(12) United States Patent
Han et al.

(10) Patent No.: US 12,297,193 B2
(45) Date of Patent: May 13, 2025

(54) PTPN2/PTP1B DEGRADER AND THERAPEUTIC METHOD THEREOF

(71) Applicant: NORTHRIDGE HEALTH GROUP (HONG KONG) CO., LIMITED, Hong Kong (CN)

(72) Inventors: Lei Han, Hong Kong (CN); Jinzi Jason Wu, Hong Kong (CN)

(73) Assignee: NORTHRIDGE HEALTH GROUP (HONG KONG) CO., LIMITED, Hong Kong (CN)

( * ) Notice: Subject to any disclaimer, the term of this patent is extended or adjusted under 35 U.S.C. 154(b) by 0 days.

(21) Appl. No.: 18/918,161

(22) Filed: Oct. 17, 2024

(65) Prior Publication Data
US 2025/0129058 A1    Apr. 24, 2025

Related U.S. Application Data

(60) Provisional application No. 63/544,959, filed on Oct. 20, 2023.

(30) Foreign Application Priority Data

| Oct. 18, 2023 | (CN) | .................. 202311350130.3 |
| Apr. 26, 2024 | (CN) | .................. 202410517098.1 |
| Jul. 12, 2024 | (CN) | .................. 202410935322.9 |
| Oct. 12, 2024 | (CN) | .................. 202411424577.5 |

(51) Int. Cl.
| C07D 409/14 | (2006.01) |
| A61K 31/4545 | (2006.01) |
| A61K 31/4725 | (2006.01) |
| C07D 401/14 | (2006.01) |
| C07D 413/14 | (2006.01) |
| C07D 417/14 | (2006.01) |
| C07D 471/08 | (2006.01) |

(52) U.S. Cl.
CPC ........ *C07D 409/14* (2013.01); *A61K 31/4545* (2013.01); *A61K 31/4725* (2013.01); *C07D 401/14* (2013.01); *C07D 413/14* (2013.01); *C07D 417/14* (2013.01); *C07D 471/08* (2013.01)

(58) Field of Classification Search
CPC .................................................... C07D 409/14
USPC ........................................................... 514/316
See application file for complete search history.

(56) References Cited

U.S. PATENT DOCUMENTS 11,407,732 B1 *    8/2022    Henderson ........... C07D 487/08

FOREIGN PATENT DOCUMENTS

| WO | 2021/127586 A1 | 6/2021 |
| WO | 2022271727 A1 | 12/2022 |
| WO | 2023019166 A1 | 2/2023 |

OTHER PUBLICATIONS

Baumgartner et al., The PTPN2/PTPN1 inhibitor ABBV-CLS-484 unleashes potent anti-tumour immunity, Nature, (2023), 622:850-894.

Hao et al., Mechanistic insights into a heterobifunctional degrader-induced PTPN2/N1 complex, Communications Chemistry, (2024), 7:1-16.

* cited by examiner

*Primary Examiner* — Niloofar Rahmani
(74) *Attorney, Agent, or Firm* — Nevrivy Patent Law Group P. L.L.C.

(57) ABSTRACT

The present disclosure describes a PTPN2/PTP1B degrader compounds having the structure of Formula (I), that are useful for treating PTPN2/PTP1B-mediated disorders or conditions, Formula (I)

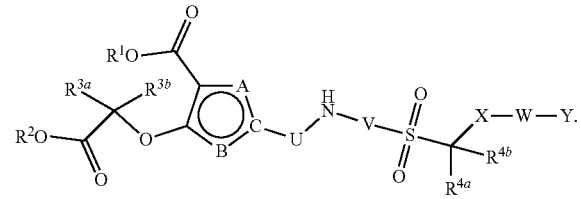

8 Claims, 1 Drawing Sheet

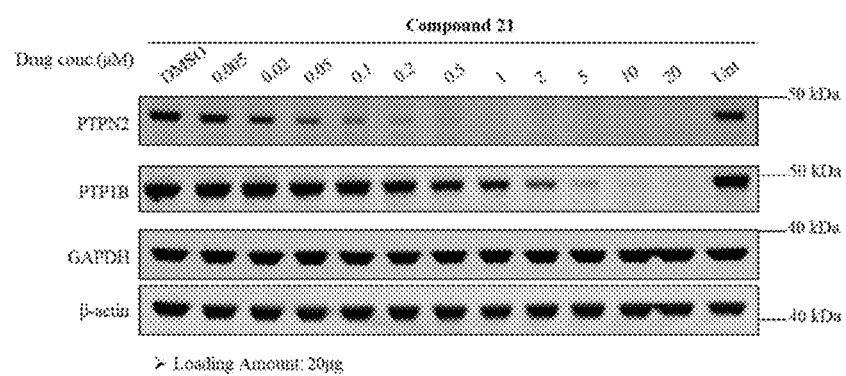

PTPN2/PTP1B DEGRADER AND THERAPEUTIC METHOD THEREOF

CROSS-REFERENCE TO RELATED APPLICATIONS

The present disclosure claims the benefits of the Chinese patent application No. 202311350130.3 entitled "PTPN2/PTP1B Agonist and Therapeutic Method Thereof" filed Oct. 18, 2023 with the China National Intellectual Property Administration, the U.S. provisional application No. 63/544,959 entitled "PTPN2/PTP1B Degrader and Therapeutic Method Thereof" filed Oct. 20, 2023 with the U.S. Patent and Trademark Office, the Chinese patent application No. 202410517098.1 entitled "PTPN2/PTP1B Degrader and Therapeutic Method Thereof" filed Apr. 26, 2024, the Chinese patent application No. 202410935322.9 entitled "PTPN2/PTP1B Degrader and Therapeutic Method Thereof" filed Jul. 12, 2024 with the China National Intellectual Property Administration, and the Chinese patent application No. 202411424577.5 entitled "PTPN2/PTP1B Degrader and Therapeutic Method Thereof" filed Oct. 12, 2024 with the China National Intellectual Property Administration, which are incorporated herein by their entireties.

FIELD

The present disclosure generally relates to compounds that bind to and act as degraders of PTPN2/PTP1B, as well as the use of such compounds for the treatment and/or prevention of PTPN2/PTP1B-mediated diseases and conditions.

BACKGROUND

Cancer immunotherapy regimens targeting immune evasion mechanisms, including checkpoint blockade (e.g., PD-1/PD-L1 and CTLA-4 blocking antibodies), have proven effective in treating a variety of cancers and have significantly improved outcomes in some populations that are refractory to conventional treatments. However, incomplete clinical responses and the development of intrinsic or acquired resistance continue to limit the subject population that may benefit from checkpoint blockade; Protein tyrosine phosphatase non-receptor type 2 (PTPN2), also known as T-cell protein tyrosine phosphatase (TC-PTP), is an intracellular member of a subfamily of tyrosine phosphatases that control multiple cellular regulatory processes by removing phosphate groups from tyrosine substrates.

Protein tyrosine phosphatase non-receptor type 1 (PTPN1), also known as protein tyrosine 5 phosphatase-1B (PTP1B), has been shown to play a key role in insulin and leptin signaling and is a major mechanism for down-regulating insulin and leptin receptor signaling pathways. Animals lacking PTP1B improved glucose regulation and lipid profiles, and decreased body weight gain was observed in high-fat diet induced animal models.

Therefore, compounds that are involved in binding to PTPN2/PTP1B and acting as degraders thereof may provide therapeutic benefit in the treatment of PTPN2/PTP1B-mediated diseases.

SUMMARY

One aspect of the present disclosure provides a compound of Formula (I),

Formula (I)

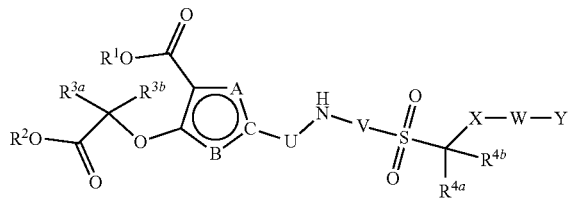

or a stereoisomer, a pharmaceutically acceptable salt, or a deuterated compound thereof, wherein, $R^1$ and $R^2$ are each independently selected from the group consisting of H, CN, $C_{1-22}$ alkyl, $C_{1-22}$ haloalkyl, $C_{2-22}$ alkenyl, $C_{2-22}$ alkynyl, $C_{1-22}$ alkoxy, $C_{1-22}$ haloalkoxy, cycloalkyl and heterocycloalkyl, or

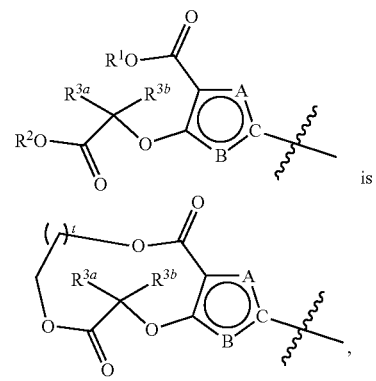

is wherein t is an integer selected from 9 to 29;

$R^{3a}$ and $R^{3b}$ are each independently selected from the group consisting of H and halogen;

$R^{4a}$ and $R^{4b}$ are each independently selected from the group consisting of H, halogen, $C_{1-6}$ alkyl, and $C_{1-6}$ alkoxy, or $R^{4a}$ and $R^{4b}$ together with carbon atom to which they are attached form cyclopropyl, cyclobutyl, or oxetanyl;

A and B are each independently selected from the group consisting of $NR^a$, $CR^b$, N, O, and S;

C is selected from the group consisting of carbon atom and nitrogen atom;

$R^a$ is selected from the group consisting of H, $C_{1-6}$ alkyl, $C_{1-6}$ alkoxy, $C_{1-6}$ haloalkyl, $C_{1-6}$ haloalkoxy, cycloalkyl, and heterocycloalkyl;

$R^b$ is selected from the group consisting of H, halogen, —CN, —$CF_3$, $C_{1-6}$ alkyl, $C_{1-6}$ alkoxy, $C_{1-6}$ haloalkyl, $C_{1-6}$ haloalkoxy, cycloalkyl, and heterocycloalkyl, wherein the cycloalkyl or heterocycloalkyl is optionally substituted with one to more halogens;

X is selected from the group consisting of

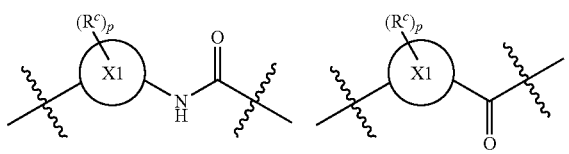

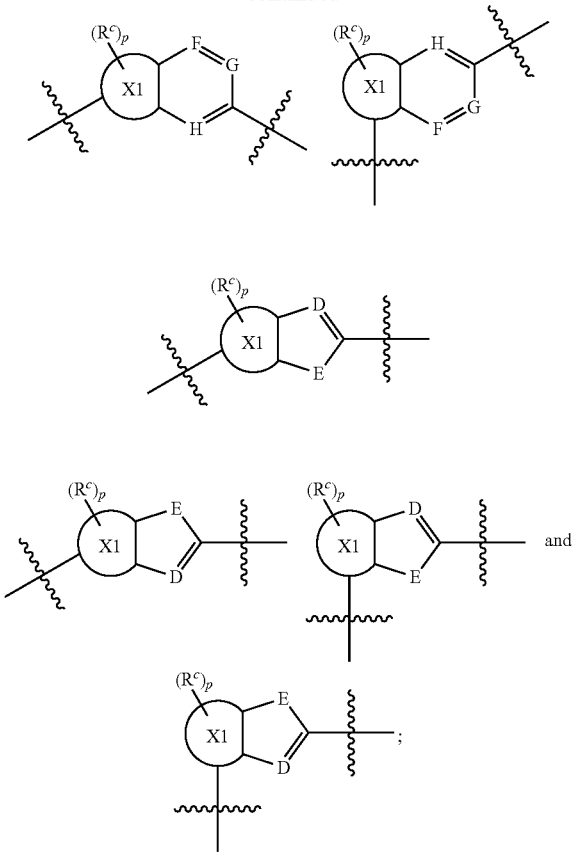
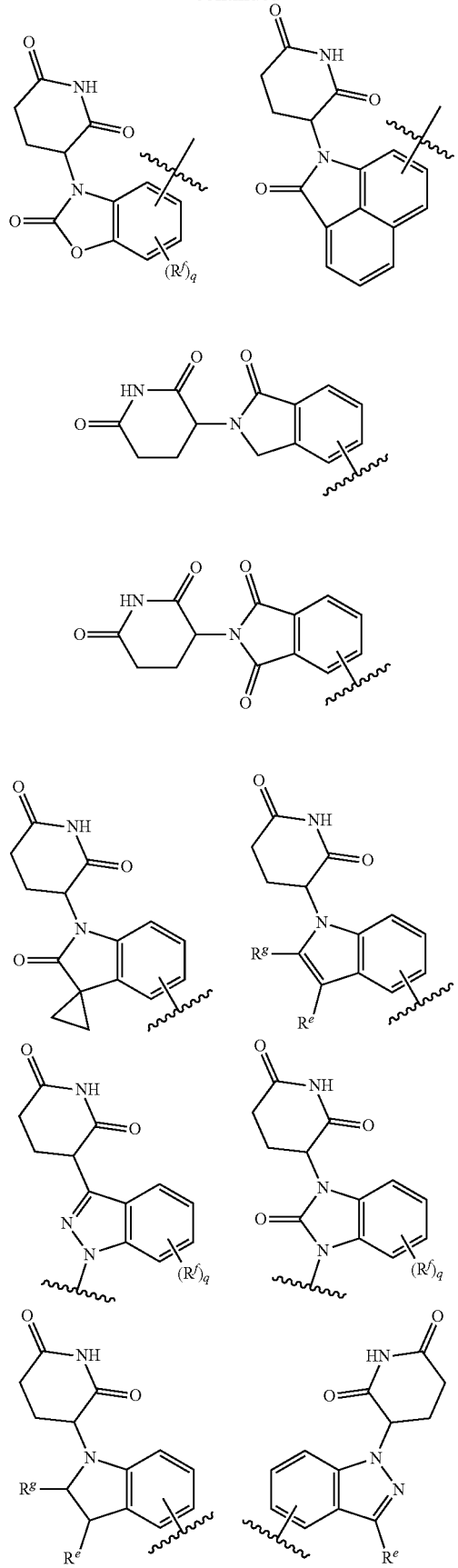

X1 is selected from the group consisting of 6-membered aryl and 6-membered heteroaryl comprising 1-4 nitrogen atoms;

$R^c$ is selected from the group consisting of H, halogen, —CN, $C_{1-6}$ alkyl, $C_{1-6}$ alkoxy, $C_{1-6}$ haloalkoxy, cycloalkyl, and heterocycloalkyl;

p is 0, 1, 2, 3 or 4;

D is selected from the group consisting of carbon atom and nitrogen atom;

E is selected from the group consisting of O, S, and $NR^d$;

$R^d$ is selected from the group consisting of H, $C_{1-6}$ alkyl, cycloalkyl, and heterocycloalkyl;

F, G, and H are each independently selected from the group consisting of C, N, O, and S;

Y is selected from the group consisting of

-continued

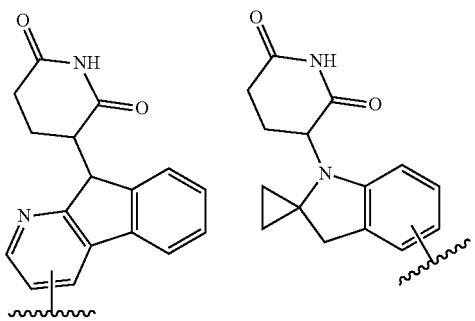

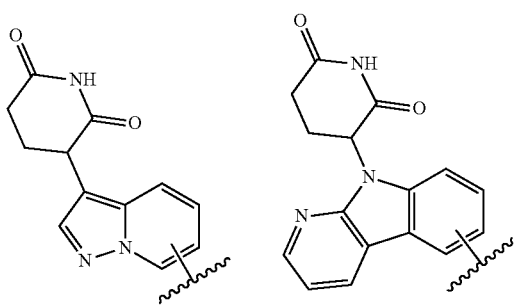

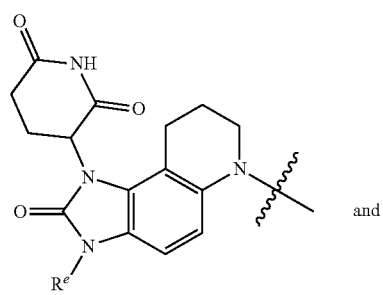

each R$^e$ is independently selected from the group consisting of hydrogen and C$_{1-6}$ alkyl, wherein C$_{1-6}$ alkyl is optionally substituted with one or more substituents independently selected from the group consisting of C$_{1-6}$ alkoxy, C$_{1-6}$ haloalkyl, C$_{3-6}$ cycloalkyl, and 4- to 6-membered heterocyclyl;

each R$^f$ is independently selected from the group consisting of halogen, —CN, C$_{1-6}$ alkyl, C$_{1-6}$ haloalkyl, C$_{1-6}$ alkoxy, and C$_{3-5}$ cycloalkoxy;

R$^g$ is selected from the group consisting of hydrogen and C$_{1-6}$ alkyl;

q is 0, 1, 2, 3 or 4;

R$^h$ is selected from the group consisting of H, halogen,

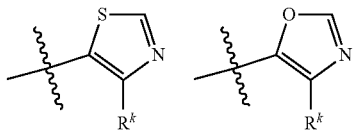

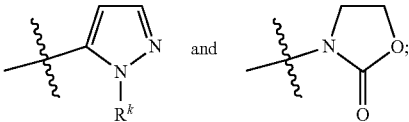

R$^k$ is selected from the group consisting of H and C$_{1-3}$ alkyl, wherein C$_{1-3}$ alkyl is optionally substituted with hydroxyl;

R$^i$ and R$^j$ are each independently selected from the group consisting of H and C$_{1-3}$ alkyl, wherein C$_{1-3}$ alkyl is optionally substituted with one or more substituents independently selected from the group consisting of F, OH, and —N(CH$_3$)$_2$; or R$^i$ and R$^j$ together with carbon atoms to which they are attached form cyclopropyl;

R$^m$ is selected from the group consisting of ethyl, isopropyl, tert-butyl, and C$_{3-6}$ cycloalkyl;

U is

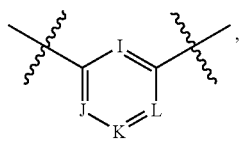

I, J, K, and L are each independently selected from the group consisting of nitrogen atom and CR$^n$;

each R$^n$ is independently selected from the group consisting of H, halogen, —CN, pseudohalogen, —CF$_3$, —OCH$_3$, and —OCF$_3$;

V is 5- to 15-membered heterocycle, wherein 5- to 15-membered heterocycle is optionally substituted with one or more substituents independently selected from the group consisting of alkyl and cycloalkyl; and W is 5- to 15-membered heterocycle, wherein 5- to 15-membered heterocycle is optionally substituted with one or more substituents independently selected from the group consisting of alkyl and cycloalkyl.

Another aspect of the present disclosure provides a compound of Formula (IX),

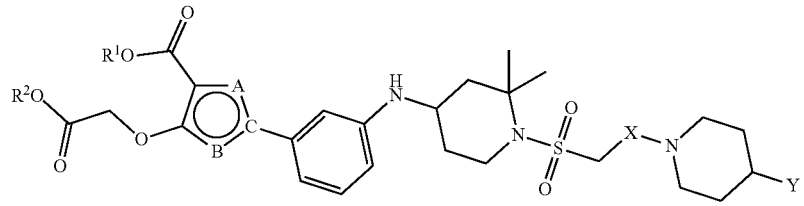

Formula (IX)

or a stereoisomer, a pharmaceutically acceptable salt, or a deuterated compound thereof,
wherein,
R¹ and R² are each independently selected from the group consisting of H, CN, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cycloalkyl, and heterocycloalkyl;
A and B are each independently selected from the group consisting of $NR^a$, $CR^b$, N, O, and S;
C is selected from the group consisting of carbon atom and nitrogen atom;
$R^a$ is selected from the group consisting of H, $C_{1-6}$ alkyl, $C_{1-6}$ alkoxy, $C_{1-6}$ haloalkoxy, cycloalkyl and heterocycloalkyl;
$R^b$ is selected from the group consisting of H, halogen, —CN, $C_{1-6}$ alkyl, $C_{1-6}$ alkoxy, $C_{1-6}$ haloalkoxy, cycloalkyl and heterocycloalkyl;
X is selected from the group consisting of $R^c$ is selected from the group consisting of H, halogen, —CN, $C_{1-6}$ alkyl, $C_{1-6}$ alkoxy, $C_{1-6}$ haloalkoxy, cycloalkyl, and heterocycloalkyl;
p is 0, 1, 2, 3 or 4;
D is selected from the group consisting of carbon atom and nitrogen atom;
E is selected from the group consisting of O, S, and $NR^d$;
$R^d$ is selected from the group consisting of H, $C_{1-6}$ alkyl, cycloalkyl and heterocycloalkyl;
F, G, and H are each independently selected from the group consisting of C, N, O, and S;
Y is selected from the group consisting of

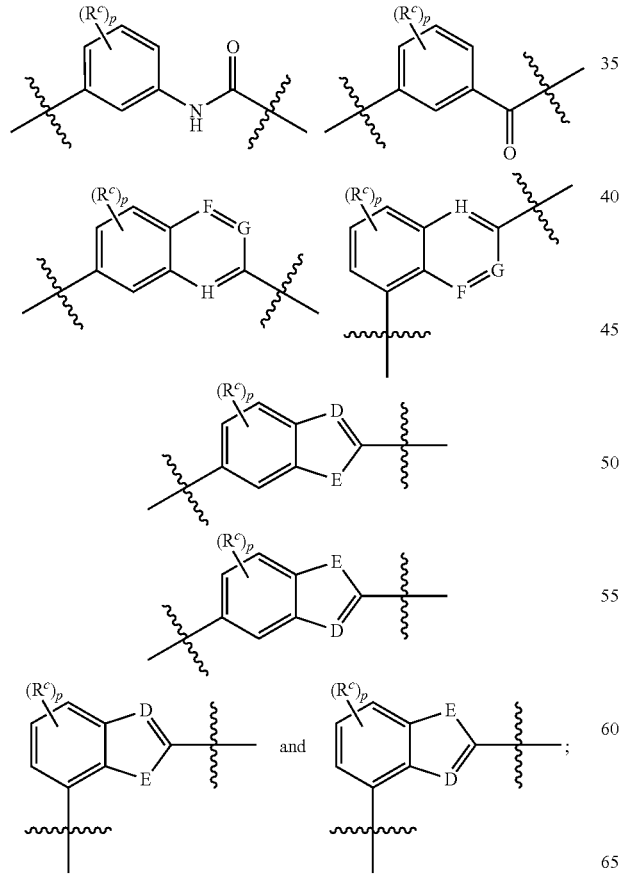

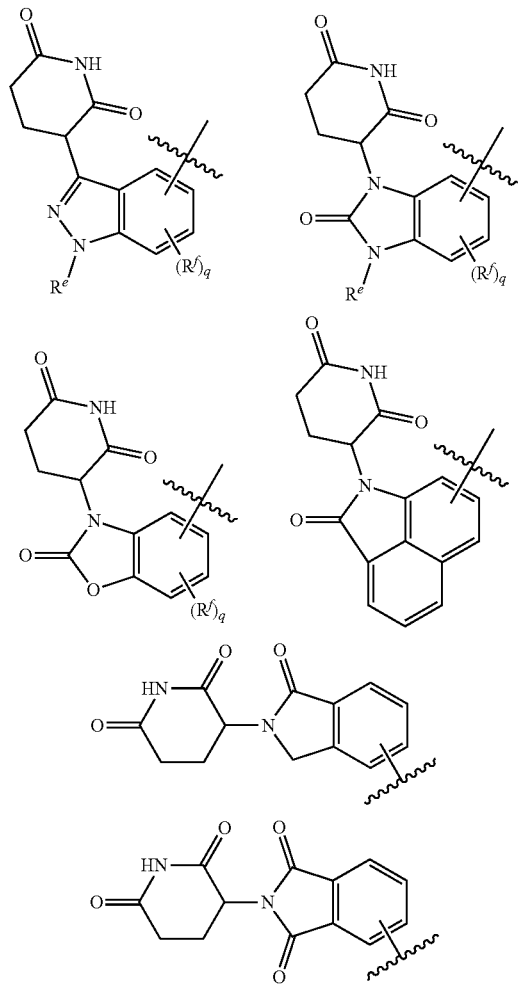

-continued

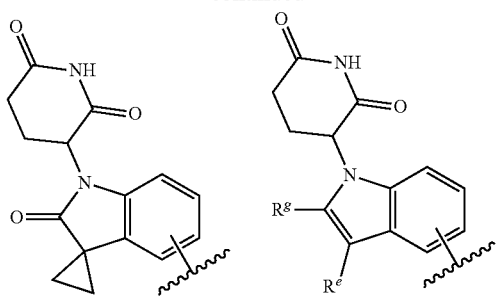

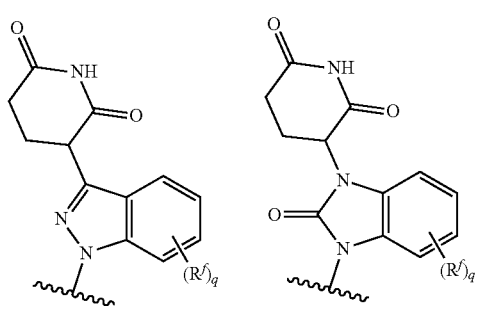

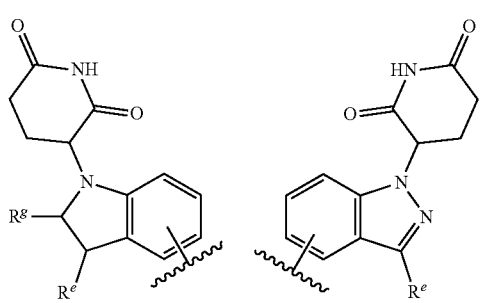

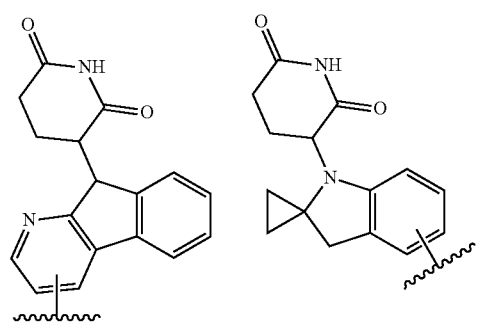

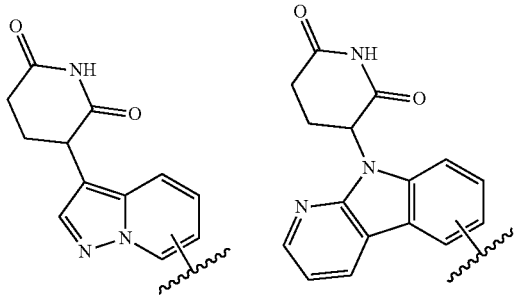

-continued

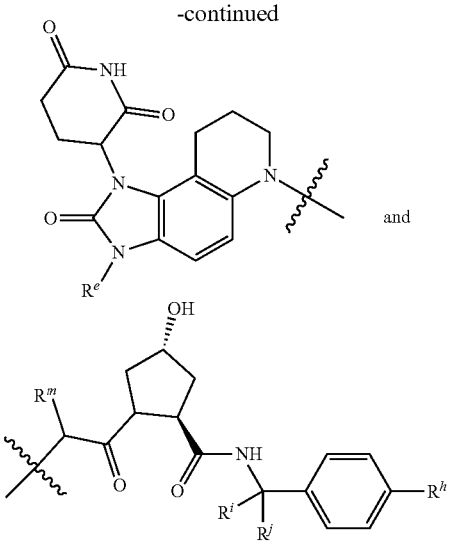

each $R^e$ is independently selected from the group consisting of hydrogen, and $C_{1\text{-}6}$ alkyl, wherein $C_{1\text{-}6}$ alkyl is optionally substituted with one or more substituents independently selected from the group consisting of $C_{1\text{-}6}$ alkoxy, $C_{1\text{-}6}$ haloalkyl, $C_{3\text{-}6}$ cycloalkyl, and 4- to 6-membered heterocyclyl;

each $R^f$ is independently selected from the group consisting of halogen, —CN, $C_{1\text{-}6}$ alkyl, $C_{1\text{-}6}$ haloalkyl, $C_{1\text{-}6}$ alkoxy, and $C_{3\text{-}5}$ cycloalkoxy;

$R^g$ is selected from the group consisting of hydrogen and $C_{1\text{-}6}$ alkyl;

q is 0, 1, 2, 3 or 4;

$R^h$ is selected from the group consisting of H, halogen,

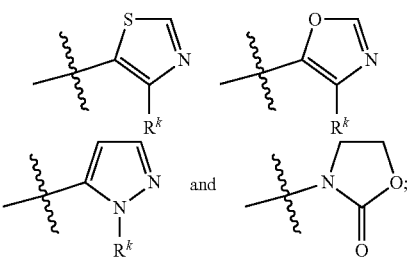

$R^k$ is selected from the group consisting of H and $C_{1\text{-}3}$ alkyl, wherein $C_{1\text{-}3}$ alkyl is optionally substituted with hydroxyl;

$R^i$ and $R^j$ are each independently selected from the group consisting of H and $C_{1\text{-}3}$ alkyl, wherein $C_{1\text{-}3}$ alkyl is optionally substituted with one or more substituents independently selected from the group consisting of F, OH, and —N(CH$_3$)$_2$; or $R^i$ and $R^j$ together with carbon atoms to which they are attached form cyclopropyl; and $R^m$ is selected from the group consisting of ethyl, isopropyl, tert-butyl, and $C_{3\text{-}6}$ cycloalkyl.

still another aspect of the present disclosure provides a compound, a pharmaceutically acceptable salt thereof, wherein the compound is selected from the group consisting of

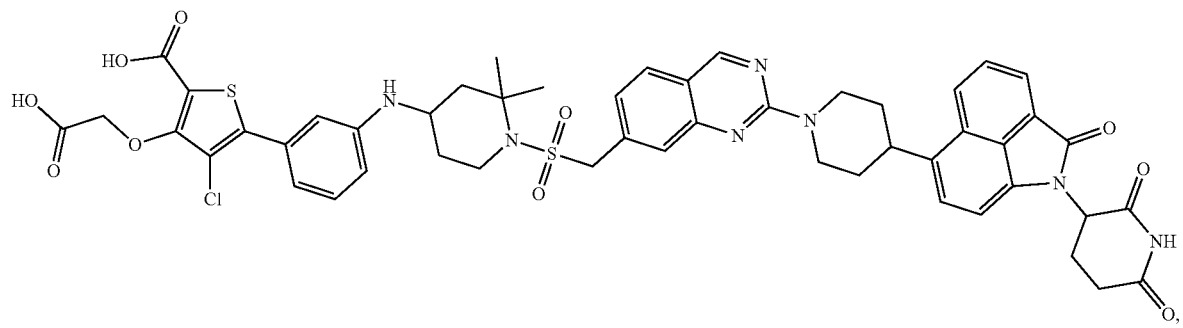
16
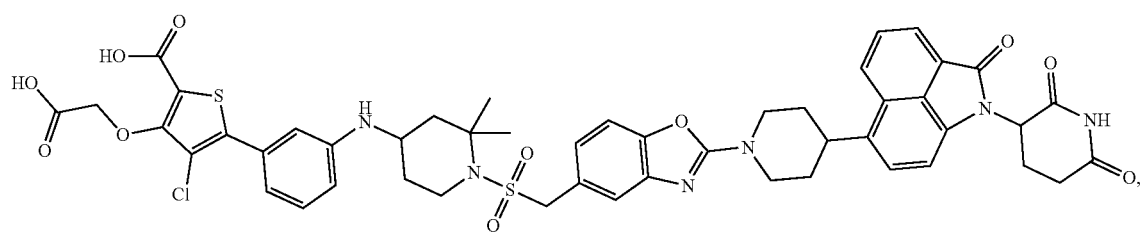
21
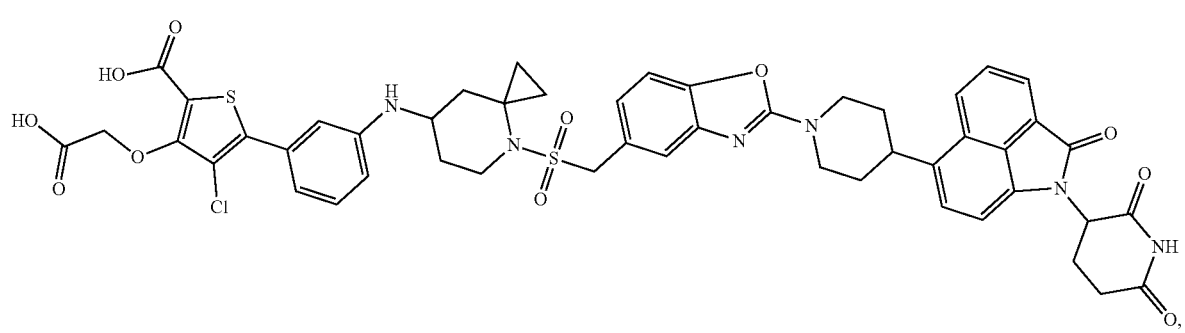
57
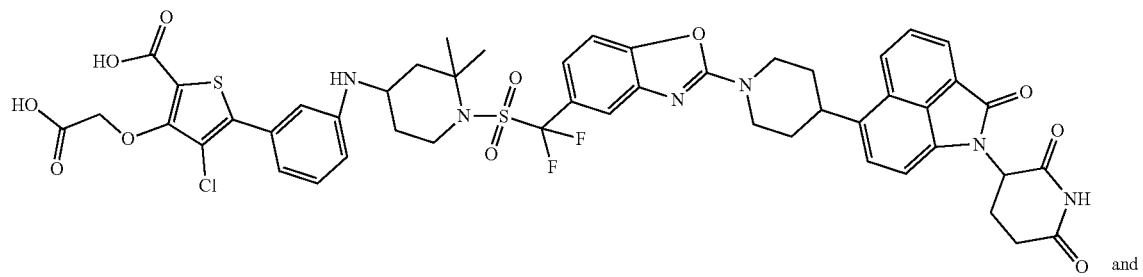
78
and
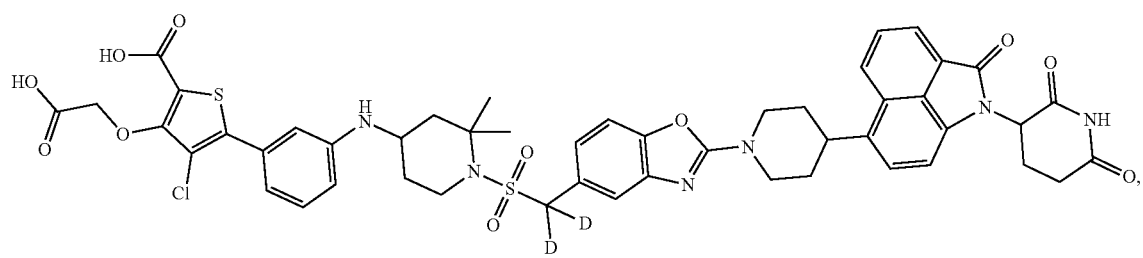
151

Yet still another aspect of the present disclosure provides a composition comprising the compound, the stereoisomer, the pharmaceutically acceptable salt, or the deuterated compound thereof of the present disclosure, and a pharmaceutically acceptable excipient.

Yet still another aspect of the present disclosure provides for use of the compound, the stereoisomer, the pharmaceutically acceptable salt, or the deuterated compound thereof, or a pharmaceutical composition of the present disclosure, in preparation of a medicament for the treatment of PTPN2/PTP1B-mediated disease or disorder.

Yet still another aspect of the present disclosure provides a method for treating PTPN2/PTP1B-mediated diseases or conditions, comprising administering to a subject in need thereof a therapeutically effective amount of the compound, the stereoisomer, the pharmaceutically acceptable salt, or the deuterated compound thereof, or the pharmaceutical composition of the present disclosure.

BRIEF DESCRIPTION OF THE DRAWINGS

FIG. 1: The degradation ability of compound 21 at different concentrations on PTPN2 and PTP1B proteins. The study shows that compound 21 has good degradation ability on PTPN2 protein in a dose-dependent manner. At the same time, the degradation ability of PTPN2 is better than that of PTP1B.

DETAILED DESCRIPTION

In the following description, certain specific details are included to provide a comprehensive understanding of the various disclosed embodiments. However, those skilled in the art will recognize that embodiments may be achieved without the use of one or more of these specific details and with the use of other methods, components, materials, etc.

Unless otherwise required in this disclosure, throughout the specification and subsequent claims, the words "including" and "comprising" are to be interpreted in an open-ended, inclusive sense, i.e., "including, without limitation".

As used in this disclosure and the appended claims, singular referents without indication of quantity include plural referents unless the context clearly indicates otherwise.

Throughout this specification, references to "an embodiment" or "embodiments" or "in another embodiment" or "in some embodiments" means to include in at least one embodiment a specific reference element, structure or feature related to that embodiment as described in that embodiment. Accordingly, the phrases "in an embodiment" or "in an embodiment" or "in another embodiment" or "in some embodiments" appearing at various places throughout the specification are intended to mean that at least one embodiment includes a specific reference element or feature related to that embodiment as described therein. "in some embodiments" need not all refer to the same embodiment. In addition, specific elements, structures, or features may be combined in one or more embodiments in any suitable manner.

It should be understood that the singular form of the article "one" (corresponding to the English words "a", "an", and "the") is used in the specification of the present disclosure and the appended claims. "the") is used in the claims in the singular form to include objects in the plural unless the context explicitly states otherwise. Thus, for example, reference to an extended-release tablet comprising "pharmaceutically acceptable excipients" includes one pharmaceutically acceptable excipient or two or more pharmaceutically acceptable excipients.

It should be understood that the singular form of the article "a" (corresponding to the English "a", "an", and "the") used in this disclosure and the accompanying claims includes plural objects unless otherwise explicitly stated in the text. Therefore, for example, a sustained-release tablet containing "pharmaceutically acceptable excipients" includes one pharmaceutically acceptable excipient or two or more pharmaceutically acceptable excipients.

Definition

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning.

A prefix such as "$C_{u\text{-}v}$" or "$C_u\text{-}C_v$" indicates that the following group has from u to v carbon atoms, where u and v are integers. For example, "$C_{1\text{-}6}$ alkyl" or "$C_1\text{-}C_6$ alkyl" indicates that the alkyl group has from 1 to 6 carbon atoms. "$C_3\text{-}C_{10}$ cycloalkyl" or "$C_{3\text{-}10}$ cycloalkyl" describes a cycloalkyl group having a total of 3 to 10 carbon atoms.

The terms "and/or" are used in this disclosure to denote "and" or "or" unless otherwise indicated.

"Optional" or "optionally" means that the subsequently described event or circumstance may, but need not occur, and the description includes instances where the event or circumstance occurs and instances in which it does not.

The terms "optionally substituted" and "substituted or unsubstituted" are used interchangeably to indicate that the particular group being described may have no nonhydrogen substituents (i.e., unsubstituted), or the group may have one or more non-hydrogen substituents (i.e., substituted). If not otherwise specified, the total number of substituents that may be present is equal to the number of H atoms present on the unsubstituted form of the group being described. Where an optional substituent is attached via a double bond, such as an oxo (=O) substituent, the group occupies two available valences, so the total number of other substituents that are included is reduced by two. In the case where optional substituents are selected independently from a list of alternatives, the selected groups may be the same or different. Throughout the disclosure, it will be understood that the number and nature of optional substituent groups will be limited to the extent that such substitutions make chemical sense to one of ordinary skill in the art.

"Halogen" or "halo" refers to fluoro, chloro, bromo and iodo (F, Cl, Br, I).

"Cyano" refers to a substituent having a carbon atom joined to a nitrogen atom by a triple bond, i.e., —CN.

"Hydroxy" refers to an —OH group.

"Pseudohalogen" is polyatomic analogues of halogens, whose chemistry, resembling that of the true halogens, allows them to substitute for halogens in several classes of chemical compounds. Examples of Pseudohalogens include, but are not limited to cyano, isocyano, azide, —OCN, and —SCN.

"Alkyl" refers to a hydrocarbon chain that may be a straight chain or branched chain, containing the indicated number of carbon atoms. For example, the term "$C_{1\text{-}22}$ alkyl" as used herein refers to saturated linear or branched-chain monovalent hydrocarbon radicals of 1-22 carbon atoms. Examples of $C_1$-$C_6$ alkyl include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-Propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$) CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$) CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$) CH(CH$_3$)$_2$), 3-methyl-1-butyl (—CH$_2$CH$_2$CH(CH$_3$)$_2$), 2-methyl-1-butyl (—CH$_2$CH(CH$_3$) CH$_2$CH$_3$), 1-hexyl (—CH$_2$CH$_2$CH$_2$CH$_2$CH$_2$CH$_3$), 2-hexyl (—CH(CH$_3$) CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$) CH(CH$_3$) CH$_2$CH$_3$), 4-methyl-2-pentyl (—CH(CH$_3$) CH$_2$CH(CH$_3$)$_2$), 3-methyl-3-pentyl (—C(CH$_3$) (CH$_2$CH$_3$)$_2$), 2-methyl-3-pentyl (—CH(CH$_2$CH$_3$) CH(CH$_3$)$_2$), 2,3-dimethyl-2-butyl (—C(CH$_3$)$_2$CH(CH$_3$)$_2$), 3, 3-dimethyl-2-butyl (—CH(CH$_3$) C(CH$_3$)$_3$, and octyl (—(CH$_2$)$_7$CH$_3$). "$C_n$ alkyl" is generally written as "$C_nH_{2n+1}$", for example, $C_{18}$ alkyl can also be written as "$C_{18}H_{37}$". Alkyl groups can be unsubstituted or substituted, as further defined herein.

"Alkoxy" refers to an alkyl group, as defined herein, that is single bonded to an oxygen atom. The attachment point of an alkoxy radical to a molecule is through the oxygen atom. An alkoxy radical may be depicted as "alkyl-O—". Alkoxy groups may contain, but are not limited to, 1 to 6 carbon atoms ("$C_{1-6}$ alkoxy"), 1 to 4 carbon atoms ("$C_{1-4}$ alkoxy"), or 1 to 3 carbon atoms ("$C_{1-3}$ alkoxy"). Alkoxy groups include, but are not limited to, methoxy, ethoxy, n-propoxy, isobutoxy, and the like. Alkoxy groups can be unsubstituted or substituted, as further defined herein.

"Haloalkyl" is an alkyl as defined herein, wherein one or more hydrogen atoms of the alkyl are independently replaced by a halogen, which may be the same or different, such that the alkyl is divalent. The alkyl group and the halogen can be any of those described above. In some embodiments, the haloalkyl defines the number of carbon atoms in the alkyl portion, e.g., $C_{1-4}$ haloalkyl includes CF$_3$, CH$_2$F, CHF$_2$, CH$_2$CF$_3$, CH$_2$CH$_2$CF$_3$, CCl$_2$CH$_2$CH$_2$CH$_3$, and C(CH$_3$)$_2$ (CF$_2$H). Haloalkyl groups can be unsubstituted or substituted, as further defined herein.

"Haloalkoxy" is an alkoxy as defined herein, wherein one or more hydrogen atoms of the alkyl in the alkyoxy are independently replaced by a halogen, which may be the same or different. The alkoxy group and the halogen can be any of those described above. In some embodiments, the haloalkoxy defines the number of carbon atoms in the alkyl portion, e.g., $C_{1-4}$ haloalkoxy includes OCF$_3$, OCH$_2$F, OCH$_2$CF$_3$, OCH$_2$CH$_2$CF$_3$, OCCl$_2$CH$_2$CH$_2$CH$_3$, and OC(CH$_3$)$_2$ (CF$_2$H). Haloalkoxy groups can be unsubstituted or substituted, as further defined herein.

"Alkenyl" refers to an alkyl group, as defined herein, consisting of at least two carbon atoms and at least one carbon-carbon double bond. For example, as used herein, the term "$C_2$-$C_6$ alkenyl" means straight or branched chain unsaturated radicals of 2 to 6 carbon atoms, including, but not limited to, ethenyl, 1-propenyl, 2-propenyl, 1-, 2-, or 3-butenyl, and the like. Alkenyl groups can be unsubstituted or substituted, as further defined herein.

"Alkynyl" refers to an alkyl group, as defined herein, consisting of at least two carbon atoms and at least one carbon-carbon triple bond. Examples include, but are not limited to, ethynyl, 1-propynyl, 2-propynyl, 1-, 2-, or 3-butynyl, and the like. Alkynyl groups can be unsubstituted or substituted, as further defined herein.

"Cycloalkyl" refers to a fully saturated hydrocarbon ring system that has the specified number of carbon atoms, which may be a monocyclic, bridged or fused bicyclic, spirocyclic or polycyclic ring system that is connected to the base molecule through a carbon atom of the cycloalkyl ring. Cycloalkyl groups may contain, but are not limited to, 3 to 8 carbon atoms ("$C_{3-8}$ cycloalkyl"), 3 to 6 carbon atoms ("$C_{3-6}$ cycloalkyl"), 3 to 5 carbon atoms ("$C_{3-5}$ cycloalkyl") or 3 to 4 carbon atoms ("$C_{3-4}$ cycloalkyl"). Examples include, but are not limited to, cyclopropyl, cyclobutyl, cyclopentyl, cyclohexyl, cycloheptyl, adamantanyl, and the like. Cycloalkyl groups may be optionally substituted or substituted, as further defined herein.

"cycloalkoxy" refers to the group "—O-cycloalkyl".

"Heterocycloalkyl" refers to a fully saturated ring system containing the specified number of ring atoms and containing at least one heteroatom selected from N, O and S as a ring member, where ring S atoms are optionally substituted by one or two oxo groups (i.e., S(O) q, where q is 0, 1 or 2) and where the heterocycloalkyl ring is connected to the base molecule via a ring atom, which may be C or N. Heterocycloalkyl rings include rings which are spirocyclic, bridged, or fused to one or more other heterocycloalkyl or carbocyclic rings. Heterocycloalkyl rings may be optionally unsubstituted or substituted, as further defined herein. Such substituents may be present on the heterocyclic ring attached to the base molecule, or on a spirocyclic, bridged or fused ring attached thereto. Heterocycloalkyl rings may include, but are not limited to, 3-10 membered heterocyclyl groups, for example 4-10, 3-8 or 4-8 membered heterocycloalkyl groups, in accordance with the definition herein.

"Aryl" or "Aromatic" refers to monocyclic, bicyclic (e.g., biaryl, fused) or polycyclic ring systems that contain the specified number of ring atoms, in which all carbon atoms in the ring are of sp$^2$ hybridization and in which the pi electrons are in conjugation. Aryl groups may contain, but are not limited to, 6 to 10 carbon atoms ("$C_6$-$C_{10}$ aryl"). Fused aryl groups may include an aryl ring (e.g., a phenyl ring) fused to another aryl ring. Examples include, but are not limited to, phenyl, naphthyl, indanyl, and indenyl. Aryl groups may be optionally substituted, unsubstituted or substituted, as further defined herein.

"Heteroaryl" or "Heteroaromatic" refer to monocyclic, bicyclic (e.g., heterobiaryl, fused) or polycyclic ring systems that contain the specified number of ring atoms and include at least one heteroatom selected from N, O and S as a ring member in a ring in which all carbon atoms in the ring are of sp$^2$ hybridization and in which the pi electrons are in conjugation. Heteroaryl groups may contain, but are not limited to, 5 to 10 ring atoms ("5- to 10-membered heteroaryl"), 5 to 9 ring atoms ("5- to 9-membered heteroaryl"), or 5 to 6 ring atoms ("5- to 6-membered heteroaryl"). Heteroaryl rings are attached to the base molecule via a ring atom of the heteroaromatic ring. Thus, either 5- or 6-membered heteroaryl rings, alone or in a fused structure, may be attached to the base molecule via a ring C or N atom. Examples of heteroaryl groups include, but are not limited to, pyrrolyl, furanyl, thiophenyl, pyrazolyl, imidazolyl, isoxazolyl, oxazolyl, isothiazolyl, thiazolyl, triazolyl, oxadiazolyl, thiadiazolyl, tetrazolyl, pyridinyl, pyridizinyl, pyrimidinyl, pyrazinyl, benzofuranyl, benzothiophenyl, indolyl, benzamidazolyl, indazolyl, quinolinyl, isoquinolinyl, purinyl, triazinyl, naphthyridinyl, cinnolinyl, quinazolinyl and quinoxalinyl. Examples of 5- or 6-membered heteroaryl groups include, but are not limited to, pyrrolyl, furanyl, thiophenyl, pyrazolyl, imidazolyl, isoxazolyl, oxazolyl, isothiazolyl, thiazolyl, triazolyl, pyridinyl, pyrimidinyl, pyrazinyl and pyridazinyl rings. Heteroaryl groups may be optionally unsubstituted or substituted, as further defined herein.

"Heterocyclyl" or "heterocycle" or "heterocyclic" or "heterocyclic ring" as used herein refers to a single saturated or partially unsaturated non-aromatic ring or a non-aromatic multiple ring system that has at least one heteroatom in the ring (i.e., at least one annular (i.e., ring-shaped) heteroatom selected from oxygen, nitrogen, and sulfur). Unless otherwise specified, a heterocyclyl group has from 3 to about 20 annular atoms, for example from 3 to 15 annular atoms, for example from 5 to 15 annular atoms, 3 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring (e.g. bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine,2-oxa-6-azaspiro[3. 3]heptan-6-yl, 6-oxa-1-azaspiro[3. 3]heptan-1-yl, 2-thia-6-azaspiro[3. 3]heptan-6-yl, 2, 6-diazaspiro[3. 3]heptan-2-yl, 2-azabicyclo[3. 1. 0]hexan-2-yl, 3-azabicyclo[3. 1. 0]hexanyl, 2-azabicyclo[2. 1. 1]hexanyl, 2-azabicyclo[2. 2. 1]heptan-2-yl, 4-azaspiro[2. 4]heptanyl, 5-azaspiro[2. 4]heptanyl,

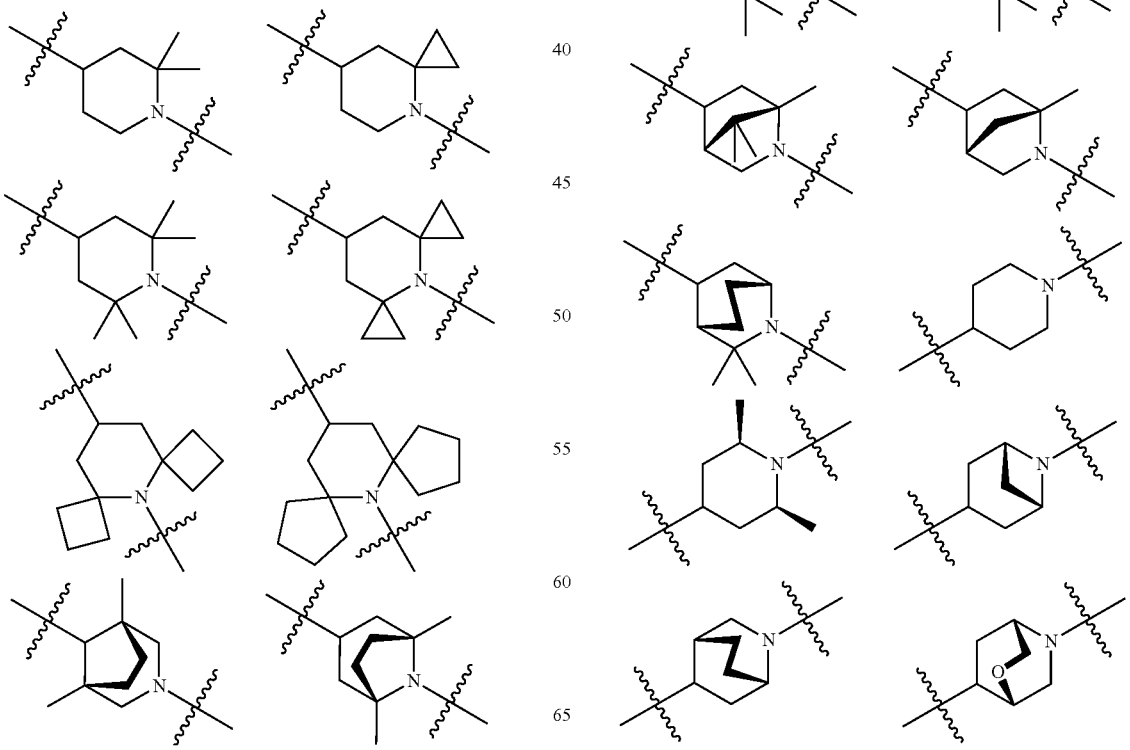

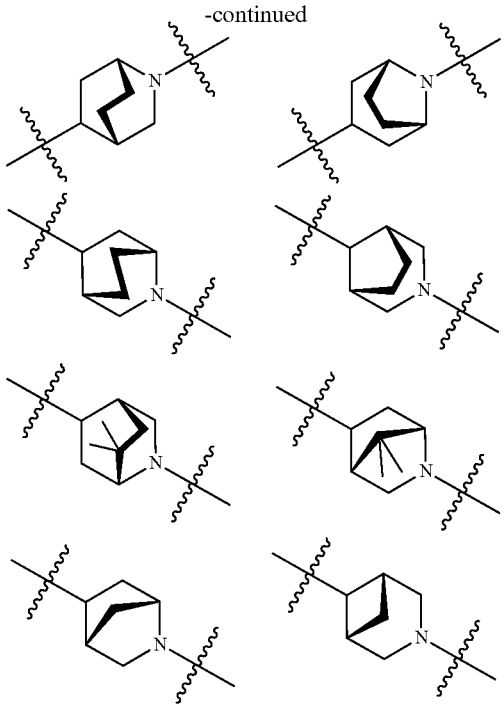

and the like. Heterocyclyl groups can be unsubstituted or substituted, as further defined herein.

A "compound of the present disclosure" includes compound disclosed herein, for example a compound of the present disclosure includes the compound of Formula (I), (II), (III), (IV), (V), (VI), (VII), (VIII), and (IX), but also includes the compound of the examples.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Therapeutically effective amount" or "effective amount" as used herein refers to an amount that is effective to elicit the desired biological or medical response, including the amount of a compound that, when administered to a subject for treating a disease, is sufficient to affect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the subject.

Provided are also pharmaceutically acceptable salts, hydrates, solvates, tautomeric forms, polymorphs, and prodrugs of the compounds described herein.

"Pharmaceutically acceptable" refers to compounds, salts, compositions, dosage forms and other materials which are useful in preparing a pharmaceutical composition that is suitable for veterinary or human pharmaceutical use.

The compounds described herein may be prepared and/or formulated as pharmaceutically acceptable salts or when appropriate as a free base. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, y-hydroxybutyrates, glycolates, tartrates, and mandelates. Lists of other suitable pharmaceutically acceptable salts are found in Remington: The Science and Practice of Pharmacy, 21st Edition, Lippincott Wiliams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $N(C_1-C_4$ alkyl$)$ 4+. Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5 (12): 524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Substitution with positron emitting isotopes, such as $^{11}$C, 18F, 15O and $^{13}$N, can be useful in Positron Emission Topography (PET) studies for examining substrate receptor occupancy. Isotopically-labeled compounds of Formula I can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, tautomer, diastereomers, and other stereoisomeric forms that may be defined, in terms of absolute stereochemistry, as (R)- or(S)- or, as (D)- or (L)- for amino acids, as well as deuterated analogs thereof. The chemical formula shown in the present disclosure is meant to include all such possible isomers, as well as their racemic and optically pure forms. Optically active (+) and (−), (R)- and(S)—, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

"Stereoisomer" as used herein refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

"Tautomer" as used herein refers to a proton shift from one atom of a molecule to another atom of the same molecule. In some embodiments, the present disclosure includes tautomers of said compounds.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Prodrug" as used herein refers to a derivative of a drug that upon administration to the human body is converted to the parent drug according to some chemical or enzymatic pathway. In some embodiments, a prodrug is a biologically inactive derivative of a drug that upon administration to the human body is converted to the biologically active parent drug according to some chemical or enzymatic pathway.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival. "At risk individual" as used herein refers to an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

Compound

One aspect of the present disclosure provides a compound of Formula (I),

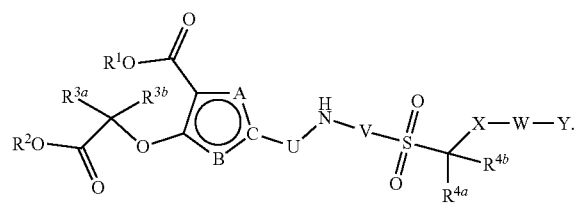

Formula (I)

or a stereoisomer, a pharmaceutically acceptable salt, or a deuterated compound thereof, wherein, $R^1$ and $R^2$ are each independently selected from the group consisting of H, CN, $C_{1-22}$ alkyl, $C_{1-22}$ haloalkyl, $C_{2-22}$ alkenyl, $C_{2-22}$ alkynyl, $C_{1-22}$ alkoxy, $C_{1-22}$ haloalkoxy, cycloalkyl and heterocycloalkyl, or

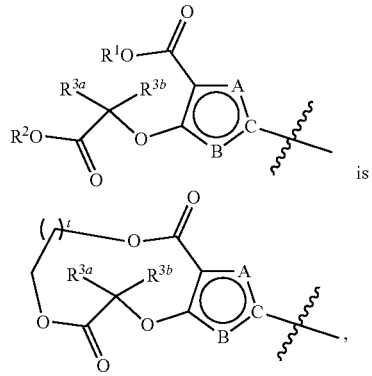

is

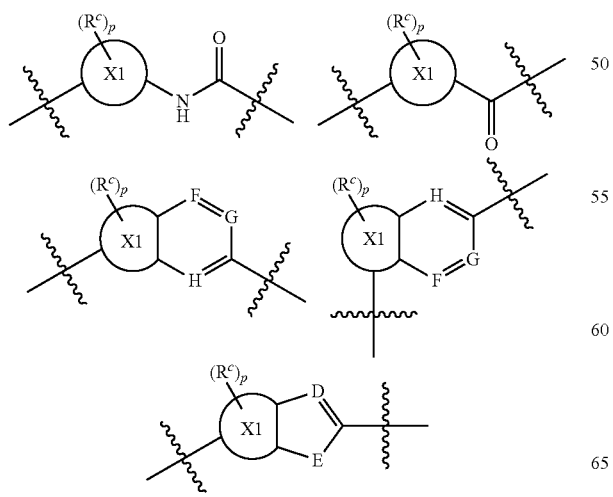

wherein t is an integer selected from 9 to 29;

$R^{3a}$ and $R^{3b}$ are each independently selected from the group consisting of H and halogen;

$R^{4a}$ and $R^{4b}$ are each independently selected from the group consisting of H, halogen, $C_{1-6}$ alkyl, and $C_{1-6}$ alkoxy, or $R^{4a}$ and $R^{4b}$ together with carbon atom to which they are attached form cyclopropyl, cyclobutyl, or oxetanyl;

A and B are each independently selected from the group consisting of $NR^a$, $CR^b$, N, O, and S;

C is selected from the group consisting of carbon atom and nitrogen atom;

$R^a$ is selected from the group consisting of H, $C_{1-6}$ alkyl, $C_{1-6}$ alkoxy, $C_{1-6}$ haloalkyl, $C_{1-6}$ haloalkoxy, cycloalkyl, and heterocycloalkyl;

$R^b$ is selected from the group consisting of H, halogen, —CN, —CF$_3$, $C_{1-6}$ alkyl, $C_{1-6}$ alkoxy, $C_{1-6}$ haloalkyl, $C_{1-6}$ haloalkoxy, cycloalkyl, and heterocycloalkyl, wherein the cycloalkyl or heterocycloalkyl is optionally substituted with one to more halogens;

X is selected from the group consisting of

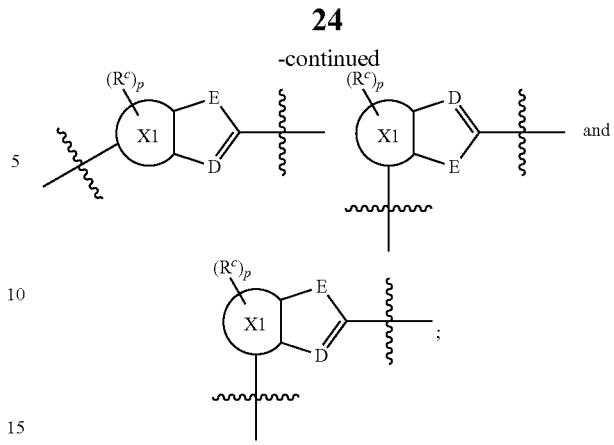

X1 is selected from the group consisting of 6-membered aryl and 6-membered heteroaryl comprising 1-4 nitrogen atoms;

$R^c$ is selected from the group consisting of H, halogen, —CN, $C_{1-6}$ alkyl, $C_{1-6}$ alkoxy, $C_{1-6}$ haloalkoxy, cycloalkyl, and heterocycloalkyl;

p is 0, 1, 2, 3 or 4;

D is selected from the group consisting of carbon atom and nitrogen atom;

E is selected from the group consisting of O, S, and $NR^d$;

$R^d$ is selected from the group consisting of H, $C_{1-6}$ alkyl, cycloalkyl, and heterocycloalkyl;

F, G, and H are each independently selected from the group consisting of C, N, O, and S;

Y is selected from the group consisting of

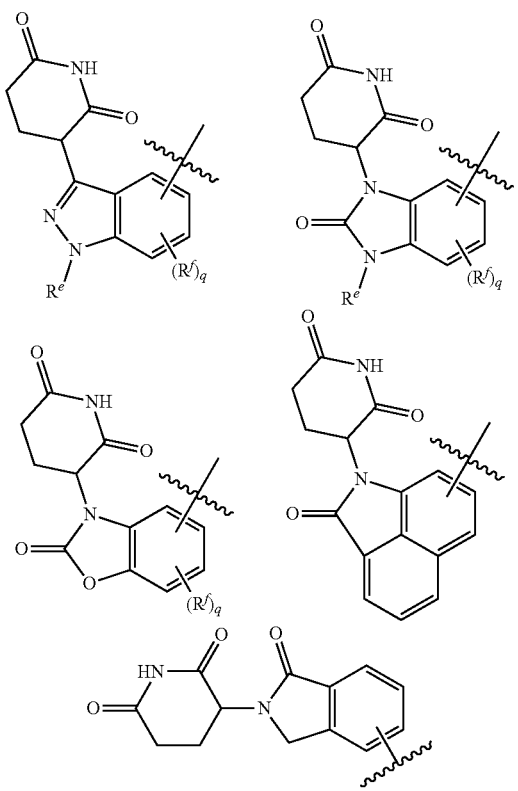

-continued

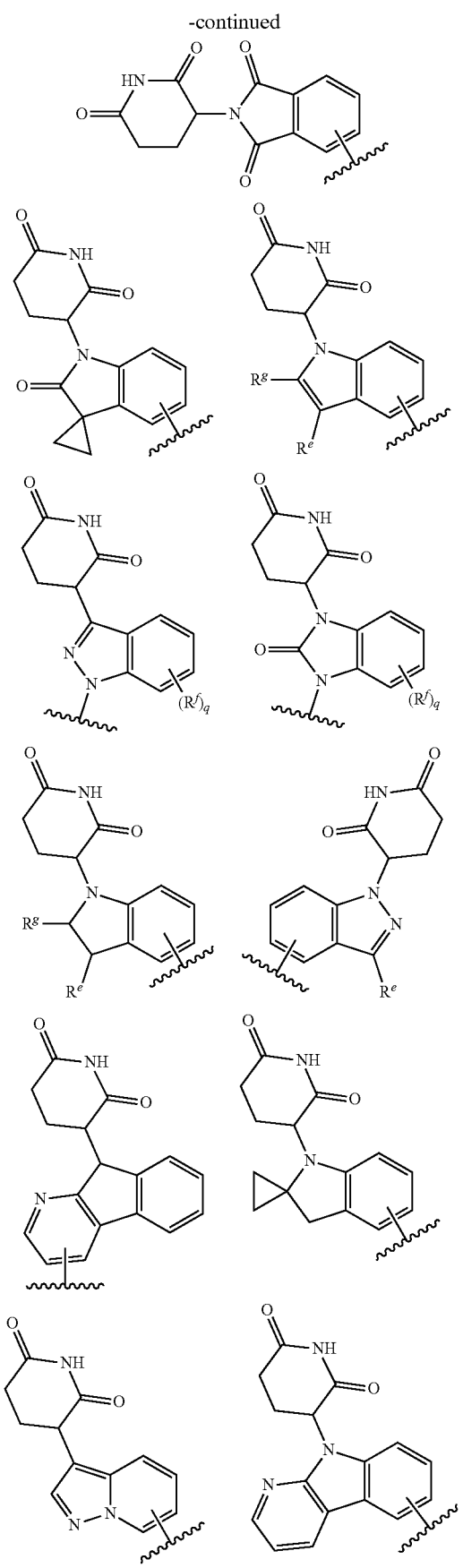

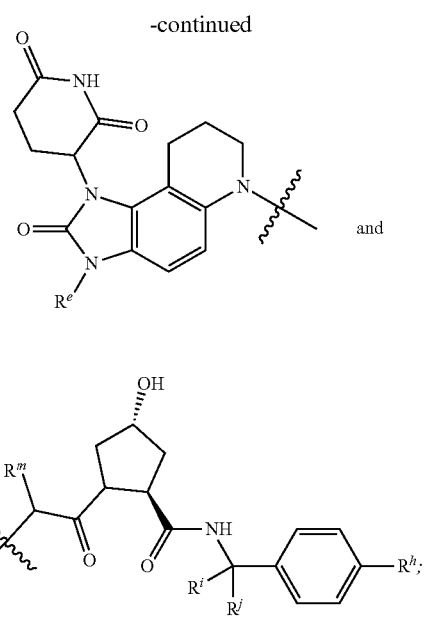 and each $R^e$ is independently selected from the group consisting of hydrogen and $C_{1-6}$ alkyl, wherein $C_{1-6}$ alkyl is optionally substituted with one or more substituents independently selected from the group consisting of $C_{1-6}$ alkoxy, $C_{1-6}$ haloalkyl, $C_{3-6}$ cycloalkyl, and 4- to 6-membered heterocyclyl;

each $R^f$ is independently selected from the group consisting of halogen, —CN, $C_{1-6}$ alkyl, $C_{1-6}$ haloalkyl, $C_{1-6}$ alkoxy, and $C_{3-5}$ cycloalkoxy;

$R^g$ is selected from the group consisting of hydrogen and $C_{1-6}$ alkyl;

q is 0, 1, 2, 3 or 4;

$R^h$ is selected from the group consisting of H, halogen,

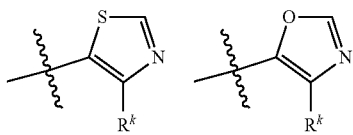

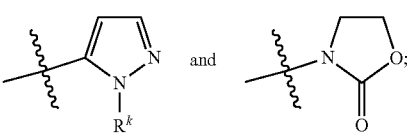 and $R^k$ is selected from the group consisting of H and $C_{1-3}$ alkyl, wherein $C_{1-3}$ alkyl is optionally substituted with hydroxyl;

$R^i$ and $R^j$ are each independently selected from the group consisting of H and $C_{1-3}$ alkyl, wherein $C_{1-3}$ alkyl is optionally substituted with one or more substituents independently selected from the group consisting of F, OH, and —N(CH$_3$)$_2$: or $R^i$ and $R^j$ together with carbon atoms to which they are attached form cyclopropyl;

$R^m$ is selected from the group consisting of ethyl, isopropyl, tert-butyl, and $C_{3-6}$ cycloalkyl;

U is

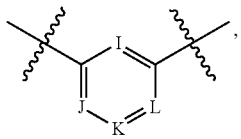

I, J, K, and L are each independently selected from the group consisting of nitrogen atom and $CR''$;
each $R''$ is independently selected from the group consisting of H, halogen, —CN, pseudohalogen, —$CF_3$, —$OCH_3$, and —$OCF_3$;
V is 5- to 15-membered heterocycle, wherein 5- to 15-membered heterocycle is optionally substituted with one or more substituents independently selected from the group consisting of alkyl and cycloalkyl; and
W is 5- to 15-membered heterocycle, wherein 5- to 15-membered heterocycle is optionally substituted with one or more substituents independently selected from the group consisting of alkyl and cycloalkyl.

In some embodiments, in the compound of Formula (I), $R^1$ and $R^2$ are each independently selected from the group consisting of H, —CN, $C_{1-6}$ alkyl, $C_{1-6}$ haloalkyl, $C_{1-6}$ alkoxy, and $C_{1-6}$ haloalkoxy.

In some embodiments, in the compound of Formula (I), $R^1$ and $R^2$ are each independently selected from the group consisting of H, —CN, methyl, ethyl, n-propyl, isopropyl, n-butyl, isobutyl, and tert-butyl.

In some embodiments, in the compound of Formula (I), $R^{3a}$, $R^{3b}$, $R^{4a}$, and $R^{4b}$ are each independently selected from the group consisting of H and F.

In some embodiments, in the compound of Formula (I),
A is selected from the group consisting of N, O, S, and NH;
B is selected from the group consisting of N, O, S, $NR^a$, and $CR^b$;
C is selected from the group consisting of carbon atom and nitrogen atom;
$R^a$ is selected from the group consisting of H, $C_{1-3}$ alkyl, $C_{1-3}$ alkoxy, $C_{1-3}$ haloalkyl, and $C_{1-3}$ haloalkoxy; and
$R^b$ is selected from the group consisting of H, F, Cl, methyl, ethyl, —CN, —$CF_3$, —$CHF_2$, and —$CH_2F$.

In some embodiments, in the compound of Formula (I), A is S; B is $CR^b$; and C is carbon atom; $R^b$ is selected from the group consisting of H, F, Cl, —$CH_3$, and —$CF_3$.

In some embodiments, in the compound of Formula (I), U is

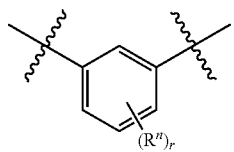

each $R''$ is independently selected from the group consisting of halogen, —CN, —$CF_3$, —$OCH_3$, and —$OCF_3$; and
r is 0, 1, 2, 3 or 4.

In some embodiments, in the compound of Formula (I), $R''$ is halogen, and r is 0 or 1.

In some embodiments, in the compound of Formula (I), V is

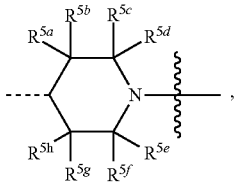

$R^{5a}$, $R^{5b}$, $R^{5c}$, $R^{5d}$, $R^{5e}$, $R^{5f}$, $R^{5g}$, and $R^{5h}$ are each independently selected from the group consisting of H and $C_{1-6}$ alkyl; or
$R^{5a}$ and $R^{5b}$ together with carbon atom to which they are attached form $C_{3-6}$ cycloalkyl, and/or $R^{5c}$ and $R^{5d}$ together with carbon atom to which they are attached form $C_{3-6}$ cycloalkyl, and/or $R^{5e}$ and $R^{5f}$ together with carbon atom to which they are attached form $C_{3-6}$ cycloalkyl, and/or $R^{5g}$ and $R^{5h}$ together with carbon atom to which they are attached form $C_{3-6}$ cycloalkyl; or
two or three of $R^{5a}$, $R^{5b}$, $R^{5c}$, $R^{5d}$, $R^{5e}$, $R^{5f}$, $R^{5g}$, and $R^h$ together with the carbon atoms to which they are attached form $C_{3-6}$ cycloalkyl, the $C_{3-6}$ cycloalkyl is optionally substituted with one to six $C_{1-6}$ alkyl;

wherein "---" is a bond connected to "—NH—"; "⸺ξ⸺" is a bond connected to "—$S(O)_2$—".

In some embodiments, in the compound of Formula (I), V is selected from the group consisting of

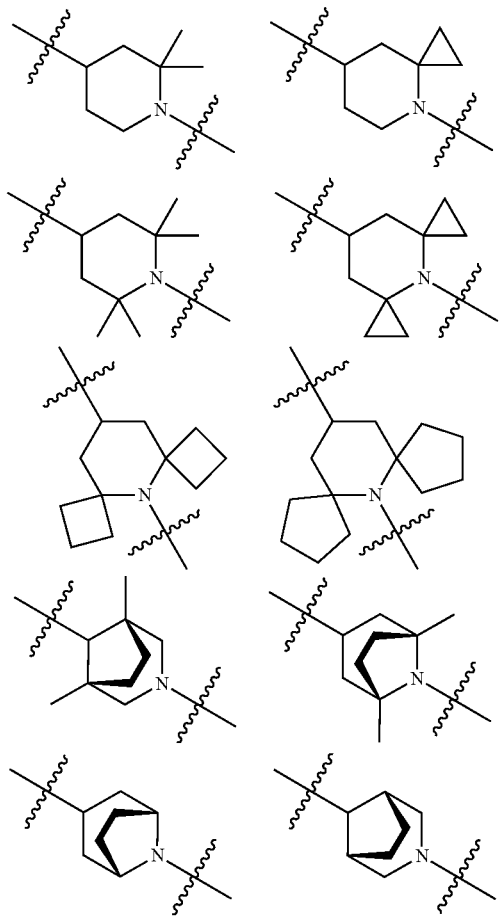

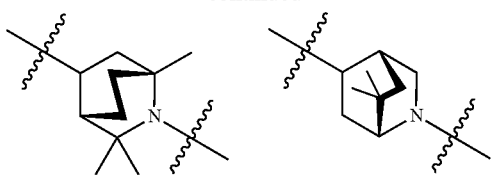
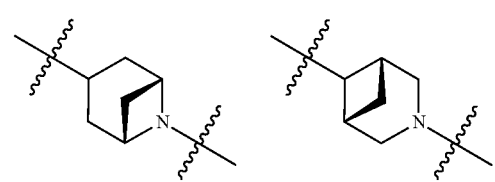
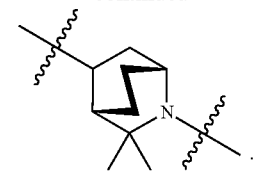
In some embodiments, in the compound of Formula (I), V is selected from the group consisting of
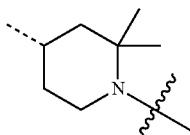 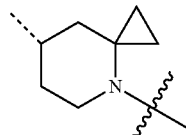
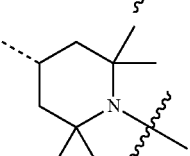 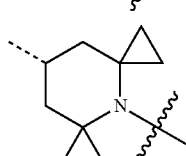
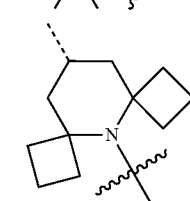 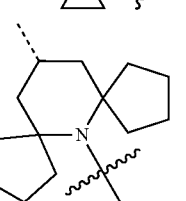
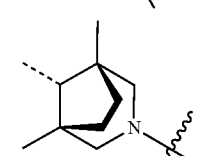 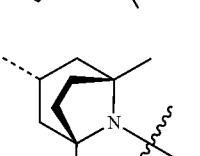
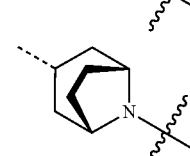 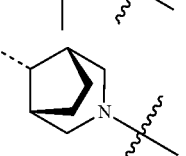
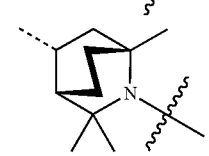 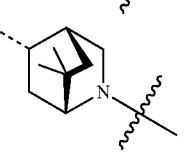
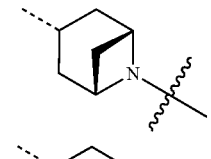 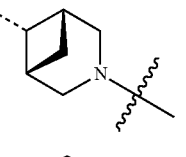
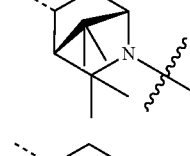 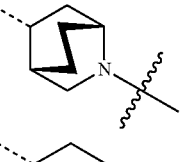
and
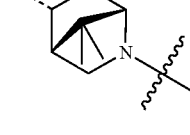 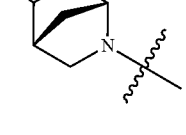

-continued

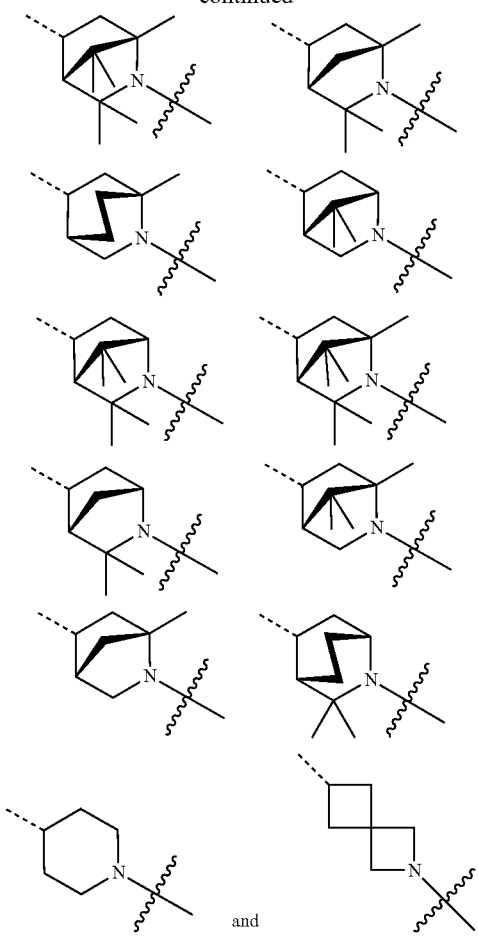

wherein "---" is a bond connected to "—NH—"; "⸹" is a bond connected to "—S(O)₂—".

In some embodiments, in the compound of Formula (I), W is

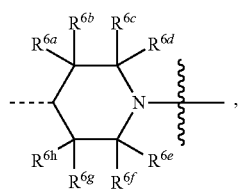

$R^{6a}$, $R^{6b}$, $R^{6c}$, $R^{6d}$, $R^{6e}$, $R^{6f}$, $R^{6g}$ and $R^{6h}$ are each independently selected from the group consisting of H and $C_{1-6}$ alkyl; or two or three of $R^{6a}$, $R^{6b}$, $R^{6c}$, $R^{6d}$, $R^{6e}$, $R^{6f}$, $R^{6g}$, and $R^{6h}$ together with the carbon atoms to which they are attached form $C_{3-6}$ cycloalkyl, the $C_{3-6}$ cycloalkyl is optionally substituted with one to six $C_{1-6}$ alkyl;

"---" is a bond connected to Y, "⸹" is a bond connected to X.

In some embodiments, in the compound of Formula (I), W is selected from the group consisting of:

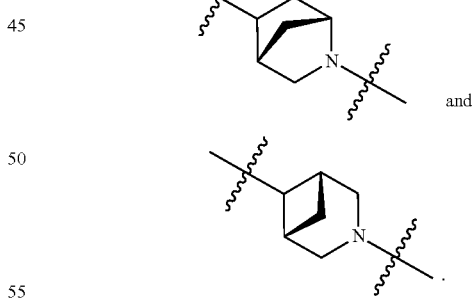

In some embodiments, in the compound of Formula (I), W is selected from the group consisting of

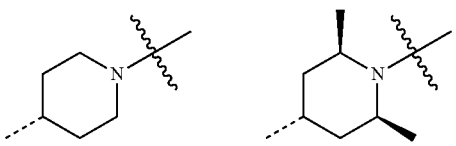

-continued

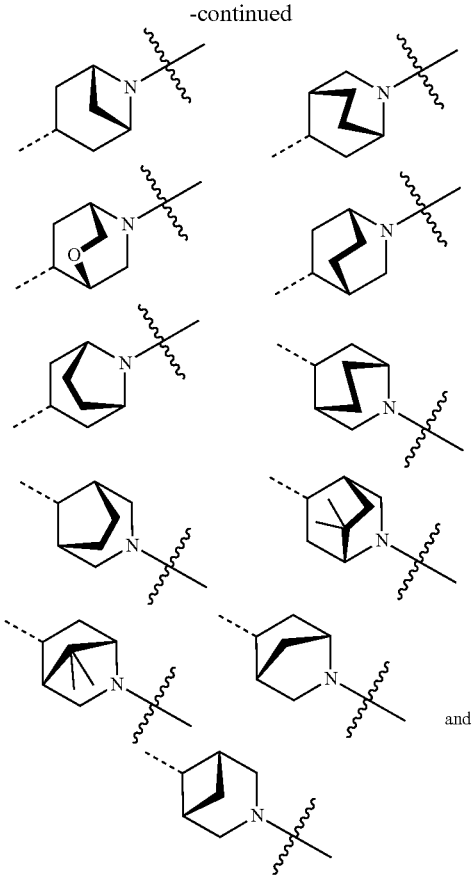

"---" is a bond connected to Y, "-ξ-" is a bond connected to X.

In some embodiments, in the compound of Formula (I), X is selected from the group consisting of J¹, J², and J³ are each independently selected from the group consisting of N and CR$^c$;
D is selected from the group consisting of carbon atom and nitrogen atom;
E is selected from the group consisting of O, S, and NR$^d$;
F, G, and H are each independently selected from the group consisting of CH and N;
R$^c$ is selected from the group consisting of H, halogen, —CN, $C_{1-6}$ alkyl, $C_{1-6}$ alkoxy, and $C_{1-6}$ haloalkoxy;
R$^d$ is selected from the group consisting of H and $C_{1-6}$ alkyl; and "---" is a bond connected to "—C(R$^{4a}$R$^{4b}$)—"; "-ξ-" is a bond connected to W.

In some embodiments, in the compound of Formula (I), X is selected from the group consisting of

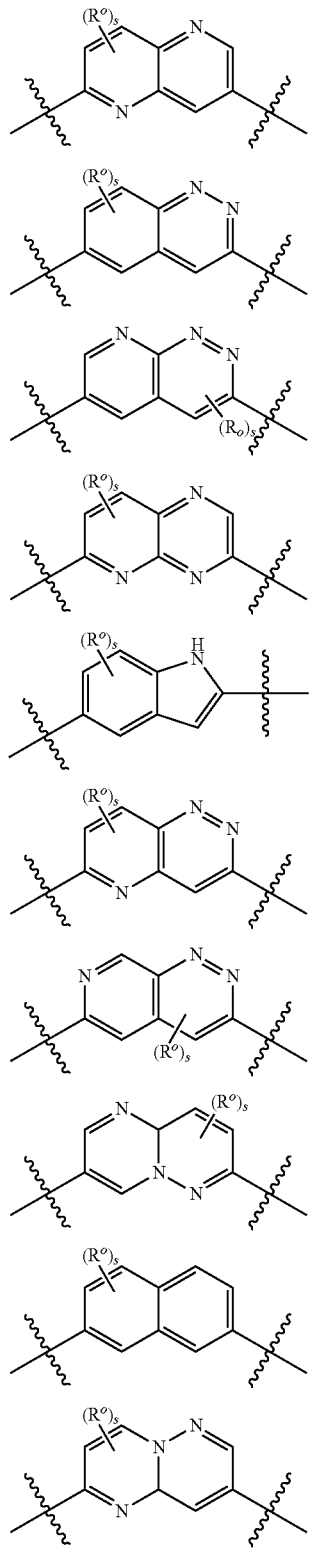

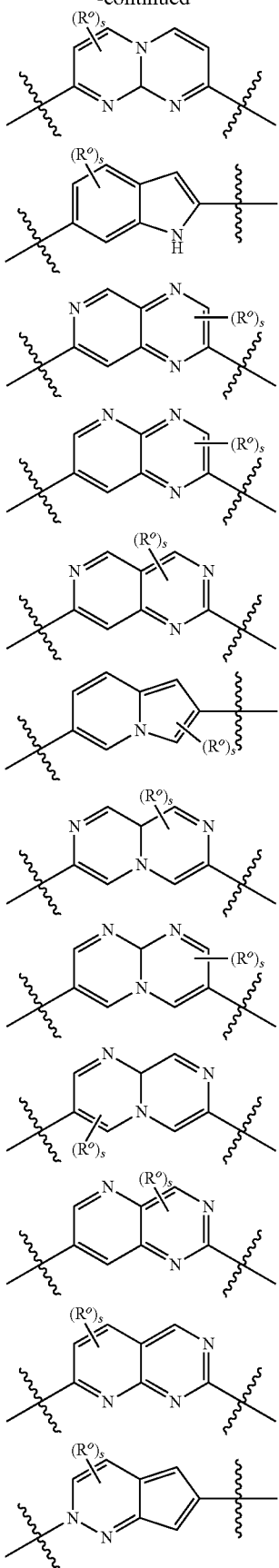
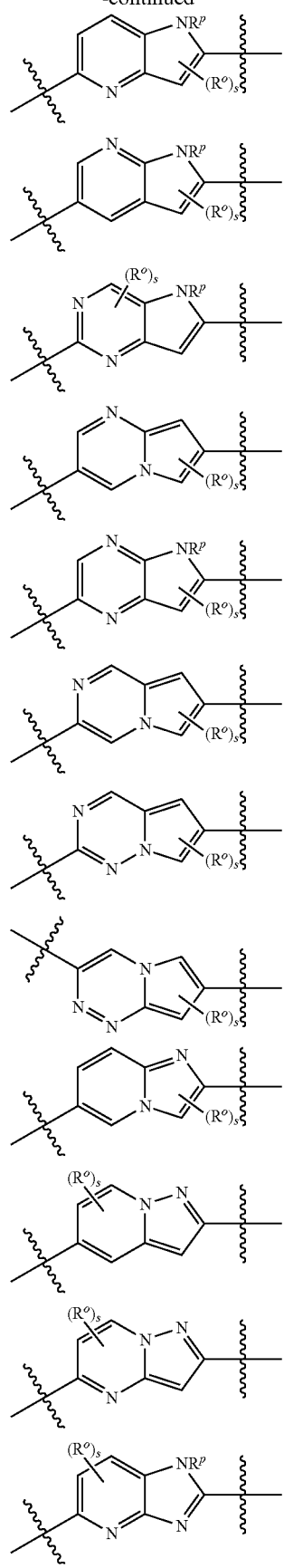

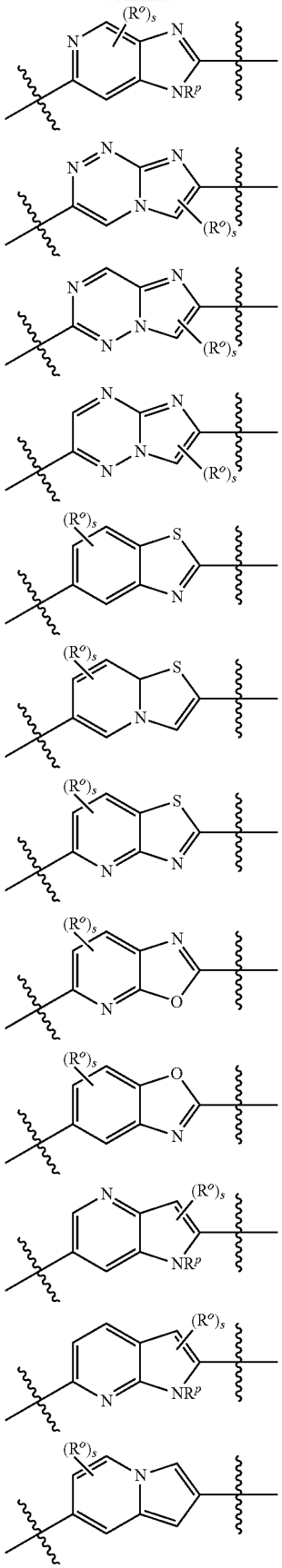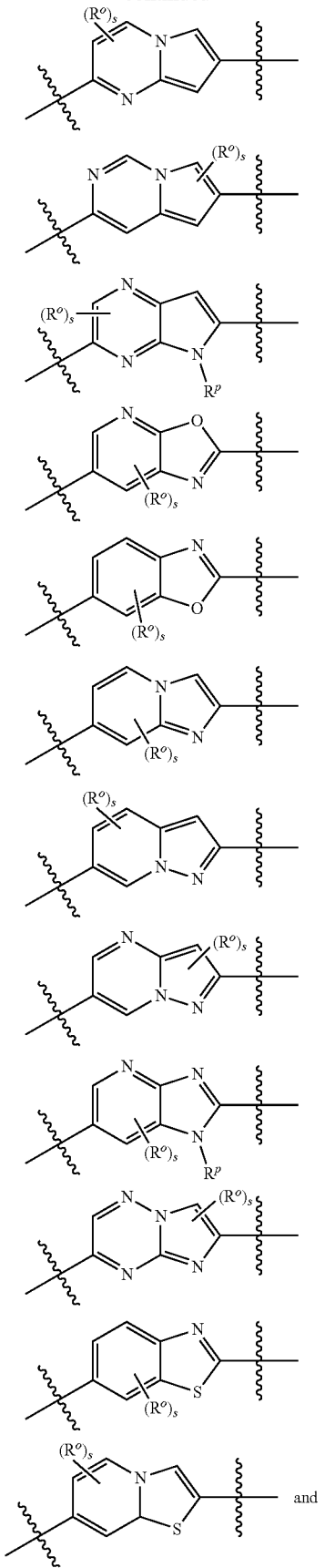

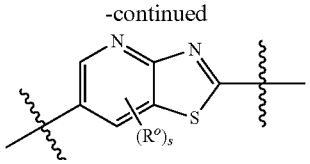
R° is selected from the group consisting of H, halogen, —CN, $C_{1-6}$ alkyl, $C_{1-6}$ alkoxy, $C_{1-6}$ haloalkoxy, cycloalkyl, and heterocycloalkyl;
s is 0, 1, 2, 3 or 4; and
$R^p$ is selected from the group consisting of H, $C_{1-6}$ alkyl, $C_{1-6}$ alkoxy, cycloalkyl, and heterocycloalkyl.
In some embodiments, in the compound of Formula (I), X is selected from the group consisting of
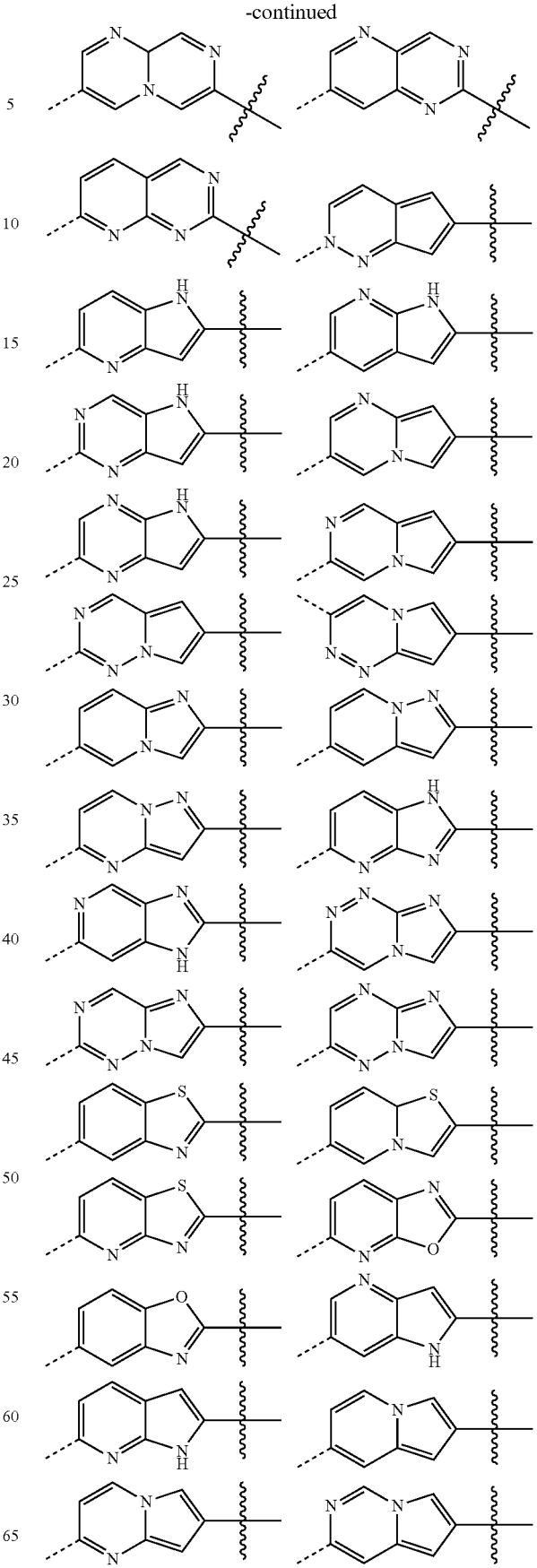

-continued

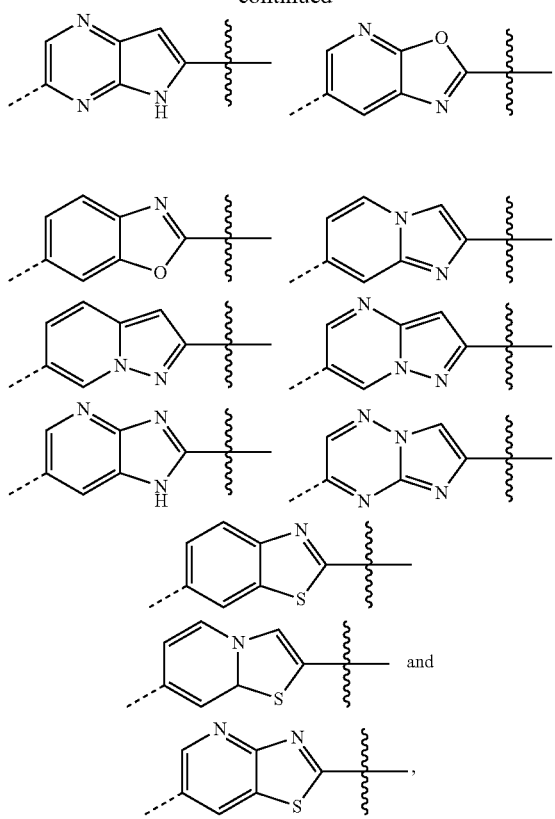

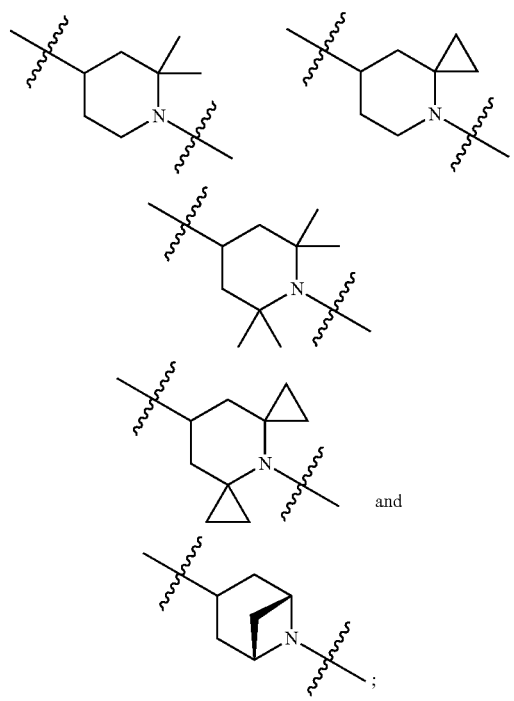

wherein "---" is a bond connected to —C(R$^{4a}$R$^{4b}$)—; "⸺" is a bond connected to W.

In some embodiments, the compound of Formula (I) has a structure of Formula (II), Formula (II)

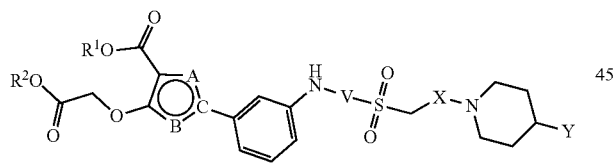

wherein,

R$^1$ and R$^2$ are each independently selected from the group consisting of H, CN, C$_{1-6}$ alkyl, C$_{1-6}$ haloalkyl, C$_{2-6}$ alkenyl, C$_{2-6}$ alkynyl, C$_{1-6}$ alkoxy, C$_{1-6}$ haloalkoxy, cycloalkyl, and heterocycloalkyl;

A and B are each independently selected from the group consisting of NR$^a$, CR$^b$, N, O, and S;

C is selected from the group consisting of carbon atom and nitrogen atom;

R$^a$ is selected from the group consisting of H, C$_{1-6}$ alkyl, C$_{1-6}$ alkoxy, C$_{1-6}$ haloalkoxy, cycloalkyl and heterocycloalkyl;

R$^b$ is selected from the group consisting of H, halogen, —CN, —CF$_3$, C$_{1-6}$ alkyl, C$_{1-6}$ alkoxy, C$_{1-6}$ haloalkoxy, cycloalkyl and heterocycloalkyl;

V is selected from the group consisting of

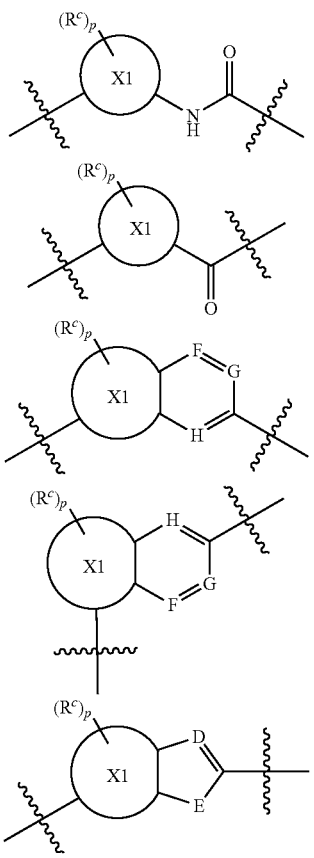

X is selected from the group consisting of

-continued

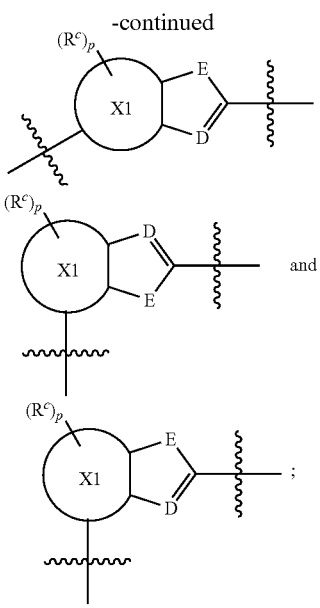

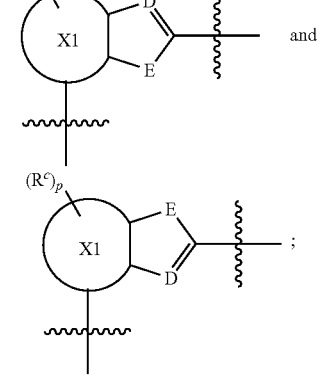

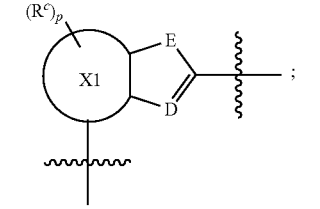

X1 is selected from the group consisting of 6-membered aryl and 6-membered heteroaryl comprising 1-4 nitrogen atoms;

$R^c$ is selected from the group consisting of H, halogen, —CN, $C_{1-6}$ alkyl, $C_{1-6}$ alkoxy, $C_{1-6}$ haloalkoxy, cycloalkyl, and heterocycloalkyl;

p is 0, 1, 2, 3 or 4;

D is selected from the group consisting of carbon atom and nitrogen atom;

E is selected from the group consisting of O, S, and $NR^d$;

$R^d$ is selected from the group consisting of H, $C_{1-6}$ alkyl, cycloalkyl, and heterocycloalkyl;

F, G, and H are each independently selected from the group consisting of C, N, O, and S;

Y is selected from the group consisting of

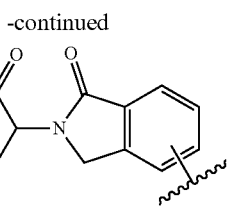

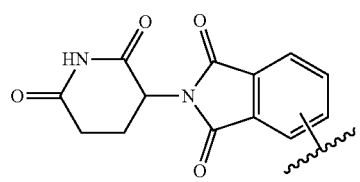

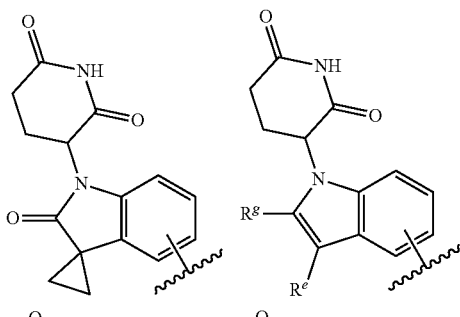

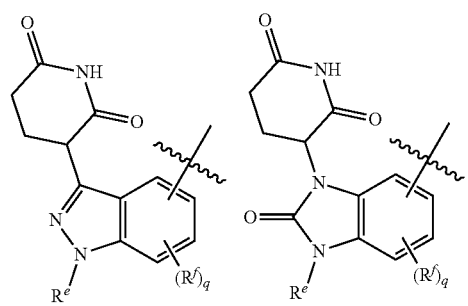

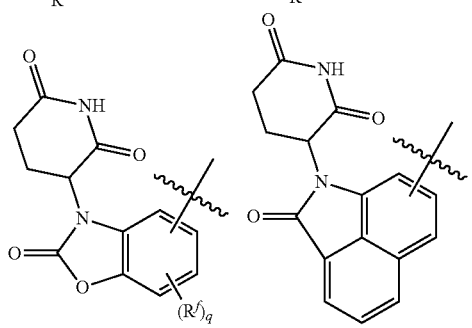

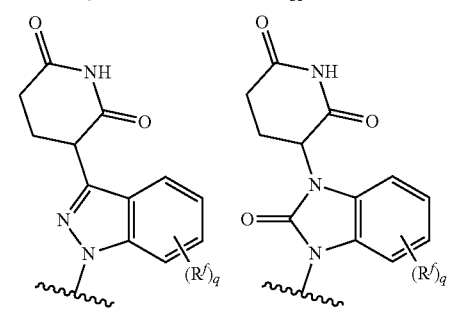

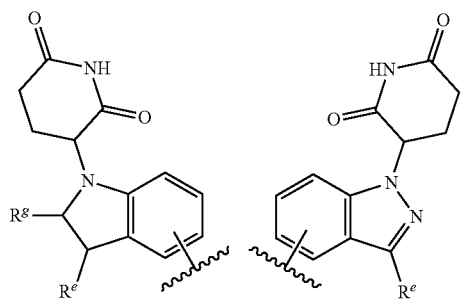

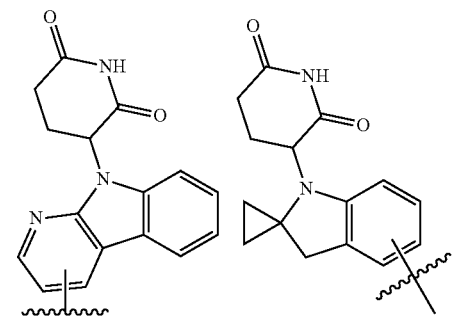

-continued

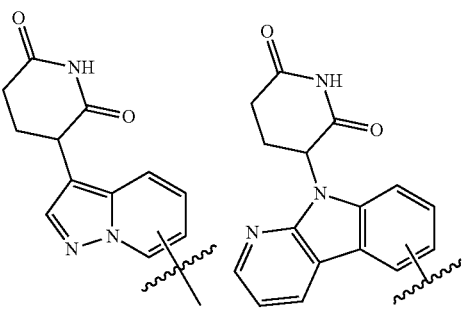

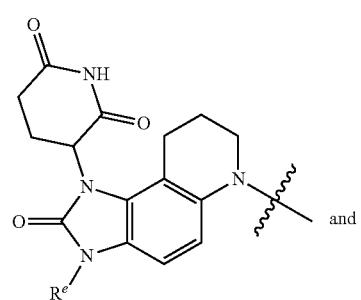 and

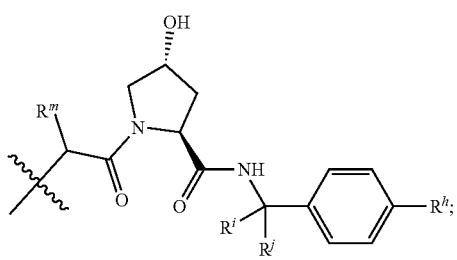

each $R^e$ is independently selected from the group consisting of hydrogen and $C_{1-6}$ alkyl optionally substituted with one or more substituents independently selected from the group consisting of $C_{1-6}$ alkoxy, $C_{1-6}$ haloalkyl, $C_{3-6}$ cycloalkyl, and 4- to 6-membered heterocyclyl;

each $R^f$ is independently selected from the group consisting of halogen, —CN, $C_{1-6}$ alkyl, $C_{1-6}$ haloalkyl, $C_{1-6}$ alkoxy, and $C_{3-5}$ cycloalkoxy;

$R^g$ is selected from the group consisting of hydrogen and $C_{1-6}$ alkyl.

q is 0, 1, 2, 3 or 4;

$R^h$ is selected from the group consisting of H, halogen,

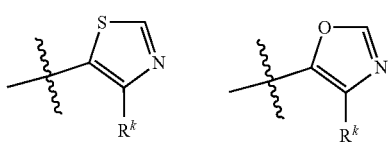

-continued

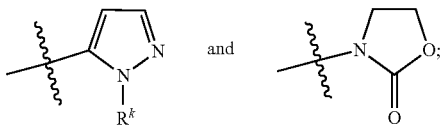 and $R^k$ is selected from the group consisting of H and $C_{1-3}$ alkyl optionally substituted with hydroxyl;

$R^i$ and $R^j$ are each independently selected from the group consisting of H and $C_{1-3}$ alkyl, wherein $C_{1-3}$ alkyl is optionally substituted with one or more substituents independently selected from the group consisting of F, OH, and —N(CH$_3$)$_2$; or $R^i$ and $R^j$ together with carbon atoms to which they are attached form cyclopropyl; and $R^m$ is selected from the group consisting of ethyl, isopropyl, tert-butyl, and $C_{3-6}$ cycloalkyl.

In some embodiments, in the compound of Formula (II), $R^1$ and $R^2$ are each independently selected from the group consisting of H, CN, methyl, ethyl, n-propyl, isopropyl, n-butyl, isobutyl, and tert-butyl;

A is S;

B is $CR^b$, $R^b$ is selected from the group consisting of H, F, Cl, —CH$_3$, and —CF$_3$; C is carbon atom;

V is selected from the group consisting of

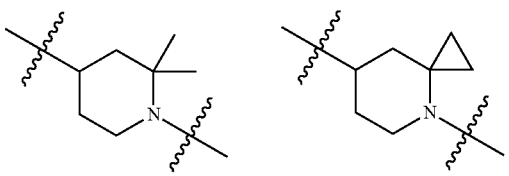

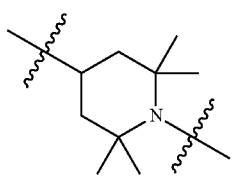

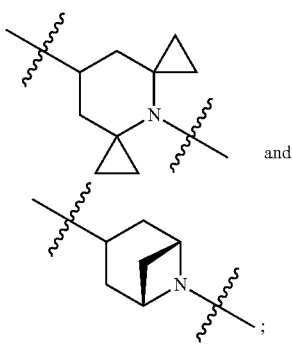

wherein "---" is a bond connected to "—NH—"; "⸺ξ⸺" is a bond connected to "—S(O)$_2$—";

X is selected from the group consisting of
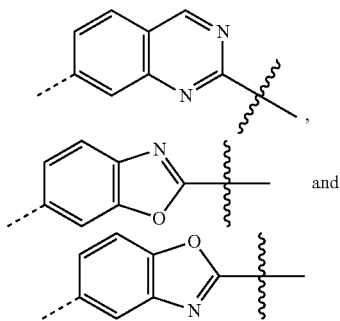
and
wherein "---" is a bond connected to "—CH$_2$—"; "⸾" is a bond connected to the "N" of
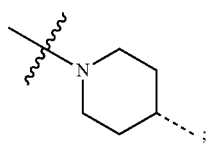
and
Y is selected from the group consisting of
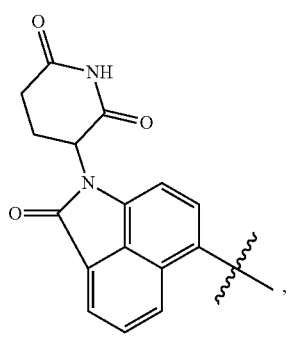
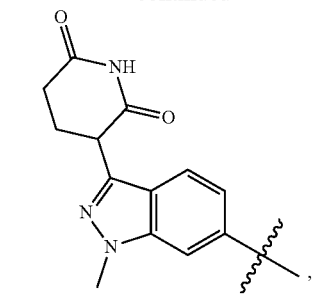
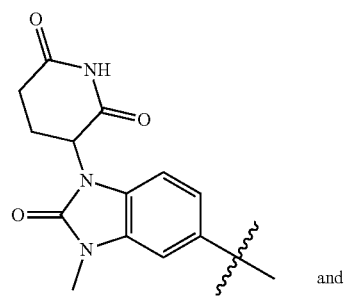
and
In some embodiments, the compound of Formula (I) has a structure of Formula (III),
Formula (III)
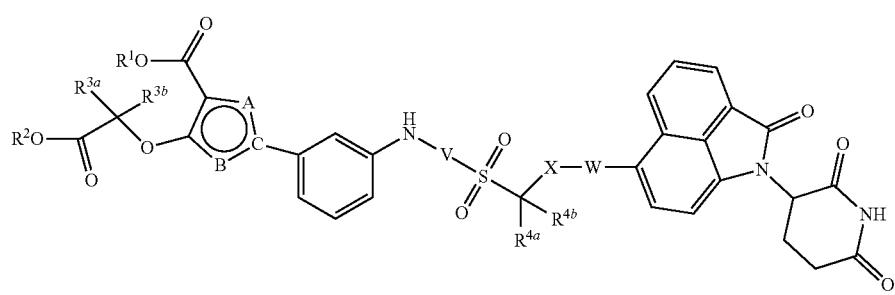

wherein, $R^1$, $R^2$, $R^{3a}$, $R^{3b}$, $R^{4a}$, $R^{4b}$, A, B, C, V, X, and W are defined as Formula (I).

In some embodiments, in the compound of Formula (III), $R^1$ and $R^2$ are each independently selected from the group consisting of H, CN, $C_{1-6}$ alkyl, $C_{1-6}$ haloalkyl, $C_{1-6}$ alkoxy and $C_{1-6}$ haloalkoxy;

$R^{3a}$, $R^{3b}$, $R^{4a}$, and $R^{4b}$ are each independently selected from the group consisting of H and F;

A is selected from the group consisting of N, O, S, and NH;

B is selected from the group consisting of N, O, S, $NR^a$, and $CR^b$;

C is selected from the group consisting of carbon atom and nitrogen atom;

$R^a$ is selected from the group consisting of H, $C_{1-3}$ alkyl, $C_{1-3}$ alkoxy, $C_{1-3}$ haloalkyl, and $C_{1-3}$ haloalkoxy;

$R^b$ is selected from the group consisting of H, F, Cl, methyl, ethyl, —CN, —$CF_3$, —$CHF_2$, and —$CH_2F$;

V is selected from the group consisting of

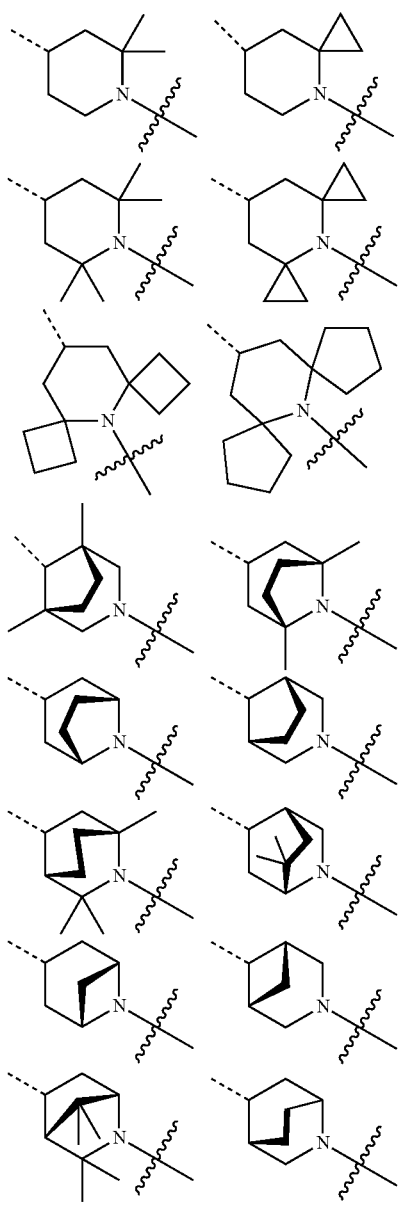

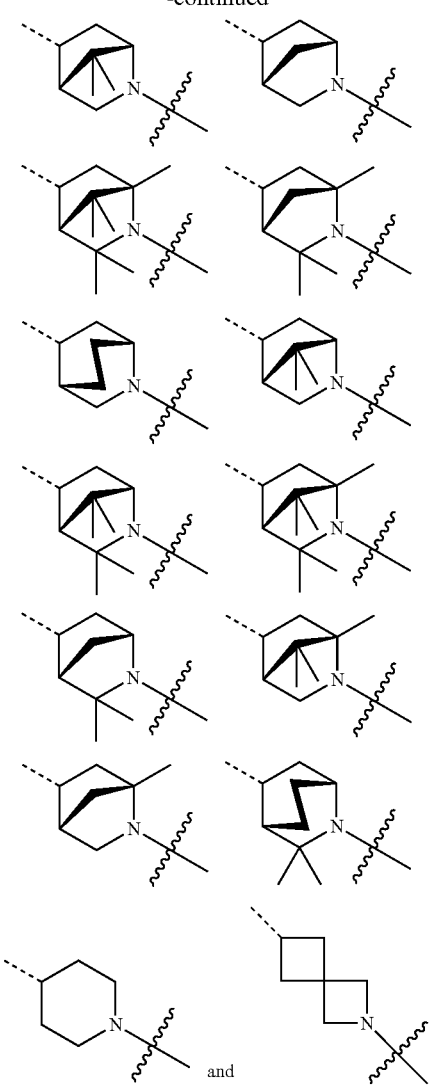

"---" is a bond connected to "—NH—"; "-ξ-" is a bond connected to "—S(O)$_2$—";

W is selected from the group consisting of

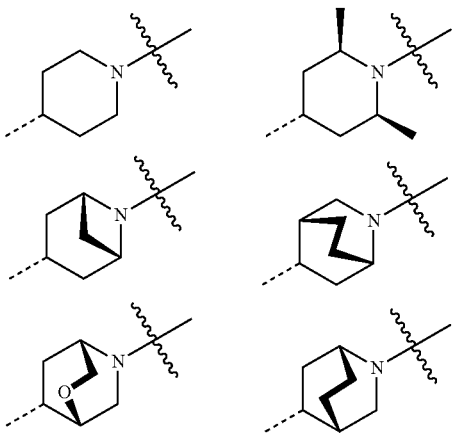

-continued

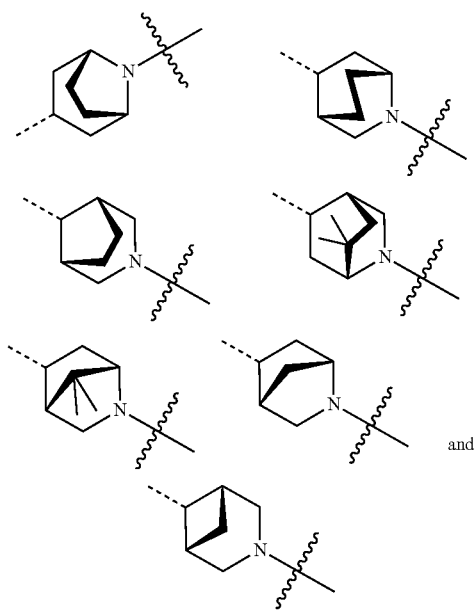

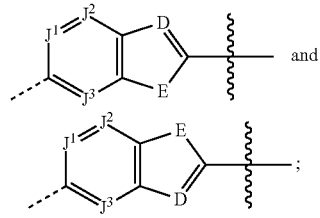

and $J^1$, $J^2$, and $J^3$ are each independently selected from the group consisting of N and $CR^c$;

D is selected from the group consisting of carbon atom and nitrogen atom;

E is selected from the group consisting of O, S, and $NR^d$;

F, G, and H are each independently selected from the group consisting of CH and N;

$R^c$ is selected from the group consisting of H, halogen, —CN, $C_{1-6}$ alkyl, $C_{1-6}$ alkoxy, and $C_{1-6}$ haloalkoxy;

$R^d$ is selected from the group consisting of H and $C_{1-6}$ alkyl; and

"---" is a bond connected to "—C($R^{4a}R^{4b}$)—"; "⸹" is a bond connected to W. In some embodiments, the compound of Formula (I) has a structure of Formula (IV), Formula (IV)

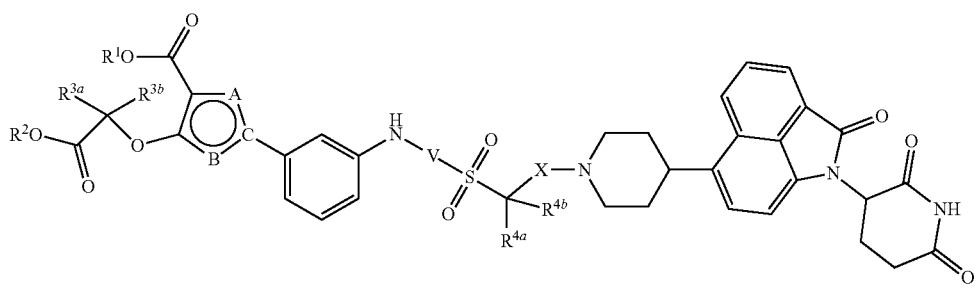

wherein "⸹" is a bond connected to X; "---" is a bond connected to

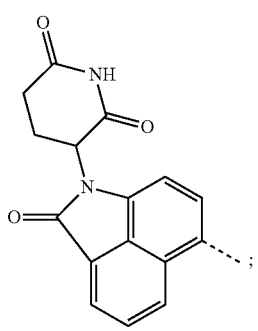

X is selected from the group consisting of

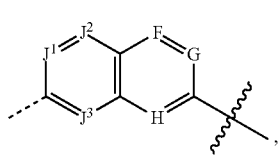

wherein $R^1$, $R^2$, $R^{3a}$, $R^{3b}$, $R^{4a}$, $R^{4b}$, A, B, C, V, and X are defined as Formula (I).

In some embodiments, in the compound of Formula (IV), $R^1$ and $R^2$ are each independently selected from the group consisting of H, —CN, $C_{1-6}$ alkyl, $C_{1-6}$ haloalkyl, $C_{1-6}$ alkoxy, and $C_{1-6}$ haloalkoxy;

$R^{3a}$, $R^{3b}$, $R^{4a}$, and $R^{4b}$ are each independently selected from the group consisting of H and F;

A is selected from the group consisting of N, O, S, and NH;

B is selected from the group consisting of N, O, S, $NR^a$, and $CR^b$;

C is selected from the group consisting of carbon atom and nitrogen atom;

$R^a$ is selected from the group consisting of H, $C_{1-3}$ alkyl, $C_{1-3}$ alkoxy, $C_{1-3}$ haloalkyl, and $C_{1-3}$ haloalkoxy, $R^b$ is selected from the group consisting of H, F, Cl, methyl, ethyl, —CN, —$CF_3$, —$CHF_2$, and —$CH_2F$;

V is selected from the group consisting of
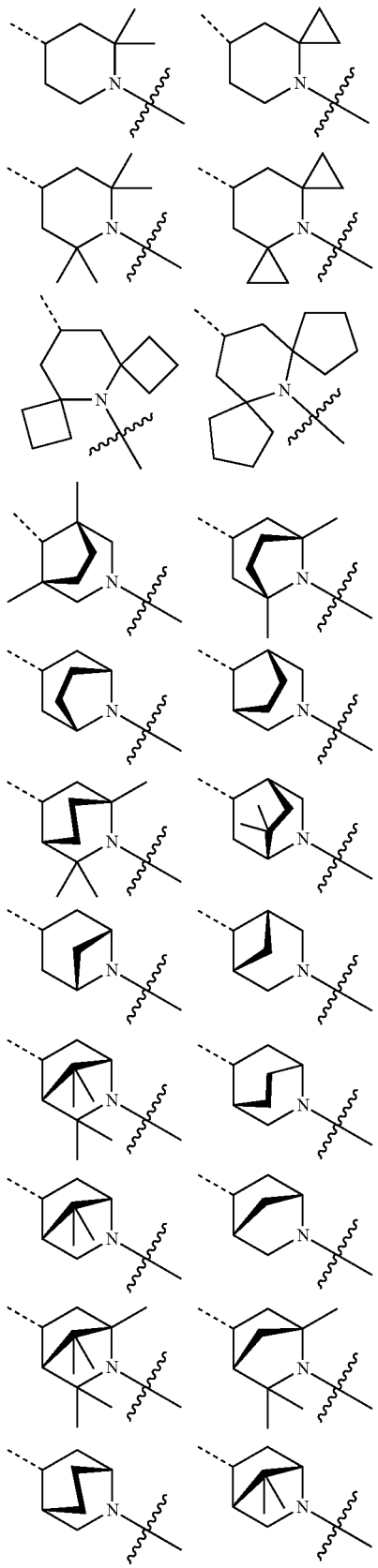
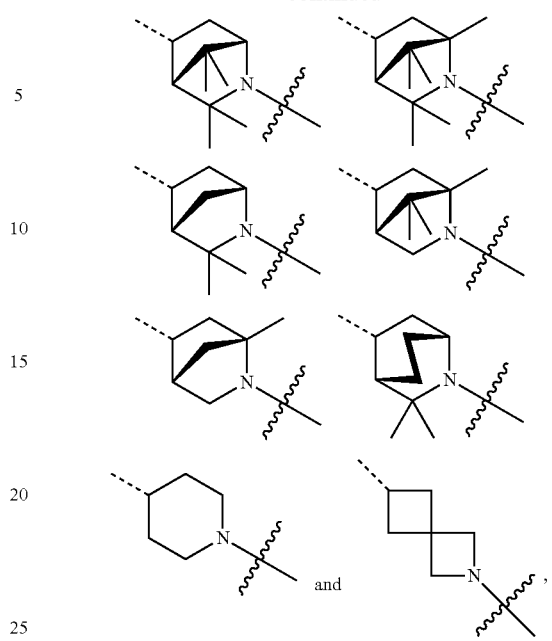
wherein "---" is a bond connected to "—NH—"; "⸾" is a bond connected to "—S(O)₂—";
X is selected from the group consisting of
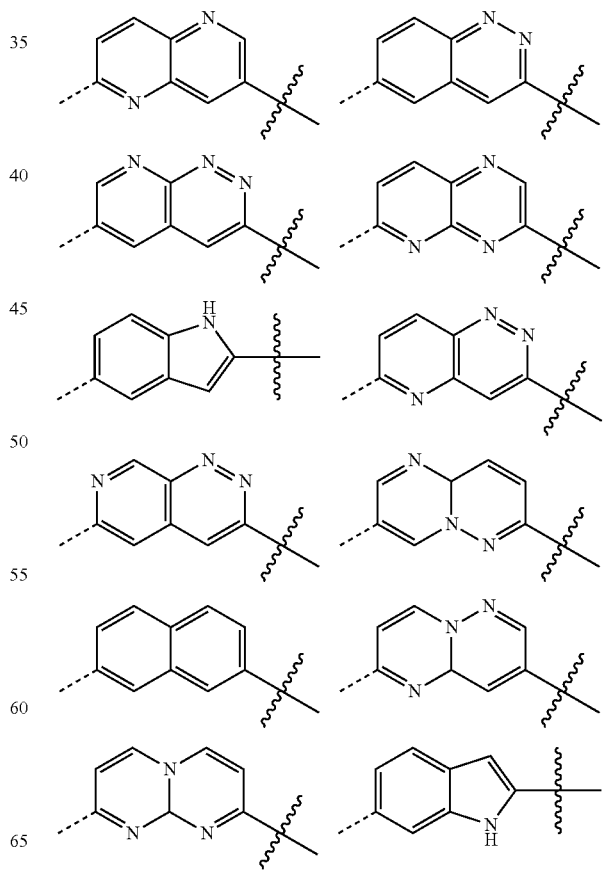

-continued
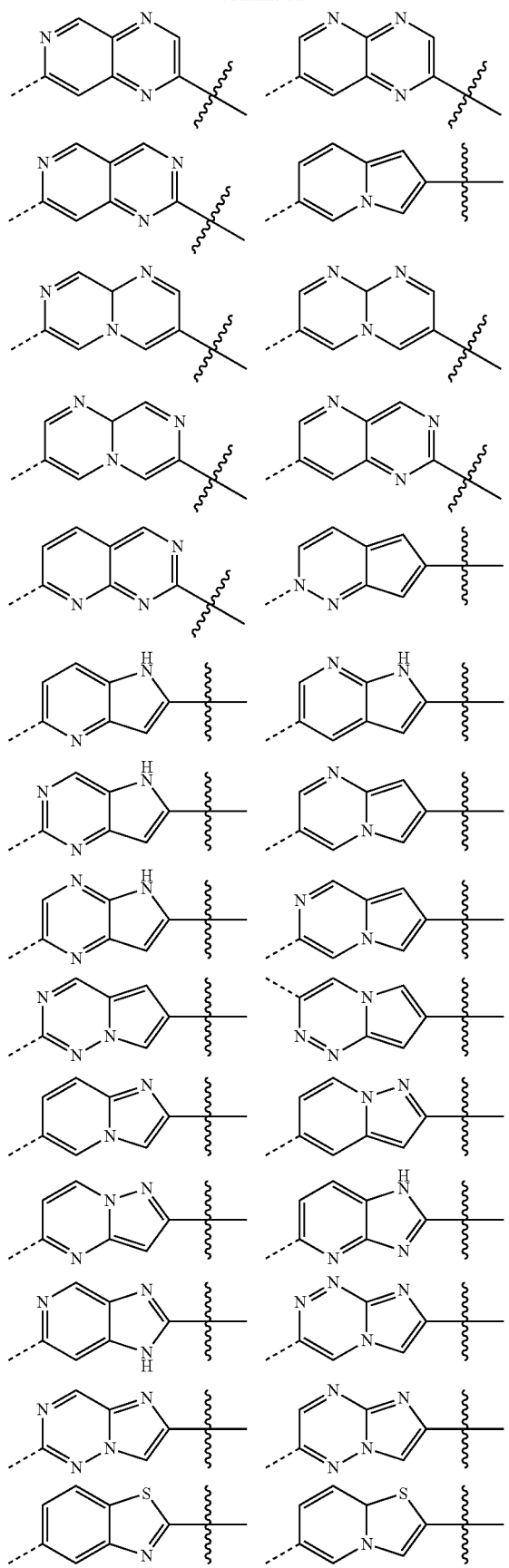
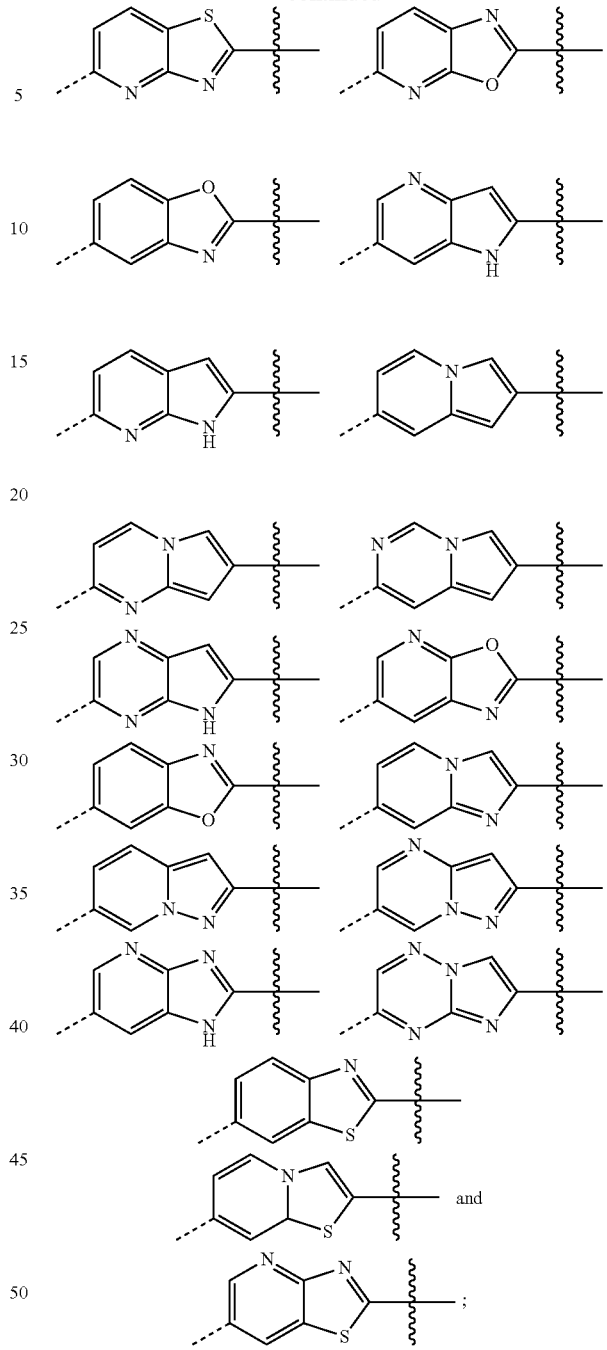
wherein "---" is a bond connected to "—C(R$^{4a}$R$^{4b}$)—"; " 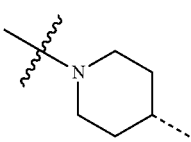 " is a bond connected to the "N" of
In some embodiments, the compound of Formula (I) has a structure of Formula (V) or Formula (VI), Formula (V)

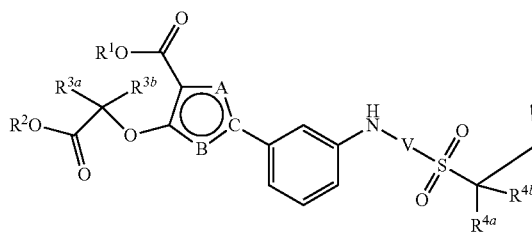 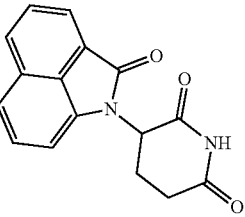

Formula (VI)

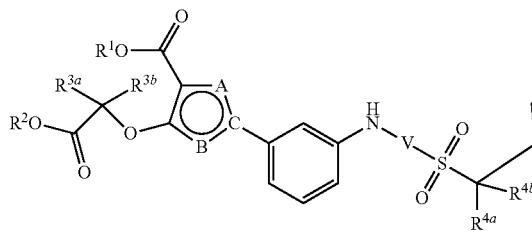 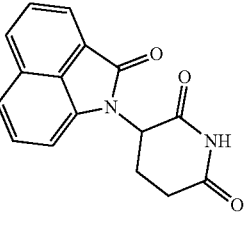

wherein, $R^1$, $R^2$, $R^{3a}$, $R^{3b}$, $R^{4a}$, $R^{4b}$, A, B, C, and V are defined as Formula (I).

In some embodiments, in the compound of Formula (V) or Formula (VI), $R^1$ and $R^2$ are each independently selected from the group consisting of H, CN, methyl, ethyl, n-propyl, isopropyl, n-butyl, isobutyl, and tert-butyl;

$R^{3a}$, $R^{3b}$, $R^{4a}$, and $R^{4b}$ are each independently selected from the group consisting of H and F;

A is S;

B is $CR^b$, $R^b$ is selected from the group consisting of H, F, Cl, —$CH_3$, and —$CF_3$;

C is carbon atom; and

V is selected from the group consisting of

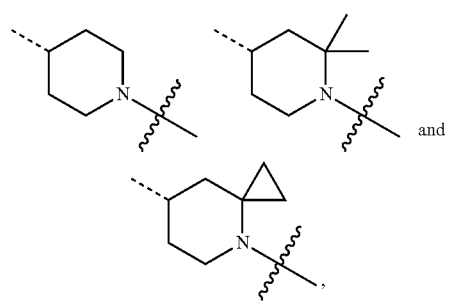

wherein "---" is a bond connected to "—NH—"; "⸺" is a bond connected to "—$S(O)_2$—".

In some embodiments, the compound of Formula (I) has a structure of Formula (VII), Formula (VII)

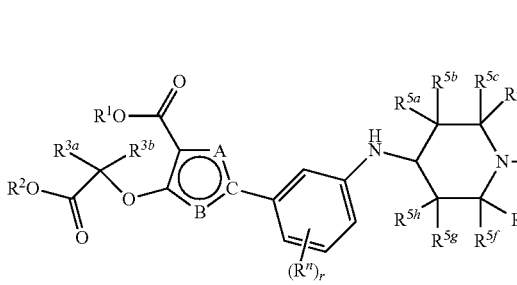 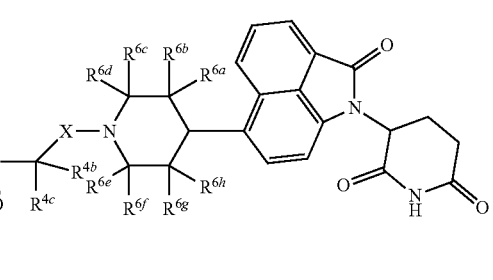

wherein, $R^1$ and $R^2$ are each independently selected from the group consisting of H, —CN, $C_{1-6}$ alkyl, $C_{1-6}$ haloalkyl, $C_{1-6}$ alkoxy, and $C_{1-6}$ haloalkoxy;

$R^{3a}$ and $R^{3b}$ are independently selected from the group consisting of H and halogen;

$R^{4a}$ and $R^{4b}$ are independently selected from the group consisting of H, halogen, $C_{1-6}$ alkyl, or $R^{4a}$ and $R^{4b}$ together with carbon atoms to which they are attached form cyclopropyl, cyclobutyl or oxetanyl;

$R^{5a}$, $R^{5b}$, $R^{5c}$, $R^{5d}$, $R^{5e}$, $R^{5f}$, $R^{5g}$, and $R^{5h}$ are each independently selected from the group consisting of H and $C_{1-6}$ alkyl; or $R^{5a}$ and $R^{5b}$ together with carbon atom to which they are attached form a $C_{3-6}$ cycloalkyl, and/or $R^{5c}$ and $R^{5d}$ together with carbon atom to which they are attached form a $C_{3-6}$ cycloalkyl, and/or $R^{5e}$ and $R^{5f}$ together with carbon atom to which they are attached form a $C_{3-6}$ cycloalkyl, and/or $R^{5g}$ and $R^{5h}$ together with carbon atom to which they are attached form a $C_{3-6}$ cycloalkyl; or two or three of $R^{5a}$, $R^{5b}$, $R^{5c}$, $R^{5d}$, $R^{5e}$, $R^{5f}$, $R^{5g}$, and $R^h$ together with carbon atoms to which they are attached form $C_{3-6}$ cycloalkyl, wherein the $C_{3-6}$ cycloalkyl is optionally substituted with one to six $C_{1-6}$ alkyl;

$R^{6a}$, $R^{6b}$, $R^{6c}$, $R^{6d}$, $R^{6e}$, $R^{6f}$, $R^{6g}$, and $R^{6h}$ are each independently selected from the group consisting of H and $C_{1-6}$ alkyl; or two or three of $R^{6a}$, $R^{6b}$, $R^{6c}$, $R^{6d}$, $R^{6e}$, $R^{6f}$, $R^{6g}$, and $R^{6h}$ together with carbon atoms to which they are attached form $C_{3-6}$ cycloalkyl, wherein the $C_{3-6}$ cycloalkyl is optionally substituted with one to six $C_{1-6}$ alkyl;

each $R^n$ is independently selected from the group consisting of halogen, —CN, —$CF_3$, —$OCH_3$, and —$OCF_3$;

r is 0, 1, 2, 3 or 4;

A is selected from the group consisting of N, O, S, and NH;

B is selected from the group consisting of N, O, S, $NR^a$, and $CR^b$;

C is selected from the group consisting of carbon atom and nitrogen atom;

$R^a$ is selected from the group consisting of H, $C_{1-3}$ alkyl, $C_{1-3}$ alkoxy, $C_{1-3}$ haloalkyl, and $C_{1-3}$ haloalkoxy;

$R^b$ is selected from the group consisting of H, F, Cl, methyl, ethyl, —CN, —$CF_3$, —$CHF_2$, and —$CH_2F$;

F, G, and H are each independently selected from the group consisting of CH and N;

$R^c$ is selected from the group consisting of H, halogen, —CN, $C_{1-6}$ alkyl, $C_{1-6}$ alkoxy, and $C_{1-6}$ haloalkoxy; and $R^d$ is selected from the group consisting of H and $C_{1-6}$ alkyl, wherein "---" is a bond connected to "—$C(R^{4a}R^{4b})$—"; "

$-\xi-$"; is a bond connected to the N of

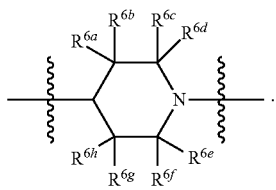

In some embodiments, the compound of Formula (I) has the structure of Formula (VIII),

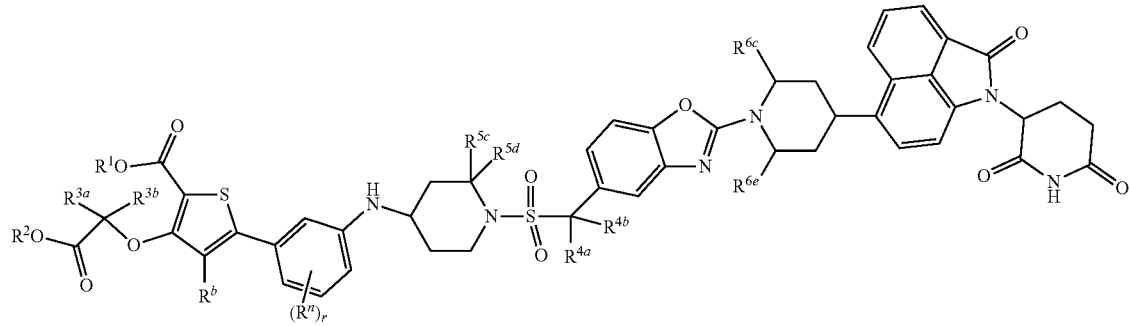

Formula (VIII)

wherein, $R^1$ and $R^2$ are each independently selected from the group consisting of H, —CN, methyl, ethyl, n-propyl, isopropyl, n-butyl, isobutyl and tert-butyl;

$R^b$ is selected from the group consisting of H, F, Cl, methyl, ethyl, —CN, —$CF_3$, —$CHF_2$, and —$CH_2F$;

$R^{3a}$, $R^{3b}$, $R^{4a}$, and $R^{4b}$ are each independently selected from the group consisting of H and halogen;

$R^{5c}$ and $R^{5d}$ are each independently selected from the group consisting of H, methyl, ethyl, n-propyl, and isopropyl, or $R^{5c}$ and $R^{5d}$ together with carbon atom to which they are attached form a $C_{3-6}$ cycloalkyl, wherein the $C_{3-6}$ cycloalkyl is optionally substituted with 1-3 $C_{1-6}$ alkyl;

$R^{6c}$ and $R^{6e}$ are each independently selected from the group consisting of H, methyl, and ethyl;

$R^n$ is selected from the group consisting of F, Cl, and —CN; and r is 0 or 1.

X is selected from the group consisting of

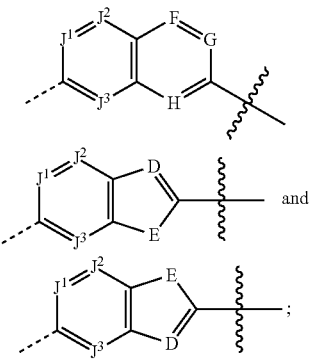

$J^1$, $J^2$, and $J^3$ are each independently selected from the group consisting of N and $CR^c$;

D is selected from the group consisting of carbon atom and nitrogen atom;

E is selected from the group consisting of O, S, and $NR^d$;

Another aspect of the present disclosure provides a compound of Formula (IX),

Formula (IX)

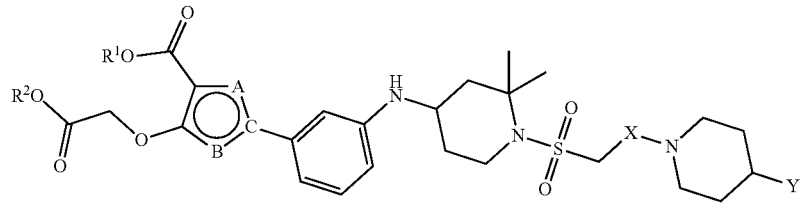

or a stereoisomer, a pharmaceutically acceptable salt, or a deuterated compound thereof, wherein, $R^1$ and $R^2$ are each independently selected from the group consisting of H, CN, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cycloalkyl, and heterocycloalkyl;

A and B are each independently selected from the group consisting of $NR^a$, $CR^b$, N, O, and S;

C is selected from the group consisting of carbon atom and nitrogen atom;

$R^a$ is selected from the group consisting of H, $C_{1-6}$ alkyl, $C_{1-6}$ alkoxy, $C_{1-6}$ haloalkoxy, cycloalkyl and heterocycloalkyl;

$R^b$ is selected from the group consisting of H, halogen, —CN, $C_{1-6}$ alkyl, $C_{1-6}$ alkoxy, $C_{1-6}$ haloalkoxy, cycloalkyl and heterocycloalkyl;

X is selected from the group consisting of

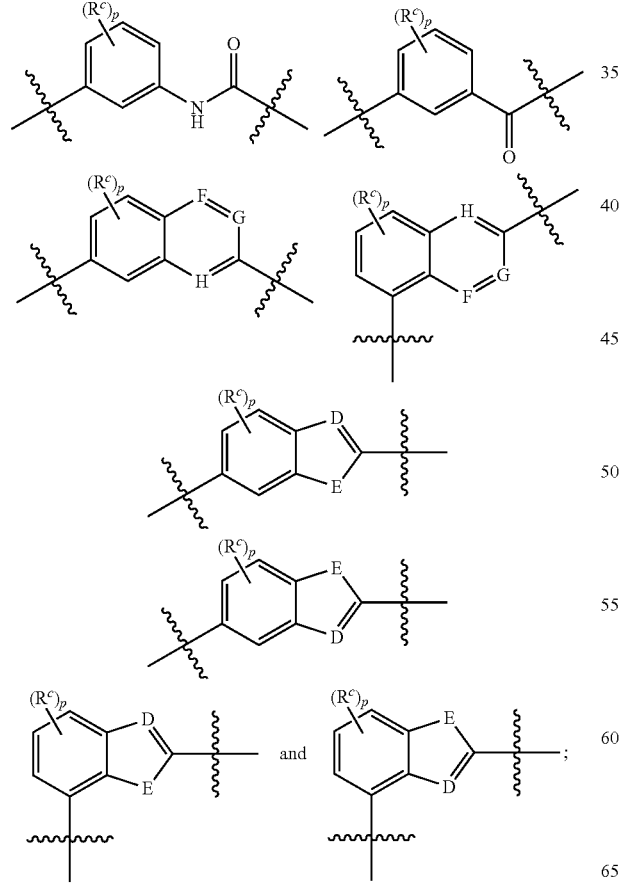

and $R^c$ is selected from the group consisting of H, halogen, —CN, $C_{1-6}$ alkyl, $C_{1-6}$ alkoxy, $C_{1-6}$ haloalkoxy, cycloalkyl, and heterocycloalkyl;

p is 0, 1, 2, 3 or 4;

D is selected from the group consisting of carbon atom and nitrogen atom;

E is selected from the group consisting of O, S, and $NR^d$;

$R^d$ is selected from the group consisting of H, $C_{1-6}$ alkyl, cycloalkyl and heterocycloalkyl;

F, G, and H are each independently selected from the group consisting of C, N, O, and S;

Y is selected from the group consisting of

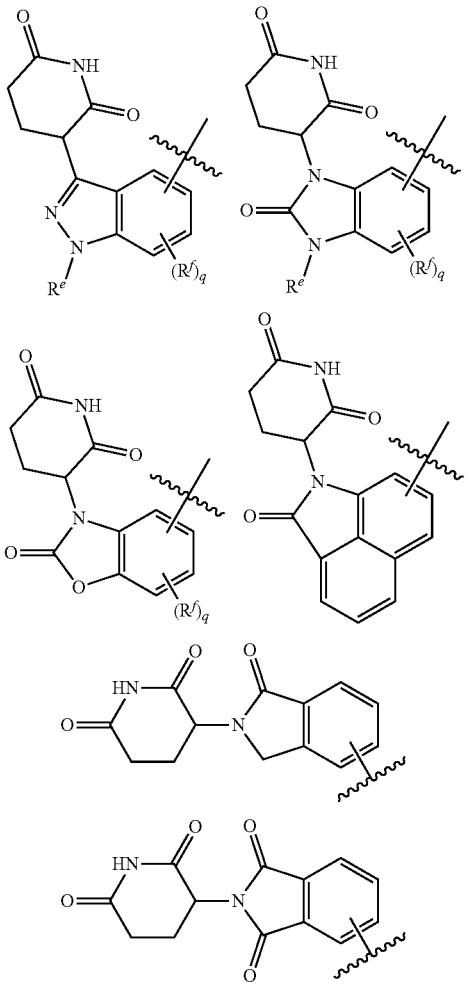

-continued

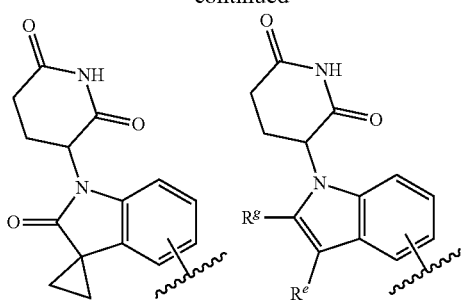
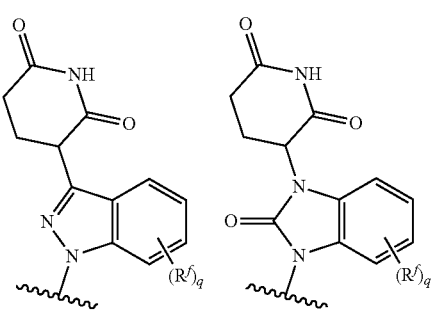
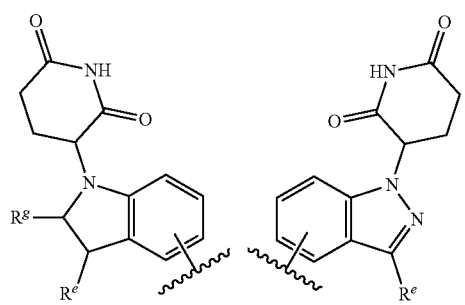
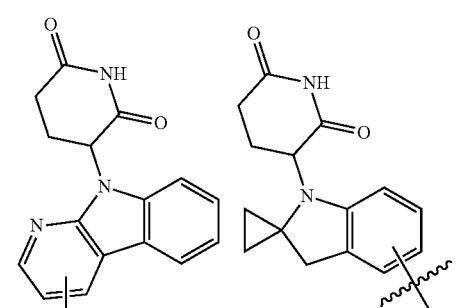
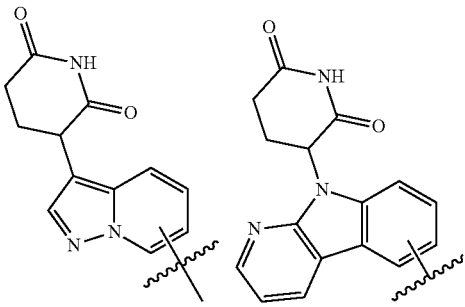

-continued

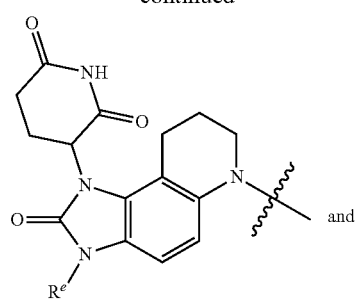

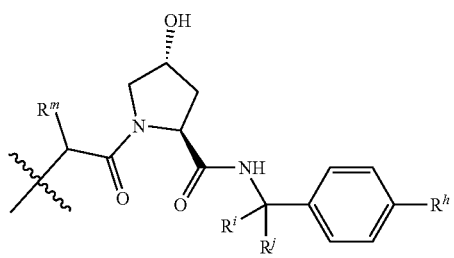

each $R^e$ is independently selected from the group consisting of hydrogen, and $C_{1\text{-}6}$ alkyl, wherein $C_{1\text{-}6}$ alkyl is optionally substituted with one or more substituents independently selected from the group consisting of $C_{1\text{-}6}$ alkoxy, $C_{1\text{-}6}$ haloalkyl, $C_{3\text{-}6}$ cycloalkyl, and 4- to 6-membered heterocyclyl;

each $R^f$ is independently selected from the group consisting of halogen, —CN, $C_{1\text{-}6}$ alkyl, $C_{1\text{-}6}$ haloalkyl, $C_{1\text{-}6}$ alkoxy, and $C_{3\text{-}5}$ cycloalkoxy;

$R^g$ is selected from the group consisting of hydrogen and $C_{1\text{-}6}$ alkyl;

q is 0, 1, 2, 3 or 4;

$R^h$ is selected from the group consisting of H, halogen,

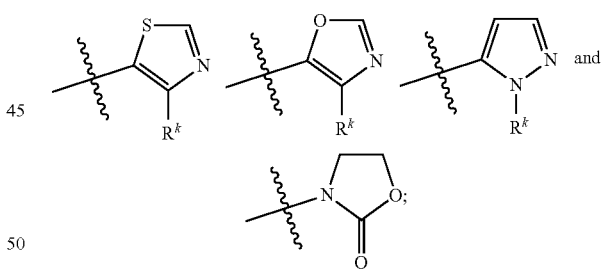

$R^k$ is selected from the group consisting of H and $C_{1\text{-}3}$ alkyl, wherein $C_{1\text{-}6}$ alkyl is optionally substituted with hydroxyl;

$R^i$ and $R^j$ are each independently selected from the group consisting of H and $C_{1\text{-}3}$ alkyl, wherein $C_{1\text{-}6}$ alkyl is optionally substituted with one or more substituents independently selected from the group consisting of F, OH, and —N(CH$_3$)$_2$; or $R^i$ and $R^j$ together with carbon atoms to which they are attached form cyclopropyl; and $R^m$ is selected from the group consisting of ethyl, isopropyl, tert-butyl, and $C_{3\text{-}6}$ cycloalkyl.

In some embodiments, in the compound of Formula (IX), X is selected from the group consisting of

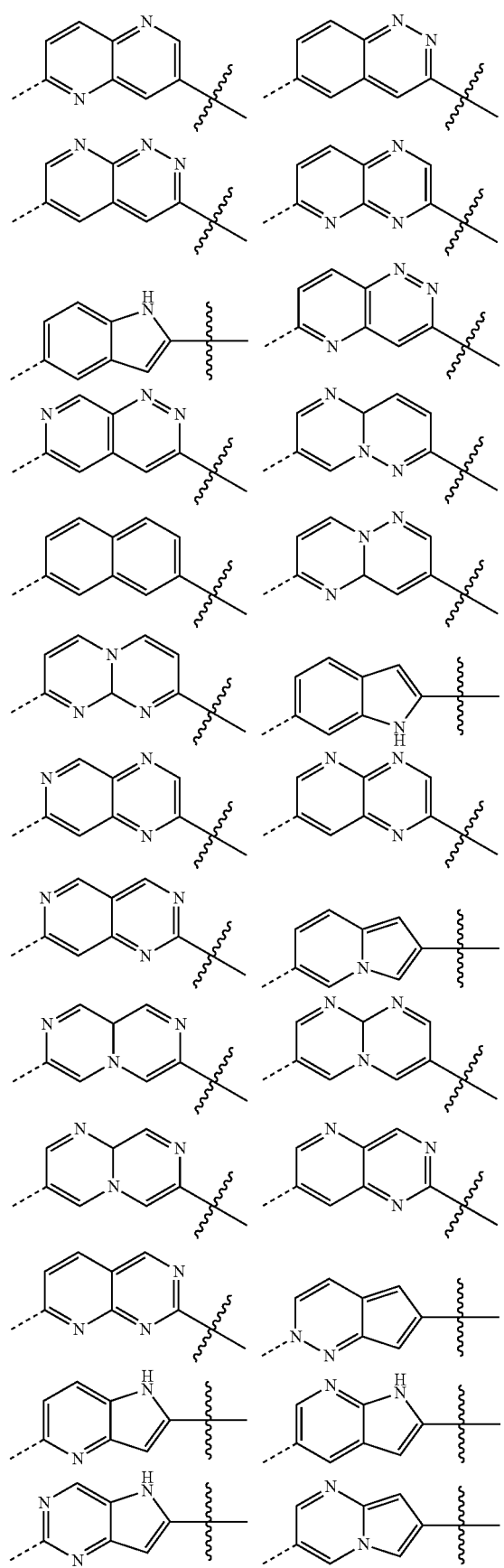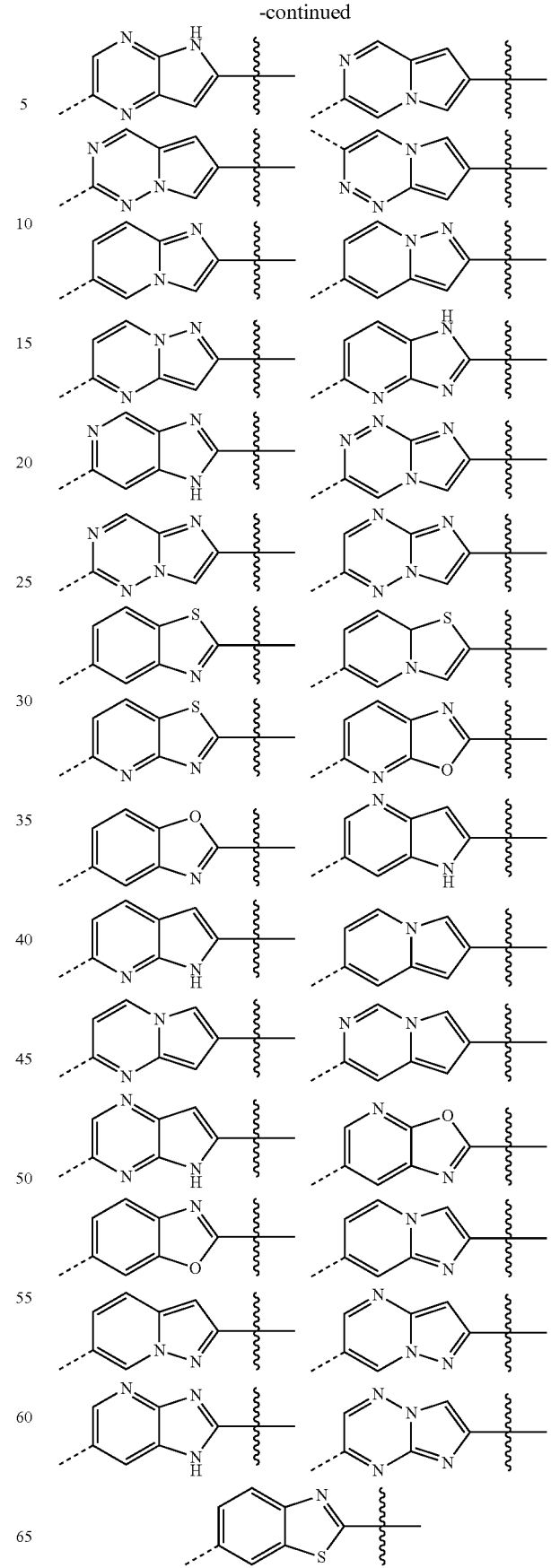

67
-continued
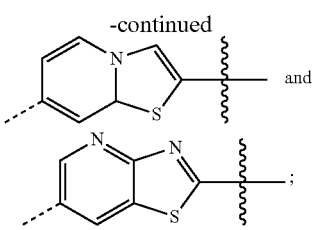
and;
wherein "---" is a bond connected to "—CH$_2$—"; "-ξ-" is a bond connected to the "N" of
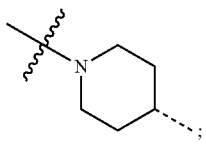
Y is selected from the group consisting of
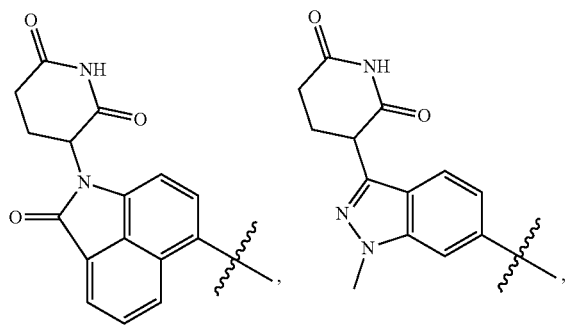
68
-continued
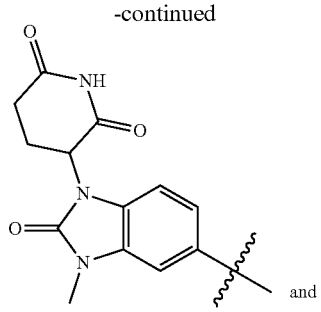
and
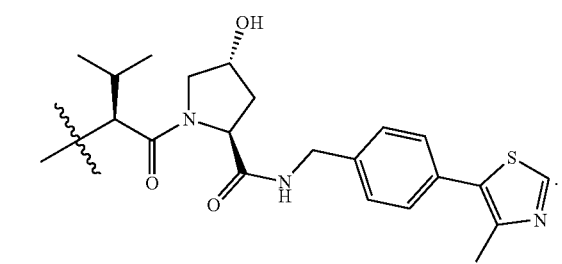
Still another aspect of the present disclosure provides a compound, wherein the compound is selected from the group consisting of
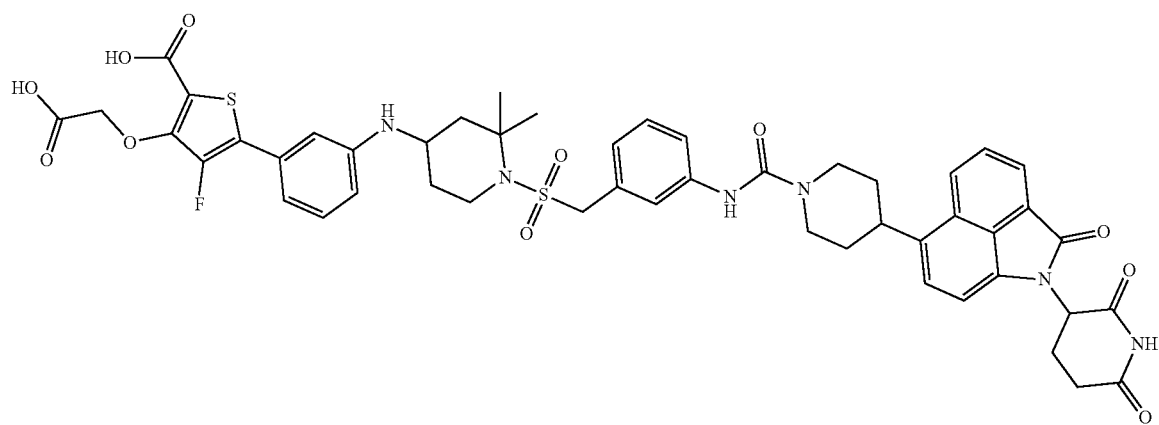
1

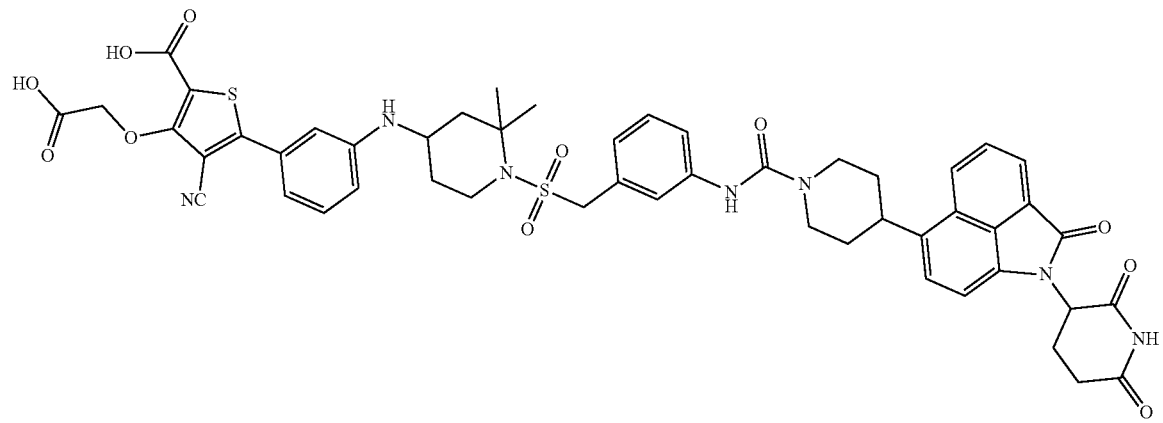
2
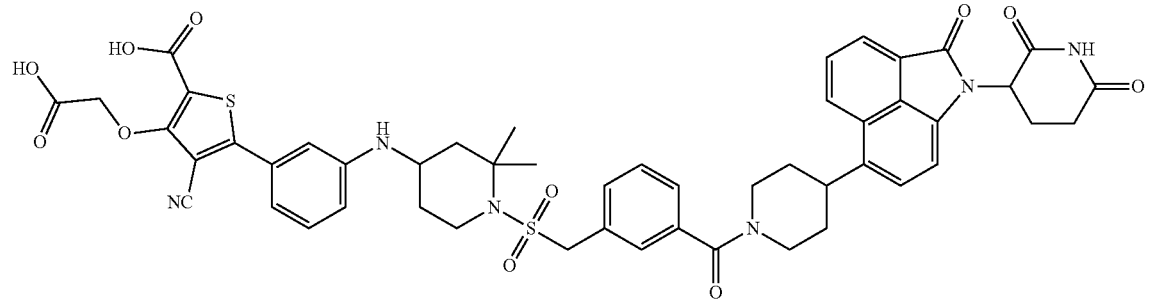
3
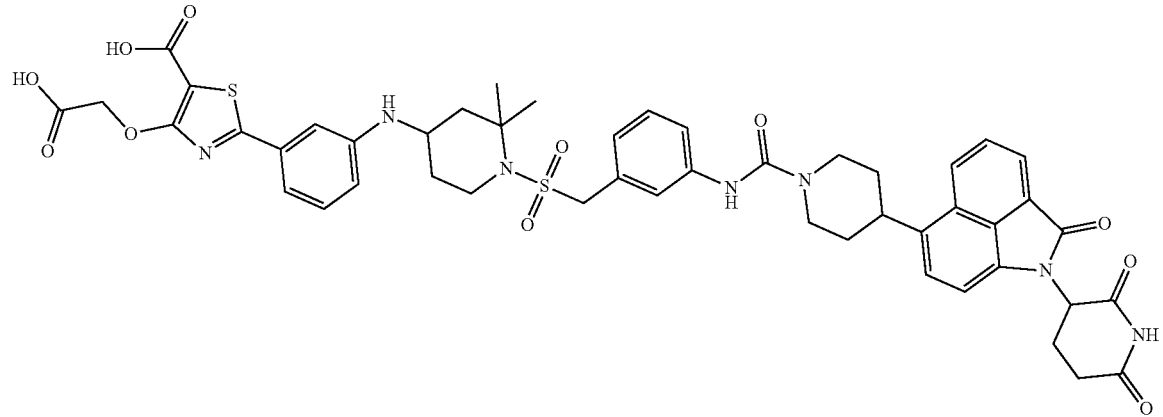
4
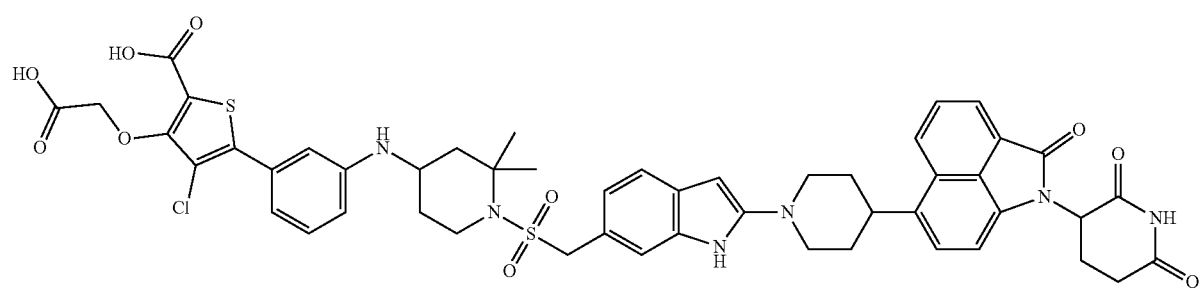
5

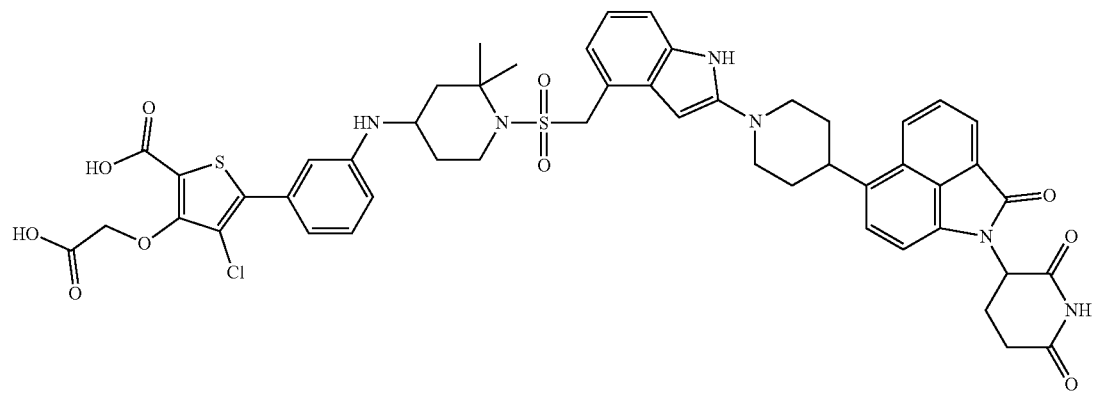
6
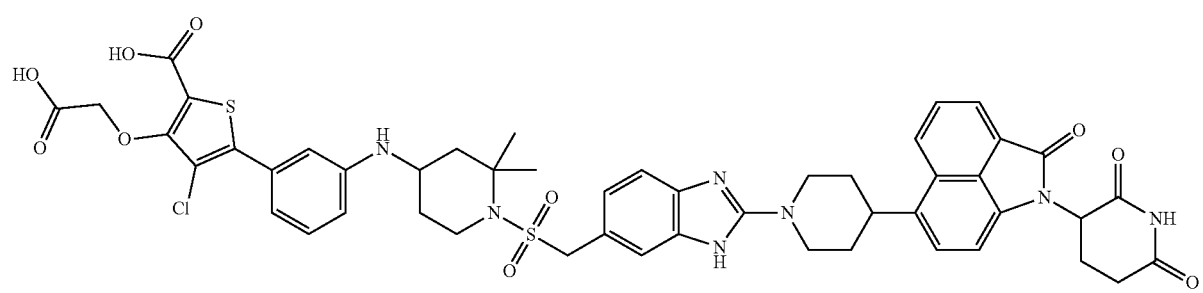
7
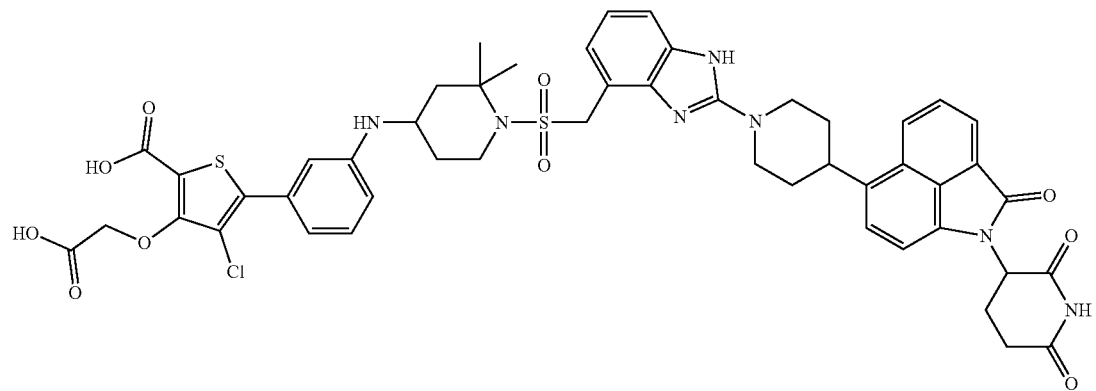
8
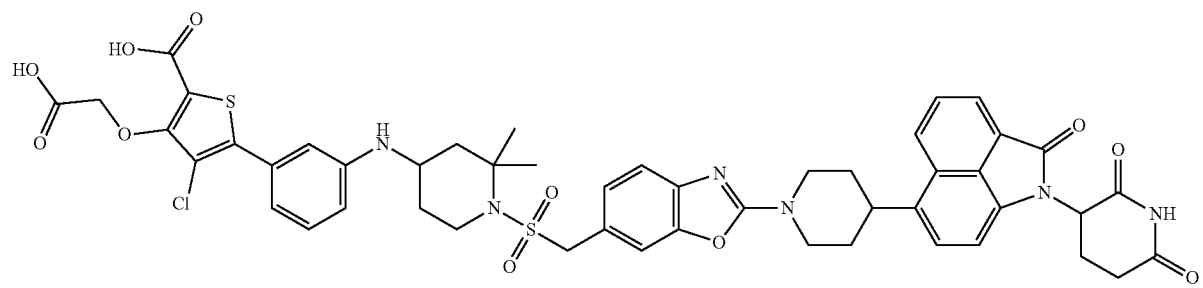
9

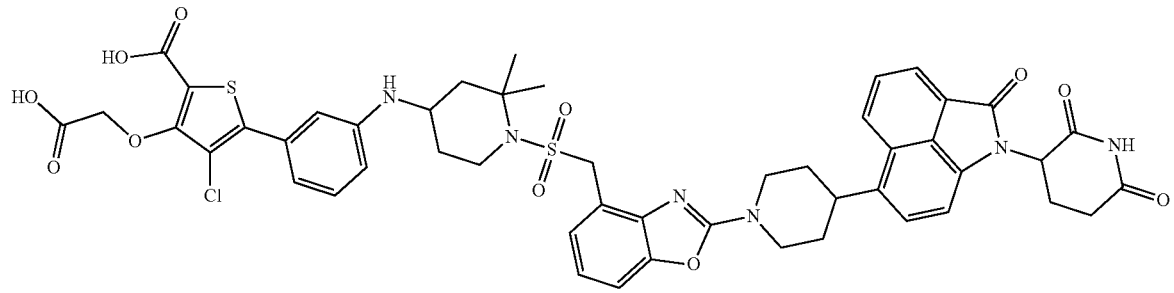
10
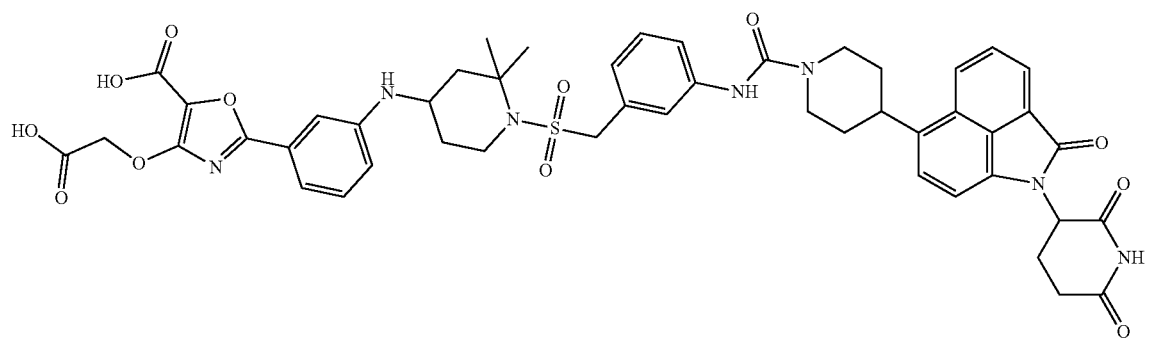
11
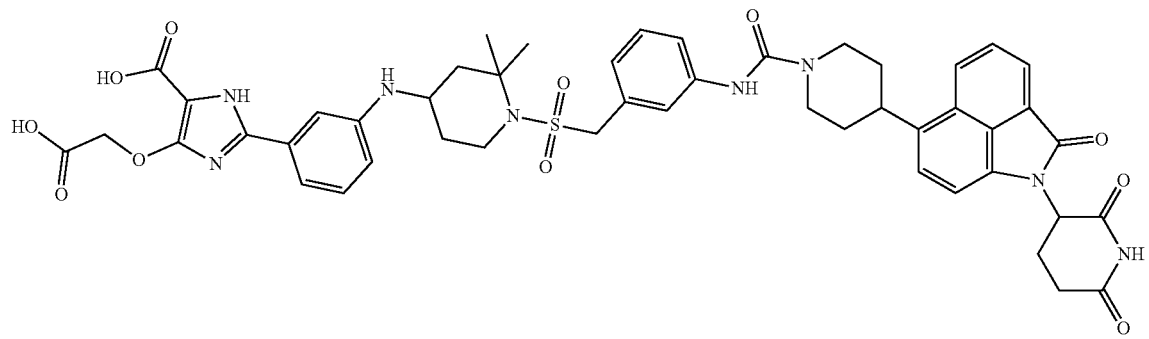
12
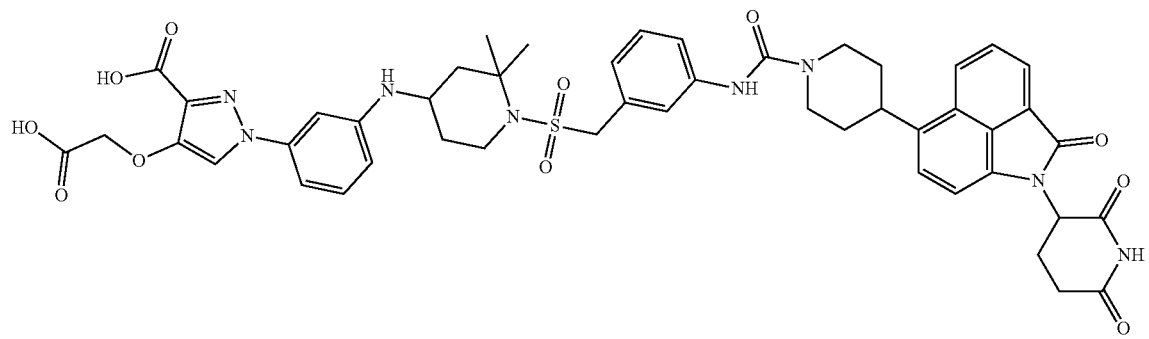
13

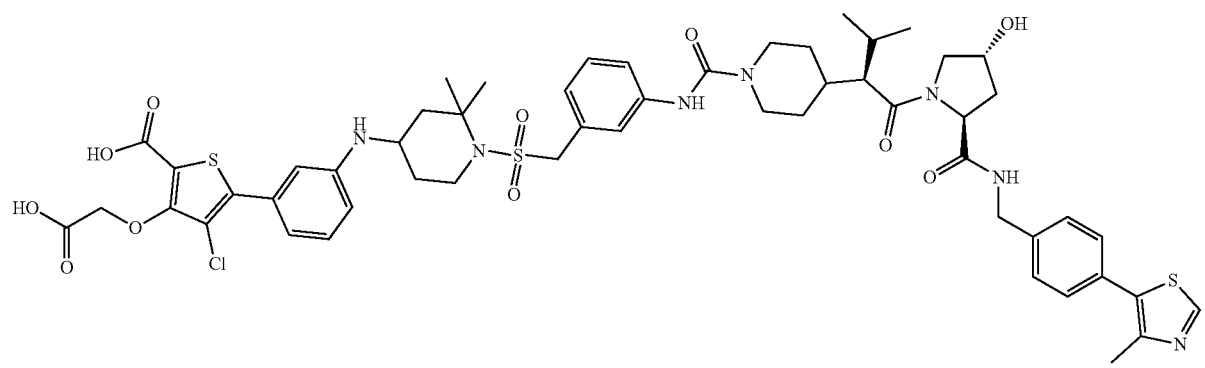
14
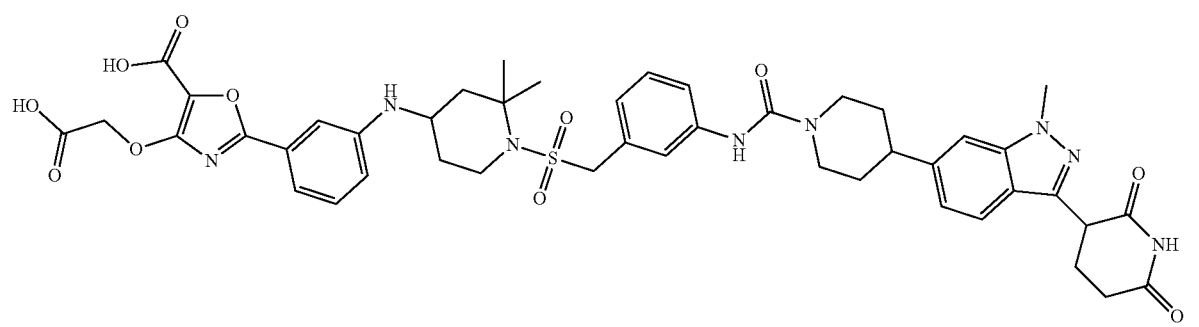
15
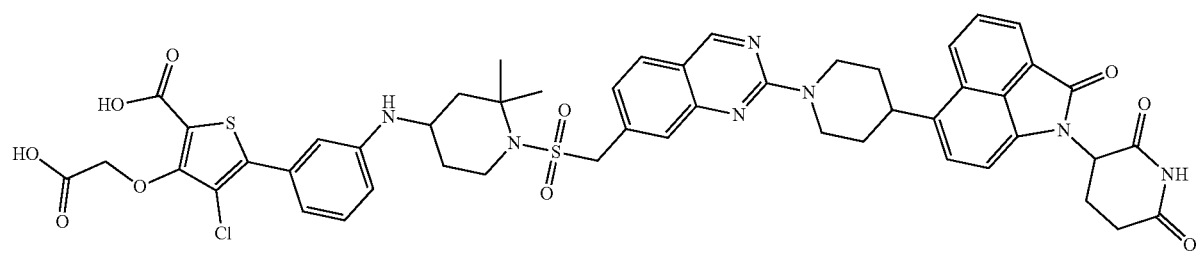
16
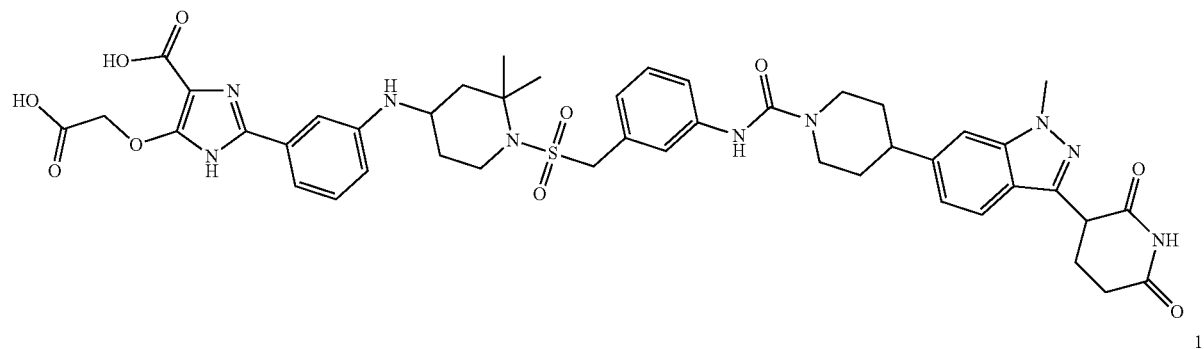
17
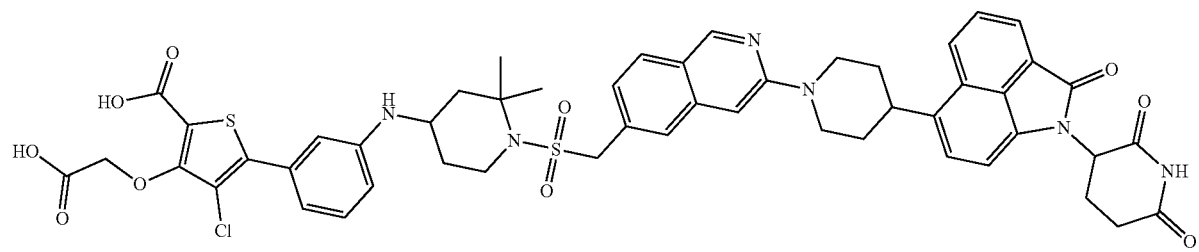
18

19
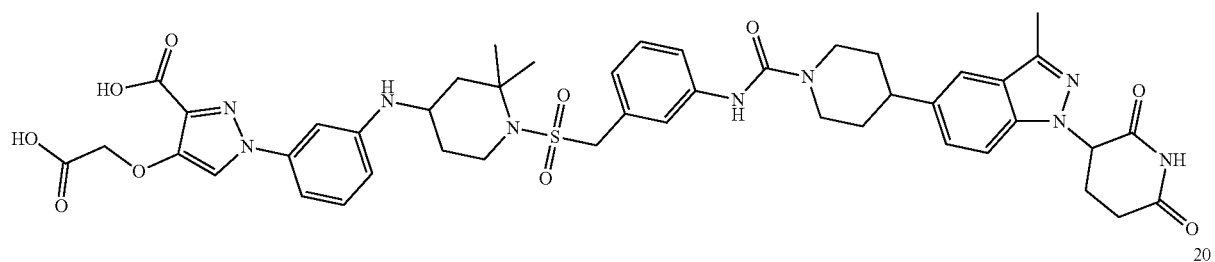
20
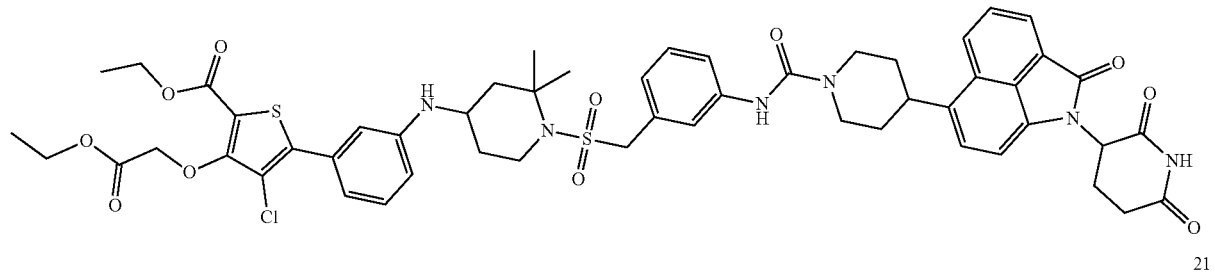
21
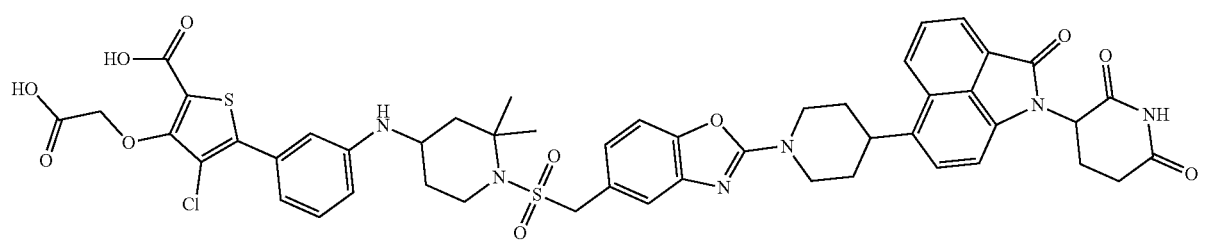
22
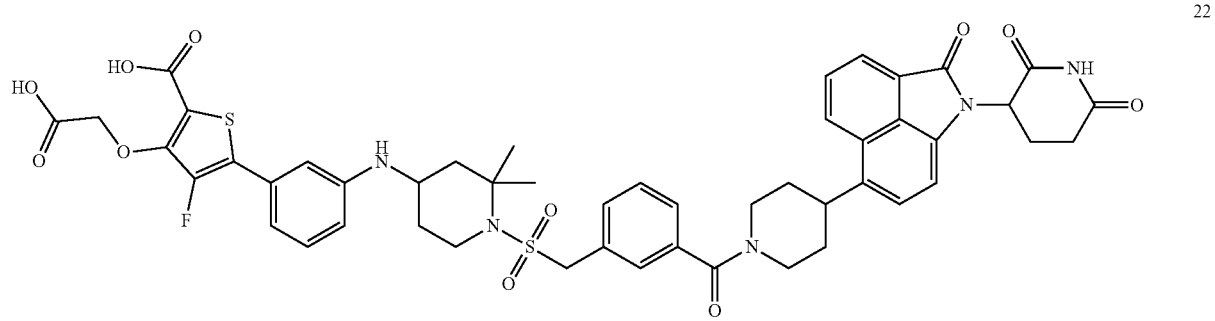
23
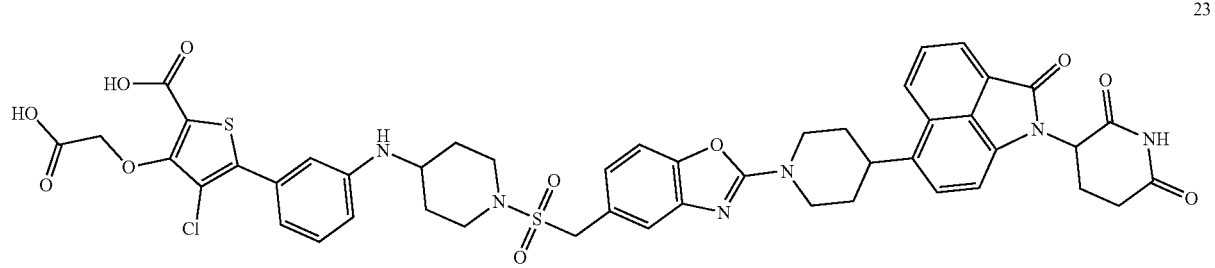
24
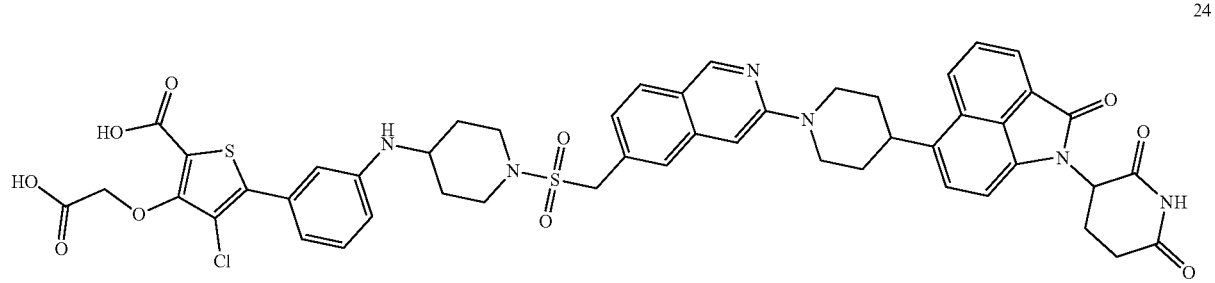

25
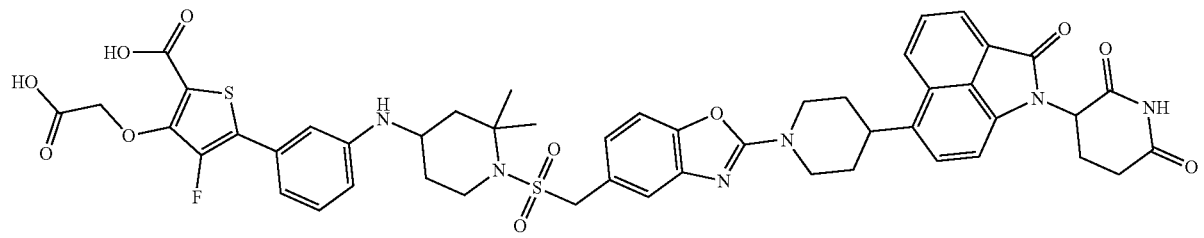
26
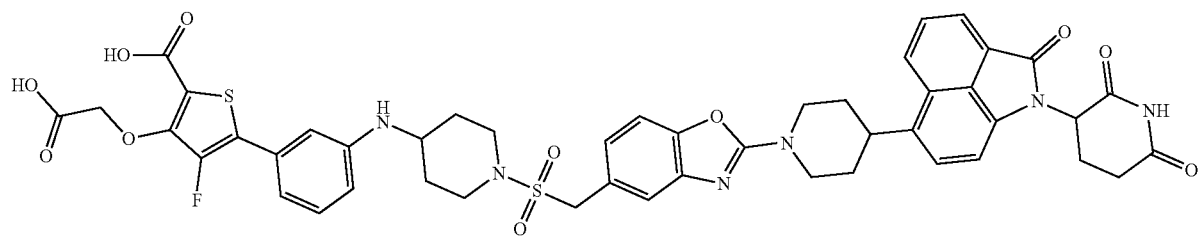
27
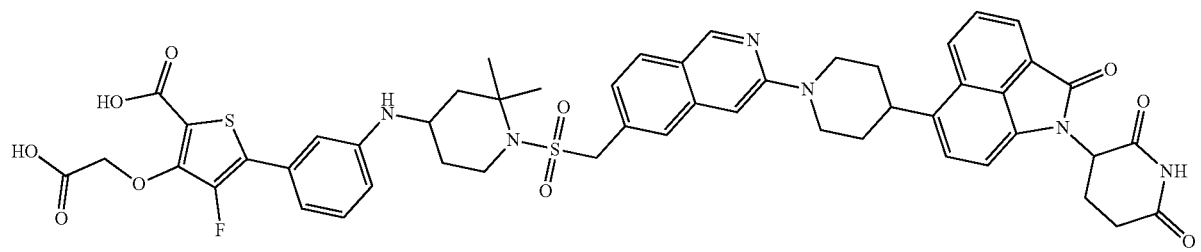
28
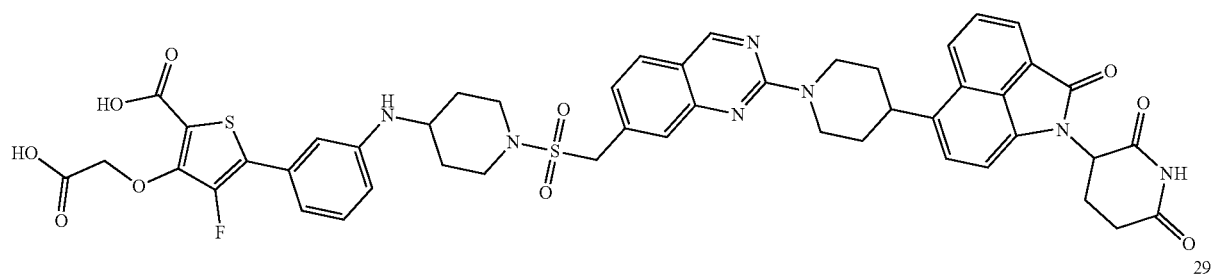
29
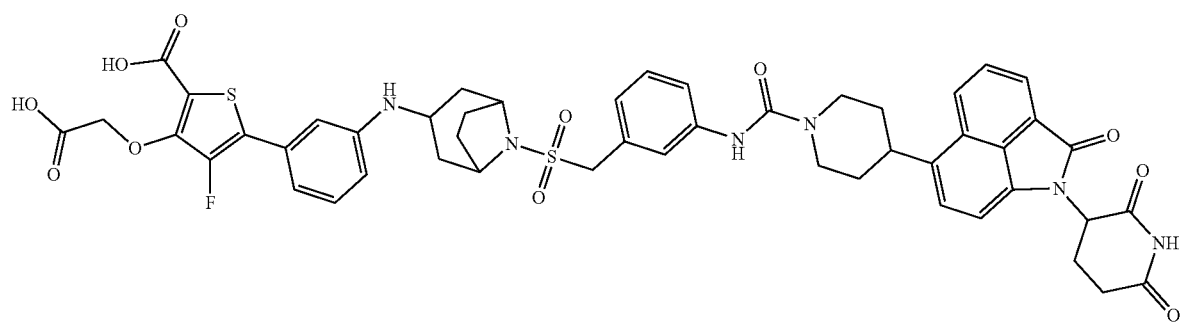

-continued
30
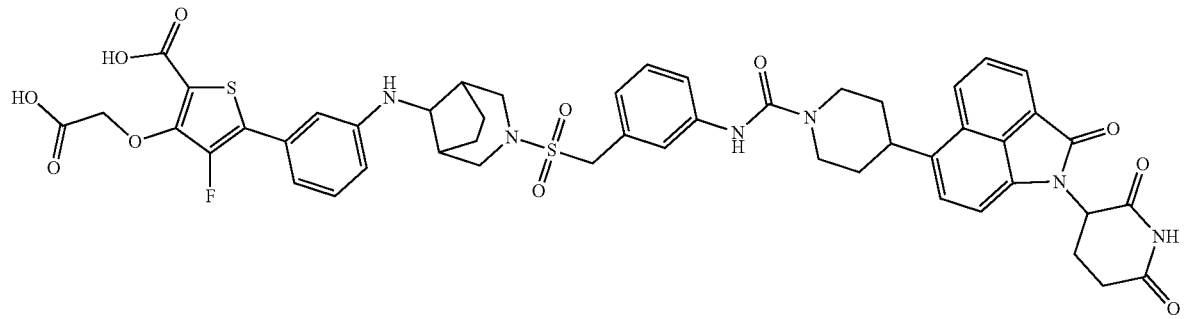
31
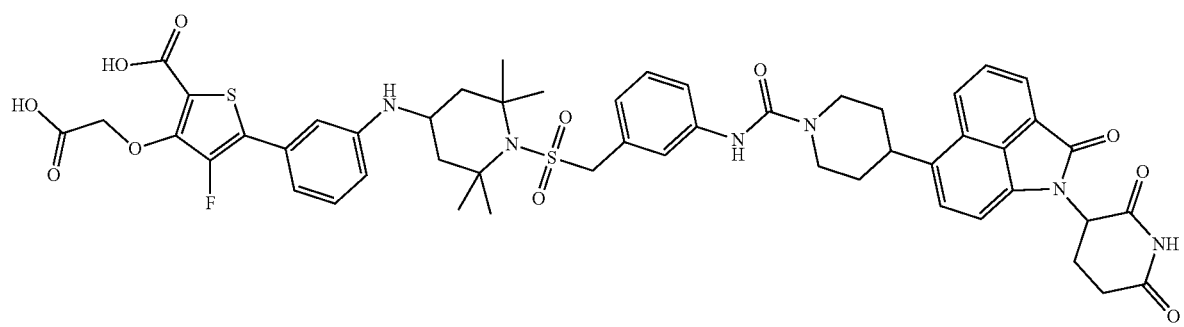
32
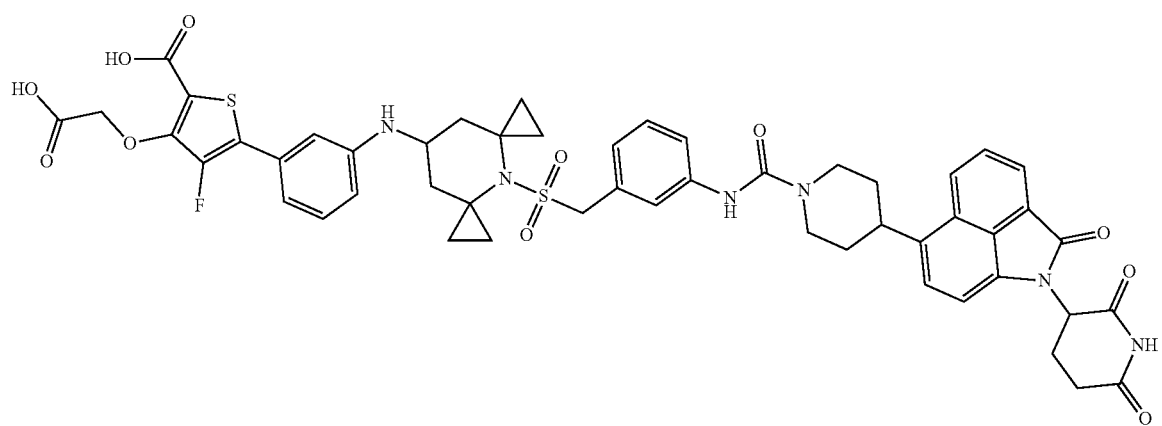
33
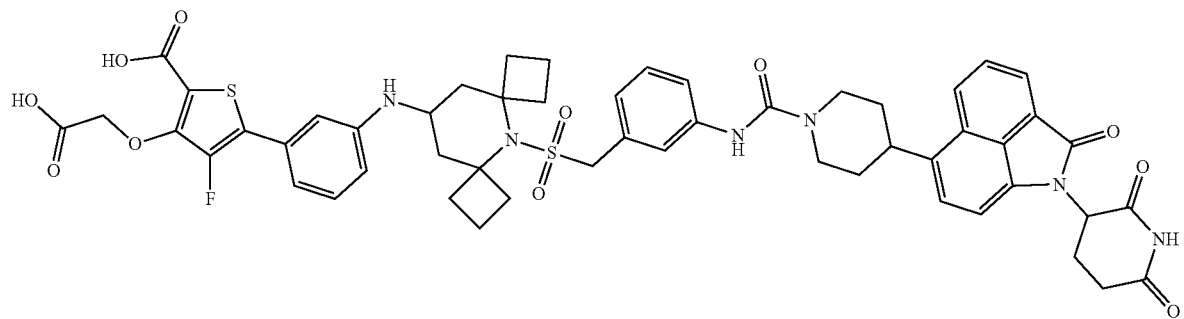

34
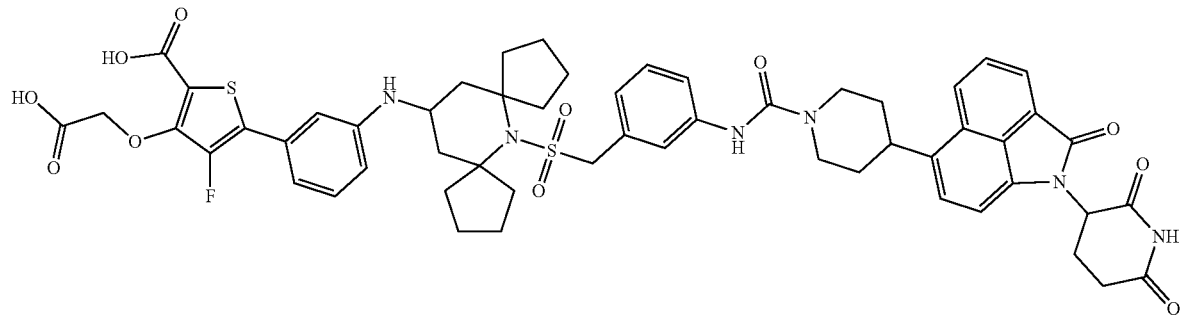
35
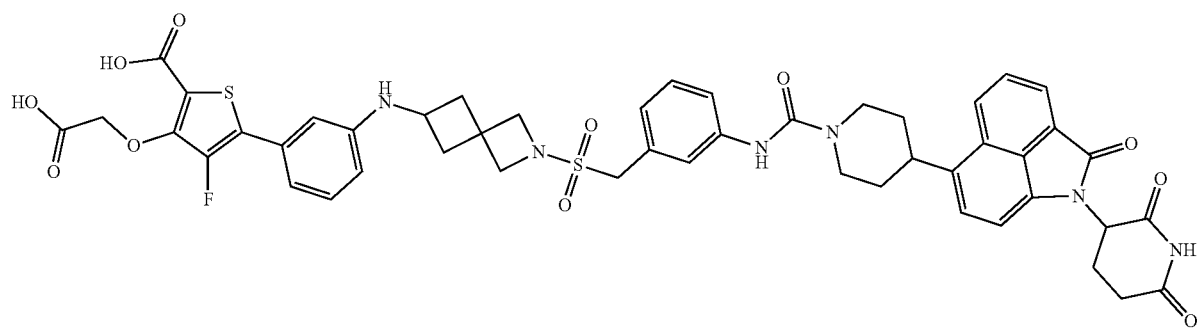
36
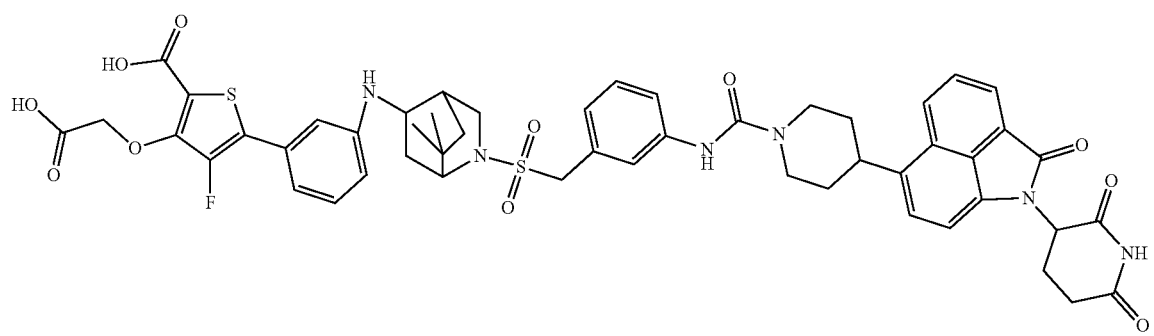
37
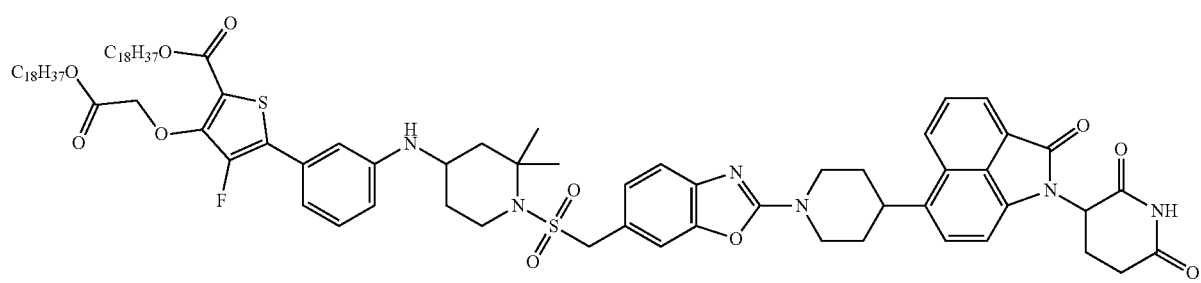

-continued
38
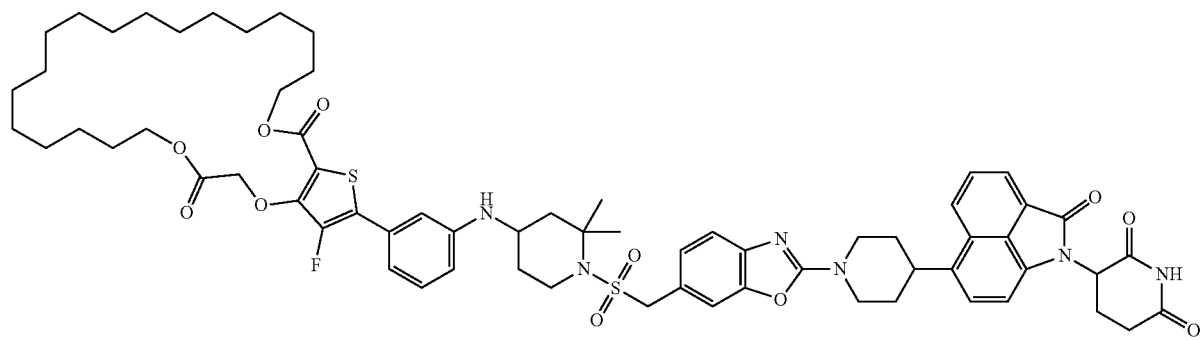
39
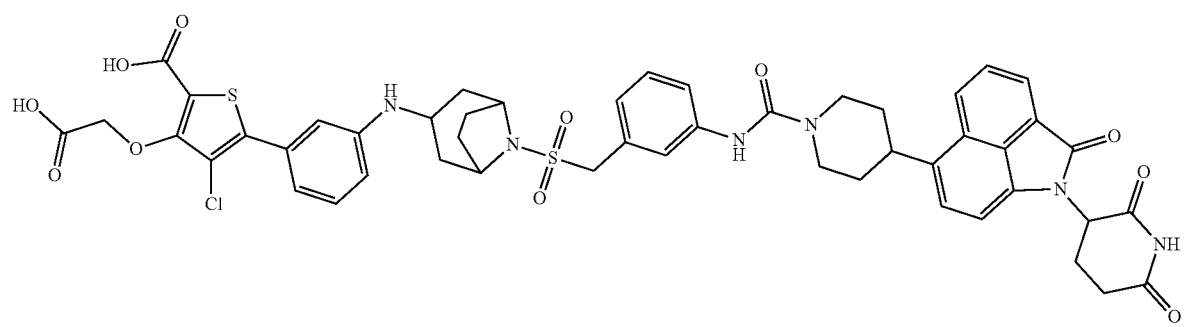
40
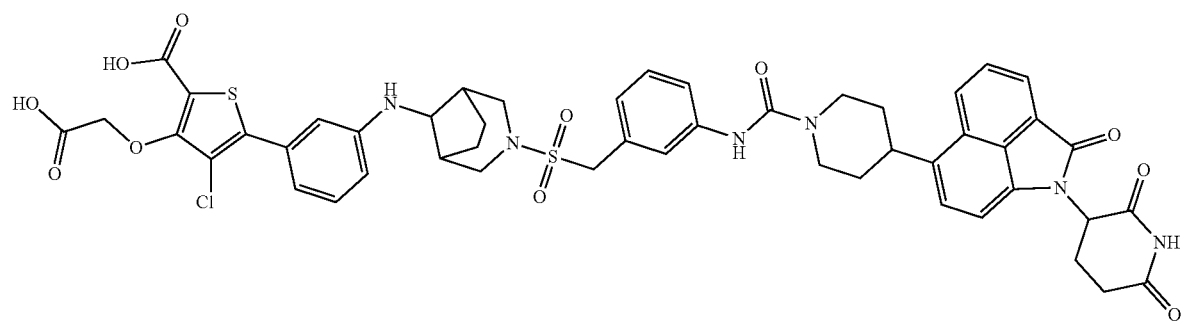
41
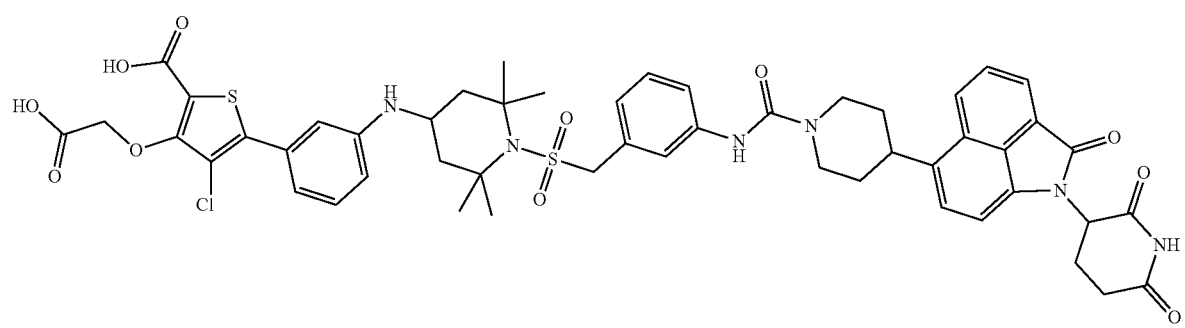

42
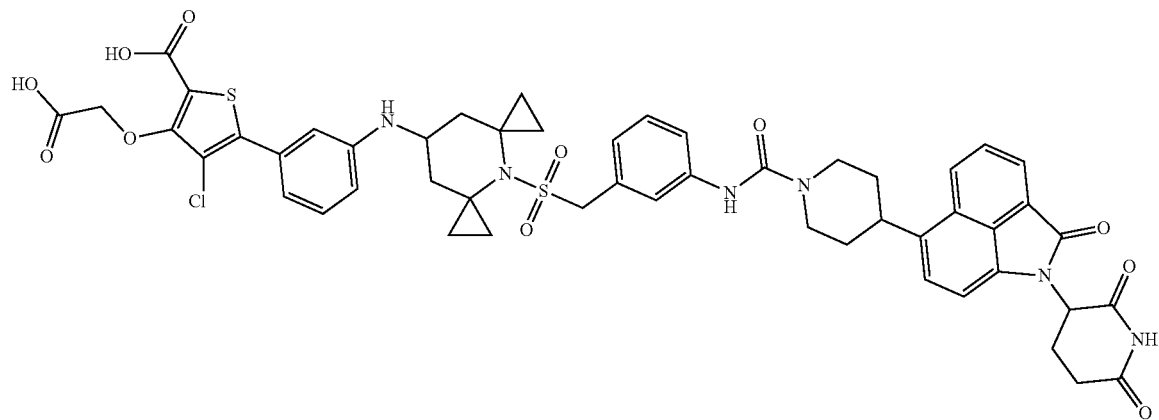
43
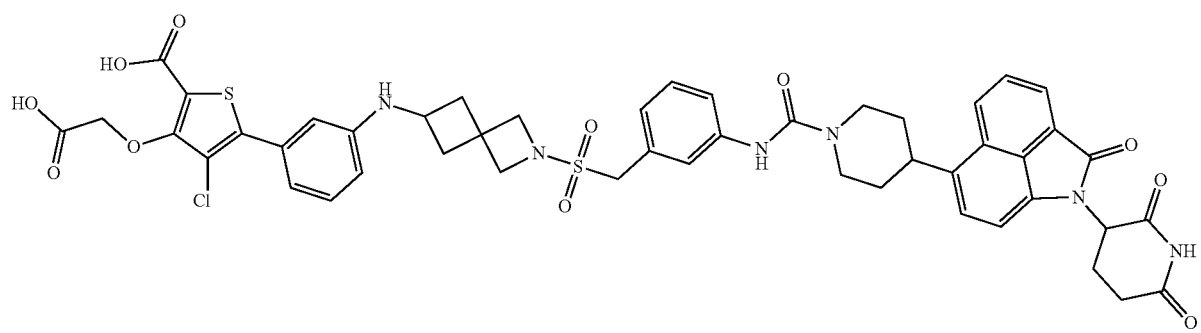
44
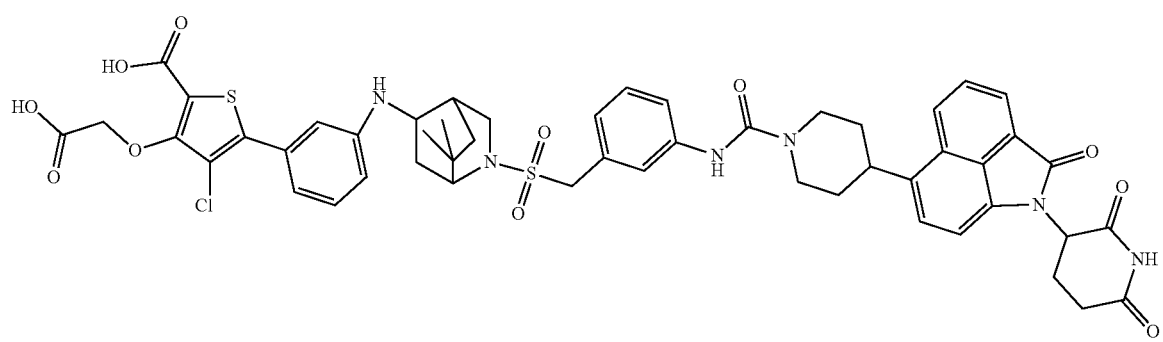
45
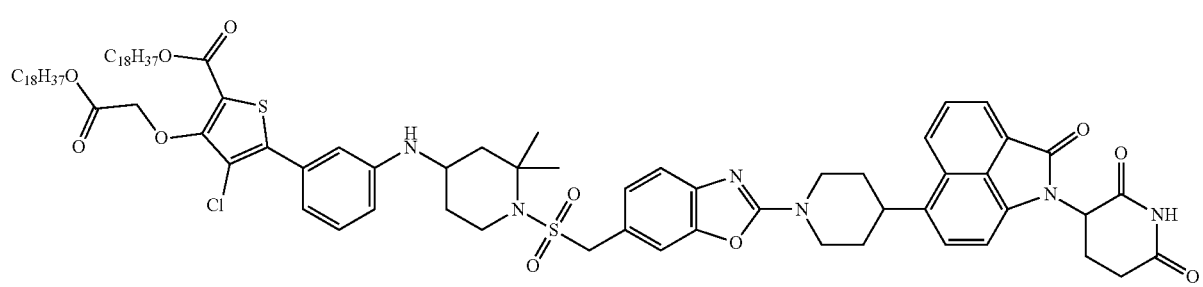

46
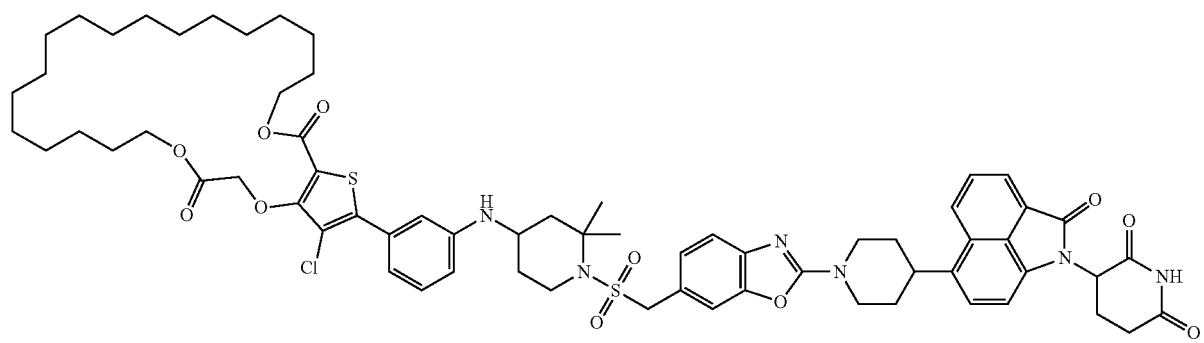
47
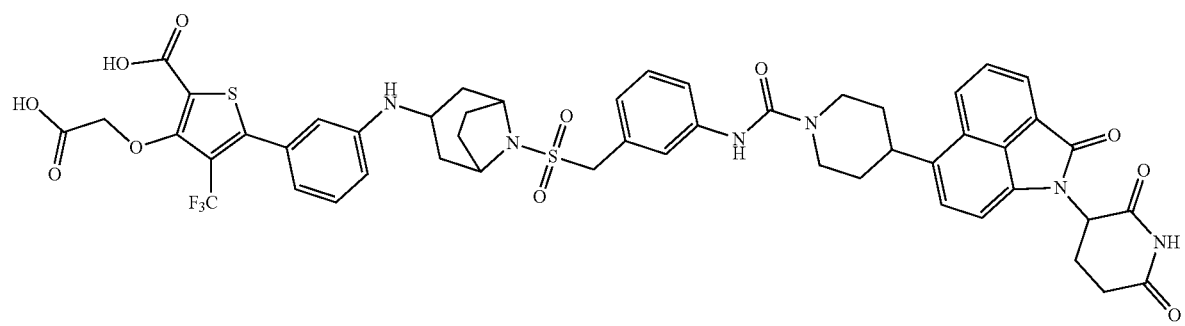
48
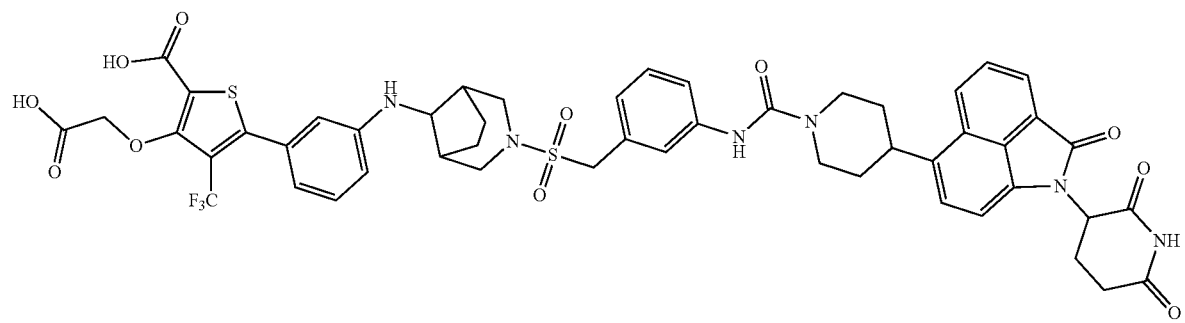
49
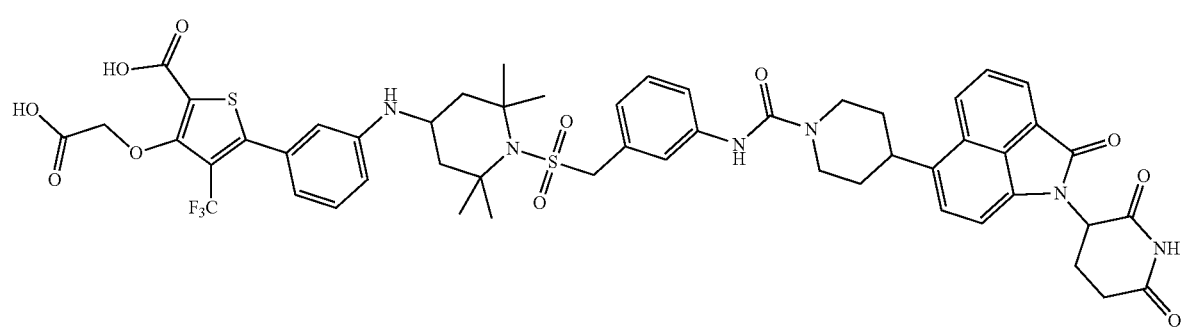

50
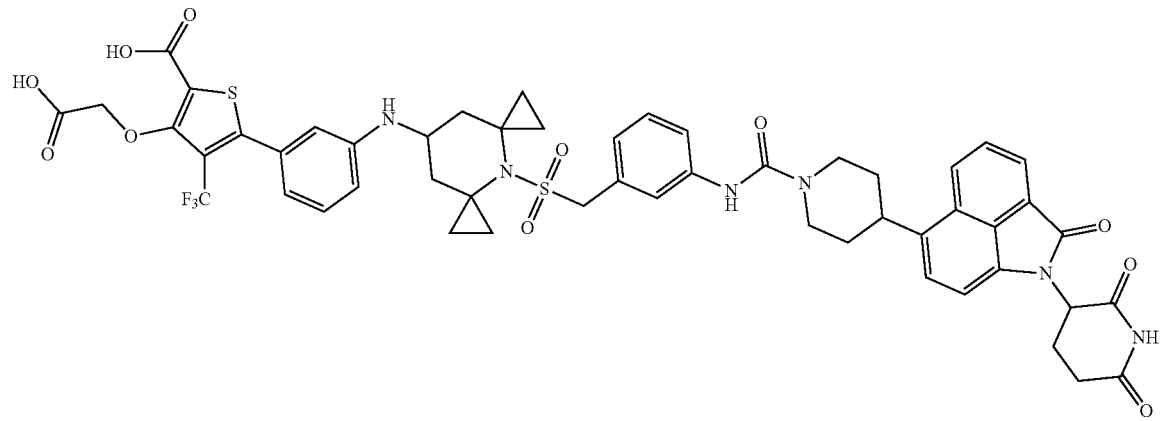
51
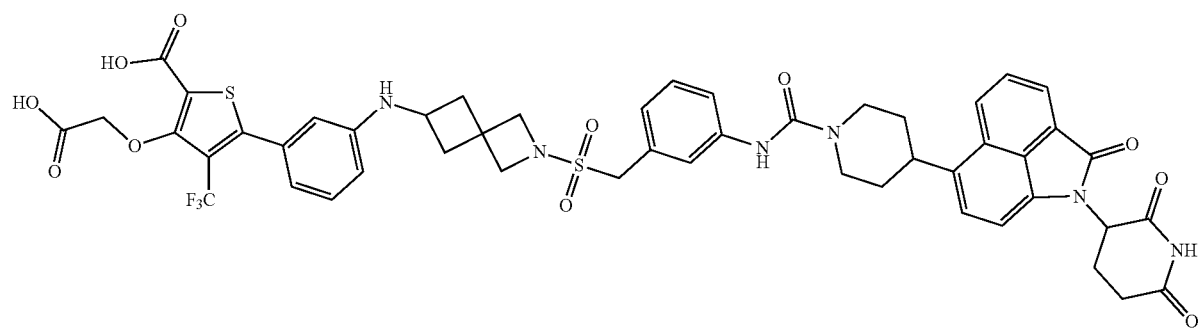
52
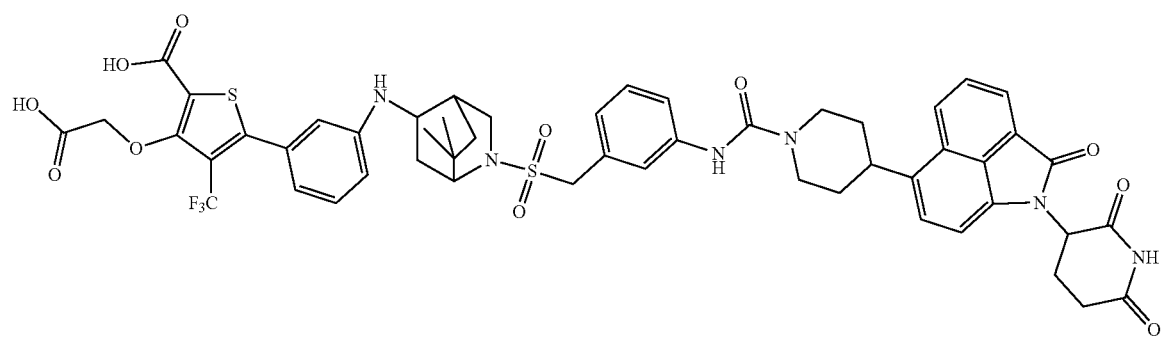
53
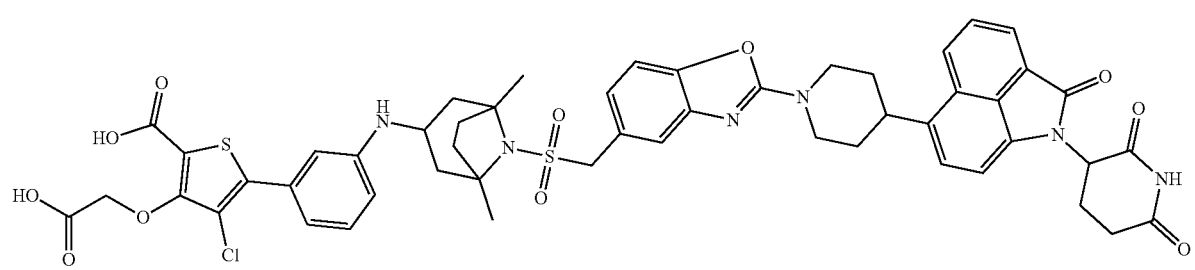

54
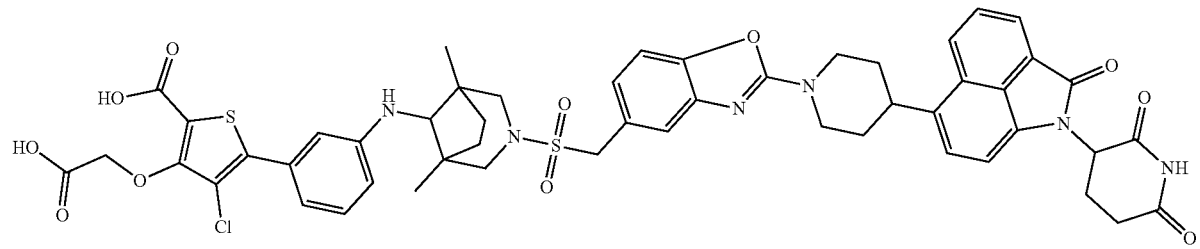
55
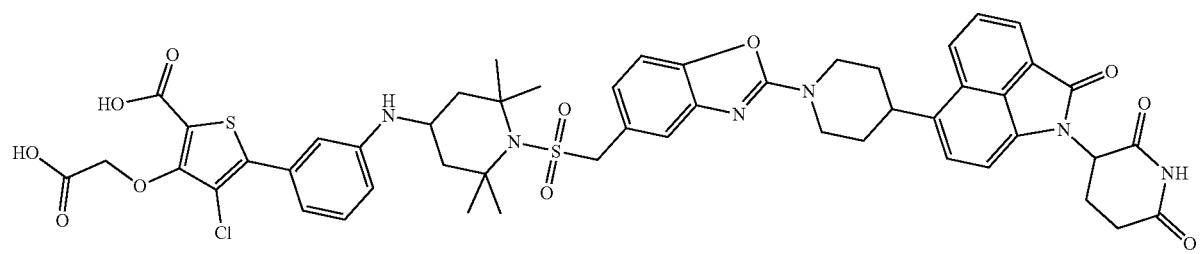
56
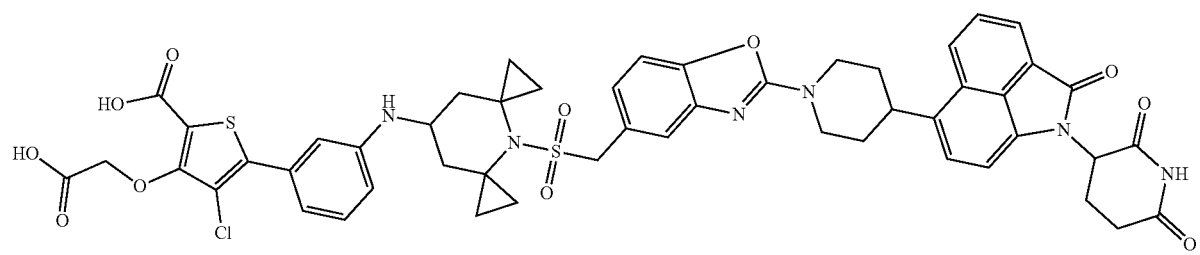
57
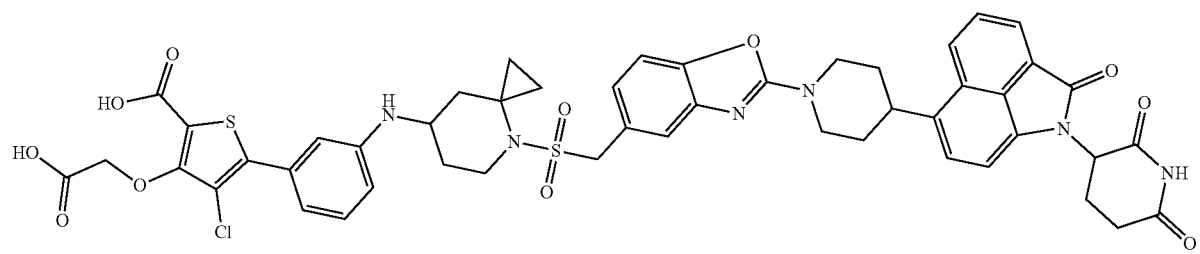
58
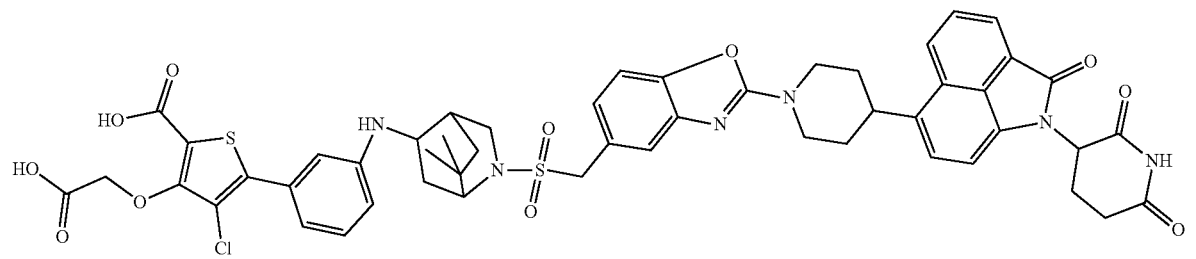

59
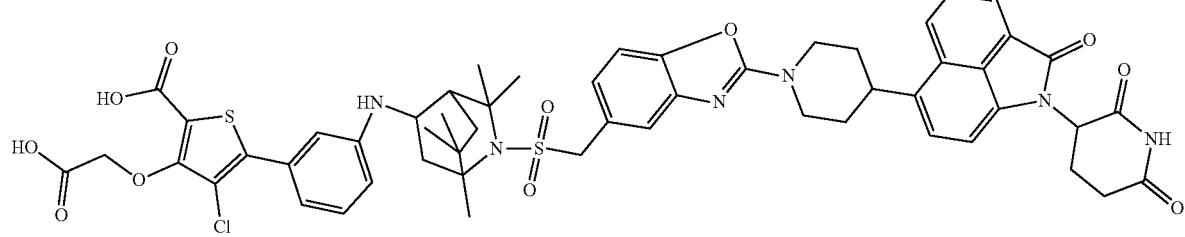
60
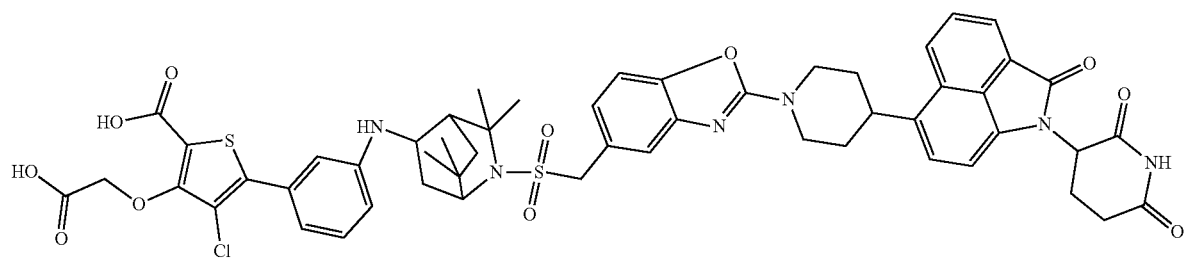
61
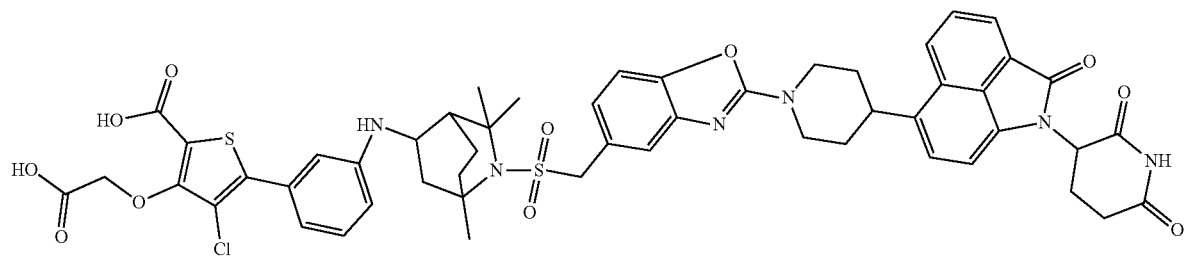
62
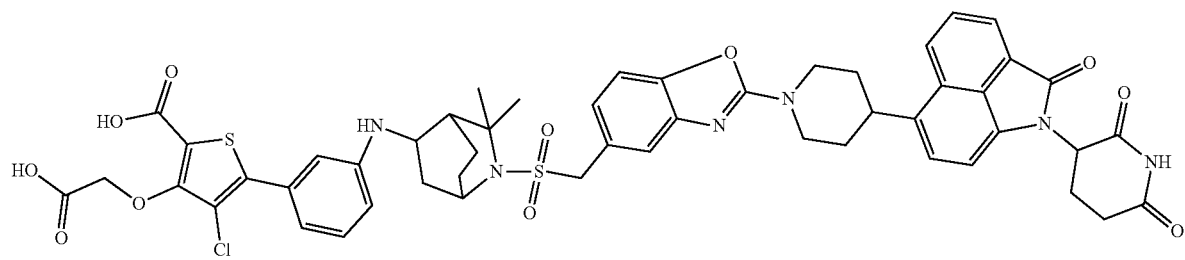
63
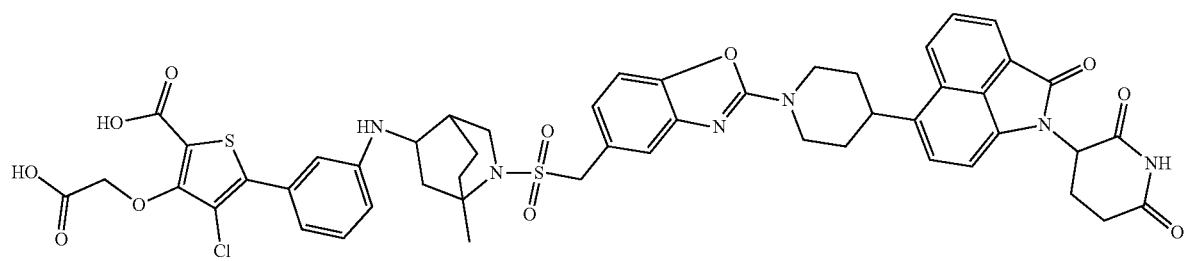

64
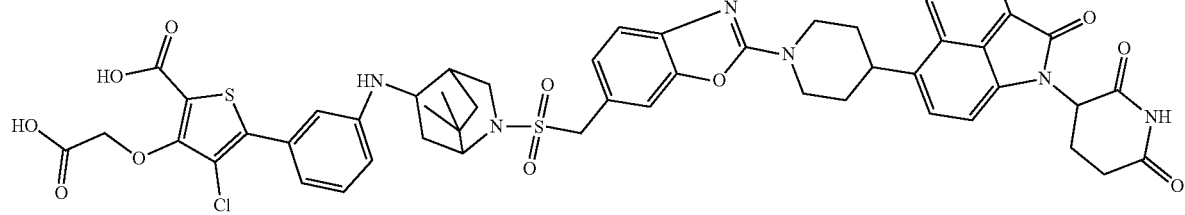
65
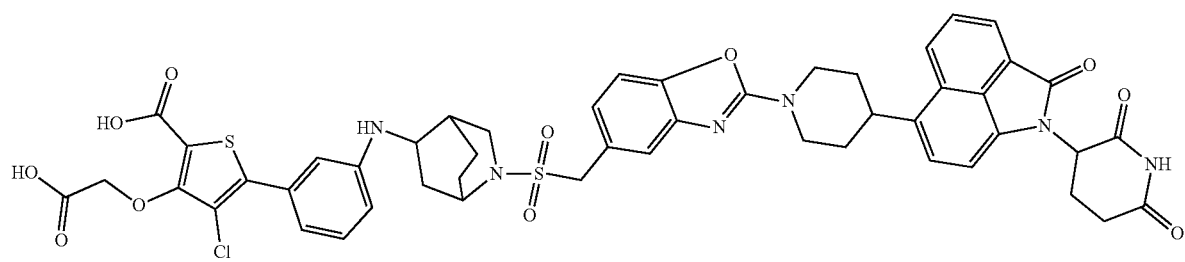
66
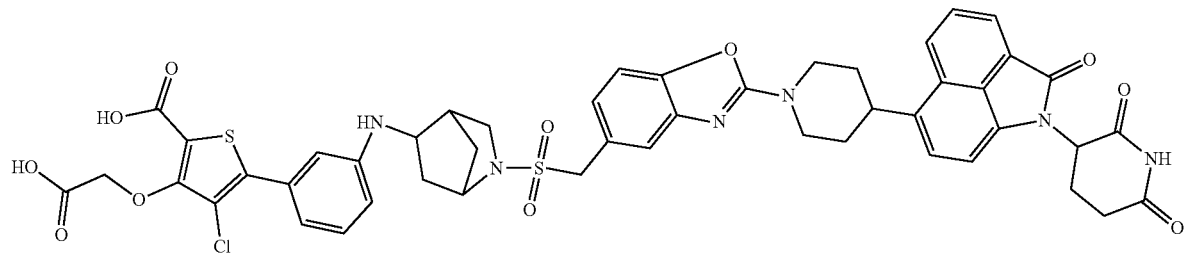
67
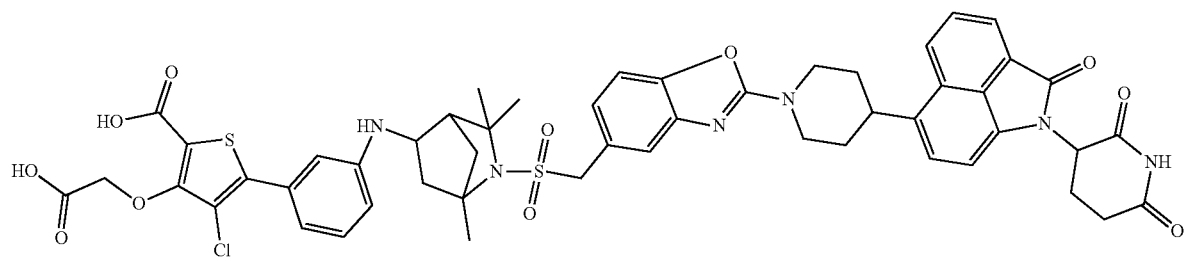
68
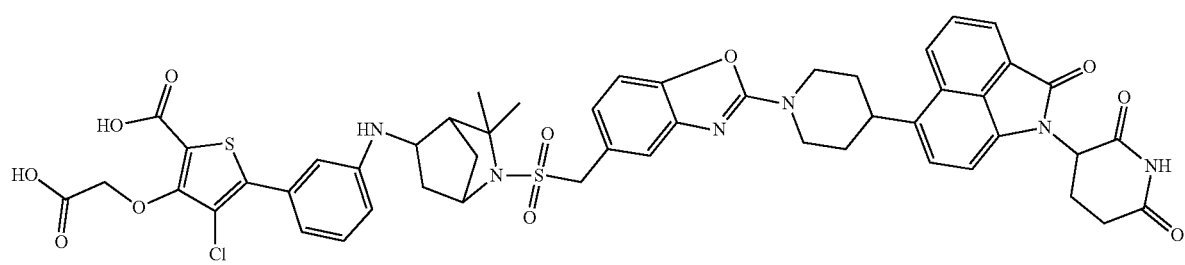

69
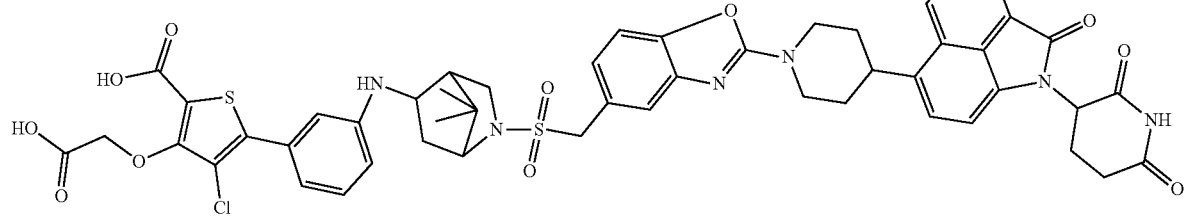
70
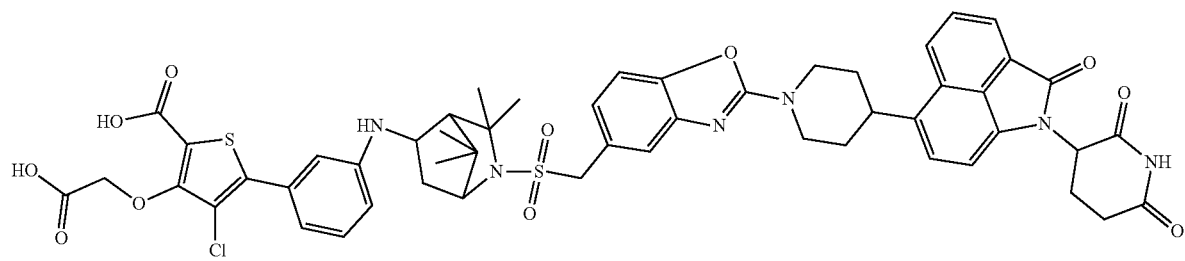
71
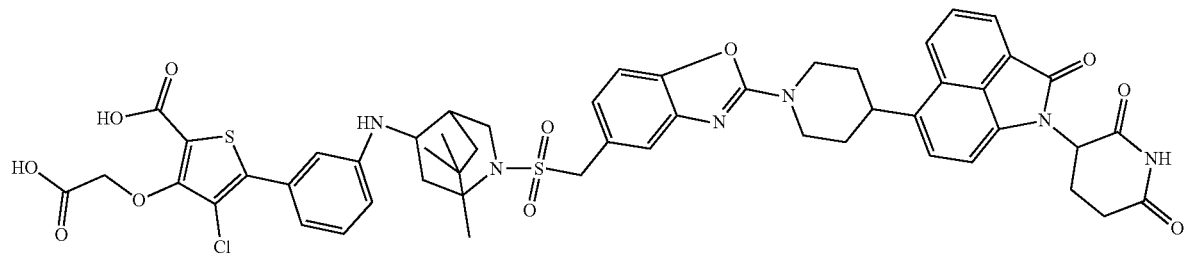
72
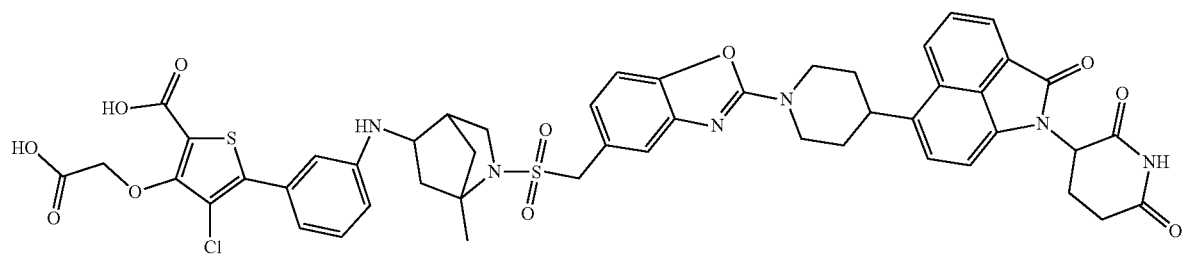
73
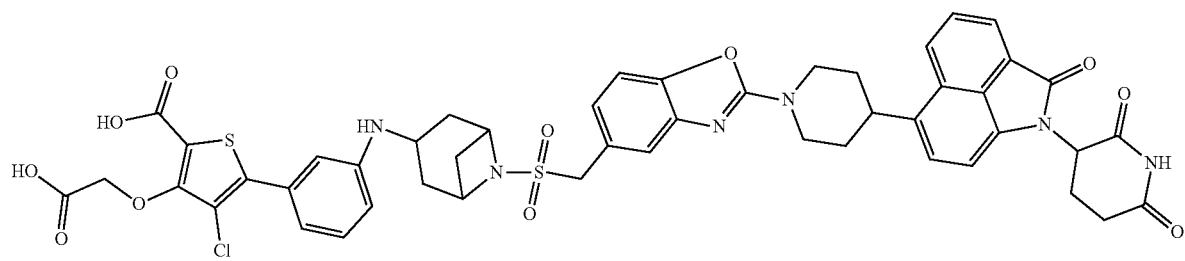

74
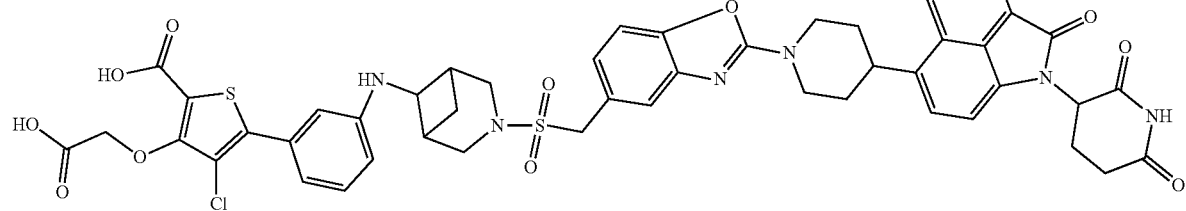
75
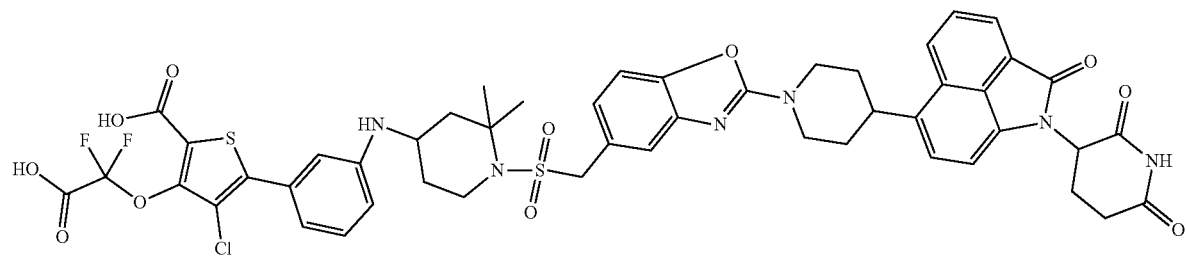
76
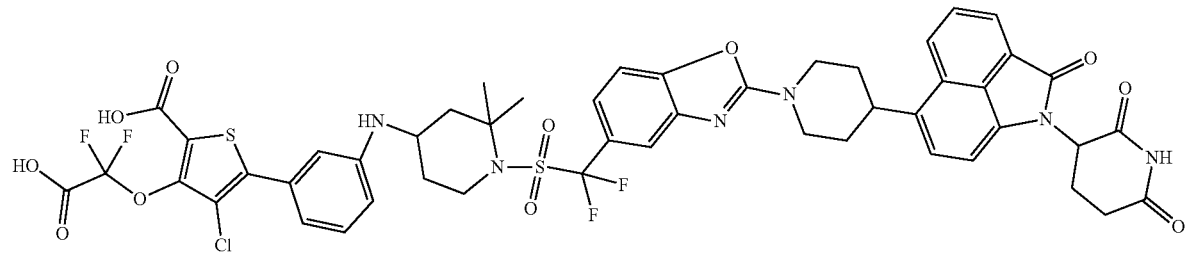
77
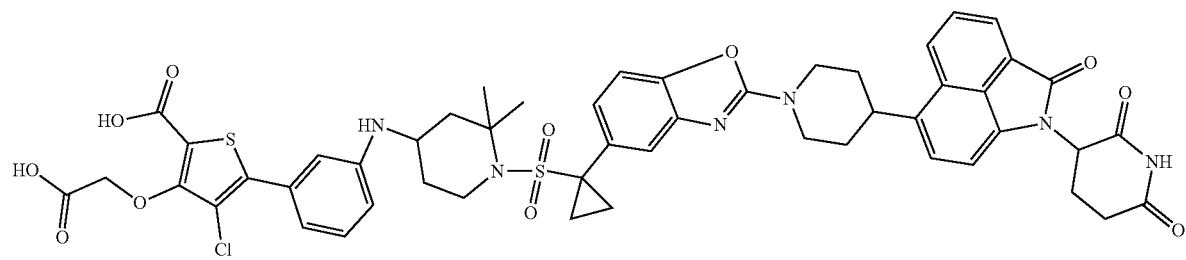
78
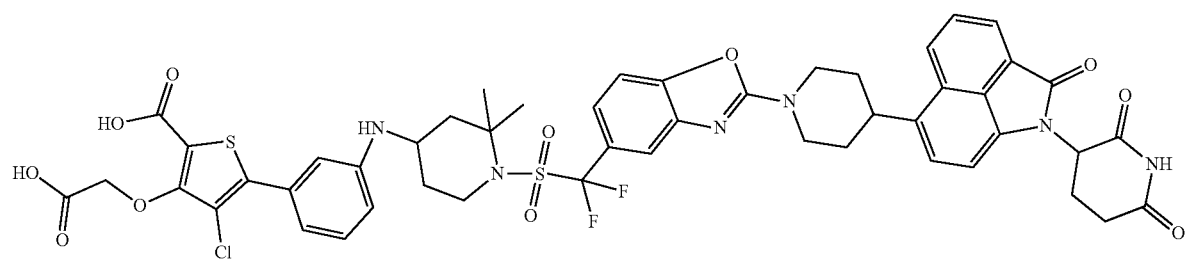

79
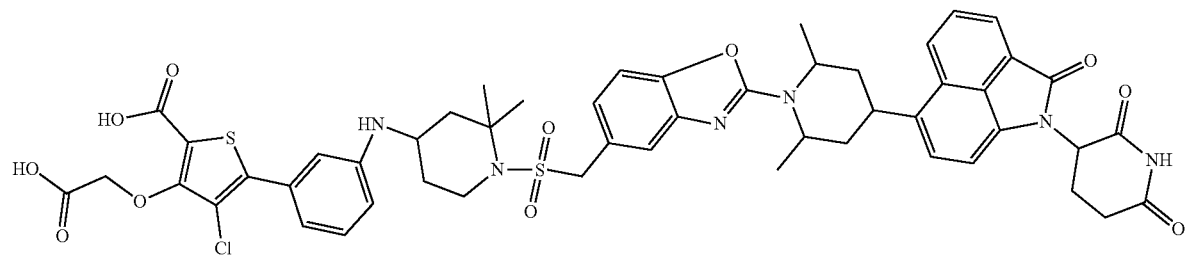
80
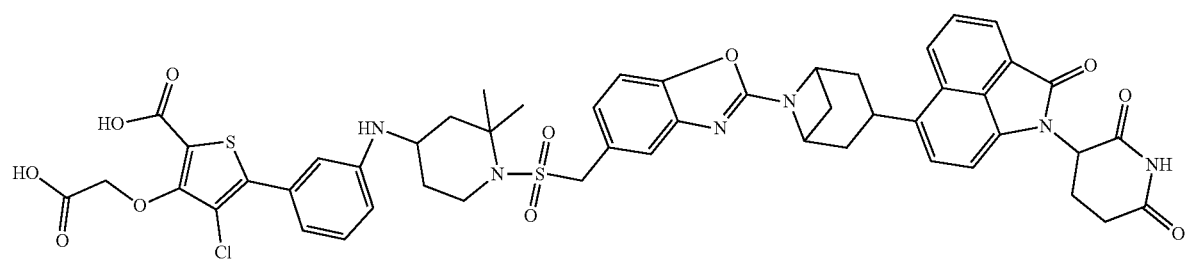
81
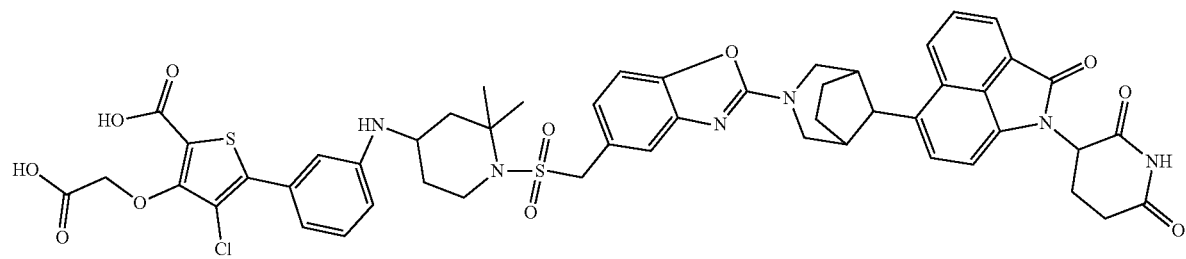
82
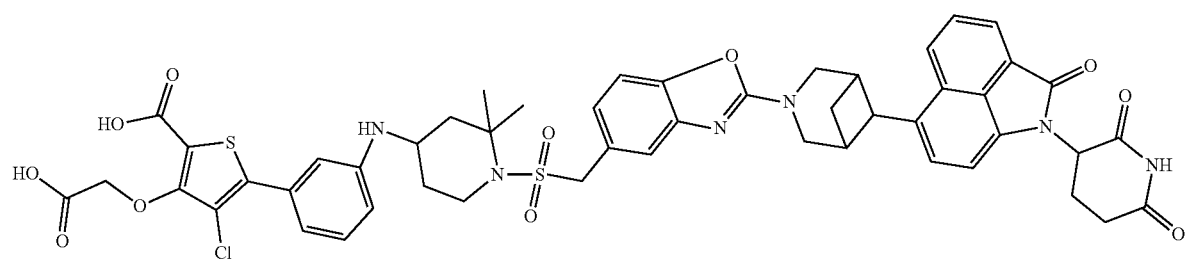
83
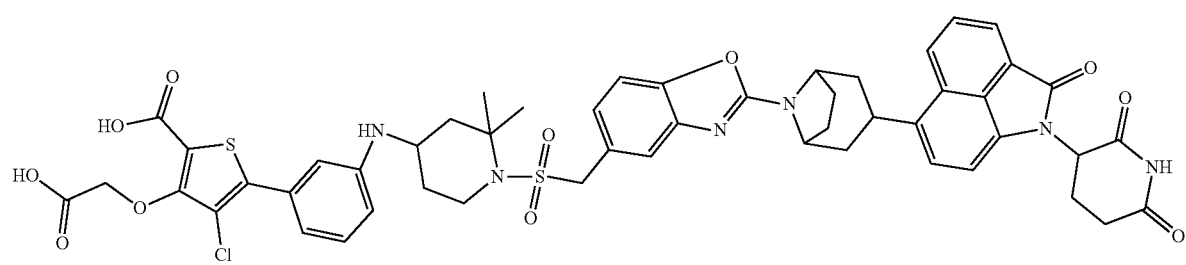

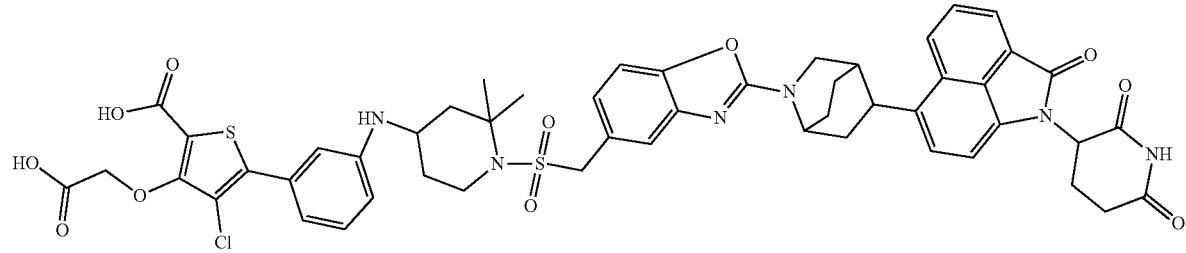
84
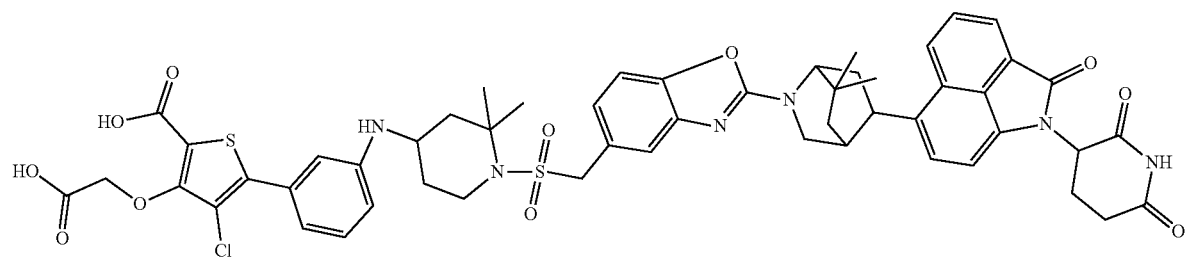
85
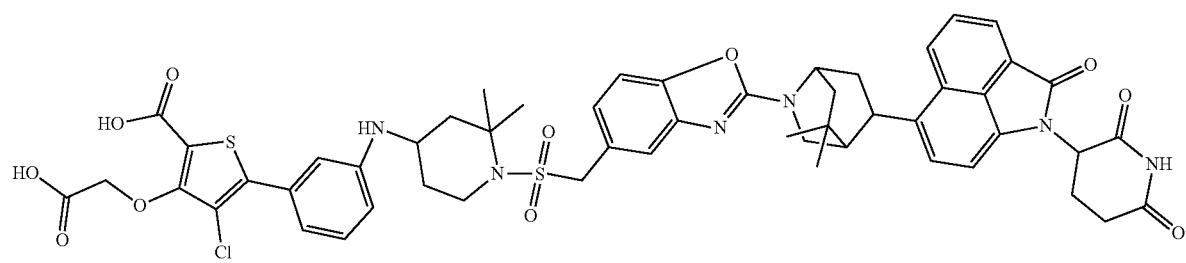
86
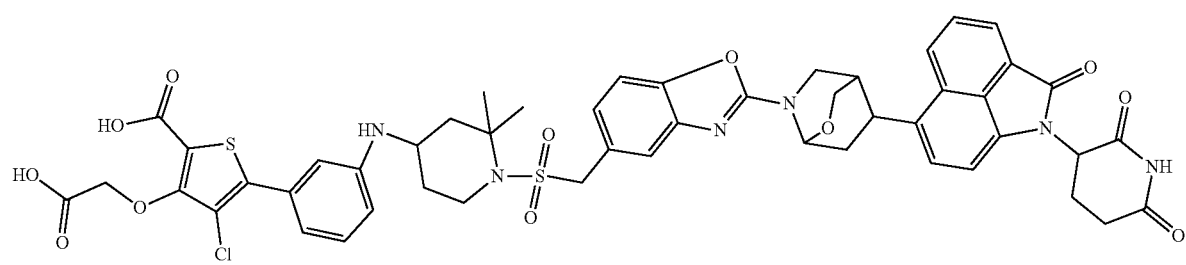
87
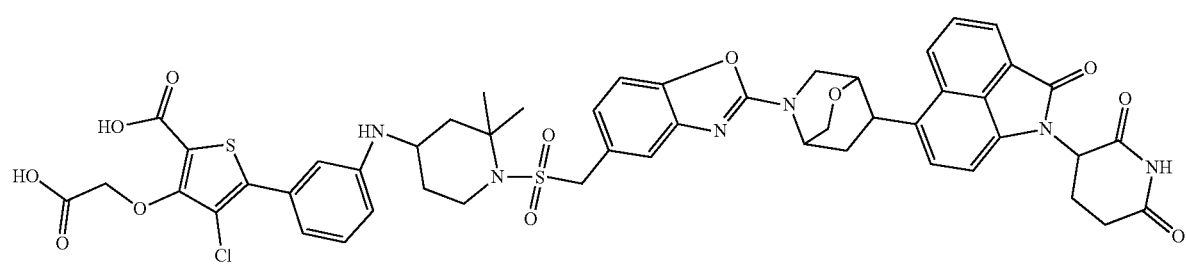
88

-continued
89
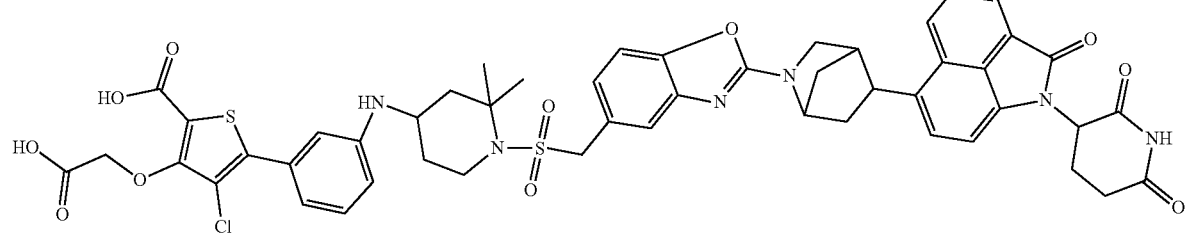
90
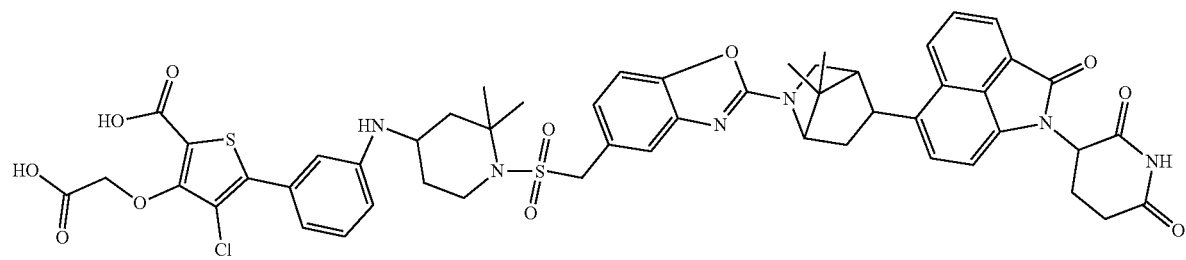
91
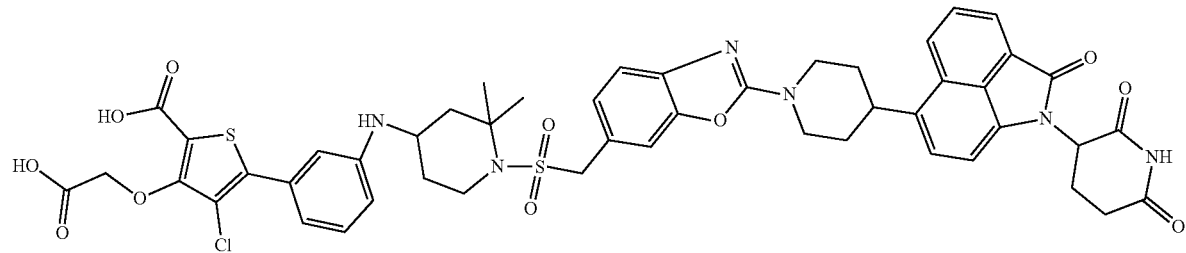
92
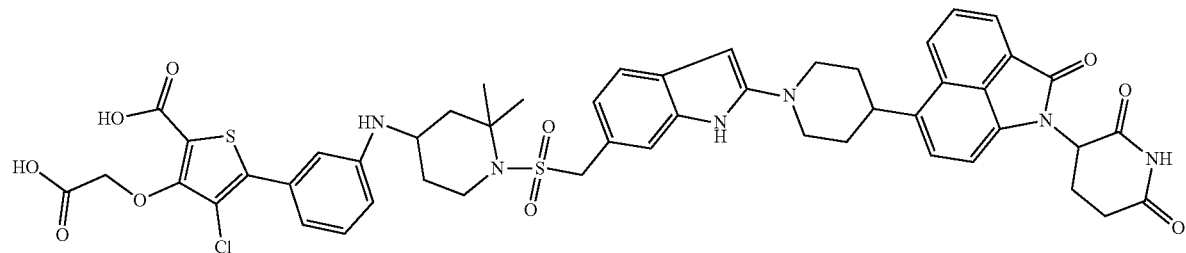
93
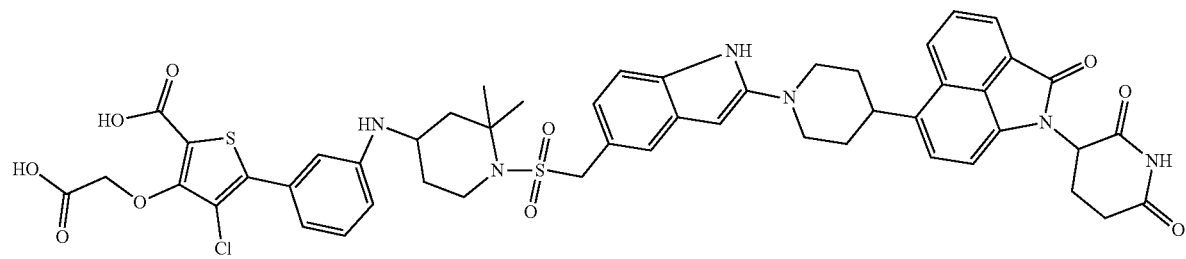

94
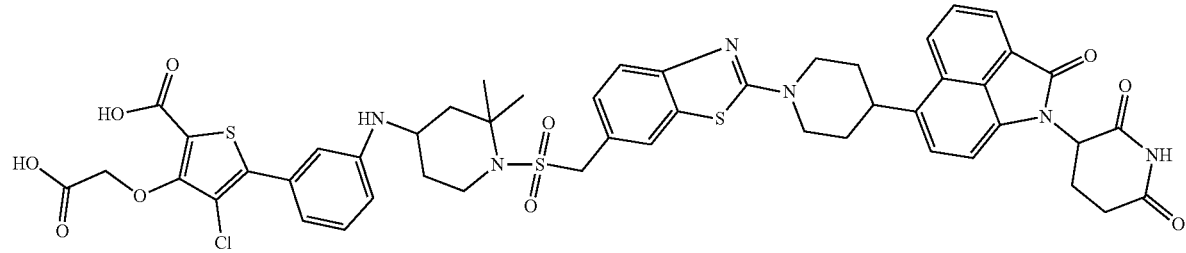
95
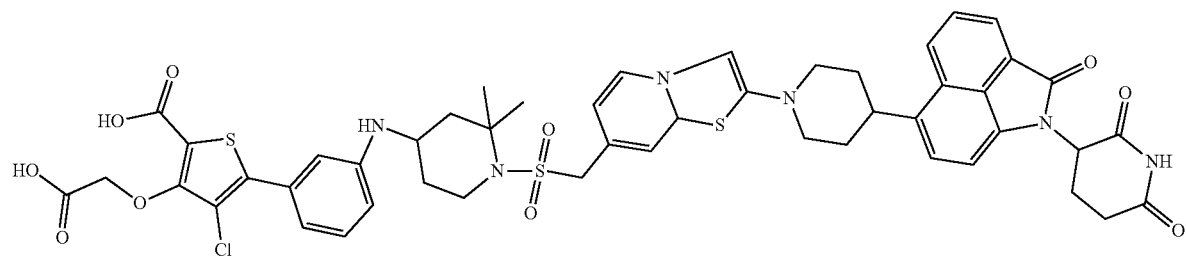
96
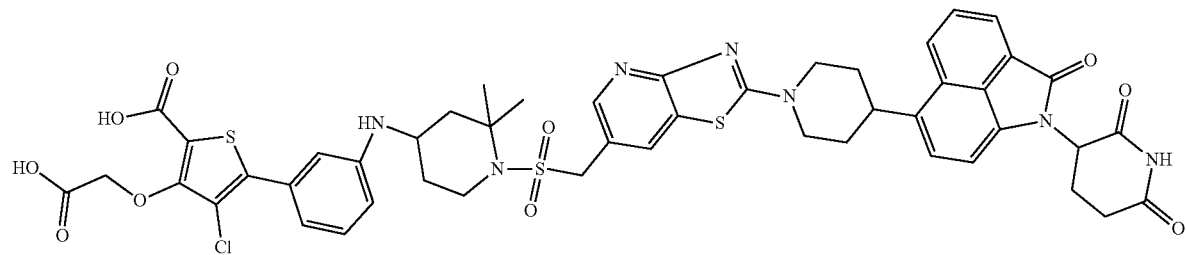
97
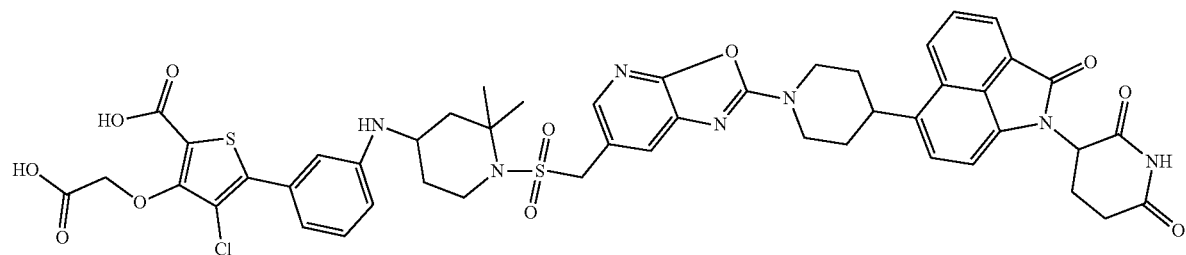
98
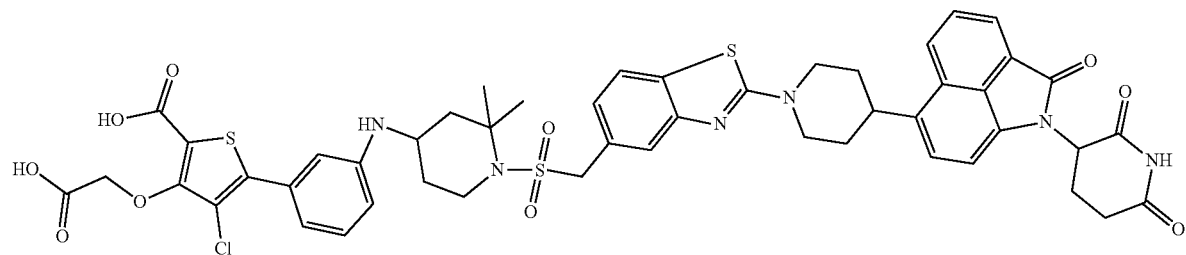

-continued
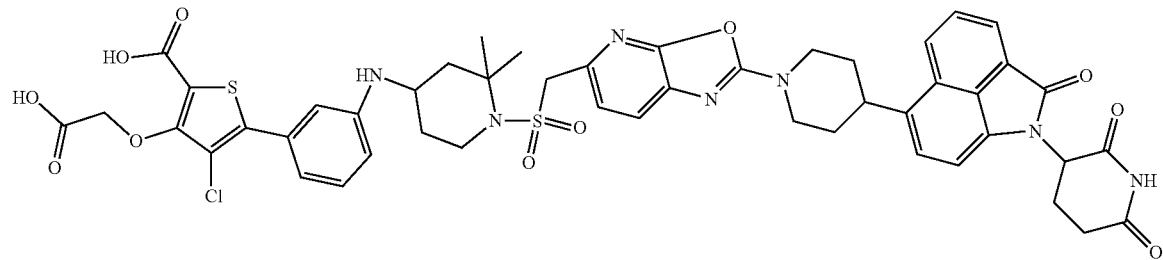
99
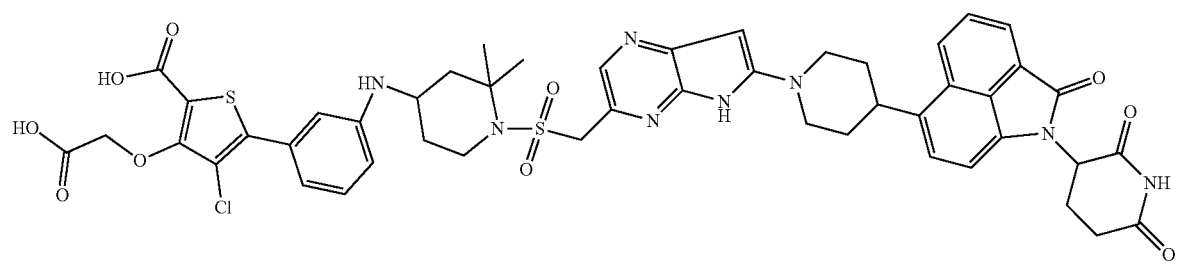
100
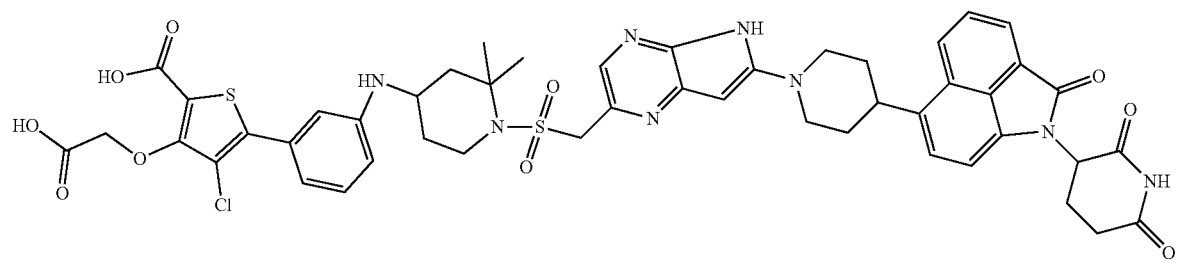
101
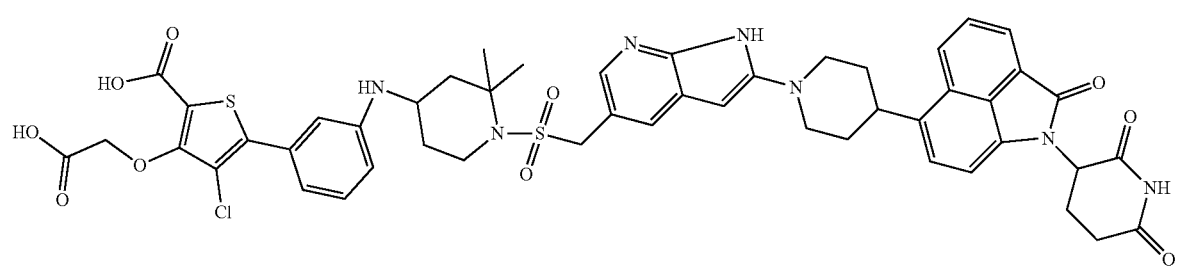
102
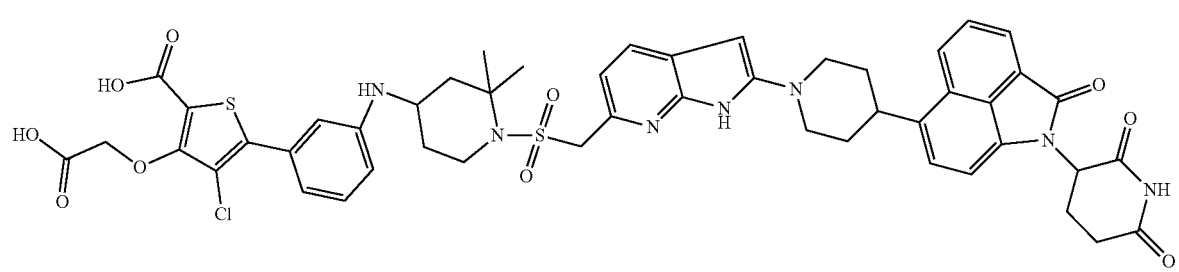
103

104
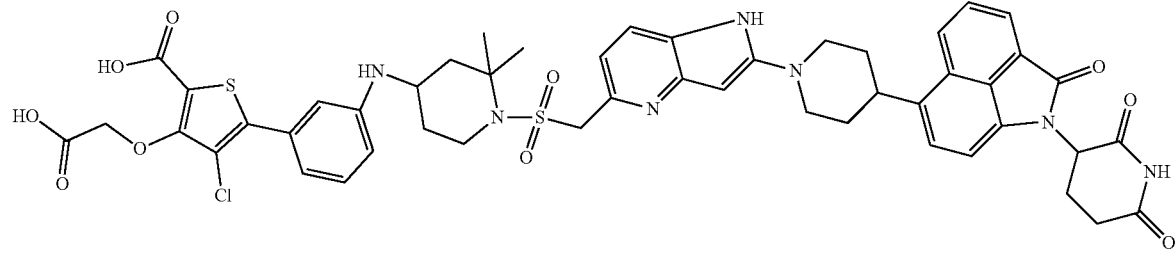
105
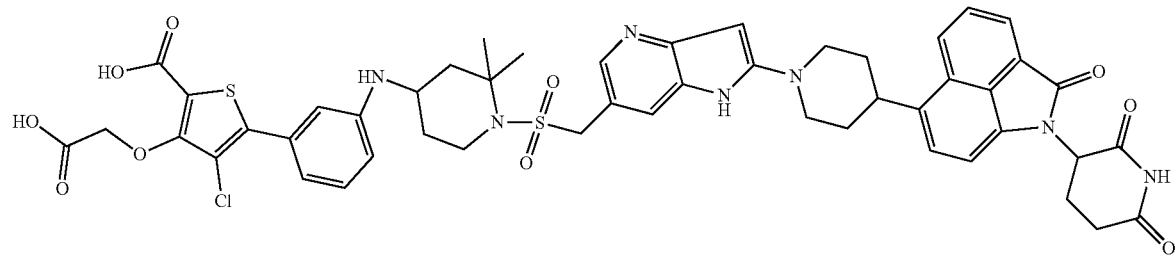
106
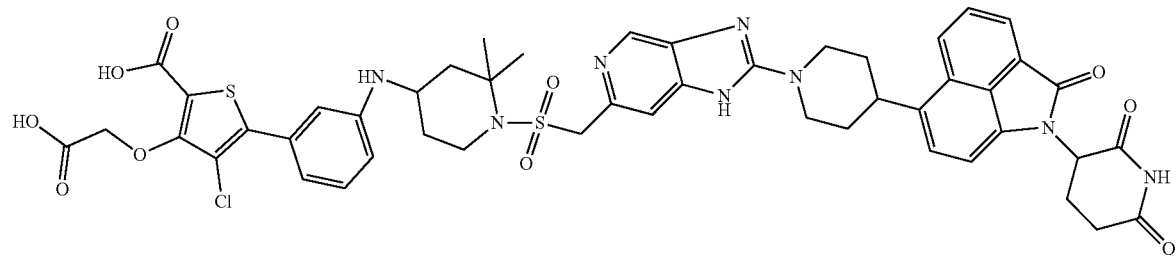
107
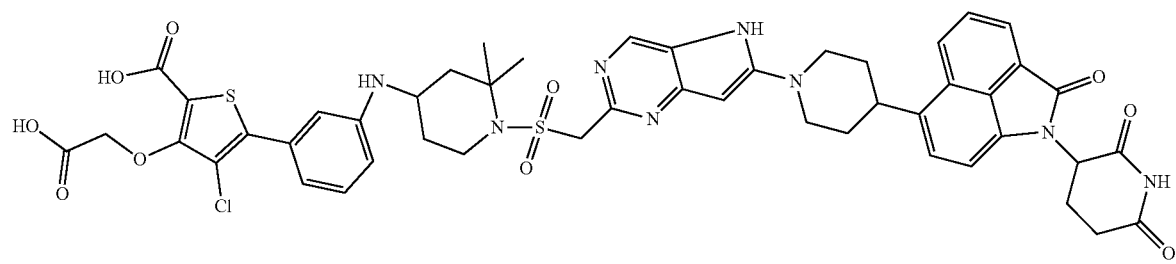
108
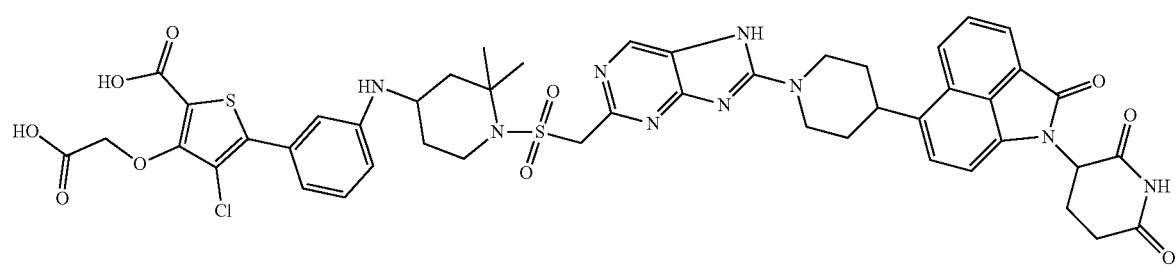

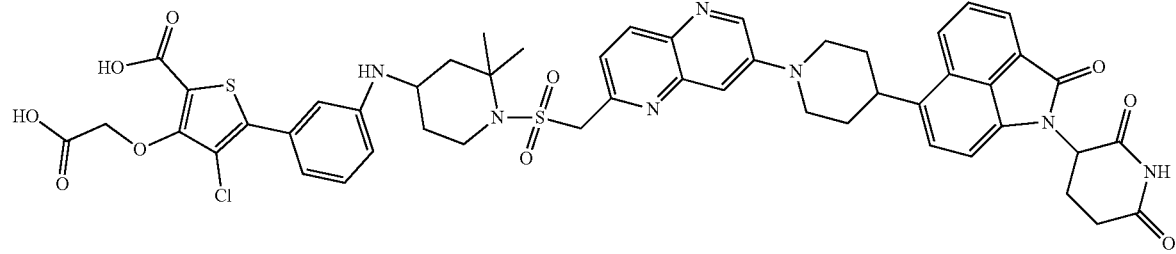
109
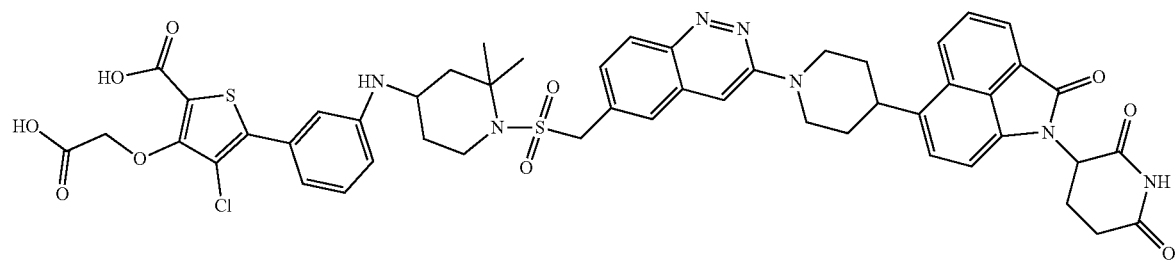
110
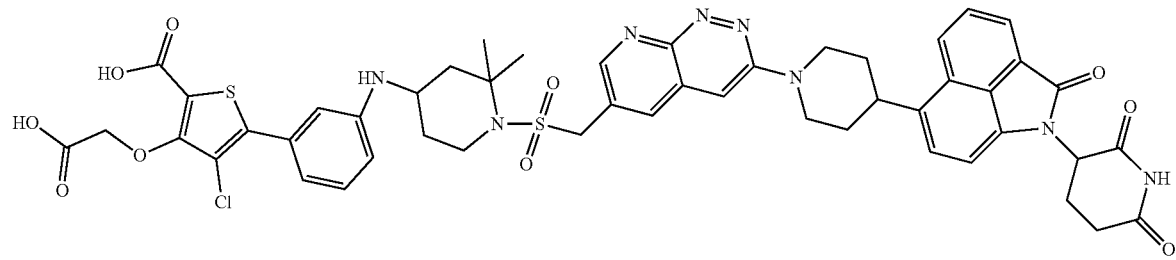
111
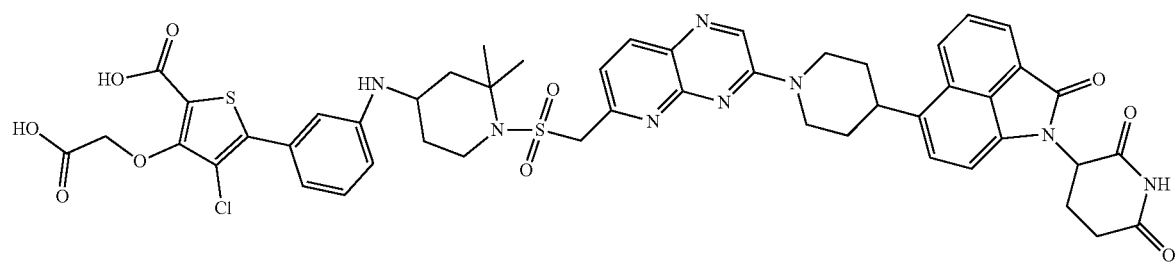
112
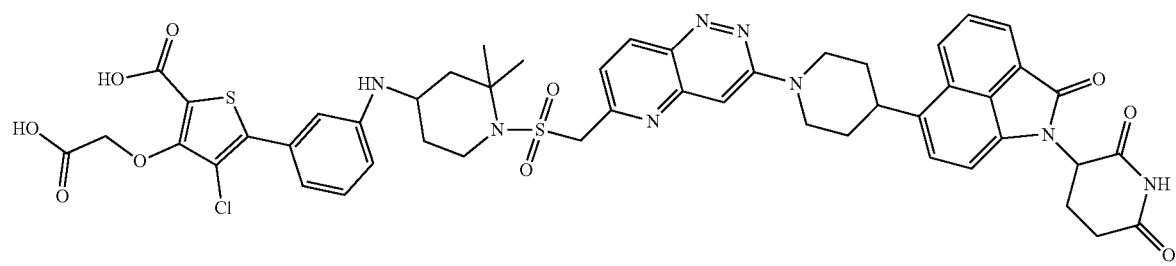
113

114
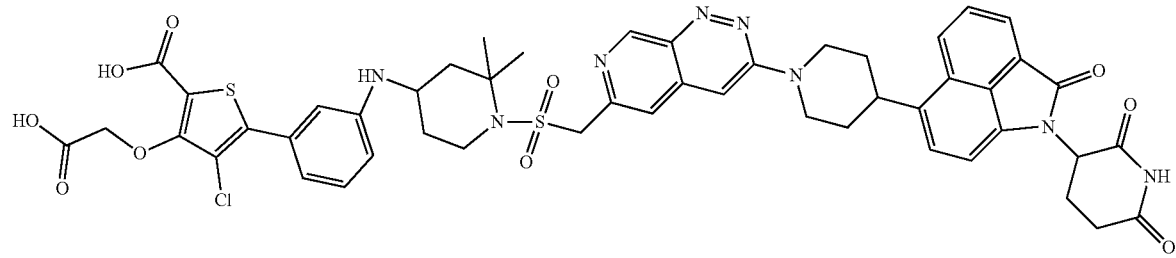
115
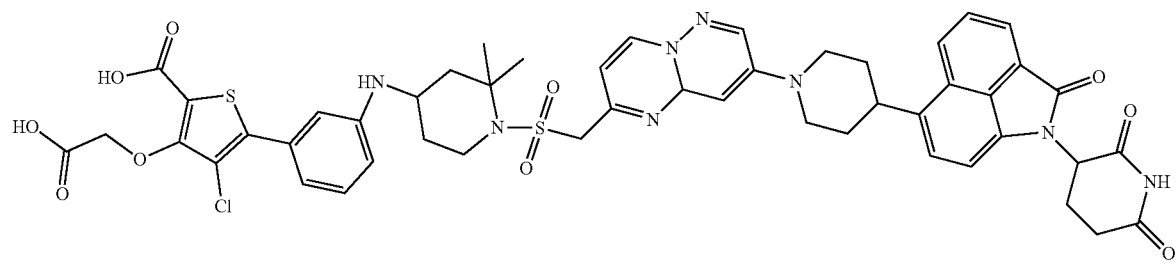
116
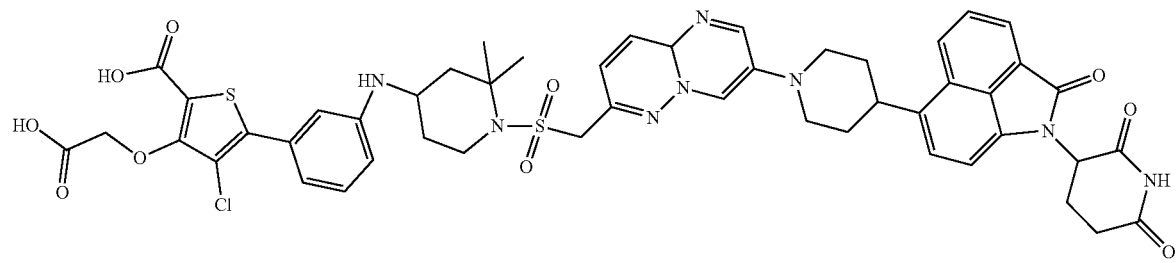
117
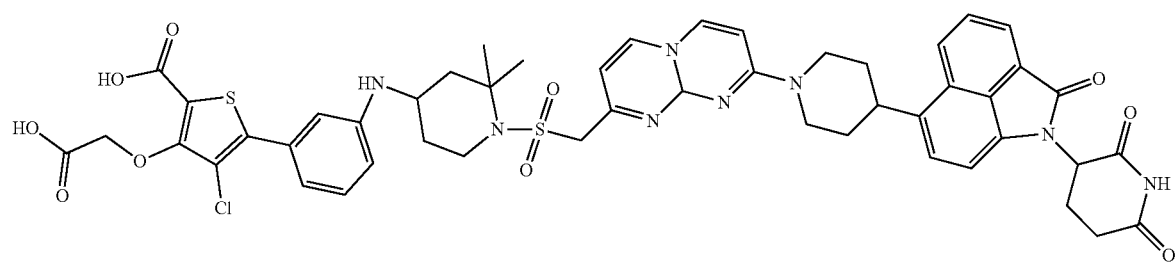
118
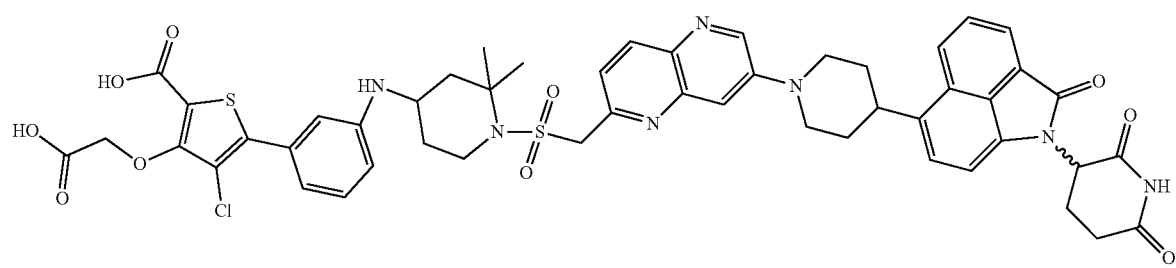

-continued
119
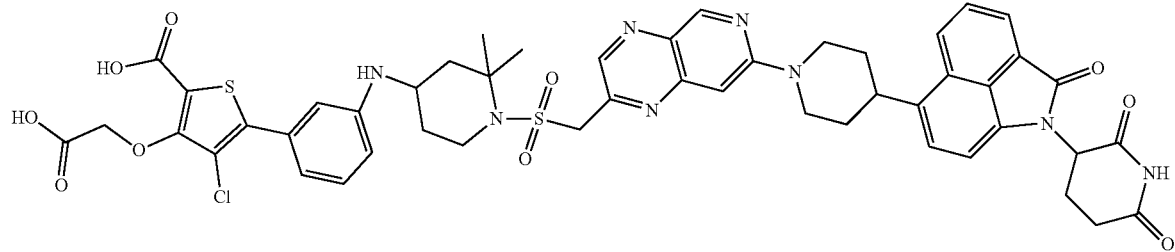
120
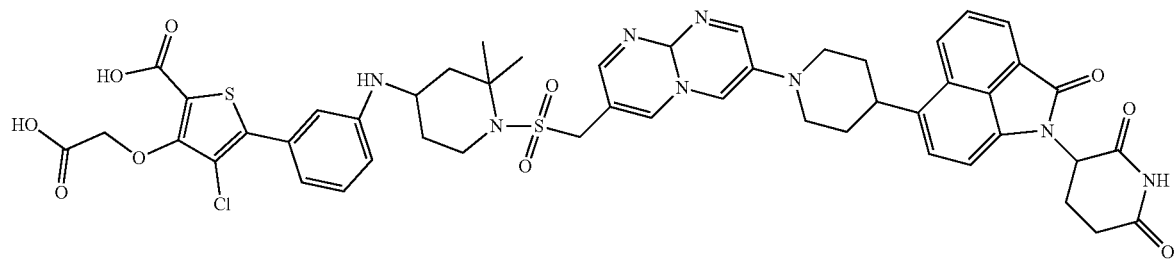
121
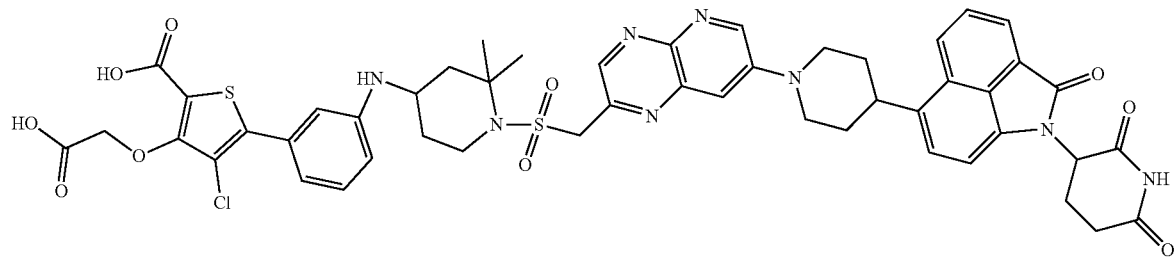
122
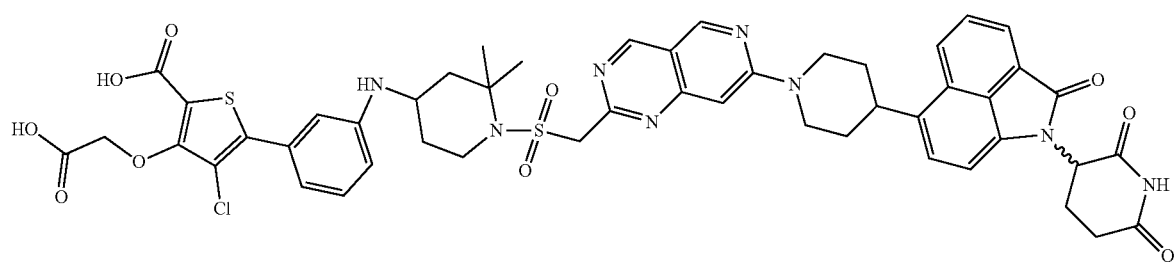
123
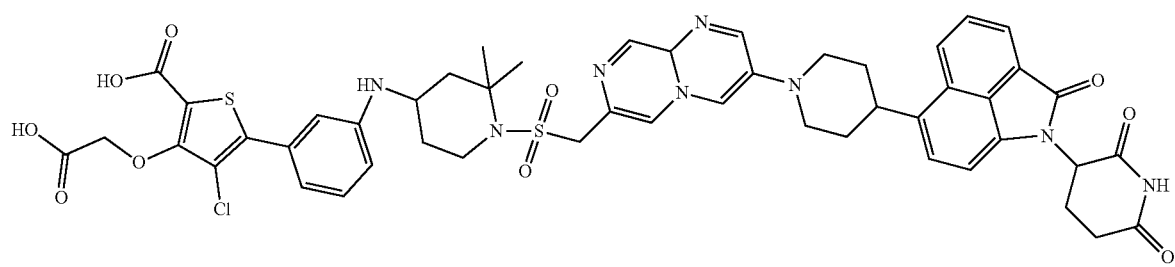

-continued
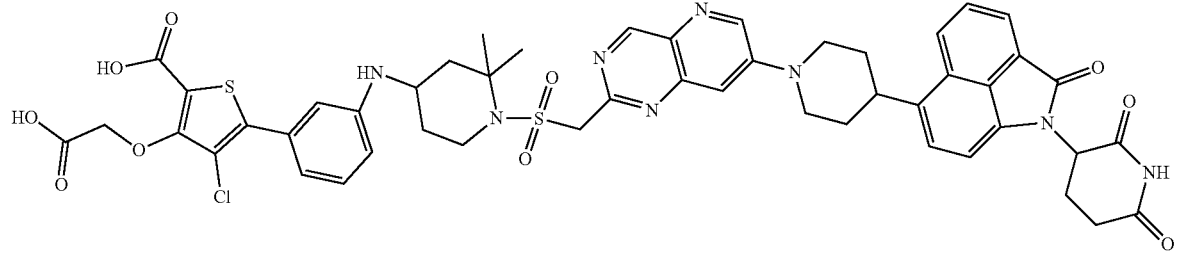
124
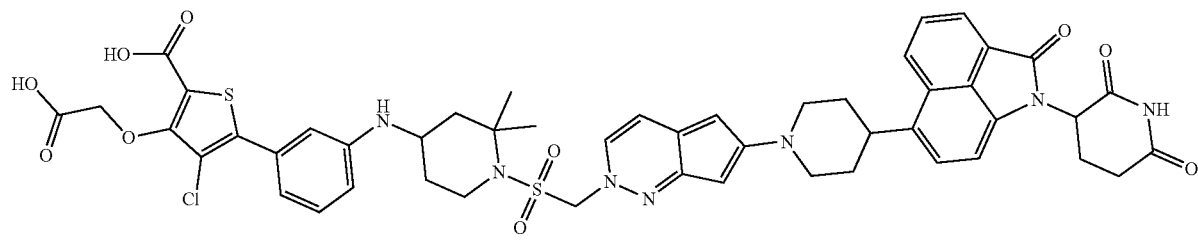
125
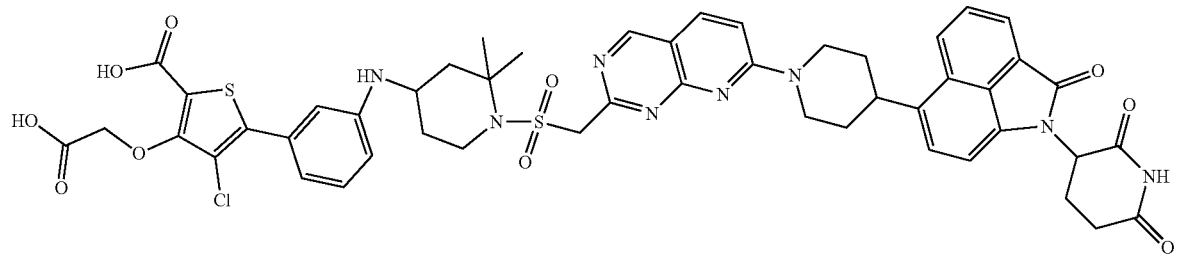
126
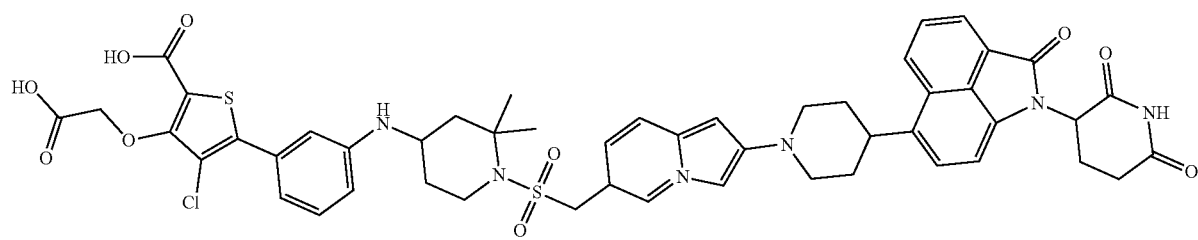
127
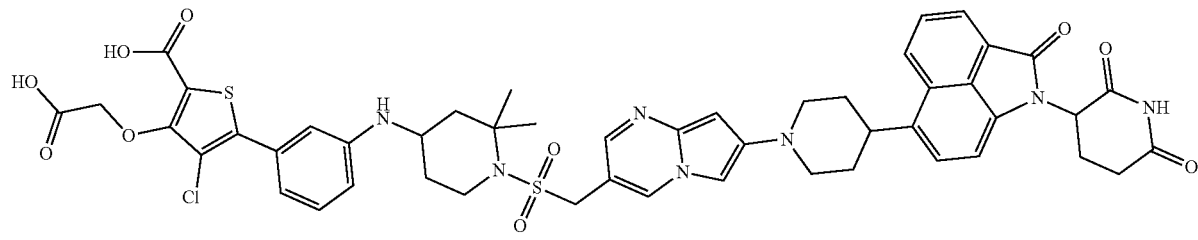
128
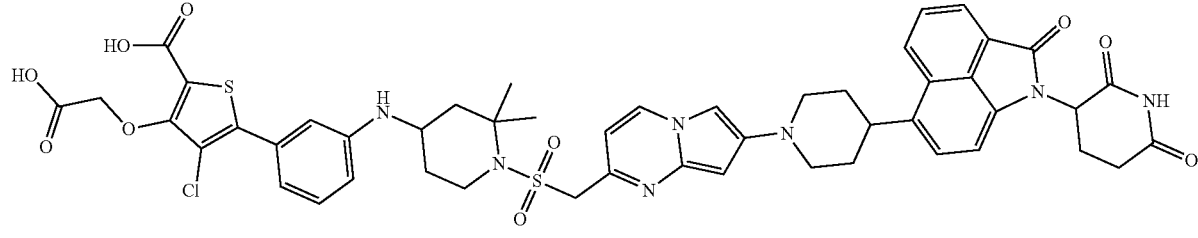
129

130
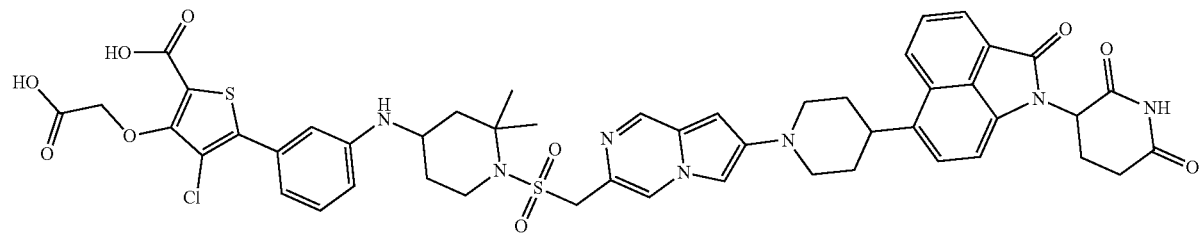
131
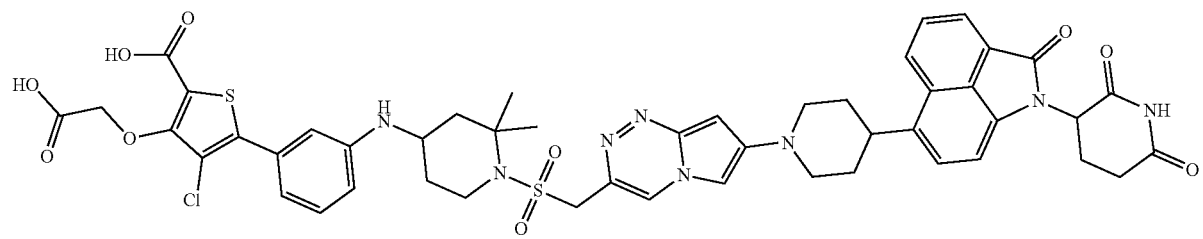
132
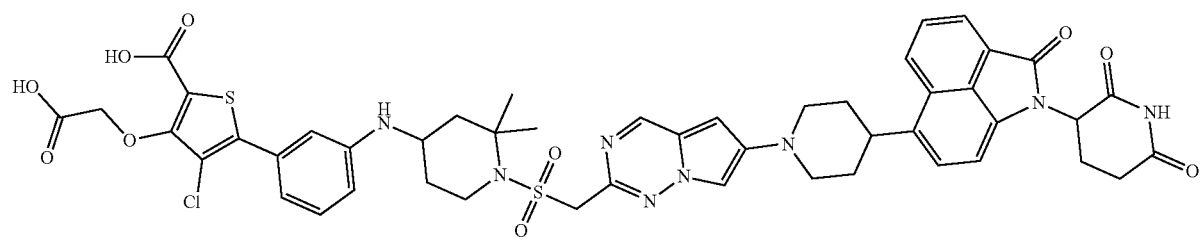
133
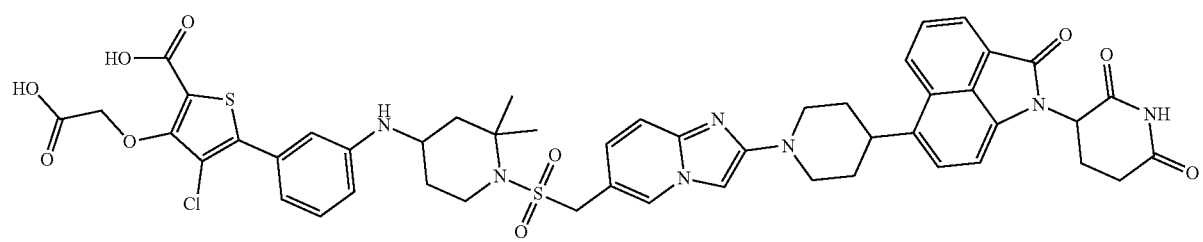
134
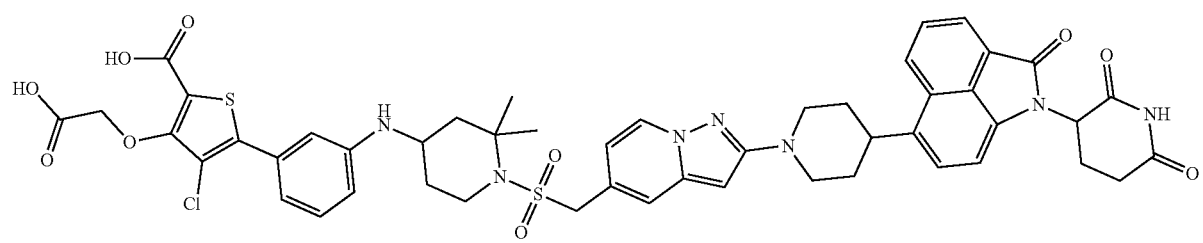
135
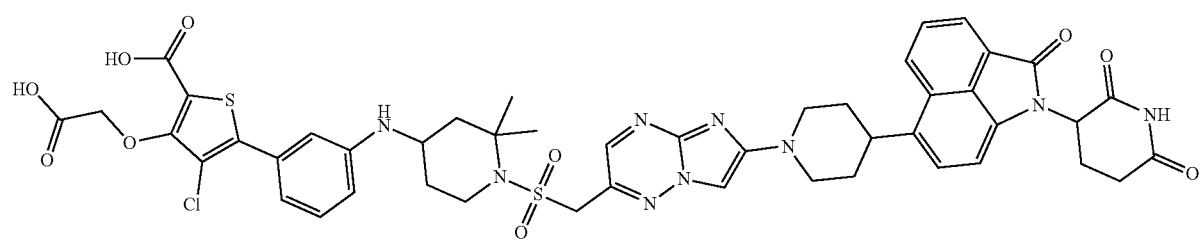

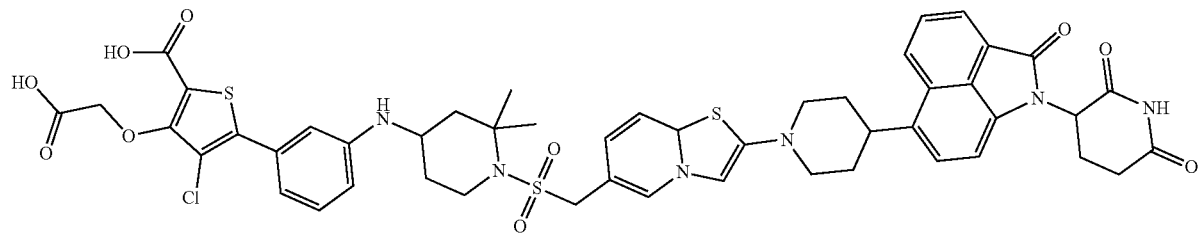
136
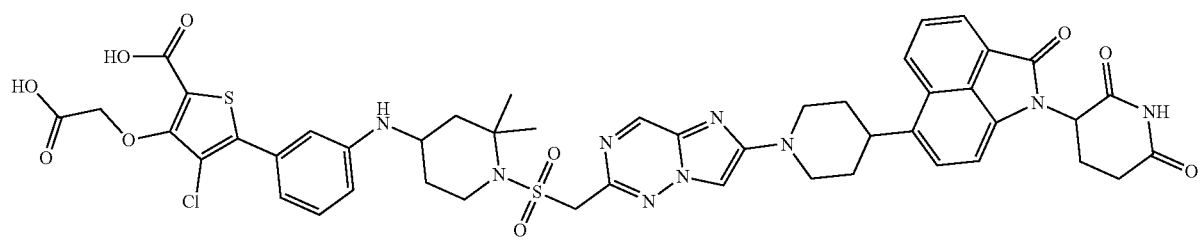
137
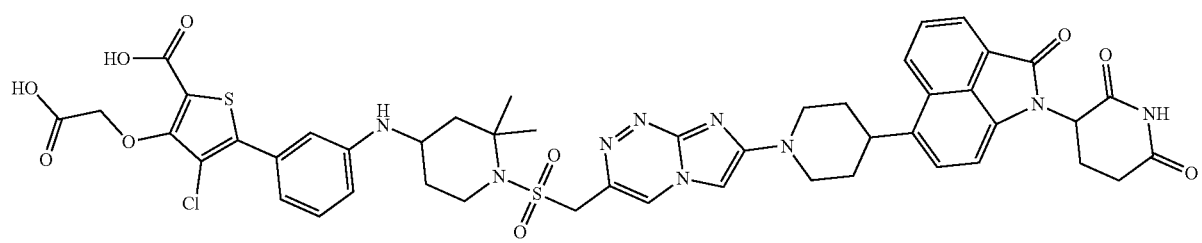
138
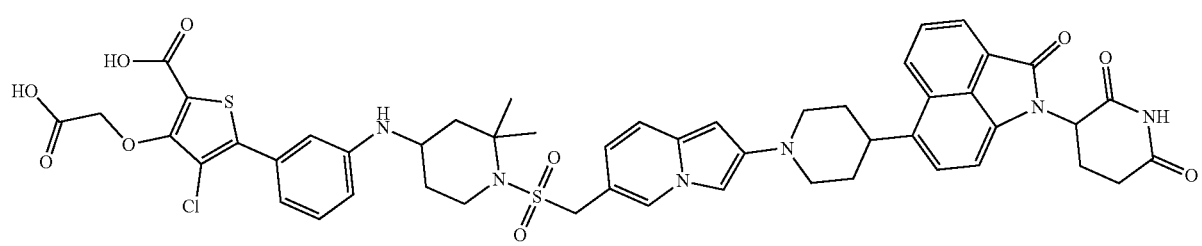
139
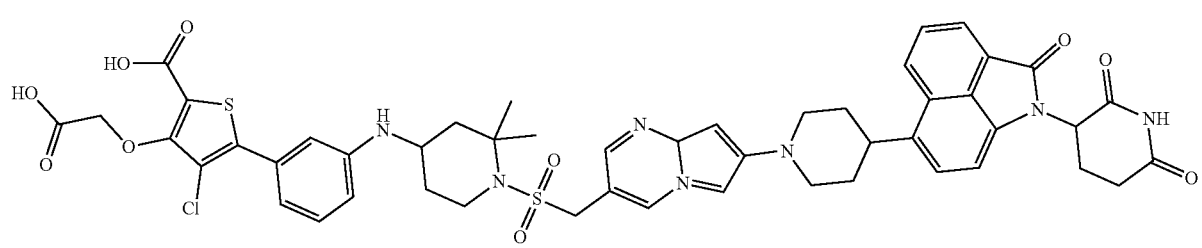
140
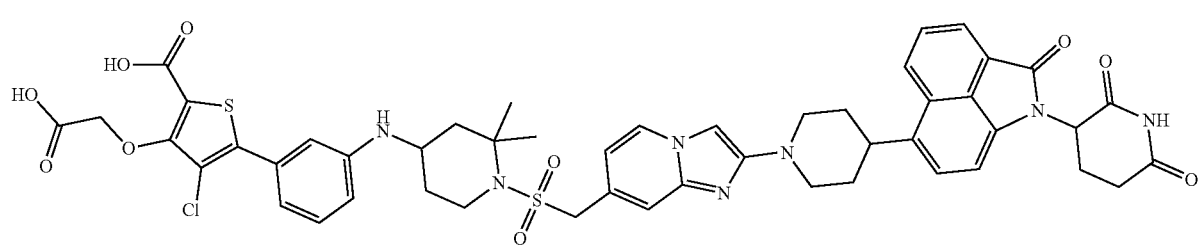
141

142
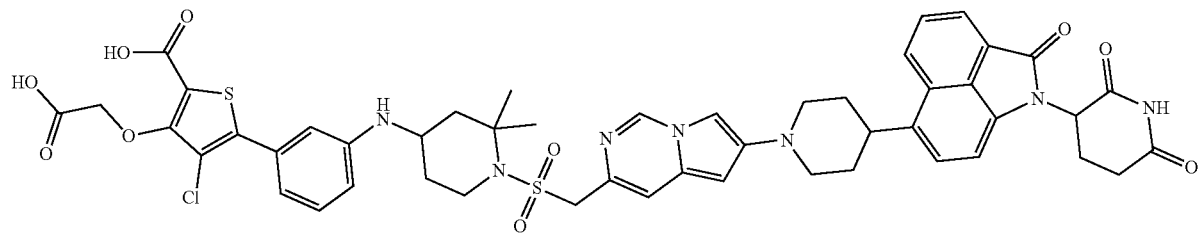
143
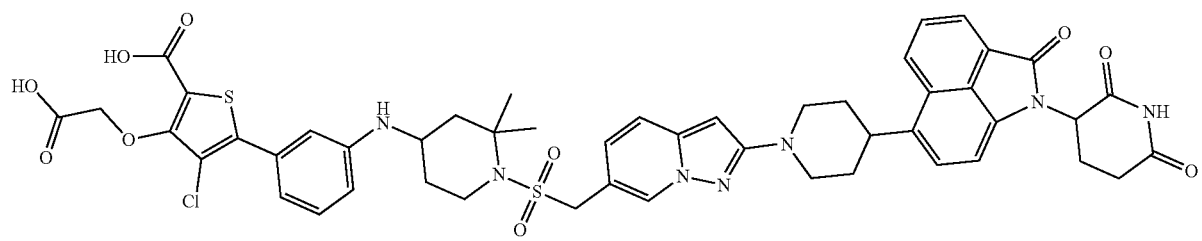
144
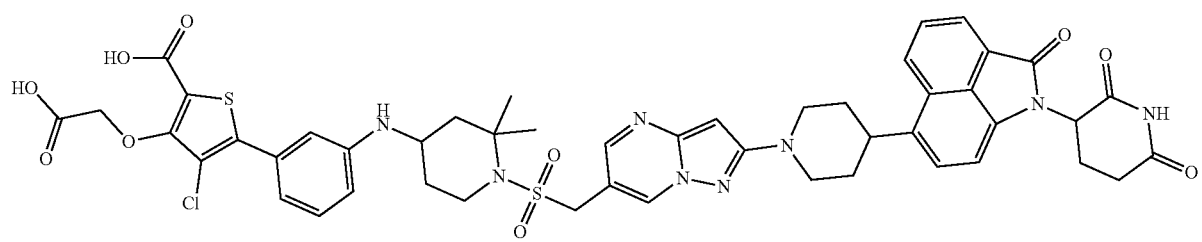
145
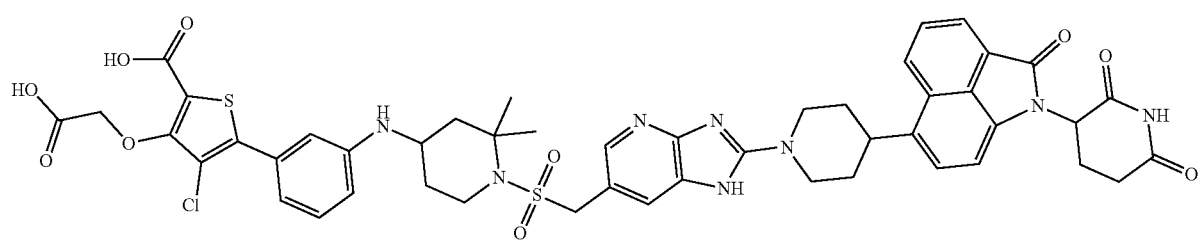
146
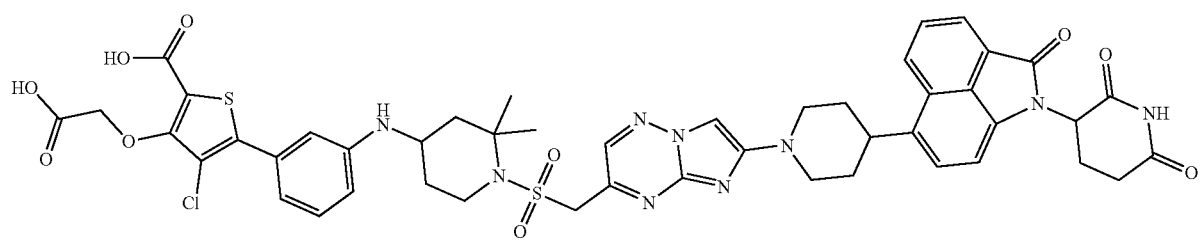
147
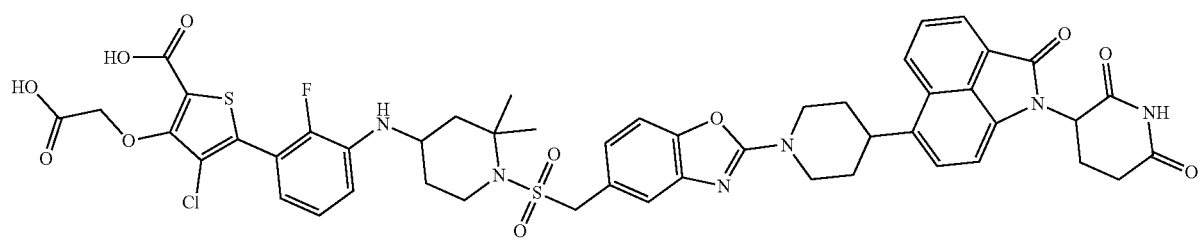

-continued

148

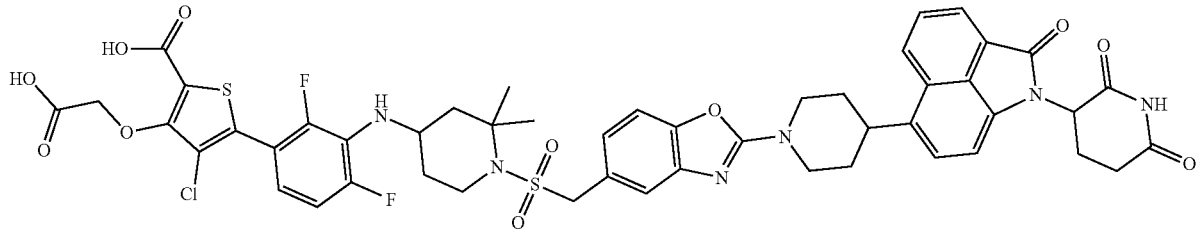

149

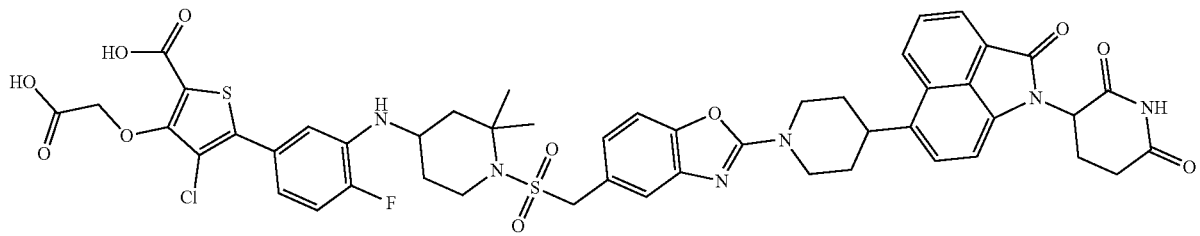

150

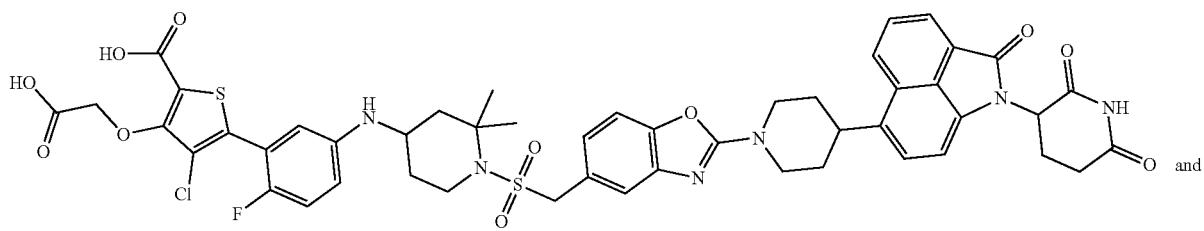

and

151

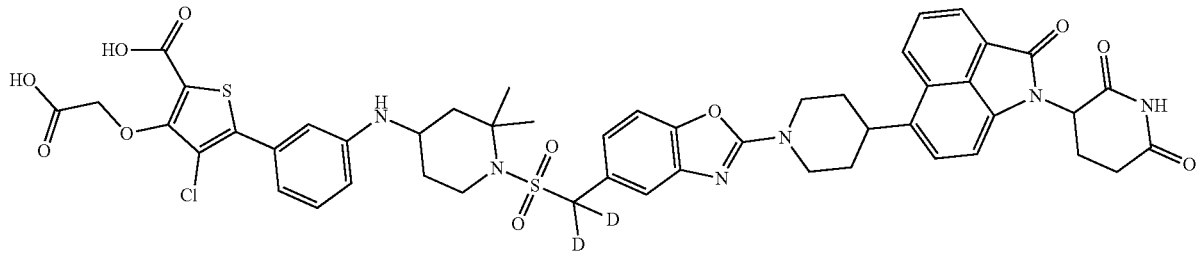

or stereoisomer, pharmaceutically acceptable salt, or deuterated compound thereof.

Yet still another aspect of the present disclosure provides a compound of Formula (Ia), Formula (Ia)

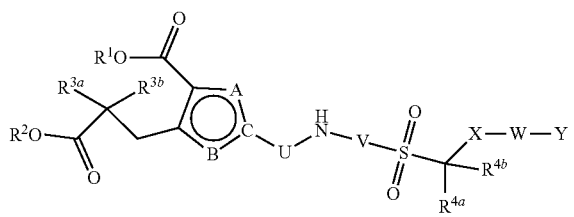

or a stereoisomer, a pharmaceutically acceptable salt, or a deuterated compound thereof,
wherein,
$R^1$ and $R^2$ are selected from the group consisting of H, CN, $C_{1-22}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cycloalkyl and heterocycloalkyl, or $R^1$ and $R^2$ are joined together to form a 10- to 30-membered heterocycle;

$R^{3a}$ and $R^{3b}$ are each independently selected from the group consisting of H and halogen;

$R^{4a}$ and $R^{4b}$ are each independently selected from the group consisting of H, halogen, $C_{1-6}$ alkyl, and $C_{1-6}$ alkoxy, or $R^{4a}$ and $R^{4b}$ together with the carbon atom to which they are attached form cyclopropyl, cyclobutyl, or oxetanyl;

A and B are selected from the group consisting of $NR^a$, $CR^b$, N, O, and S;

C is selected from the group consisting of carbon atom and nitrogen atom;

$R^a$ is selected from the group consisting of H, $C_{1-6}$ alkyl, $C_{1-6}$ alkoxy, $C_{1-6}$ haloalkoxy, cycloalkyl and heterocycloalkyl; $R^b$ is selected from the group consisting of H, halogen, —CN, —CF$_3$, $C_{1-6}$ alkyl, $C_{1-6}$ alkoxy, $C_{1-6}$ haloalkoxy, cycloalkyl and heterocycloalkyl, the $R^a$ or $R^b$ is optionally substituted with one to more halogens;

X is selected from the group consisting of

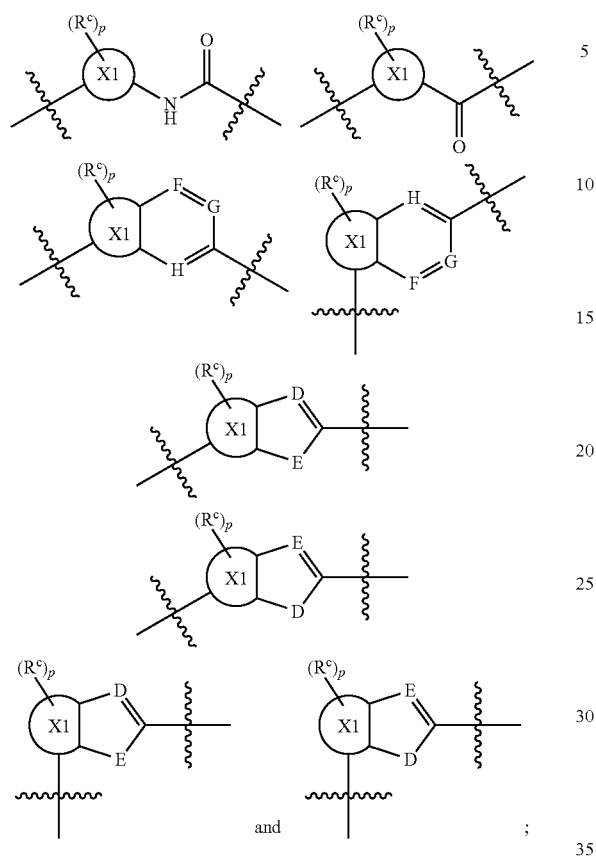

X1 is selected from the group consisting of 6-membered aryl and 6-membered heteroaryl comprising 1-4 nitrogen atoms;

$R^c$ is selected from the group consisting of H, halogen, —CN, $C_{1-6}$ alkyl, $C_{1-6}$ alkoxy, $C_{1-6}$ haloalkoxy, cycloalkyl and heterocycloalkyl;

p is 0, 1, 2, 3 or 4;

D is selected from the group consisting of C and N;

E is selected from the group consisting of O, S, and $NR^d$;

$R^d$ is selected from the group consisting of H, $C_{1-6}$ alkyl, cycloalkyl and heterocycloalkyl;

F, G, and H are each independently selected from the group consisting of C, N, O, and S;

Y is selected from the group consisting of

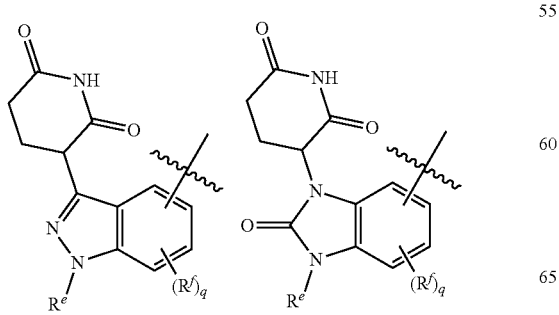

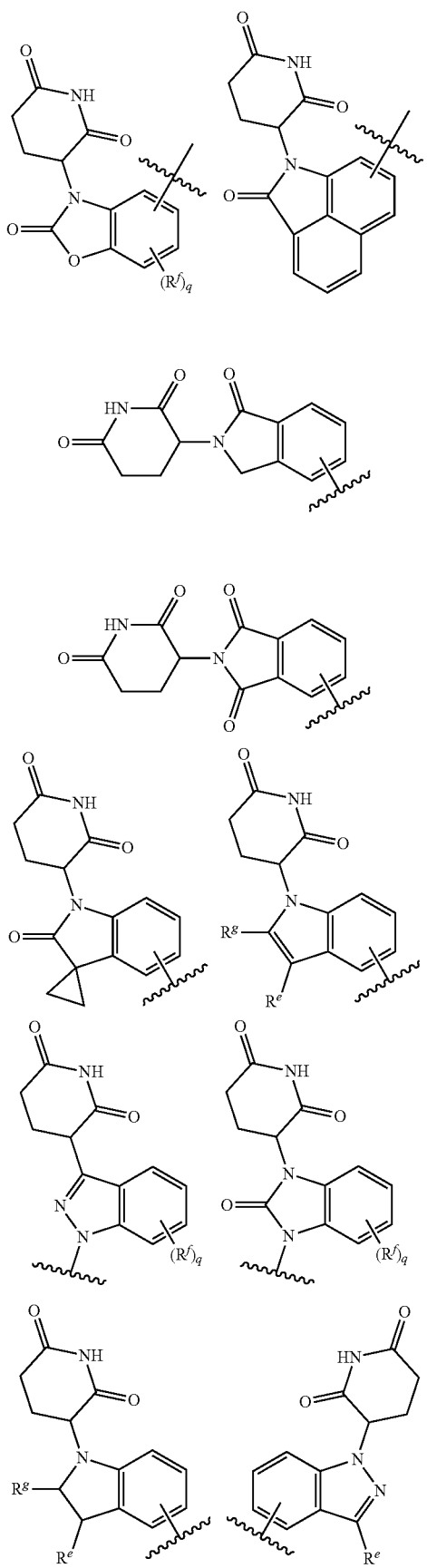

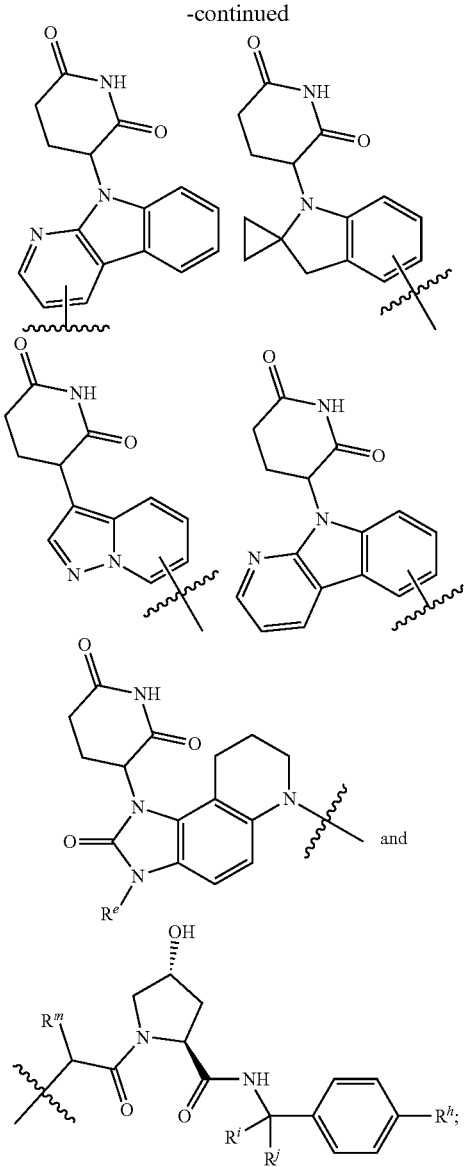

each of $R^e$ is independently selected from the group consisting of hydrogen and $C_{1-6}$ alkyl optionally substituted with one or more substituents independently selected from the group consisting of $C_{1-6}$ alkoxy, $C_{1-6}$ haloalkyl, $C_{3-6}$ cycloalkyl, and 4- to 6-membered heterocyclyl;

each of $R^f$ is independently selected from the group consisting of halogen, —CN, $C_{1-6}$ alkyl, $C_{1-6}$ haloalkyl, $C_{1-6}$ alkoxy, and $C_{3-5}$ cycloalkoxy;

$R^g$ is selected from the group consisting of hydrogen and $C_{1-6}$ alkyl;

q is 0, 1, 2, 3 or 4;

$R^h$ is selected from the group consisting of H, halogen,

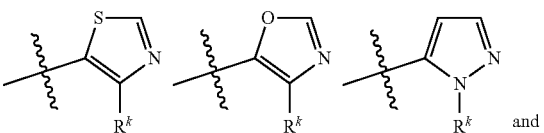

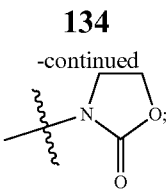

$R^k$ is selected from the group consisting of H and $C_{1-3}$ alkyl optionally substituted with hydroxyl;

$R^i$ and $R^j$ are each independently selected from the group consisting of H and $C_{1-3}$ alkyl optionally substituted with one or more substituents independently selected from the group consisting of F, OH, and —N(CH$_3$)$_2$; or $R^i$ and $R^j$ together with the carbon atoms to which they are attached form cyclopropyl;

$R^m$ is selected from the group consisting of ethyl, isopropyl, tert-butyl, and $C_{3-6}$ cycloalkyl;

U is

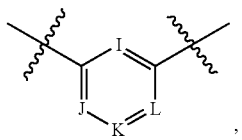

I, J, K, and L are each independently selected from the group consisting of nitrogen atom and $CR^n$;

each of $R^n$ is independently selected from the group consisting of H, halogen, —CN, pseudohalogen, —CF$_3$, —OCH$_3$, and —OCF$_3$;

V is selected from the group consisting of 5- to 15-membered heterocycle, bridged heterocycle and spirocycle, substituted with alkyl or cycloalkyl;

W is selected from the group consisting of 5- to 15-membered heterocycle, bridged heterocycle and spirocycle, substituted with alkyl or cycloalkyl.

In some embodiments, in the compound of Formula (Ia), $R^{3a}$ and $R^{3b}$ are each independently selected from the group consisting of H and F.

In some embodiments, in the compound of Formula (Ia), $R^{4a}$ and $R^{4b}$ are each independently selected from the group consisting of H and F.

In some embodiments, in the compound of Formula (Ia), U is benzene ring.

In some embodiments, in the compound of Formula (Ia), U is

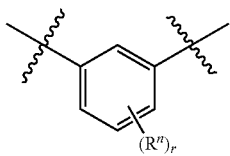

r is 0 or 1, $R^n$ is halogen;

In some embodiments, $R^n$ is F.

In some embodiments, r is 0.

In some embodiments, in the compound of Formula (Ia), V is selected from the group consisting of

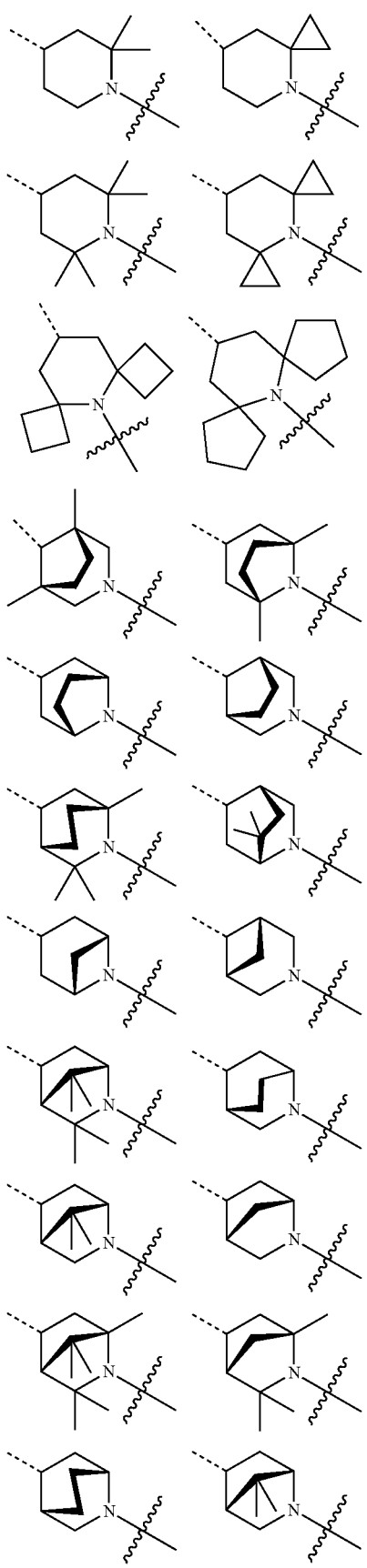
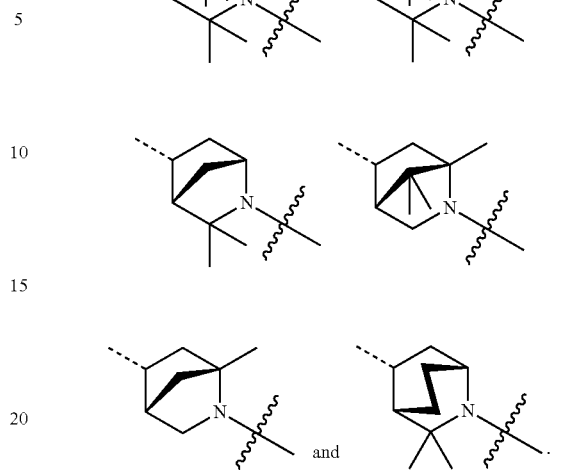
In some embodiments, in the compound of Formula (I), W is selected from the group consisting of:
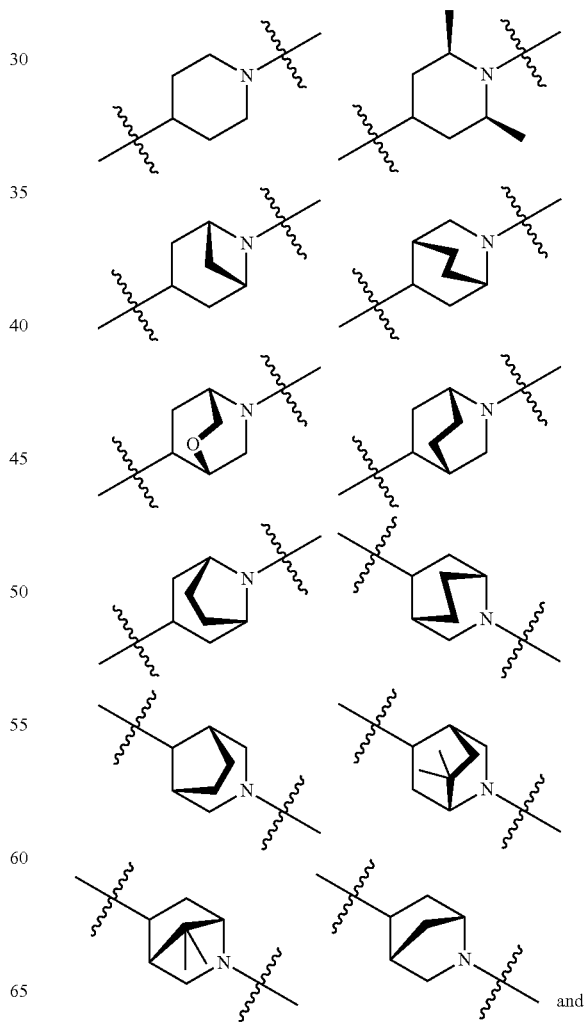

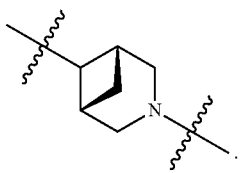
In some embodiments, in the compound of Formula (I), X is selected from the group consisting of
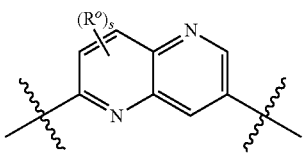
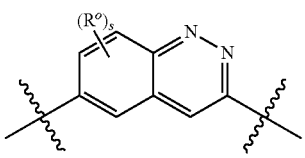
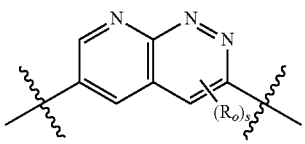
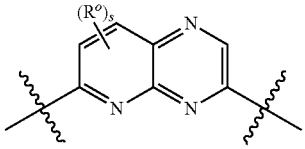
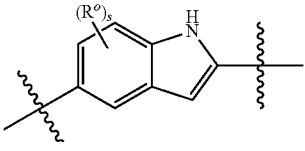
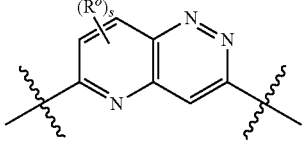
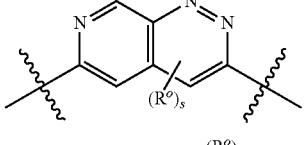
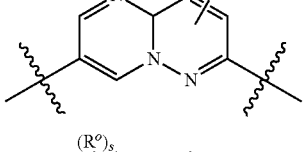
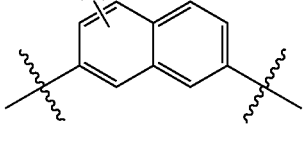
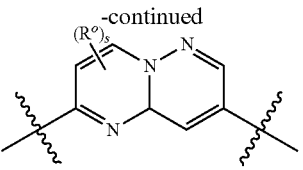
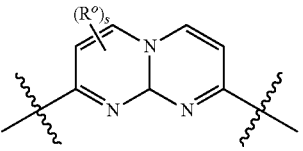
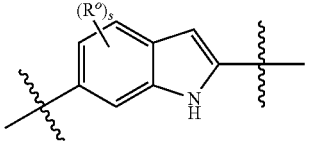
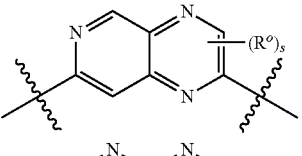
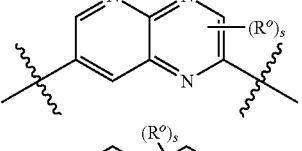
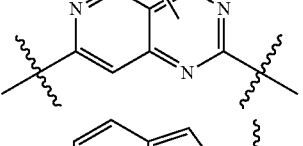
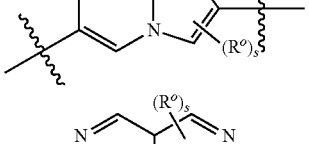
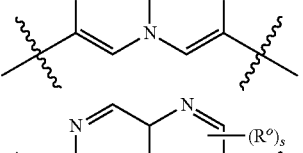
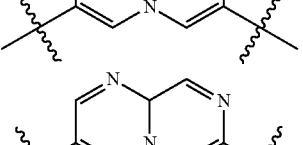
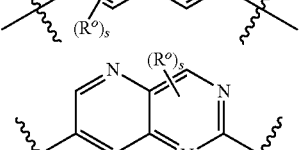
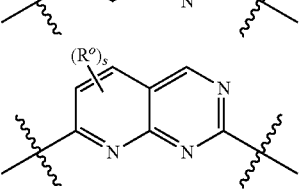

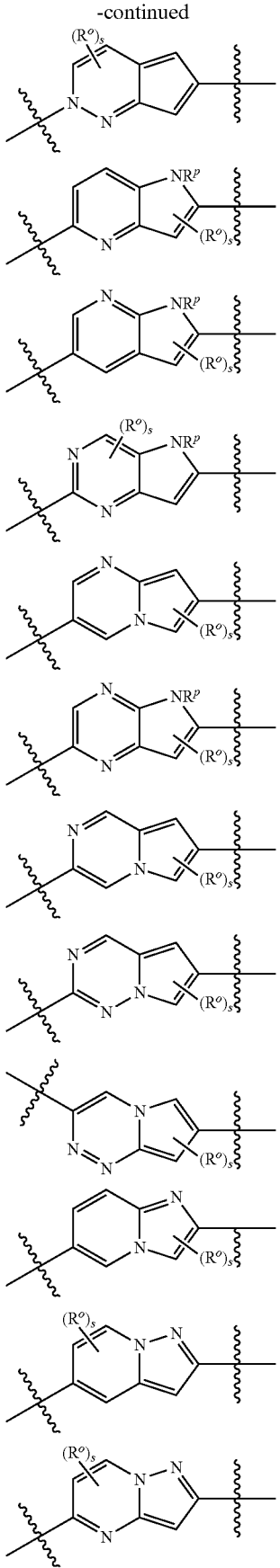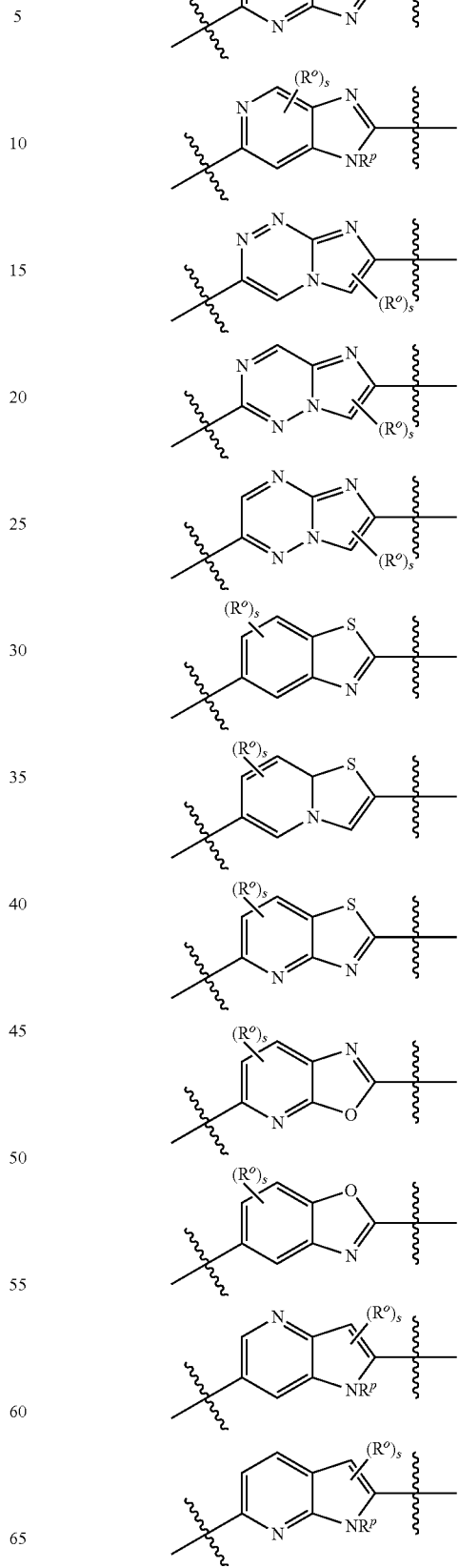

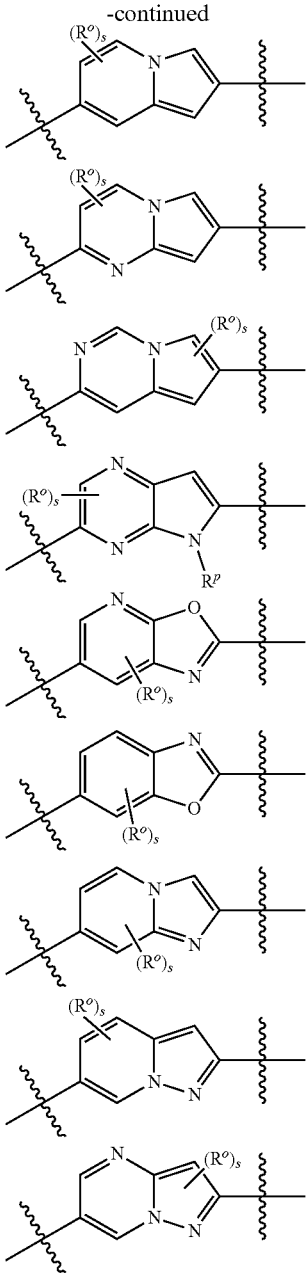

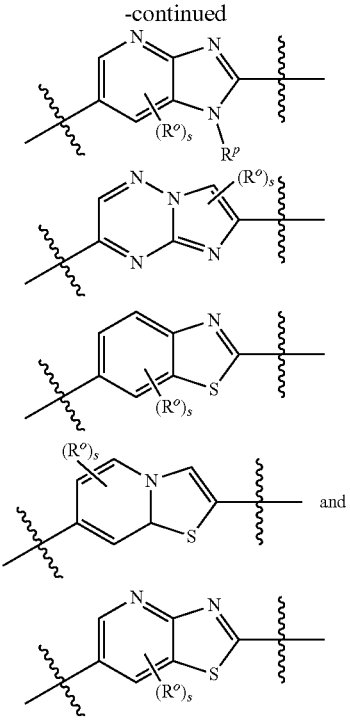

R⁰ is selected from the group consisting of H, halogen, —CN, $C_{1-6}$ alkyl, $C_{1-6}$ alkoxy, $C_{1-6}$ haloalkoxy, cycloalkyl, and heterocycloalkyl;

s is 0, 1, 2, 3 or 4;

R^p is selected from the group consisting of H, $C_{1-6}$ alkyl, $C_{1-6}$ alkoxy, cycloalkyl, and heterocycloalkyl.

In some embodiments, the pharmaceutically acceptable salt of the present disclosure, is selected from the group consisting of an acetate, a benzenesulfonate, a bromide, a camphorsulfonate, a chloride, a citrate, a fumarate, a lactate, a malate, a maleate, a fumarate, an oxalate, a phosphate, a succinate, a sulfate, a tartrate, a sodium salt, a potassium salt, an ammonium salt, a tetra-n-butylammonium salt, and an ethanolamine salt.

Yet still another aspect of the present disclosure provides a compound, a pharmaceutically acceptable salt thereof, wherein the compound is selected from the group consisting of

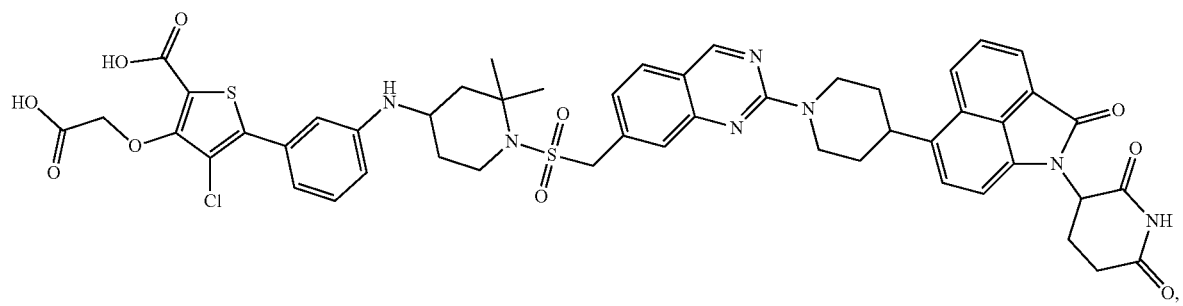

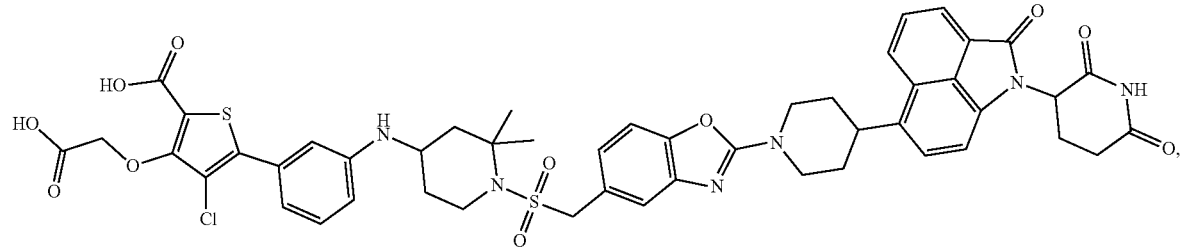
21
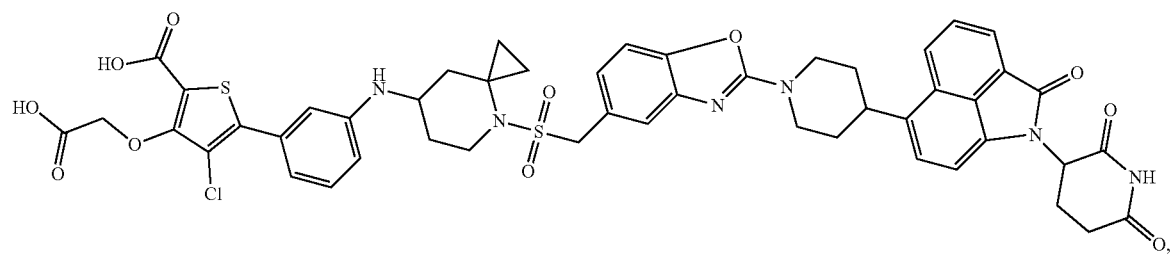
57
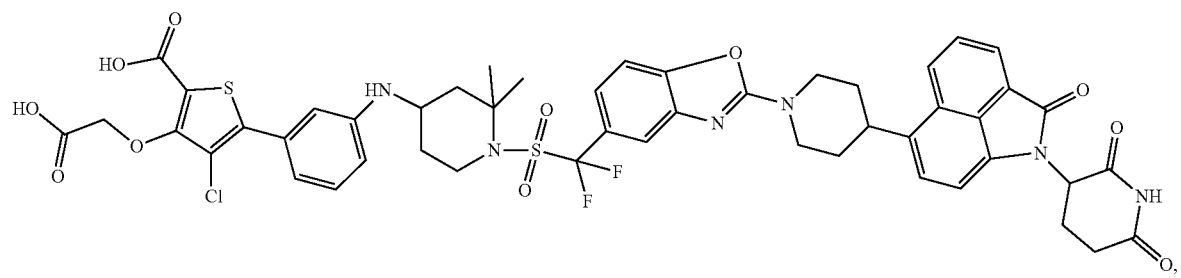
78
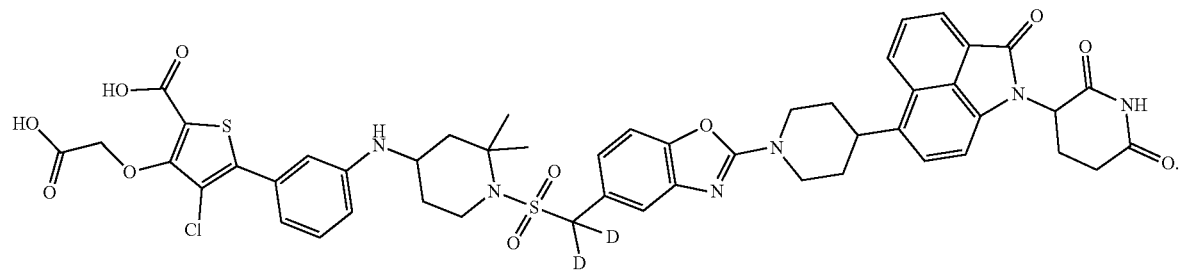
151

In certain embodiments, in the compound or the pharmaceutically acceptable salt thereof of the present disclosure, the compound is

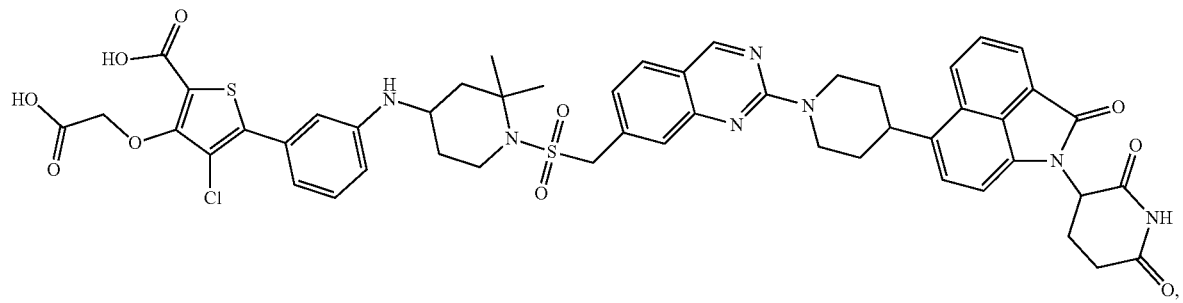

16

In certain embodiments, in the compound or the pharmaceutically acceptable salt thereof of the present disclosure, the compound is

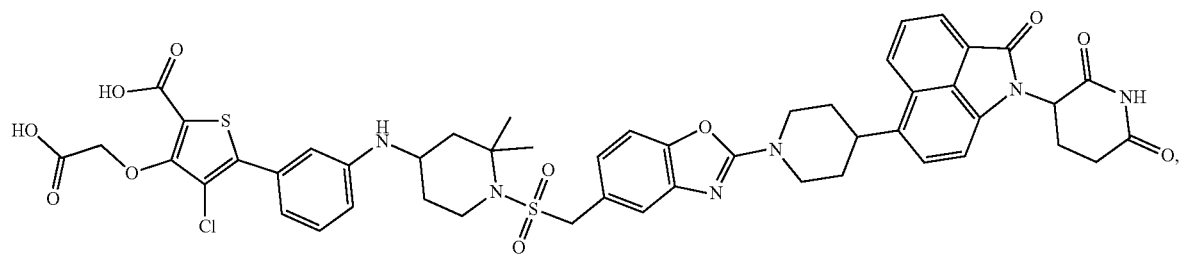

21

In certain embodiments, in the compound or the pharmaceutically acceptable salt thereof of the present disclosure, the compound is

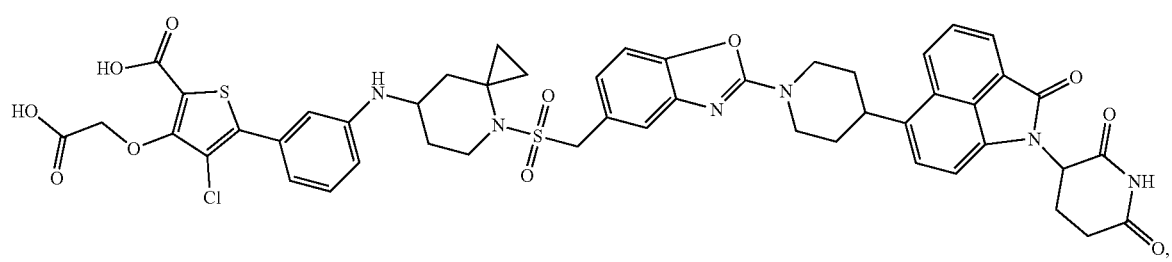

57

In certain embodiments, in the compound or the pharmaceutically acceptable salt thereof of the present disclosure, the compound is

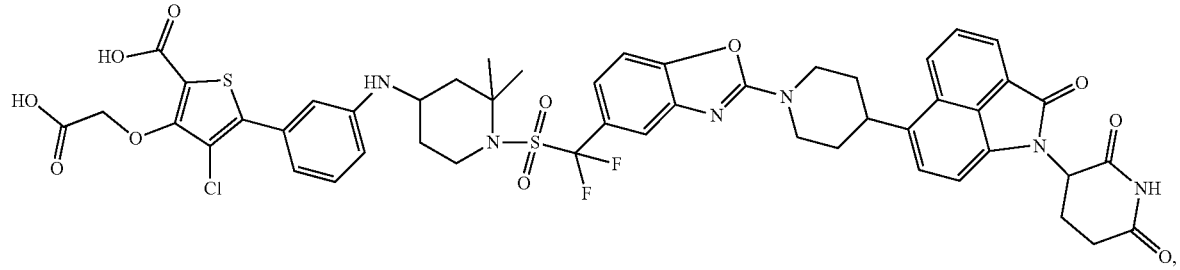

78

In certain embodiments, in the compound or the pharmaceutically acceptable salt thereof of the present disclosure, the compound is

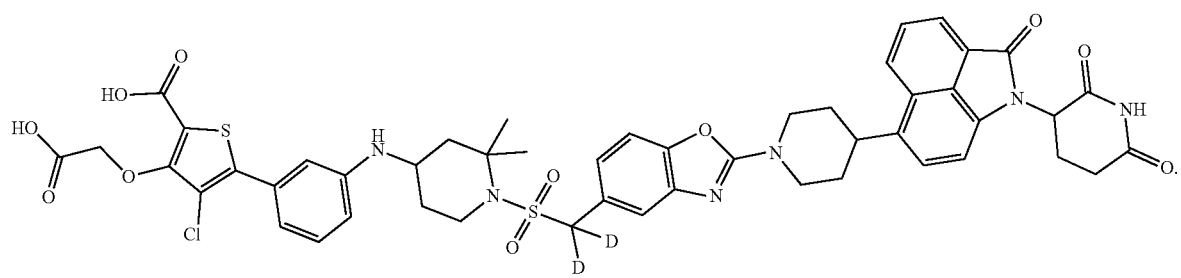

151

Pharmaceutical Composition

Another aspect of the present disclosure provides a pharmaceutical composition that comprises the compound, the stereoisomer, the pharmaceutically acceptable salt, or the deuterated compound thereof of the present disclosure, and a pharmaceutically acceptable excipient.

In some embodiments, the pharmaceutical composition comprising the compound, the stereoisomer, the pharmaceutically acceptable salt, or the deuterated compound thereof of the present disclosure may be prepared with one or more pharmaceutically acceptable excipients, the excipients may be selected in accordance with conventional practice. Tablets may contain excipients, including flow aids, fillers, binders, and the like. Aqueous compositions may be prepared in a sterile form and may generally be isotonic when intended to be delivered by means other than oral administration.

In some embodiments, the compositions may comprise excipients, such as those set forth in Rowe et al, Handbook of Pharmaceutical Excipients, 6th edition, American Pharmacists Association, 2009. Excipients may include ascorbic acid and other antioxidants, chelating agents such as ethylenediaminetetraacetic acid, carbohydrates such as dextrin, hydroxyalkylcellulose, hydroxyalkylmethylcellulose, stearic acid, and the like. In some embodiments, the compositions are provided in solid dosage forms, including solid oral dosage forms.

The pharmaceutical composition may be prepared by any of the methods well known in the art of pharmacy, including oral administration. Such methods include the step of bringing into association the active ingredient (e.g., a compound of the present disclosure or a pharmaceutical salt thereof) with one or more pharmaceutically acceptable excipients. In some embodiments, the pharmaceutical compositions are prepared by uniformly and intimately bringing into association the active ingredient with liquid excipients or finely divided solid excipients or both, and then, if desired, shaping the product. Techniques and formulations generally are found in Remington: The Science and Practice of Pharmacy, 21st Edition, Lippincott Wiliams and Wilkins, Philadelphia, Pa., 2006.

In some embodiments, the pharmaceutical compositions of the present disclosure are presented in unit dosage form, including but not limited to capsules, sachets, or tablets, each containing a predetermined amount of the active ingredient. In one embodiment, the pharmaceutical composition is a tablet.

The pharmaceutical composition disclosed herein comprises one or more of the compound, the stereoisomer, the pharmaceutically acceptable salt, or the deuterated compound thereof of the present disclosure, as well as pharmaceutically acceptable excipients and, optionally, other therapeutic agents. The pharmaceutical compositions containing the active ingredient may be in any form suitable for the intended method of administration. When intended for oral use, for example, tablets, lozenges, ingots, aqueous or oil suspensions, dispersible powders or granules, emulsions, hard or soft capsules, syrups, or elixirs may be prepared. Compositions for oral use may be prepared according to any method known in the art for the manufacture of pharmaceutical compositions, and such compositions may contain one or more excipients, including sweeteners, flavoring agents, coloring agents, and preservatives, to provide palatable formulations. Tablets containing the active ingredient with a non-toxic pharmaceutically acceptable excipient are acceptable and said excipient is suitable for the production of tablets. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredients that may be combined with the inactive ingredients to produce a dosage form may vary depending upon the intended treatment subject and the mode of administration. For example, in some embodiments, a dosage form for oral administration to humans may contain approximately 1 to 1000 mg of active material formulated with an appropriate and convenient amount of a pharmaceutically acceptable excipient. In some embodiments, the pharmaceutically acceptable excipient varies from about 5% to about 95% of the total compositions (weight: weight).

In some embodiments, the pharmaceutical composition of the present disclosure does not contain an agent that affects the rate at which the active ingredient is metabolized. Thus, it is understood that pharmaceutical compositions comprising a compound of the present disclosure in one aspect do not comprise an agent that would affect (e.g., slow, hinder or retard) the metabolism of a compound of the present disclosure or any other active ingredient administered separately, sequentially or simultaneously with a compound of the present disclosure. It is also understood that any of the methods, kits, articles of manufacture, and the like detailed herein in one aspect do not comprise an agent that would affect (e.g., slow, hinder or retard) the metabolism of a compound of the present disclosure or any other active ingredient administered separately, sequentially or simultaneously with a compound of the present disclosure.

In some embodiments, the above-described pharmaceutical compositions are for use in humans or animals.

The present disclosure also includes compounds of the present disclosure which are administered as a single active ingredient of a pharmaceutically acceptable composition that may be prepared by conventional methods known in the art, for example, by combining the active ingredient to a pharmaceutically acceptable, therapeutically inert organic and/or inorganic carrier or excipient, or by mixing therewith.

The present disclosure provided herein are uses of the compounds of the present disclosure as a second or other active ingredient, said second or other active ingredient being synergistic with other active ingredients in known drugs, or the compounds of the present disclosure being administered with such drugs.

The compounds of the present disclosure may also be used in the form of a prodrug or other suitably modified form that releases the active ingredient in vivo.

Method of Treatment

Another aspect of the present disclosure provides a method for treating a PTPN2/PTP1B-mediated disease or condition, comprising administering to a subject in need thereof a therapeutically effective amount of the compound, the stereoisomer, the pharmaceutically acceptable salt, or the deuterated compound thereof of the present disclosure, or a pharmaceutical composition of the present disclosure.

In some embodiments, the PTPN2/PTP1B-mediated disease or condition is selected from the group consisting of solid tumors, brain tumors, non-small cell lung cancer, melanoma, cardiovascular diseases, immune system disorders, metabolic disorders, neurodegenerative disorders, T1D (type 1 diabetes), T2DM (type 2 diabetes mellitus), prediabetes, idiopathic T1D (idiopathic type 1 diabetes), malnutrition-related diabetes, gestational diabetes, hyperglycemia, insulin resistance, hepatic insulin resistance, impaired glucose tolerance, diabetic neuropathy, diabetic nephropathy, nephropathy, diabetic retinopathy, adipocyte dysfunction, visceral fat deposition, sleep apnea, obesity, weight management, chronic weight management, eating disorders, weight gain induced by other medications, hyperglycemia, dyslipidemia, hyperinsulinemia, NAFLD (non-alcoholic fatty liver disease), NASH (non-alcoholic steatohepatitis), and infectious diseases.

The compound of the present disclosure (also referred to herein as the active ingredients) or the pharmaceutical composition of the present disclosure can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intratumoral, intrathecal and epidural), and the like. It will be appreciated that the preferred route may vary with for example the condition of the recipient. An advantage of certain compound disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In some embodiments, the compound is administered once daily.

The compound can be administered by any useful route and means, such as by oral or parenteral (e.g., intravenous) administration. Therapeutically effective amounts of the compound may include from about 0. 00001 mg/kg body weight per day to about 10 mg/kg body weight per day, such as from about 0. 0001 mg/kg body weight per day to about 10 mg/kg body weight per day, or such as from about 0. 001 mg/kg body weight per day to about 1 mg/kg body weight per day, or such as from about 0. 01 mg/kg body weight per day to about 1 mg/kg body weight per day, or such as from about 0. 05 mg/kg body weight per day to about 0. 5 mg/kg body weight per day, or such as from about 0. 3 mg to about 30 mg per day, or such as from about 30 mg to about 300 mg per day.

A compound of the present disclosure may be combined with one or more additional therapeutic agents in any dosage amount of the compound of the present disclosure (e.g., from 1 mg to 1000 mg of the compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose.

Other therapeutically effective amounts of the compound of the present disclosure are about 100, 125, 150, 175, 200, 225, 250, 275, 300, 325, 350, 375, 400, 425, 450, 475, or about 500 mg per dose. Other therapeutically effective amounts of the compound of the present disclosure are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In some embodiments, a single dose can be administered once every week. A single dose can also be administered once every month.

Kits that comprise the compound e, the stereoisomers, the pharmaceutically acceptable salts, or the deuterated compound thereof, are also included in the present disclosure.

In some embodiments, a kit further includes a label and/or instructions for the use of the compounds in the treatment of the indications, such as the diseases or conditions described herein.

In some embodiments, the kit comprises a compound of the present disclosure, or pharmaceutically acceptable salt thereof, in combination with one or more (e.g., one, two, three, four, one or two, or one to three, or one to four) additional therapeutic agents.

Examples

Example 1 Synthesis

The compounds of the disclosure may be prepared using methods disclosed herein and routine modifications thereof which will be apparent given the disclosure herein and methods well known in the art. Conventional and well-known synthetic methods may be used in addition to the teachings herein.

The synthesis of typical compounds of the present disclosure, e.g., compounds having structures described by one or more of Formula (I), or other formulas or compounds disclosed herein, may be accomplished as described in the following examples.

General Syntheses

Typical embodiments of compounds in accordance with the present disclosure may be synthesized using the general reaction schemes and/or examples described below. It will be apparent, given the description herein that the general schemes may be altered by substituting the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods for synthesizing compounds that are embodiments of the present disclosure, inspection of the structure of the compound to be synthesized will provide the identity of each substituent group, the identity of the final product will generally render apparent the identity of the necessary starting materials by a simple process of inspection, given the examples herein. Group labels (e.g., R1, R2) used in the reaction schemes herein are for illustrative purposes only and unless otherwise specified, do not necessarily match by name or function the labels used elsewhere to describe compounds of Formula (I), (II), (III), (IV), (V), (VI), (VII), (VIII), and (IX), or aspects or fragments thereof.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of the present disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA). Others may be prepared by procedures or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5, and Supplemental (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), N, N-dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

Compounds as provided herein may be synthesized according to the general schemes provided below. In the Schemes below, it should be appreciated that each of the compounds shown therein may have protecting groups as required present at any step. Standard protecting groups are well within the prevue of one skilled in the art.

Synthesis of Intermediates

Synthesis of intermediate A

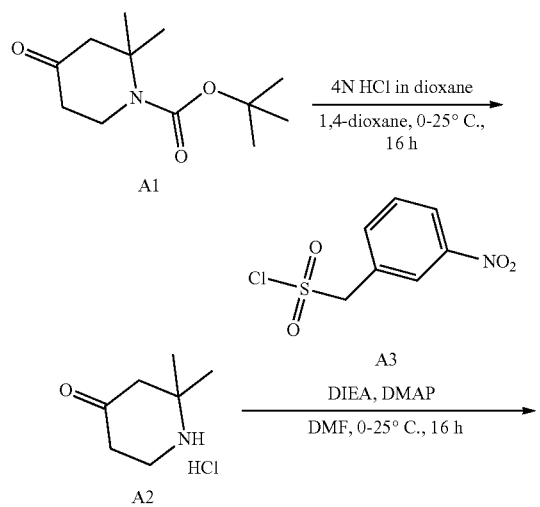

To a solution of A1 (8.0 g, 35.2 mmol) in 1,4-dioxane (80 mL) was added 4 M hydrochloric acid in 1,4-dioxane (4.0 equiv.) at 0° C., and the reaction mixture was stirred at 25° C. for 12 h. The mixture was concentrated to afford the desired product as a white powder (5.66 g, 97% yield).

To a solution of A2 (5.6 g, 34.2 mmol) in N,N-dimethylformamide (60 mL) were added N,N-diisopropylethylamine (13.3 g, 102 mmol) and 4-dimethylaminopyridine (414 mg, 3.41 mmol). 3-Nitrophenylmethane sulfonyl chloride (9.66 g, 41.0 mmol) was added dropwise at 0° C. into the mixture which was stirred for the next 6 h at 25° C. An aqueous ammonium chloride solution (10 mL) was added to the reaction mixture. The mixture was extracted with dichloromethane (3×50 mL) and the combined organic layer was washed with brine (3×10 mL) and dried over anhydrous magnesium sulfate. The organic layer was filtered and concentrated under reduced pressure. The residue was purified by chromatography on silica gel using hexanes-ether (10:1) as an eluant to afford A (4.66 g, 42.2%).

Synthesis of Intermediate B

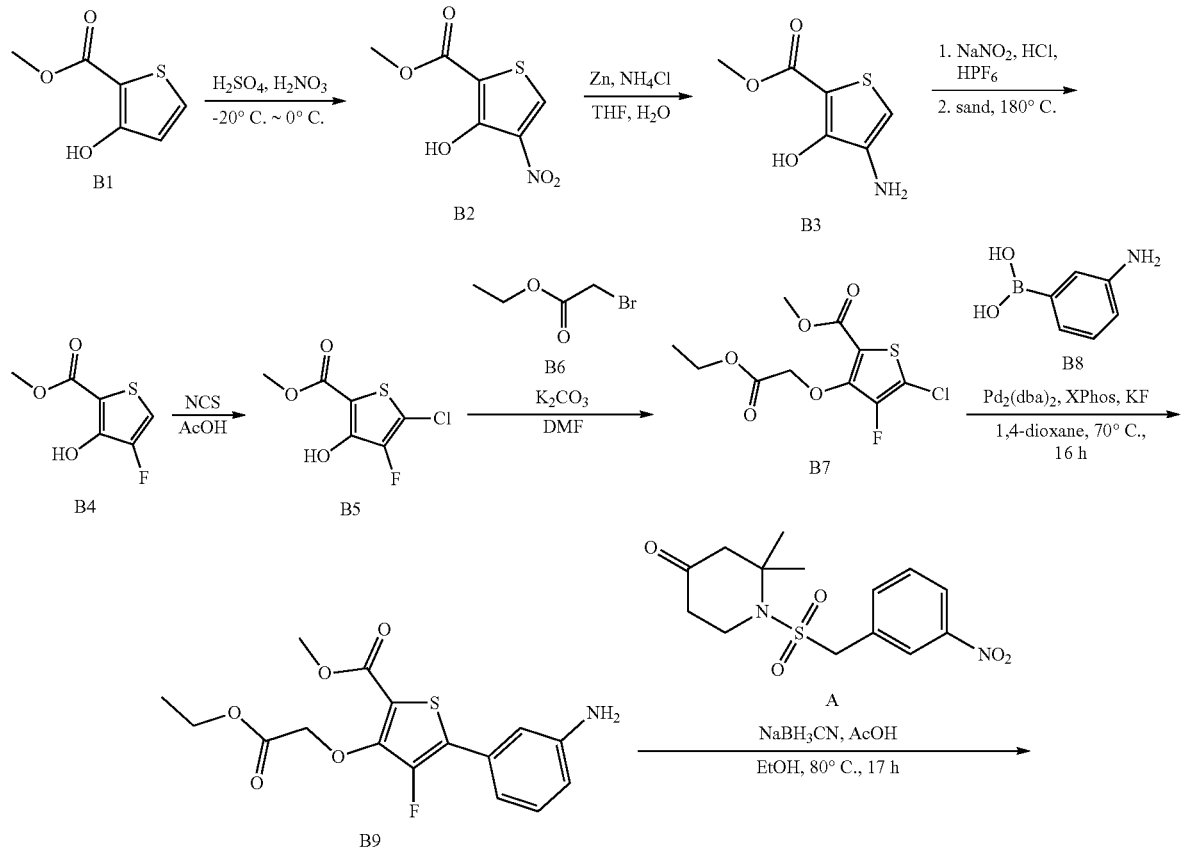

-continued

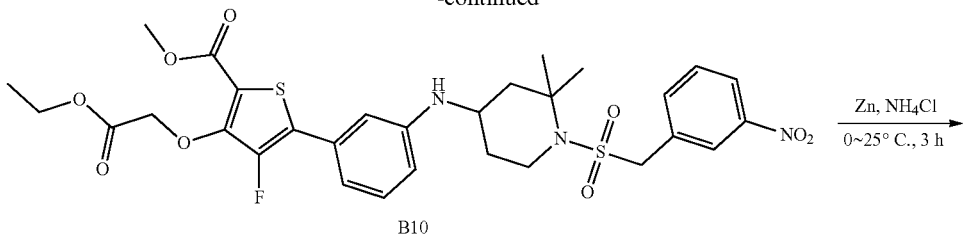

B10

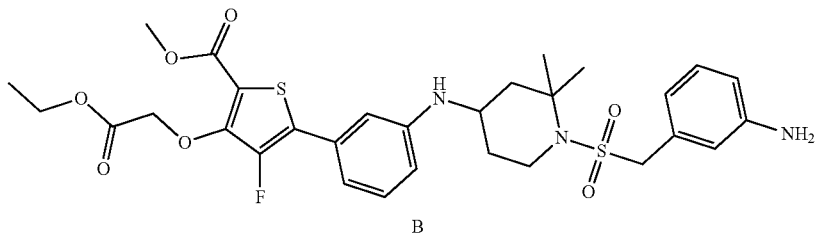

B

To a solution of B1 (20.0 g, 63.2 mmol) in concentrated sulfuric acid (96 mL) was added concentrated nitric acid (5.76 mL) at −15° C. The reaction mixture was stirred for 4 h at 0° C. before ice-water mixture (180 mL) was added. The combined mixture was extracted with ethyl acetate (300 mL) and the organic layer was washed with brine and dried over anhydrous sodium sulfate. The solvent was removed under reduced pressure, and the residue product was purified using flash chromatography to afford B2 (4.96 g, 19.2).

To a solution of B2 (4.80 g, 11.8 mmol) in tetrahydrofuran (50 mL) were added water (50 mL) and zinc powder (7.56 g, 118 mmol) and the reaction mixture was stirred at 0° C. Ammonium chloride (6.24 g, 118 mmol) was added to the reaction mixture and the mixture was stirred at room temperature for another 5 h. The reaction mixture was diluted with tetrahydrofuran, and washed with brine. The organic layer was dried over anhydrous sodium sulfate and filtered with diatomaceous earth to afford a yellow solution. The solvent was removed under reduced pressure and the crude product was purified using flash chromatography to afford B3 (3.36 g, 82.7%).

To a solution of B3 (3.32 g, 19.1 mmol) in a 6 M hydrochloric acid aqueous solution (80 mL) was added sodium nitrite (1.57 g, 22.8 mmol) at 0° C. for 1 h. Hexafluorophosphoric acid (60% aqueous solution, 12.9 mL) was added before the reaction mixture was stirred for another 10 min at 0° C. The reaction mixture was allowed to warm to 15° C. and then decanted. The solid residue was washed with diluted hexafluorophosphate (10 mL), methanol (10 mL), and methyl tert-butyl ether (10 mL). 4-Hydroxy-5-methoxycarbonylthio-phene-3-diazohexafluorophosphate was afforded as an intermediate (5.34 g, 84.9%). The obtained intermediate was heated at 200° C. with sand (30 g) and distilled under reduced pressure to afford B4 (1.65 g, 49.7%).

To a solution of B4 (1.64 g, 9.32 mmol) in acetic acid (20 mL) was added N-chlorosuccinimide (1.61 g, 12.1 mmol). The reaction mixture was stirred at 80° C. for 5 h before the solution was poured into ice water (60 mL) and treated with a saturated sodium bicarbonate aqueous solution until pH=7. The reaction mixture was extracted with ethyl acetate (120 mL×3) and the combined organic layer was washed with brine, and dried over anhydrous sodium sulfate. The solvent was removed under reduced pressure and the crude product was purified using flash chromatography to afford B5 (1.50 g, 75.7%).

To a solution of B5 (1.50 g, 7.04 mmol) in N, N-dimethylformamide (16 mL) was added potassium carbonate (1.94 g, 14.0 mmol) at 0° C. Ethyl bromoacetate (1.42 g, 8.44 mmol) was added dropwise to the reaction solution and the reaction mixture was stirred at room temperature for 2 h. A yellow solid B7 was precipitated as a product (1.74 g, 83.4%) after water (40 mL) was added to the crude mixture.

A solution of B7 (1.74 g, 5.94 mmol) in 1,4-dioxane (20 mL) was charged with a balloon filled with nitrogen. The reaction mixture was added 3-aminophenyl boronic acid (1.62 g, 11.8 mmol), potassium fluoride (1.03 mg, 17.8 mmol), XPhos (1.72 g, 0.30 mmol), and $Pd_2(dba)_3$ (270 mg, 0.30 mmol). The reaction mixture was stirred at 90° C. for 12 h. The concentrated crude mixture was purified using flash chromatography to afford B9 (926 mg, 45.1%).

To a solution of B9 (926 mg, 2.60 mmol) and A (1.02 g, 3.12 mmol) in ethanol (10 mL) was added acetic acid (780 mg, 13.0 mmol), and the reaction mixture was stirred at 80° C. for 3 h. Sodium cyanide borohydride (816 mg, 13.0 mmol) was added portion-wise and the reaction mixture was stirred at 80° C. for 5 h. The crude mixture was added ice-water mixture (20 mL) and extracted with dichloromethane (90 mL). The organic layer was washed with brine and dried over anhydrous sodium sulfate. The solvent was removed under reduced pressure and the crude product was purified using flash chromatography to afford B10 (620 mg, 35.47%).

To a solution of B10 (620 mg, 0.90 mmol) in tetrahydrofuran (6 mL) were added water (6 mL) and zinc powder (592 mg, 9.04 mmol). The reaction mixture was stirred at 0° C. Ammonium chloride (484 mg, 9.04 mmol) was added to the reaction mixture, and the reaction mixture was stirred at room temperature for 5 h. The crude mixture was diluted with tetrahydrofuran and washed with brine. The organic layer was dried over anhydrous sodium sulfate and filtered with diatomaceous earth to afford a yellow solution. The solvent was removed under reduced pressure and the crude product was purified using flash chromatography to afford B (396 mg, 66.1%).

Synthesis of C

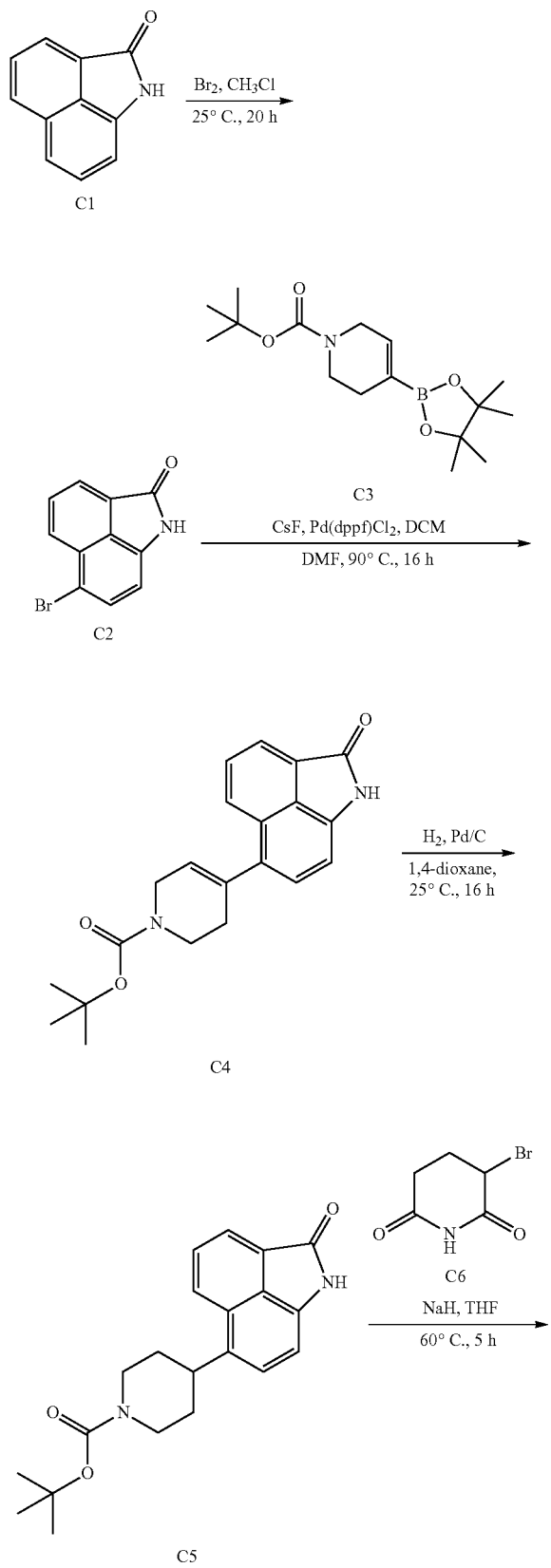

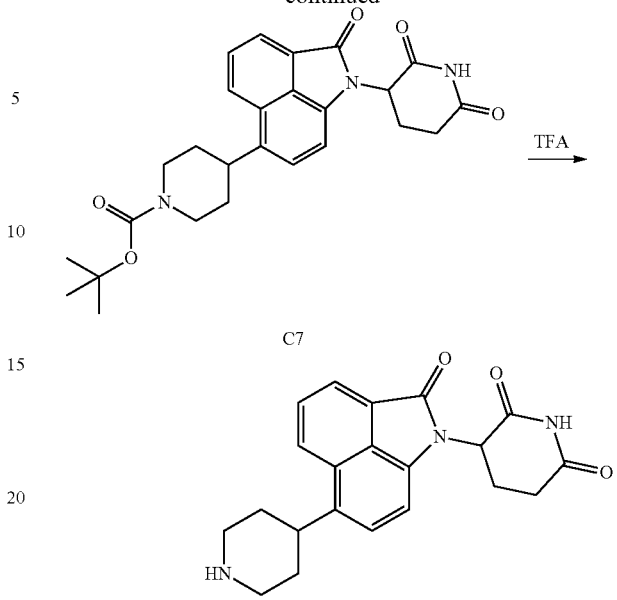

To a solution of $C_1$ (20 g, 118 mmol) in carbon tetrachloride (800 mL) was added bromine (20.7 g, 130 mmol) dropwise at 0° C. The reaction mixture was stirred at room temperature for 12 h. The yellow precipitate was isolated and washed with water (200 ml). The crude product was purified using flash chromatography to afford C2 (26 g, 72.7%).

To a solution of C2 (20 g, 80.6 mmol), C3 (27.4 g, 88.6 mmol) in N,N-dimethylformamide (200 mL) were added cesium fluoride (24.5 g, 161.3 mmol) and Pd(dppf)Cl2·DCM (7.50 g, 10.3 mmol) in an inert atmosphere. The reaction mixture was stirred at 90° C. for 12 h. The reaction mixture was filtered and the solvent was removed under reduced pressure. The crude product was purified using flash chromatography to afford C4 (6.21 g, 54.3%).

To a solution of C4 (6 g, 17.1 mmol) in 1,4-dioxane (100 mL) was added 10 wt % palladium carbon (3.65 g, 3.43 mmol). The reaction mixture was stirred at room temperature for 12 h. The crude mixture was filtered and the solvent was removed under reduced pressure. The crude product was purified using flash chromatography to afford C5 (5.61 g, 93.0%).

To a solution of C5 (4 g, 11.4 mmol) in anhydrous tetrahydrofuran (40 mL) was added sodium hydride (4.60 g, 114 mmol) at 0° C. The reaction mixture was stirred at room temperature for 1 h. 3-Bromopyridine-2,6-dione (10.9 g, 57.0 mmol) was added dropwise, and the reaction mixture was stirred at 70° C. for 5 h. The reaction mixture was added ice-water mixture (50 mL) and extracted with ethyl acetate (120 mL). The combined organic layer was washed with brine and dried over anhydrous sodium sulfate. The solvent was removed under reduced pressure and the crude product was purified using flash chromatography to afford C7 (2.42 g, 46.0%).

To a solution of C7 (2.4 g, 5.18 mmol) in dichloromethane (30 mL) was added trifluoroacetic acid (17.7 g, 155.4 mmol). The reaction mixture was stirred at room temperature for 6 h. The solvent was removed under reduced pressure and C (trifluoroacetate salt) was obtained with a yield of 94.5%.

Synthesis of D

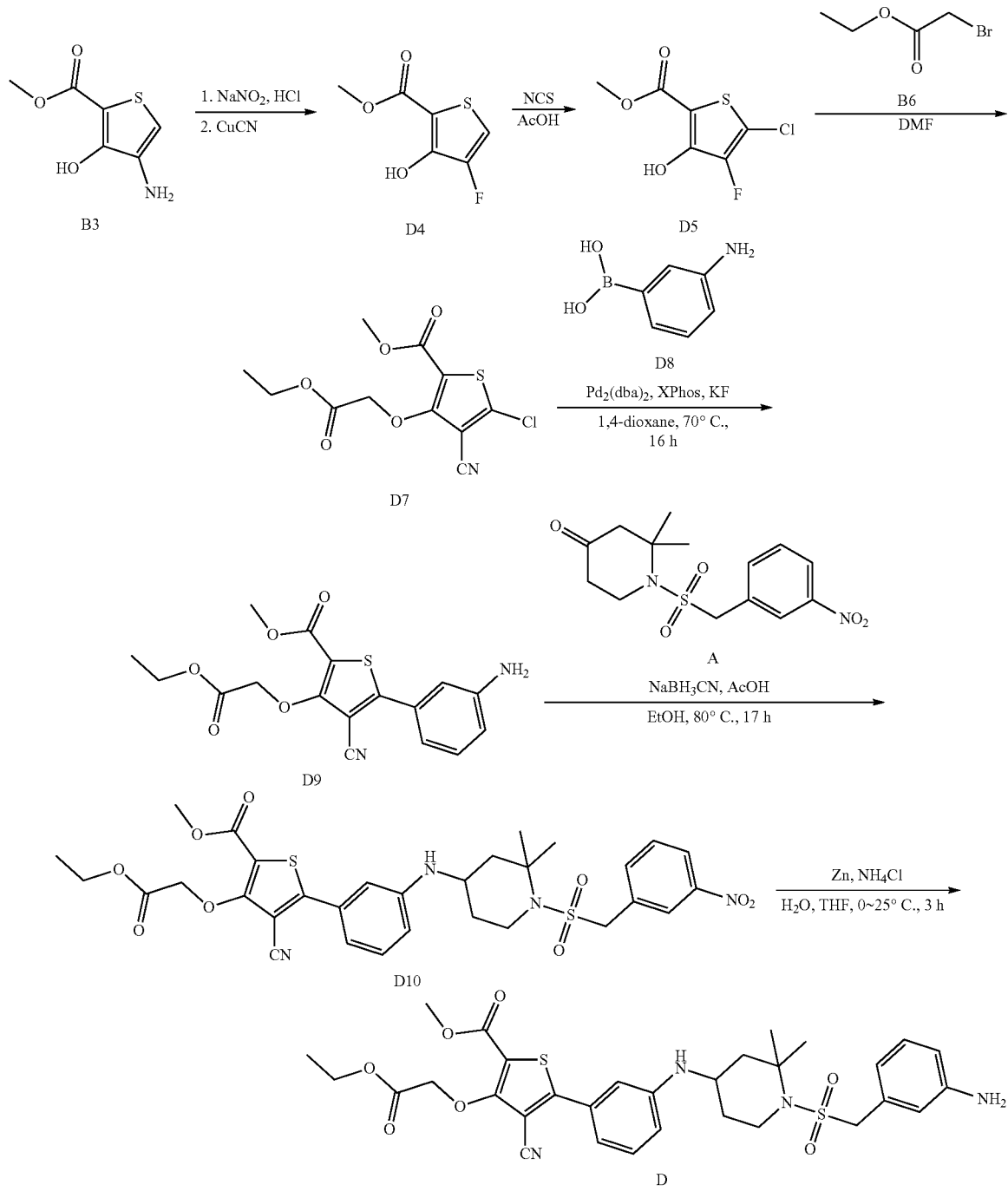

To a solution of B3 (4.0 g, 30.7 mmol) in a 6 M hydrochloric acid aqueous solution (100 mL) was added sodium nitrite (2.54 g, 36.84 mmol), and the reaction mixture was stirred at 0° C. for 1 h. Potassium carbonate (5.08 g, 36.8 mmol) and cuprous cyanide (3.27 g, 36.8 mmol) in water (50 mL) were added to the reaction mixture. The reaction mixture was stirred at 70° C. for 2 h before it was cooled to room temperature and extracted with ethyl acetate (120 mL). The organic layer was washed with brine and dried over anhydrous sodium sulfate. The solvent was removed under reduced pressure and the crude product was purified using flash chromatography to afford D4 (1.80 g, 42.6%).

To a solution of D4 (1.80 g, 9.83 mmol) in acetic acid (20 mL) was added N-chlorosuccinimide (1.96 g, 14.7 mmol). The reaction mixture was stirred at 80° C. for 5 h before it was cooled to room temperature and poured into ice-water mixture (60 mL). Saturated sodium bicarbonate aqueous solution was added to neutralize the crude mixture, and it was extracted with ethyl acetate (120 mL). The organic layer was washed with brine and dried over anhydrous sodium sulfate. The solvent was removed under reduced pressure and the crude product was purified using flash chromatography to afford D5 (1.56 g, 72.9%).

To a solution of D5 (1.50 g, 6.91 mmol) in N,N-dimethylformamide (15 mL) was added potassium carbonate (1.91 g, 13.8 mmol), and the reaction mixture was stirred at 0° C. Ethyl bromoacetate (1.39 g, 8.29 mmol) was slowly added dropwise to the solution and the reaction mixture was stirred at room temperature for 2 h. A yellow precipitate was filtered as product D7 (1.86 g 89.3%) after addition of water (40 mL).

To a solution of D7 (1.8 g, 5.94 mmol) in 1,4-dioxane (20 mL) were added 3-aminophenyl boronic acid (1.62 g, 11.8 mmol), potassium fluoride (1.03 mg, 17.8 mmol), XPhos (1.72 g, 0.30 mmol), and $Pd_2$(dba)3 (270 mg, 0.30 mmol) in an inert atmosphere. The reaction mixture was stirred at 90° C. for 12 h. The reaction mixture was filtered and the solvent was removed under reduced pressure. The crude product was purified using flash chromatography to afford D9 (1.10 g, 51.7%).

To a solution of D9 (1.0 g, 2.77 mmol) and A (1.08 g, 3.32 mmol) in ethanol (10 mL) was added acetic acid (831 mg, 13.8 mmol). The reaction mixture was stirred at 80° C. for 3 h. Sodium cyanide borohydride (816 mg, 13.0 mmol) was added portion-wise and the reaction mixture was stirred at 80° C. for 5 h. The reaction mixture was added ice-water mixture (20 mL) and extracted with dichloromethane (90 mL). The organic layer was washed with brine and dried over anhydrous sodium sulfate. The solvent was removed under reduced pressure and the crude product was purified using flash chromatography to afford D10 (711 mg, 38.3%).

To a solution of D10 (711 mg, 1.06 mmol) in tetrahydrofuran (7 mL) were added water (6 mL) and zinc powder (592 mg, 9.04 mmol). The reaction mixture was stirred at 0° C. before ammonium chloride (484 mg, 9.04 mmol) was added. Then the reaction mixture was stirred at room temperature for another 5 h before it was diluted with tetrahydrofuran, washed with brine, and extracted with ethyl acetate (120 mL×3). The combined organic layer was dried over sodium sulfate and filtered with diatomaceous earth to afford a yellow solution. The solvent was removed under reduced pressure and the crude product was purified using flash chromatography to afford D (446 mg, 65.7%).

Synthesis of Compound 1 and its 4 Stereoisomers
1a, 1b, 1c, and 1d

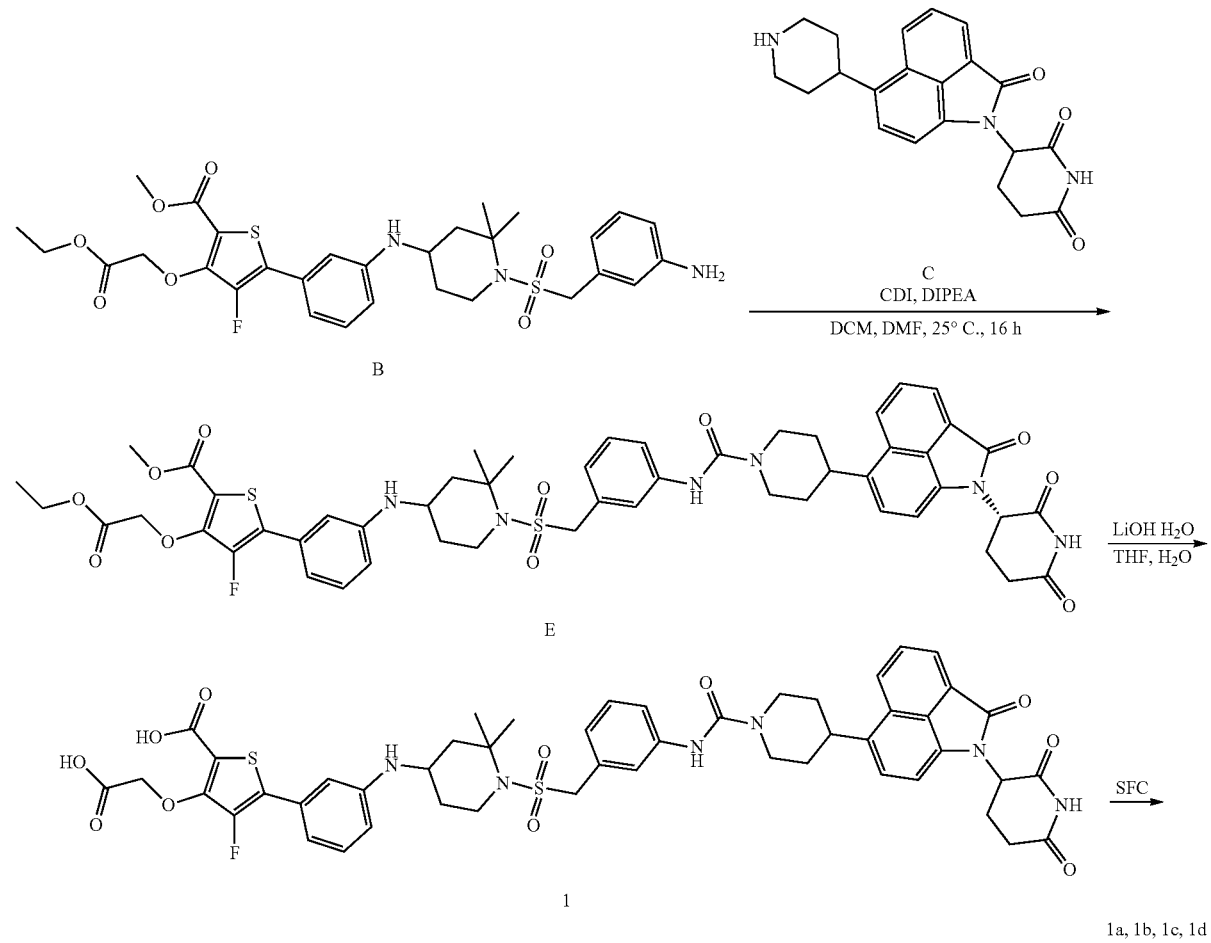

To a solution of B (194 mg, 0.30 mmol) in dichloromethane (2 mL) and N, N-dimethylformamide (0.2 mL) were added N, N-diisopropylethylamine (388 mg, 3.0 mmol) and N,N'-carbonyldiimidazole (79.0 mg, 0.48 mmol). The reaction mixture was stirred at room temperature for 2 h before a solution of C (196 mg, 0.30 mmol, trifluoroacetate) in N,N-dimethylformamide (2 mL) was added portionwise. The reaction mixture was stirred at room temperature for 12 h. The solvent was removed under reduced pressure and the crude product was purified using flash chromatography to afford E (192 mg, 61.8%).

To a solution of E (192 mg, 0.18 mmol) in tetrahydrofuran (3 mL) and water (1 mL) was added lithium hydroxide monohydrate (30.2 mg, 0.72 mmol). The reaction mixture was stirred at room temperature for 5 h. The crude mixture was added 2 M hydrochloric acid aqueous solution and the precipitation was isolated through filtration as a crude product. The crude product was purified using preparative HPLC (acetonitrile: 0.1% formic acid aqueous solution) to afford Compound 1 (128 mg, 69.8%).

4 Stereoisomers 1a, 1b, 1c, and 1d were isolated via SFC resolution of Compound 1.

Synthesis of Compound 2 and its 4 stereoisomers
2a, 2b, 2c, and 2d

To a solution of D (207 mg, 0.32 mmol) in dichloromethane (2 mL) and N, N-dimethylformamide (0.2 mL) were added N, N-diisopropylethylamine (413 mg, 3.2 mmol) and N,N'-carbonyldiimidazole (84.2 mg, 0.51 mmol). The reaction mixture was stirred at room temperature for 2 h. To a solution of C (196 mg, 0.30 mmol, trifluoroacetate salt) in N,N-dimethylformamide (2 mL) was added N, N-diisopropylethylamine (0.4 mL) slowly, and the reaction mixture was stirred at room temperature for 12 h. The reaction mixture was concentrated under reduced pressure to afford an anhydrous yellow oil, which was purified using flash chromatography to afford F (188 mg, 57.2%).

To a solution of F (180 mg, 0.18 mmol) in tetrahydrofuran (3 mL) and water (1 mL) was added lithium hydroxide monohydrate (30.2 mg, 0.72 mmol). The reaction mixture was stirred at room temperature for 5 h before 2 M hydrochloric acid was added to afford pale-yellow precipitation. The precipitation was filtered and purified using preparative HPLC (acetonitrile: 0.1% formic acid aqueous solution) to afford Compound 2 (113 mg, 62.7%).

4 Stereoisomers 2a, 2b, 2c, and 2d were isolated via SFC resolution of Compound 2.

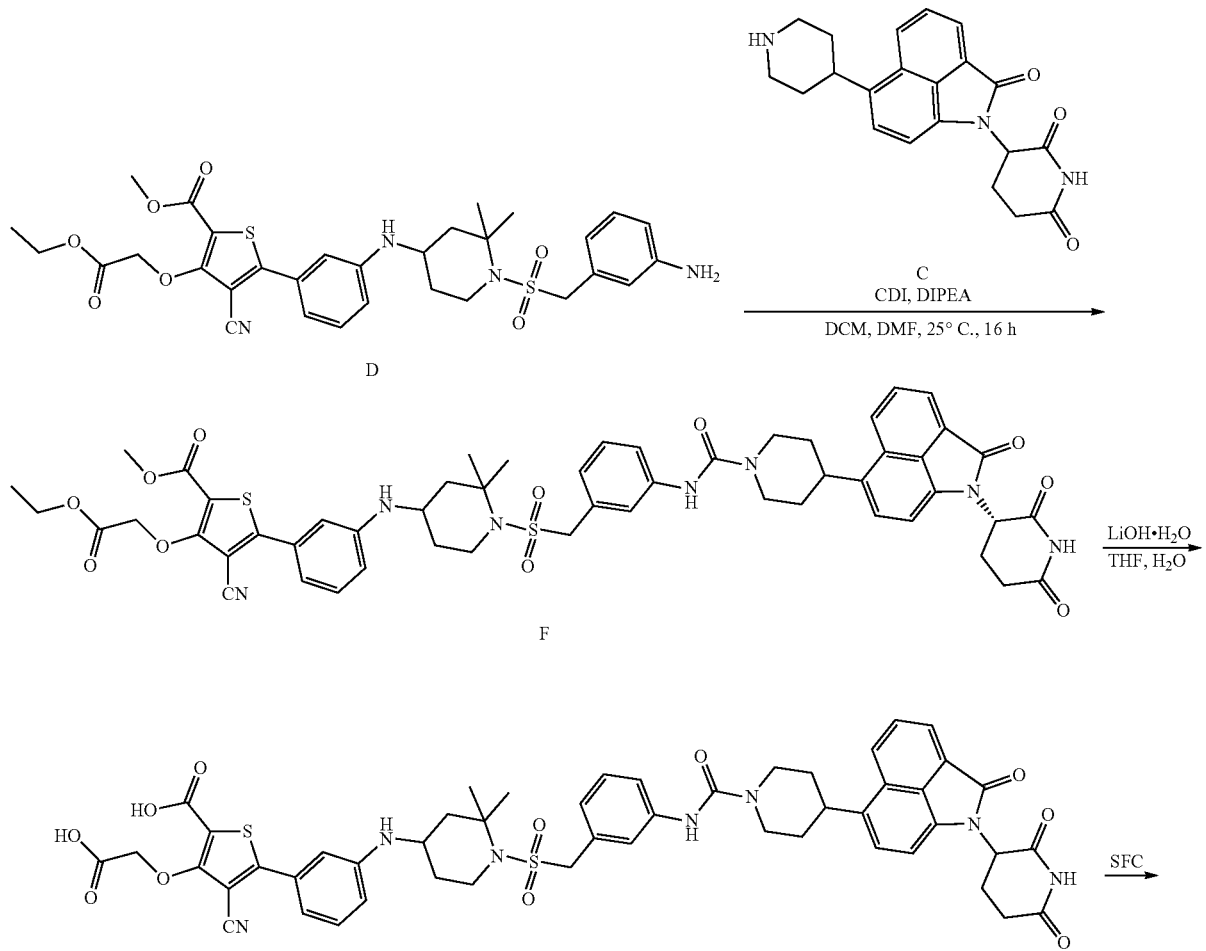

Synthesis of Compound 3 and its 4 stereoisomers 3a, 3b, 3c, and 3d
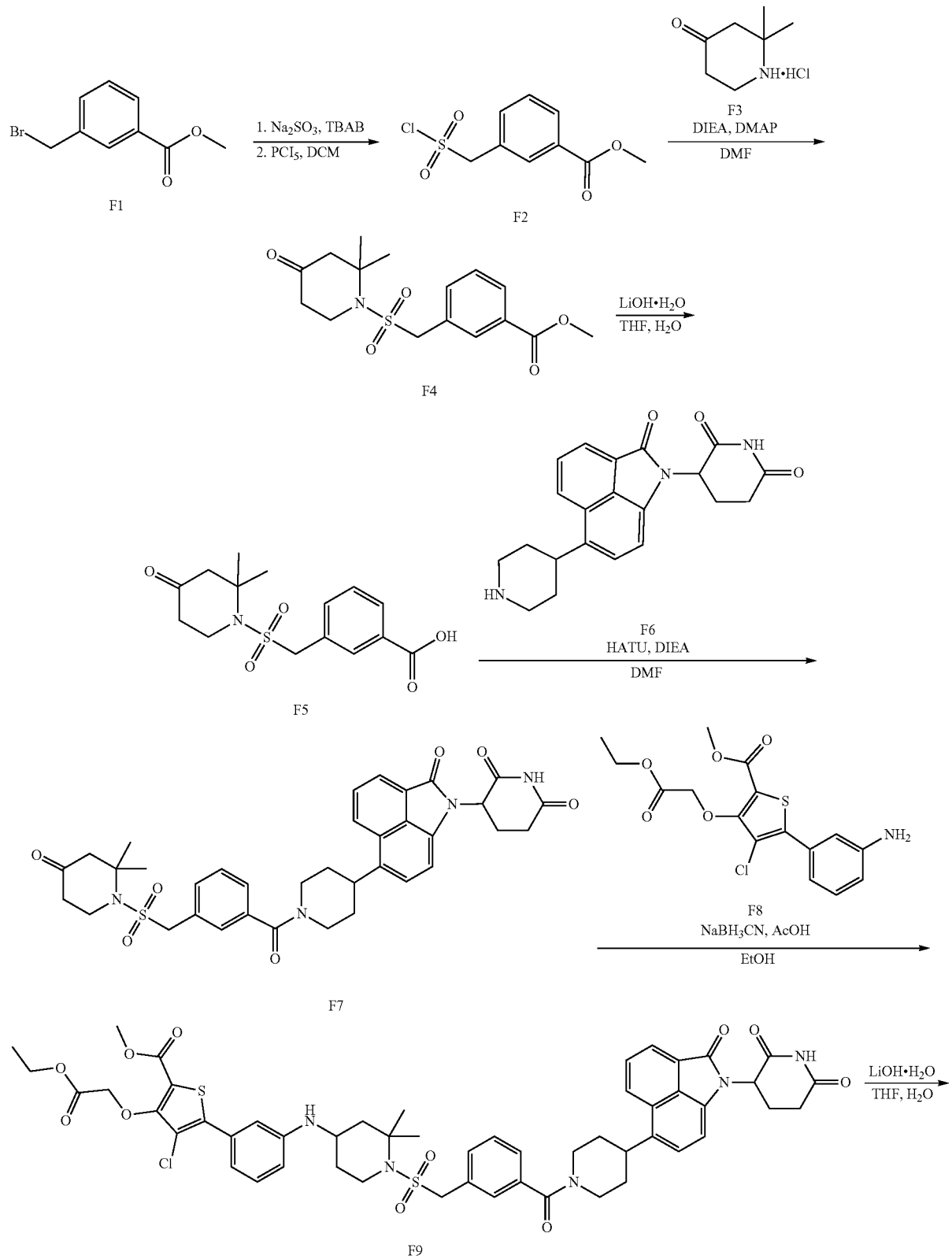

-continued

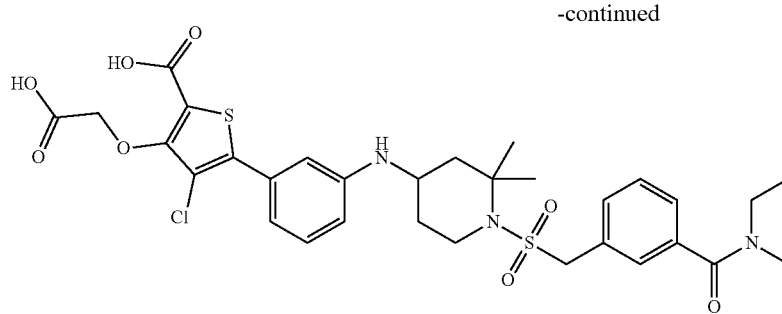

3

3a, 3b, 3c, 3d

To a solution of sodium sulfite (8.19 g, 65.0 mmol) and tetrabutylammonium bromide (2.58 g, 8.0 mmol) in water (100 mL) was added F1 (11.4 g, 50.0 mmol). The reaction mixture was stirred at 100° C. for 10 h before it was cooled to room temperature. The solvent was removed under reduced pressure and the residue was dispersed in isopropanol (100 mL) and stirred at 80° C. for 30 min. The solvent was removed under reduced pressure to afford a yellow solid (16.5 g). Dichloromethane (150 mL) was used to solve the yellow solid and phosphorus pentachloride (12.5 g, 60.0 mmol) was added dropwise at 0° C. The reaction mixture was stirred at room temperature for 12 h before it was poured into water (300 mL), and extracted with dichloromethane (300 mL). The organic layer was washed with brine and dried over anhydrous sodium sulfate. The solvent was removed under reduced pressure and the crude product was purified using flash chromatography to afford F2 (8.10 g, 65.3%).

To a solution of F3 (4.59 g, 28.2 mmol), N, N-diisopropylethylamine (11.0 g, 84.6 mmol) and 4-dimethylaminopyridine (342 mg, 2.82 mmol) in N, N-dimethylformamide (50 mL) was added F2 (7.96 g, 41.0 mmol) at 0° C. The reaction mixture was stirred at 25° C. for 12 h before it was added dropwise to an ice-water mixture (150 mL) and extracted with ethyl acetate (240 mL). The organic layer was washed with brine and dried over anhydrous sodium sulfate. The solvent was removed under reduced pressure and the crude product was purified using flash chromatography to afford F4 (4.34 g, 45.4%).

To a solution of F4 (4.30 g, 12.7 mmol) in tetrahydrofuran (30 mL) and water (10 mL) was added lithium hydroxide monohydrate (2.13 g, 50.7 mmol). The reaction mixture was stirred at room temperature for 12 h before 2 M hydrochloric acid was added to afford a precipitation. The precipitation was isolated through filtration and purified using preparative HPLC (acetonitrile: 0.1% formic acid aqueous solution) to afford Compound F5 (3.05 g, 73.8%).

To a solution of F5 (3.0 g, 9.22 mmol) and HATU (5.25 g, 13.8 mmol) in N, N-dimethylformamide (25 mL) was added N,N-diisopropylethylamine (3.74 g, 27.6 mmol) and F6 (4.03 g, 11.1 mmol). Then the reaction mixture was stirred at room temperature for 12 h. The solvent was removed under reduced pressure and the crude product was purified using flash chromatography to afford F7 (2.75 g, 43.7%).

To a solution of F7 (2.70 g, 4.03 mmol) and F8 (1.78 g, 4.84 mmol) in ethanol (15 mL) was added acetic acid (1.21 g, 20.2 mmol). The reaction mixture was stirred at 80° C. for 3 h. Sodium cyanide borohydride (1.33 g, 20.2 mmol) was added portion-wise and the reaction mixture was stirred at 80° C. for another 5 h before it was poured into an ice-water mixture (30 mL) and extracted with dichloromethane (120 mL). The organic layer was washed with brine and dried over anhydrous sodium sulfate. The solvent was removed under reduced pressure and the crude product was purified using flash chromatography to afford F9 (1.63 g, 39.7%).

To a solution of F9 (1.60 g, 1.56 mmol) in tetrahydrofuran (15 mL) and water (5 mL) was added lithium hydroxide monohydrate (302 mg, 7.2 mmol). The reaction mixture was stirred at room temperature for 5 h before the addition of 2 N hydrochloric acid to afford precipitation as a crude product. The crude product was purified using preparative HPLC (acetonitrile: 0.1% formic acid aqueous solution) to afford Compound 3 (1.18 g, 77.2%).

4 Stereoisomers 3a, 3b, 3c, and 3d were isolated via SFC resolution of Compound 3.

Synthesis of Compound 4 and its 4 Stereoisomers 4a, 4b, 4c, and 4d

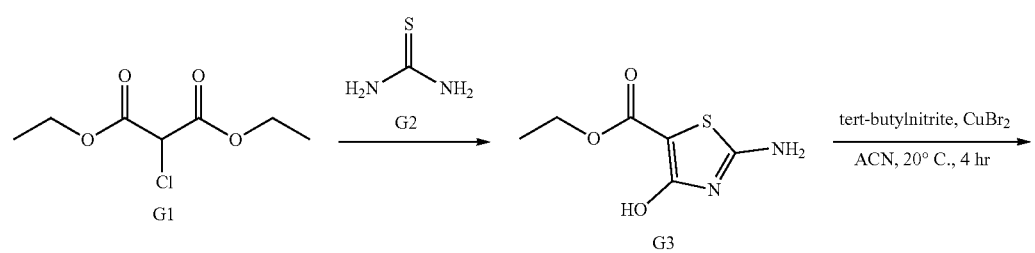

-continued
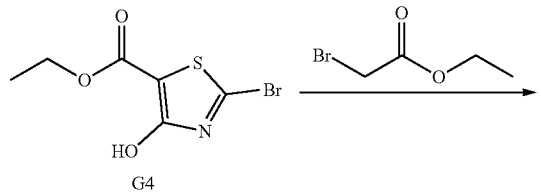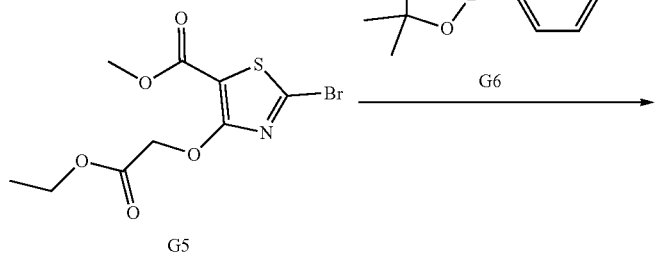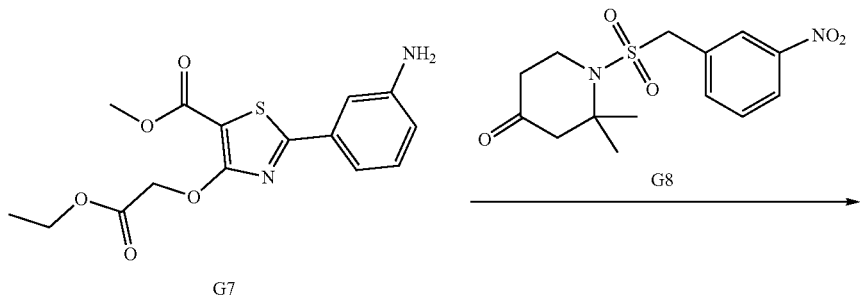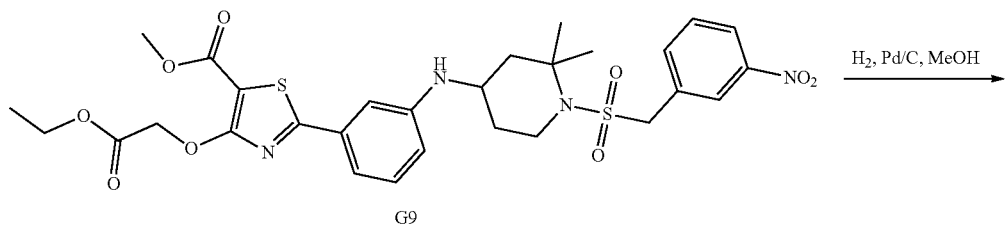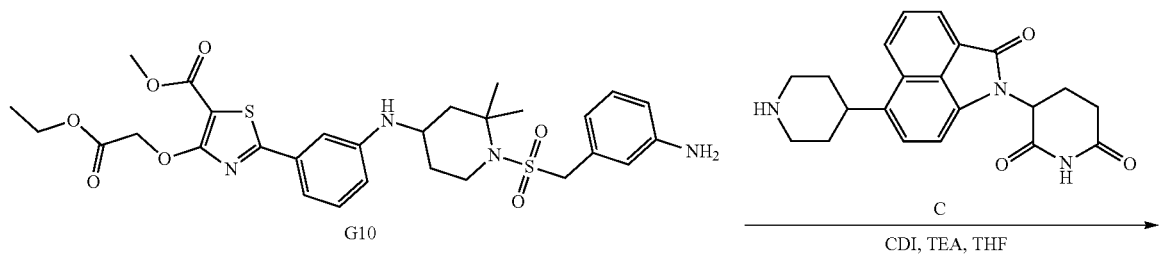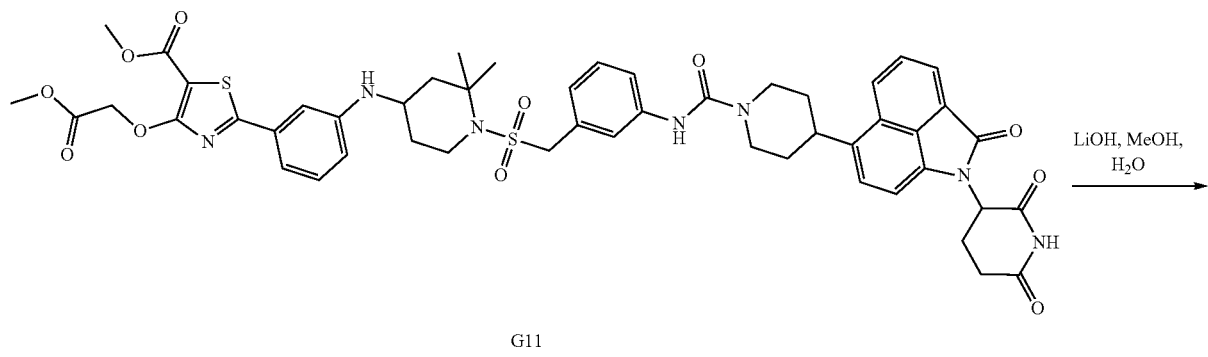

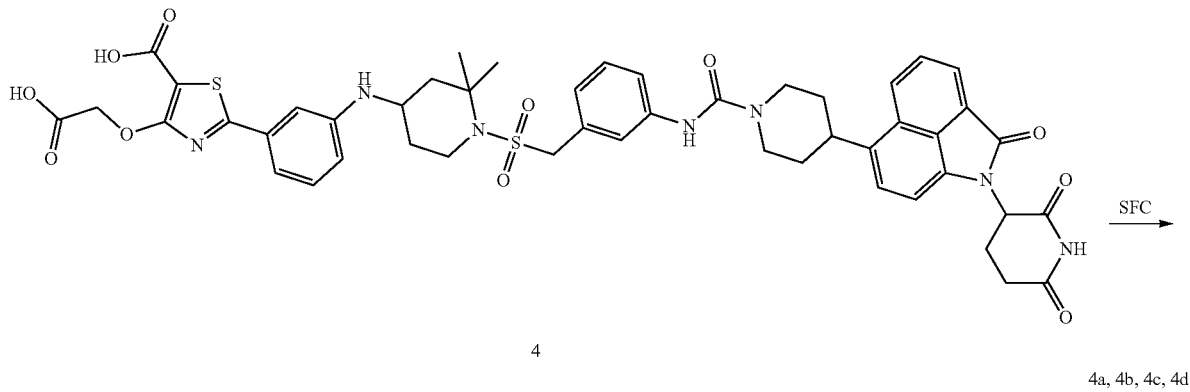

4

4a, 4b, 4c, 4d

Synthesis of G3: To a mixture of G1 (5.84 g, 30.0 mmol) and G2 (2.28 g, 30.0 mmol) was added 1-n-butyl-3-methylimidazolium trifluoromethane sulfonate (2 mL). The reaction mixture was stirred at 20° C. for 2 h. Then 40 mL water was added to quench the reaction and the crude mixture was extracted with 50 mL ethyl acetate. The organic layer was washed with brine and dried over anhydrous sodium sulfate. The solvent was removed under reduced pressure and the crude product was purified using flash chromatography to afford G3 (2.4 g, 41.2%).

Synthesis of G4: To a solution of G3 (2.4 g, 12.8 mmol) in 100 mL acetonitrile was added t-butyl nitrite (1.58 g, 15.3 mmol). The reaction mixture was stirred at 0° C. for 30 min before copper bromide (6.8 g, 30.6 mmol) was added. Then the mixture was stirred at 20° C. for 4 h, and 60 mL saturated sodium bicarbonate solution was used to quench the reaction. The crude mixture was extracted with 100 mL ethyl acetate. The organic layer was washed with brine and dried over anhydrous sodium sulfate. The solvent was removed under reduced pressure and the crude product was purified using flash chromatography to afford G4 (2.7 g, 84.6%).

Synthesis of G5: To a solution of G4 (2.7 g, 10.7 mmol) in N, N-dimethylformamide (40 mL) were added ethyl bromoacetate (2.0 g, 11.8 mmol) and potassium carbonate (2.2 g, 16.1 mmol). The mixture was stirred at 50° C. for 4 h, and 60 mL saturated sodium bicarbonate solution was used to quench the reaction. The crude mixture was extracted with 100 mL ethyl acetate. The organic layer was washed with brine and dried over anhydrous sodium sulfate. The solvent was removed under reduced pressure and the crude product was purified using flash chromatography to afford G5 (3.3 g, 95.6%).

Synthesis of G7: To a solution of G5 (3.3 g, 10.2 mmol), G6 (2.5 g, 11.2 mmol), potassium carbonate (2.1 g, 15.3 mmol) and Pd(dppf)Cl$_2$ (0.73 g, 1.0 mmol) in 1,4-dioxane (50 mL) was added water (15 mL). The reaction mixture was stirred at 100° C. for 6 h before poured into an ice-water mixture (20 mL). The crude mixture was extracted with dichloromethane (90 mL). The organic layer was washed with brine and dried over anhydrous sodium sulfate. The solvent was removed under reduced pressure and the crude product was purified using flash chromatography to afford G7 (2.9 g, 85.1%).

Synthesis of G9: To a solution of G7 (2.9 g, 8.7 mmol) and G8 (2.8 g, 8.7 mmol) in dichloromethane (150 mL) was added 1 drop of acetic acid and sodium triacetoxyborohydride (3.7 g, 17.4 mmol) under ice bath. The reaction mixture was slowly warmed to room temperature and stirred for 8 h. The reaction mixture was poured into an ice-water mixture (30 mL) and extracted with dichloromethane (120 mL). The organic layer was washed with brine and dried over anhydrous sodium sulfate. The solvent was removed under reduced pressure and the crude product was purified using flash chromatography to afford G9 (4.3 g, 76.1%).

Synthesis of G10: To a solution of G9 (4.3 g, 6.6 mmol) in methanol (150 mL) was added Pd/C (10 wt %, 1 g). Three freeze-pump-thaw cycles were used to maintain an H$_2$ atmosphere and the reaction mixture was stirred at room temperature for 8 h before it was eventually filtered. The filtrate was concentrated to afford G10 (3.26 g, 80.1%).

Synthesis of G11: A solution of G10 (0.62 g, 1.0 mmol), N,N'-carbonyldiimidazole (0.32 g, 2.0 mL) and triethylamine (0.2 g, 2.0 mmol) in tetrahydrofuran (20 mL) was stirred at 60° C. for 2 h, and the reaction mixture was cooled to 20° C. Then C (0.36 g, 1.0 mmol) was added before the reaction mixture was stirred for another 2 h. 60 mL saturated sodium bicarbonate solution was added and the crude mixture was extracted with 100 mL ethyl acetate. The organic layer was washed with brine and dried over anhydrous sodium sulfate. The solvent was removed under reduced pressure and the crude product was purified using flash chromatography to afford G11 (0.42 g 43.5%).

Synthesis of Compound 4: To a solution of G11 (0.42 g, 0.4 mmol) in tetrahydrofuran (15 mL) and water (5 mL) was added lithium hydroxide monohydrate (302 mg, 7.2 mmol). The reaction mixture was stirred at room temperature for 5 h before quenched with 2 M hydrochloric acid to afford a pale-yellow precipitation. The precipitation was filtered and purified using preparative HPLC to afford Compound 4 (0.33 g, 81.4%).

4 Stereoisomers 4a, 4b, 4c, and 4d were isolated via SFC resolution of Compound 4.

Synthesis of Compound 5 and its 4 stereoisomers 5a, 5b, 5c, and 5d
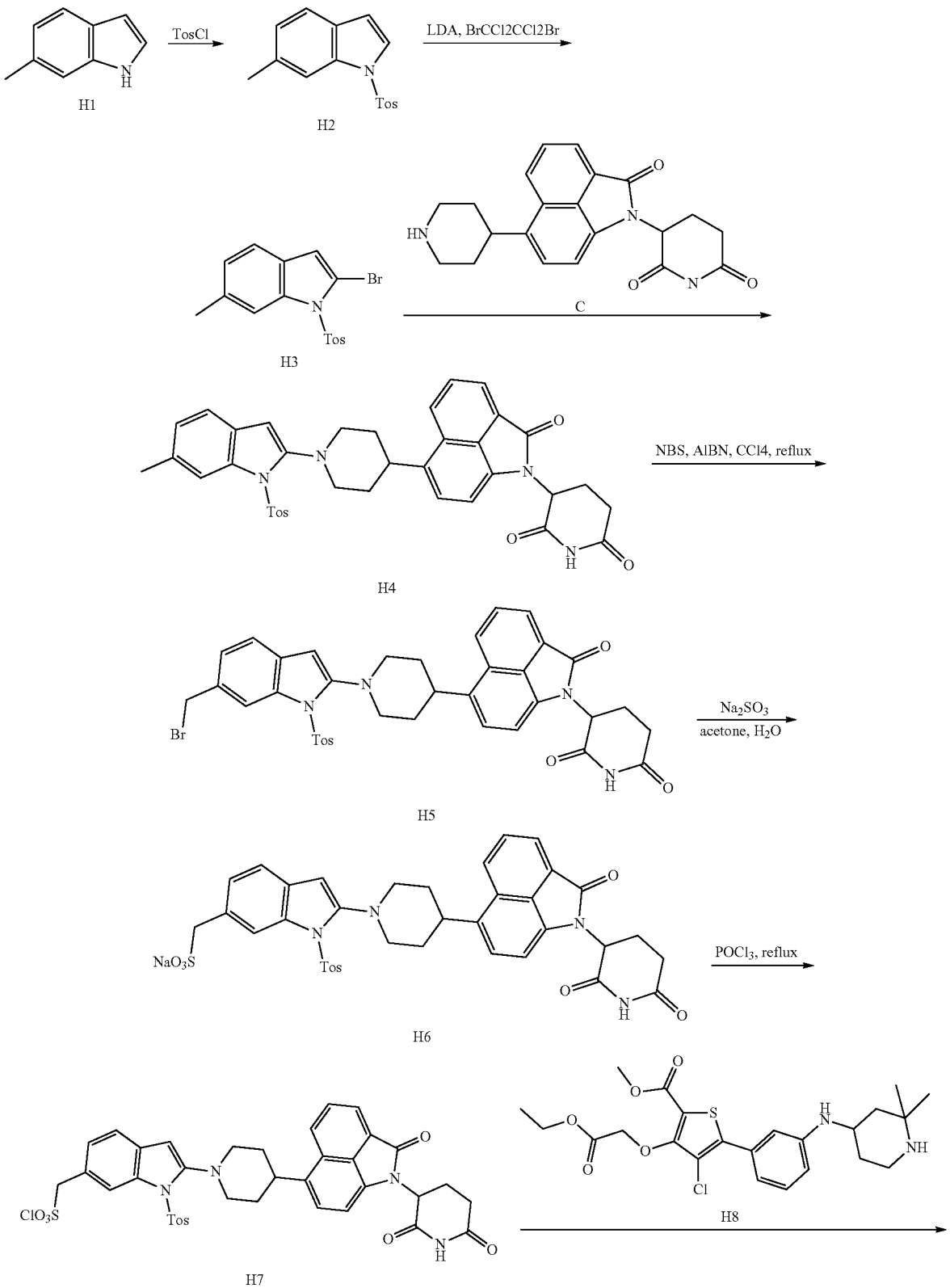

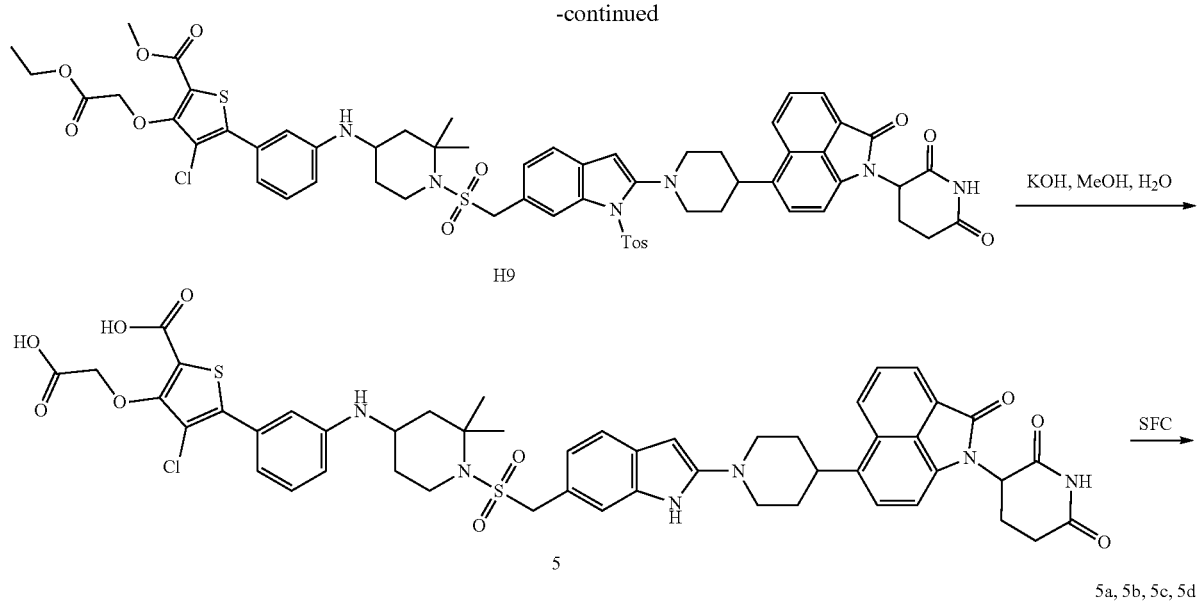

Synthesis of H₂: A solution of H₁ (2.62 g, 20 0 mmol), tosyl chloride (4.00 g, 21.0 mmol) and triethylamine (2.43 g, 24.0 mmol) in tetrahydrofuran (80 mL) was stirred at room temperature for 4 h. Ammonium chloride aqueous solution (80 mL) was used to quench the reaction, and the crude mixture was extracted with 80 mL ethyl acetate. The combined organic layer was washed with brine, dried over anhydrous magnesium sulfate, and concentrated under reduced pressure. The crude product was purified by chromatography on silica gel using hexanes-ether (10:1) as an eluant to afford H₂ (5.42 g, 95.1%).

Synthesis of H₃: To a solution of H₂ (5.28 g, 18.5 mmol) in anhydrous tetrahydrofuran (100 mL) was added lithium diisopropylamide (9.3 mL, 18.5 mmol) dropwise at −78° C. for 1 h. 1,2-Dibromotetrachloroethane (9.03 g, 27.8 mmol) was added dropwise and the reaction mixture was stirred at −78° C. for another 1 h and warmed to room temperature gradually within 4 h. The reaction mixture was quenched with 80 mL brine and the crude mixture was extracted with 80 mL ethyl acetate. The organic layer was separated and dried over anhydrous magnesium sulfate to afford a crude product. After flash chromatography purification, H₃ was obtained as a white solid (3.33 g, 49.4%).

Synthesis of intermediate H₄: To a solution of H₃ (1.82 g, 5.0 mmol), intermediate C (1.82 g, 5.0 mmol), potassium carbonate (1.04 g, 7.5 mmol) and X-Phos (0.23 g, 0.5 mmol) in 1,4-dioxane (50 mL) was added Pd₂(dba)3 (0.46 g, 0.5 mmol) in an inert atmosphere. The reaction mixture was stirred at 100° C. for 12 h. The quenched mixture was extracted with dichloromethane (3×50 mL) and the combined organic layer was washed with brine, dried over magnesium sulfate and concentrated under reduced pressure. The crude product was purified by chromatography on silica gel to afford H₄ (2.66 g, 41.2%).

Synthesis of H₅: To a solution of H₄ (2.48 g, 3.8 mmol) in 50 mL carbon tetrachloride were added N-bromosuccinimide (0.82 g, 4.6 mmol) and 2,2'-azobis(2-methylpropionitrile) (16.4 mg, 0.1 mmol) in an inert atmosphere. The reaction mixture was stirred at 90° C. for 5 h before it was cooled to room temperature. The reaction mixture was quenched with water and the crude mixture was extracted with carbon tetrachloride. The combined organic layer was dried over anhydrous sodium sulfate. The solvent was removed under reduced pressure and the crude product was purified using flash chromatography to afford H₅ (2.40 g, 87.2%).

Synthesis of H₆: To a solution of H₅ (2.21 g, 3.05 mmol) in 100 mL acetone was added an aqueous solution of sodium sulfite (0.46 g, 3.7 mmol), and the reaction mixture was heated to reflux for 5 h before it was cooled to room temperature. The solvent was removed under reduced pressure, and the crude product was purified using flash chromatography to afford H₆ (1.78 g, 77.4%).

Synthesis of H₇: A solution of H₆ (1.59 g, 2.12 mmol) in 20 mL phosphorus oxychloride was heated to reflux for 6 h. The reaction mixture was cooled to room temperature and poured into a precooled aqueous solution of sodium bicarbonate. The crude mixture was extracted with ethyl acetate (120 mL). The organic layer was washed with brine and dried over anhydrous sodium sulfate. The solvent was removed under reduced pressure and the crude product was purified using flash chromatography to afford H₇ (1.41 g, 87.2%).

Synthesis of H₉: To a solution of H₇ (0.71 g, 1.0 mmol) in 10 mL N, N-dimethylformamide were added H₈ (0.48 g, 1.0 mmol) and potassium carbonate (0.28 g, 2.0 mmol). The reaction mixture was stirred at 80° C. for 16 h before it was cooled to room temperature. The reaction was quenched with brine and the crude mixture was extracted with ethyl acetate (20 mL). The organic layer was washed with brine and dried over anhydrous sodium sulfate. The solvent was removed under reduced pressure and the crude product was purified using flash chromatography to afford H₉ (0.84 g, 71.1%).

Synthesis of Compound 5: To a solution of H₉ (0.50 g, 0.4 mmol) in methanol (6 mL) was added potassium hydroxide (8 mmol). The reaction mixture was stirred at 40° C. for 4 h. Then the reaction mixture was quenched with 2 M hydrochloric acid to afford a pale-yellow precipitation as the crude product. The crude product was purified using preparative HPLC (acetonitrile: 0.1% formic acid aqueous solution) to afford Compound 5 (0.34 g, 82.3%).

4 Stereoisomers 5a, 5b, 5c, and 5d were isolated via SFC resolution of Compound 5.
Synthesis of Compound 6 and its 4 stereoisomers 6a, 6b, 6c, and 6d: followed the synthesis of Compound 5 and its 4 isomers.
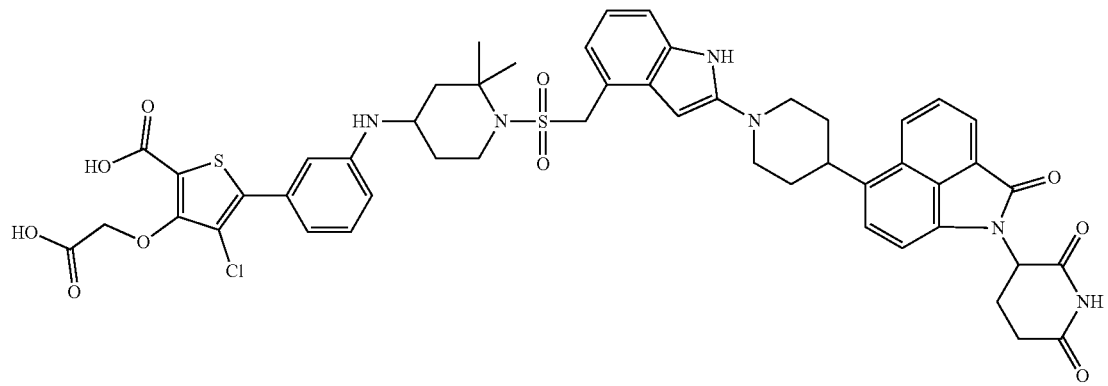
6
Synthesis of Compound 7 and its 4 stereoisomers 7a, 7b, 7c, and 7d
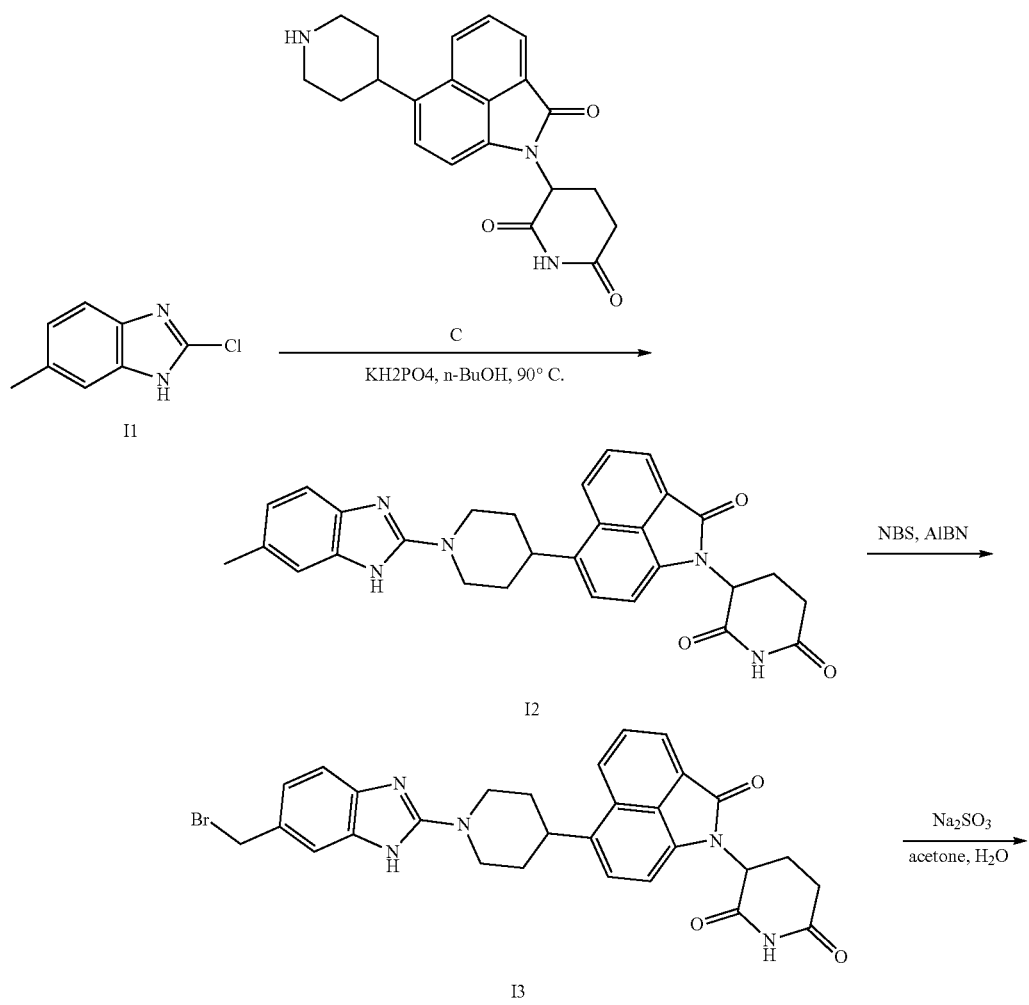

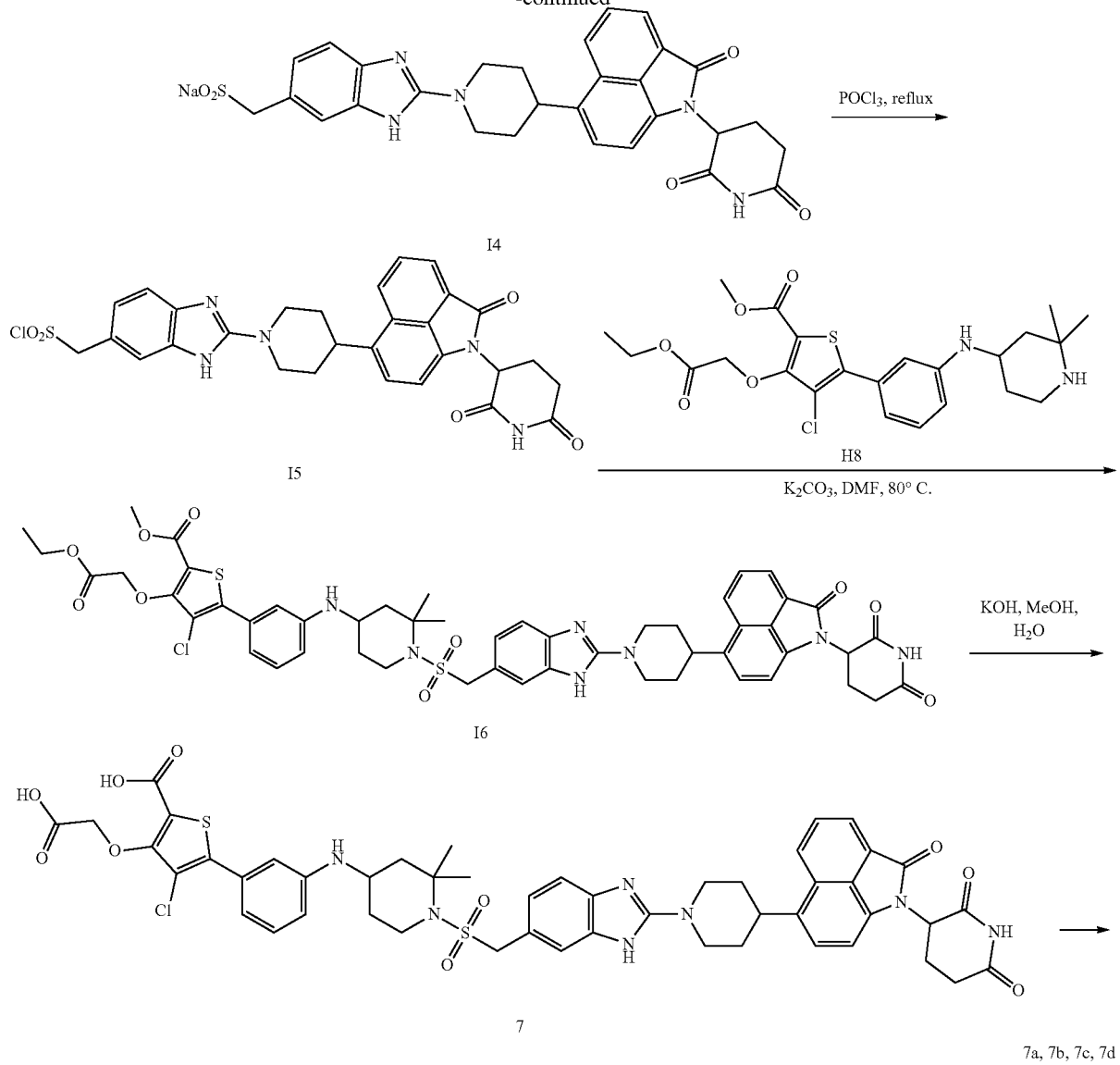

Synthesis of intermediate I2: A solution of a mixture of I1 (1.66 g, 10.0 mmol), intermediate C (3.64 g, 10.0 mmol), and potassium dihydrogen phosphate (0.07 g, 0.5 mmol) in n-butanol (20 mL) was stirred at 90° C. for 10 h. The reaction mixture was cooled to room temperature and quenched with 50 mL saturated sodium bicarbonate solution. The crude mixture was extracted with 80 mL ethyl acetate. The solvent was removed under reduced pressure and the crude product was purified using flash chromatography to afford 12 (2.06 g, 41.6%).

Synthesis of intermediate 13: To a solution of 12 (1.88 g, 3.81 mmol) in 50 mL carbon tetrachloride were added N-bromosuccinimide (0.82 g, 4.6 mmol) and 2,2'-azobis(2-methylpropionitrile) (16.4 mg, 0.1 mmol). The reaction mixture was stirred at 90° C. for 5 h before it was cooled to room temperature and quenched with water. The crude mixture was extracted with carbon tetrachloride and dried over anhydrous sodium sulfate. The solvent was removed under reduced pressure and the crude product was purified using flash chromatography to afford 13 (1.87 g, 85.8%).

Synthesis of intermediate 15: A solution of 14 (1.21 g, 2.09 mmol) in 20 mL phosphorus oxychloride was stirred at reflux condition for 6 h. After the reaction mixture was cooled to room temperature, it was poured into a precooled saturated sodium bicarbonate solution. The crude mixture was extracted with ethyl acetate and dried over anhydrous sodium sulfate. The solvent was removed under reduced pressure and the crude product was purified using flash chromatography to afford 15 (1.02 g, 82.4%).

Synthesis of intermediate 16: To a solution of 15 (0.59 g, 1.0 mmol) in 10 mL N,N-dimethylformamide were added 2 (0.48 g, 1.0 mmol) and potassium carbonate (0.28 g, 2.0 mmol). The reaction mixture was stirred at 80° C. for 16 h before it was cooled to room temperature and quenched with 100 mL water. The crude mixture was extracted with ethyl acetate. The organic layer was washed with brine and dried over anhydrous sodium sulfate. The solvent was removed under reduced pressure and the crude product was purified using flash chromatography to afford 16 (0.67 g, 64.9%).

Synthesis of Compound 7: To a solution of 16 (0.41 g, 0.4 mmol) in tetrahydrofuran (3 mL) and water (1 mL) was added lithium hydroxide monohydrate (8.0 mmol). The reaction mixture was stirred at room temperature for 5 h and quenched with 2 M hydrochloric acid solution to afford a pale-yellow precipitation as crude product. After filtration, the crude product was purified using preparative HPLC (acetonitrile: 0.1% formic acid aqueous solution) to afford Compound 7 (0.33 g, 83.8%).

4 Stereoisomers 7a, 7b, 7c, and 7d were isolated via SFC resolution of Compound 7.

Synthesis of Compound 8 and its 4 stereoisomers 8a, 8b, 8c, and 8d: followed the synthesis of Compound 7 and its 4 isomers.

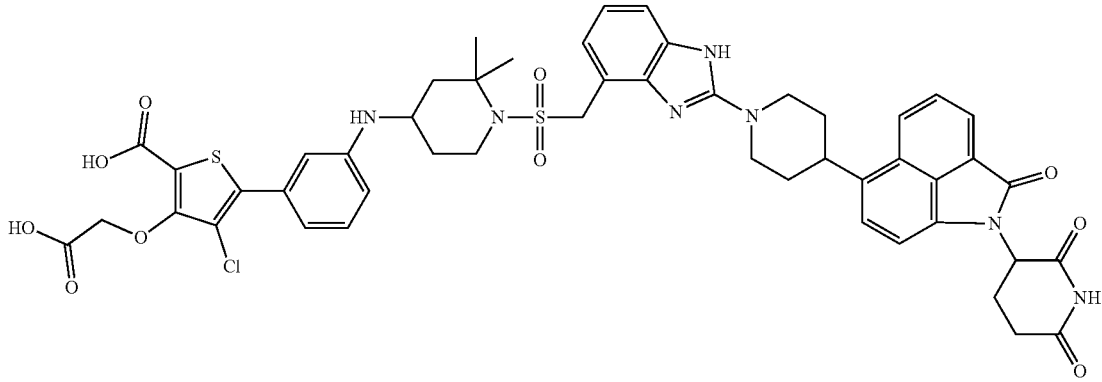

Synthesis of Compound 9 and its 4 stereoisomers 9a, 9b, 9c, and 9d

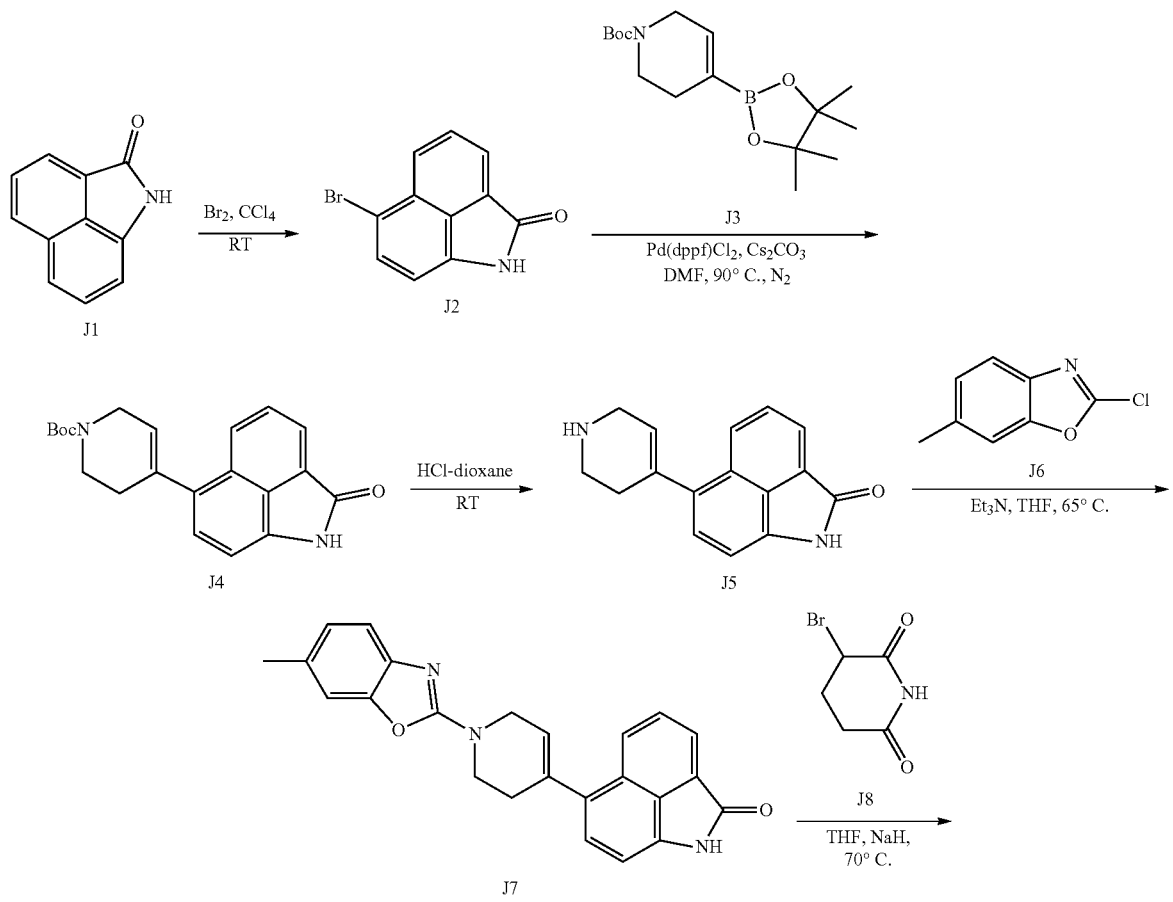

-continued
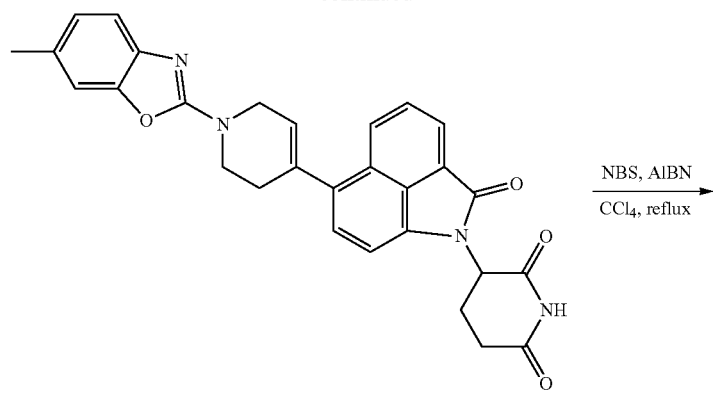
J9
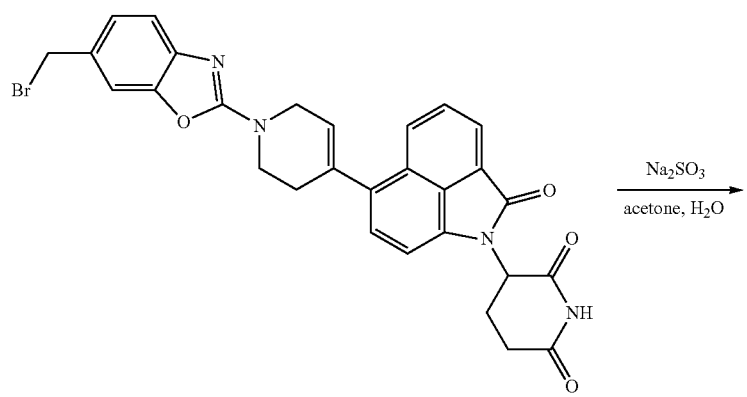
J10
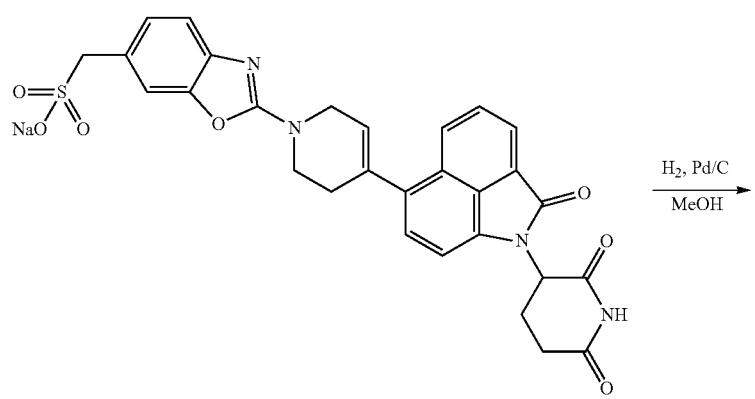
J11

-continued

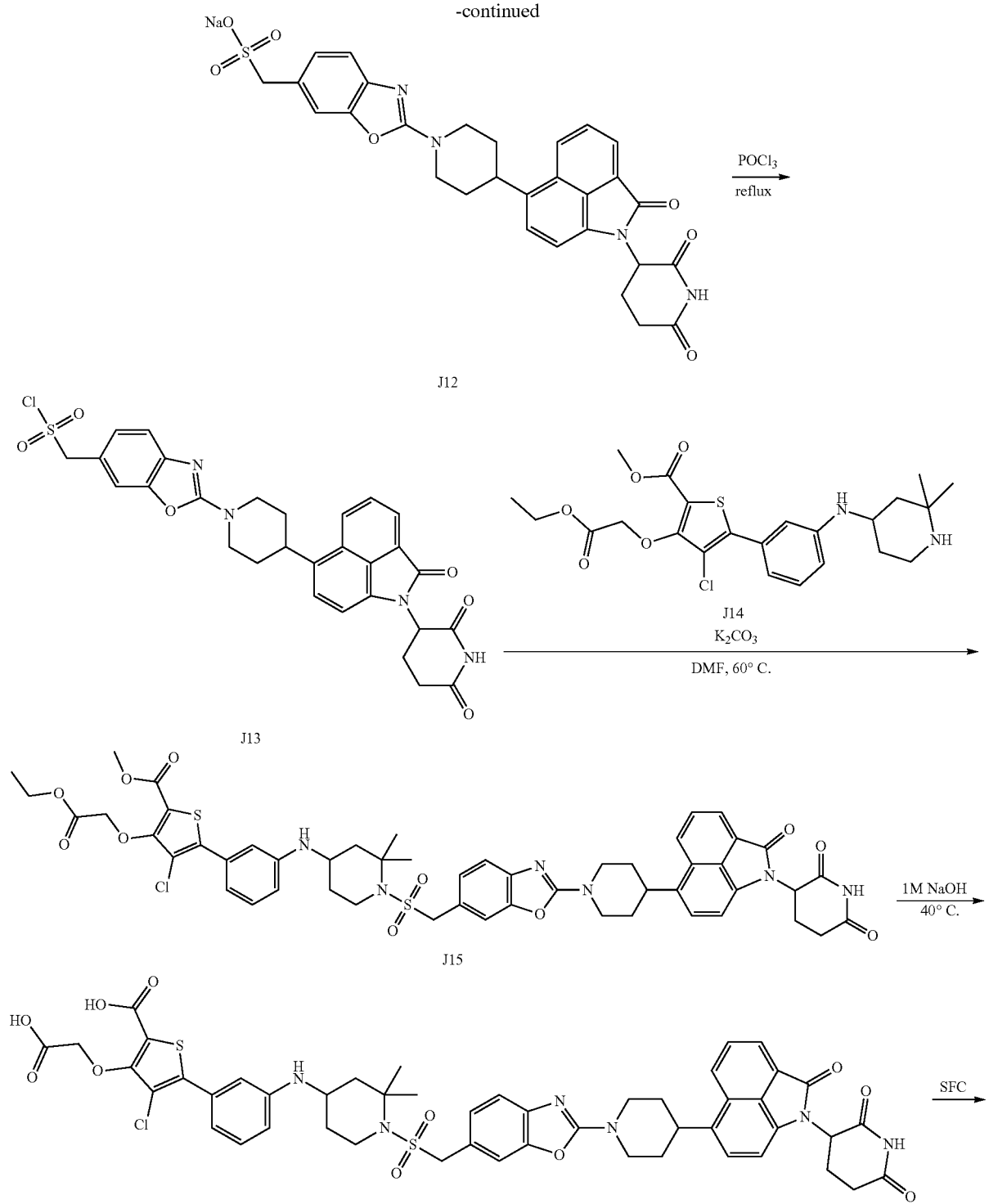

Synthesis of J2: At room temperature, a solution of J1 (20 g, 118 mmol) in 1000 mL carbon tetrachloride was added bromine (22.7 g, 142 mmol) dropwise. The reaction mixture was stirred for 16 h before quenched with saturated sodium sulfite solution. The crude mixture was purified via filtration and the residue was resuspended in water. The crude mixture was stirred at room temperature for another 30 min, and purified again via filtration to afford J2 (28 g, 95%).

Synthesis of J4: In an inert atmosphere, a solution of J2 (20 g, 80.64 mmol), J3 (37.38 g, 121 mmol), Pd(dppf)Cl$_2$ (6.37 g, 8.7 mmol), and cesium carbonate (78.82 g, 242 mmol) in 100 mL N,N-dimethylformamide was stirred at 90° C. for 15 h. The reaction mixture was cooled to room temperature before quenched with 1000 mL water. The crude mixture was extracted with ethyl acetate. The organic layer was washed with brine and dried over anhydrous sodium sulfate. The solvent was removed under reduced pressure and the crude product was purified using flash chromatography to afford J4 (24 g, 85%).

Synthesis of J5: A solution of J4 (14 g, 40 mmol) in 100 mL 4 M hydrochloric acid in 1,4-dioxane solution was stirred overnight at room temperature. The solvent was removed under reduced pressure and the crude product was purified using flash chromatography to afford J5 (9 g, 90%).

Synthesis of J7: To a solution of J5 (6 g, 24 mmol) in 300 mL tetrahydrofuran were added triethylamine (7.3 g, 72 mmol) and J6 (4.8 g, 28.8 mmol). The reaction mixture was stirred at 65° C. for 15 h before it was cooled to room temperature. The solvent was removed to afford a colorless oil, which was washed with water and extracted with ethyl acetate. The organic layer was dried over anhydrous sodium sulfate, and the crude product was purified using flash chromatography to afford J7 (7.7 g, 85%).

Synthesis of J9: In an inert atmosphere, a solution of J7 (7.62 g, 20 mmol) in 100 mL anhydrous tetrahydrofuran was stirred at 0° C. Sodium hydride (8 g, 200 mmol, 60% kerosene) was added portionwise and the reaction mixture was stirred at room temperature for 30 min. J8 (19.2 g, 100 mmol) in anhydrous tetrahydrofuran (20 mL) was added dropwise to the reaction mixture. The abovementioned mixture was stirred at 70° C. for 3 h and cooled to room temperature. Water was used to quench the reaction and the crude mixture was extracted with ethyl acetate. The organic layer was dried over anhydrous sodium sulfate. The solvent was removed under reduced pressure and the crude product was purified using flash chromatography to afford J9 (4.92 g, 50%).

Synthesis of J10: In an inert atmosphere, a solution of A9 (4.92 g, 10 mmol) in 50 mL carbon tetrachloride were added N-bromosuccinimide (2.135 g, 12 mmol) and 2,2'-azobis(2-methylpropionitrile) (16.4 mg, 0.1 mmol), and the reaction mixture was stirred at 90° C. for 5 h before it was cooled to room temperature and quenched with water. The crude mixture was extracted with carbon tetrachloride and dried over anhydrous sodium sulfate. After filtration, the solvent was removed under reduced pressure and the crude product was purified using flash chromatography to afford J10 (3.43 g, 60%).

Synthesis of J11: To a solution of J10 (3.43 g, 6 mmol) in 100 mL acetone an aqueous solution of sodium sulfite (907 mg, 7.2 mmol) (100 mL) was added. The reaction mixture was heated to reflux for 5 h before it was cooled to room temperature. The solvent was removed to afford J11 (2.71 g, 76%).

Synthesis of J12: To a solution of J11 (2.7 g, 4.54 mmol) in 50 mL methanol was added 500 mg Pd/C (10 wt %), and the reaction mixture was stirred at room temperature for 17 h in hydrogen atmosphere. The reaction mixture was filtered and concentrated to afford J12 (2.44 g, 90%).

Synthesis of J13: A solution of J12 (2.44 g, 4.09 mmol) in 30 mL phosphorus oxychloride was heated at reflux for 6 h before it was cooled to room temperature. The reaction mixture was poured into a precooled saturated sodium bicarbonate solution. The crude mixture was extracted with ethyl acetate three times. The combined organic layer was dried over anhydrous sodium sulfate. After filtration and concentration, the crude product was purified using flash chromatography to afford J13 (1.94 g, 80%).

Synthesis of J15: To a solution of J13 (1.94 g, 3.27 mmol) in 30 mL N,N-dimethylformamide were added J14 (2.36 g, 4.9 mmol) and potassium carbonate (1.36 g, 9.82 mmol). The reaction mixture was stirred at 80° C. for 16 h before it was cooled to room temperature and quenched with brine. The crude product was extracted with ethyl acetate (20 mL). The organic layer was dried over anhydrous sodium sulfate. The solvent was removed under reduced pressure and the crude product was purified using flash chromatography to afford J15 (2.88 g, 85%).

Synthesis of Compound 9: To a solution of J15 (2.88 g, 2.78 mmol) in 20 mL tetrahydrofuran was added 1 M sodium hydroxide solution (20 mL). The reaction mixture was stirred at 40° C. for 18 h before it was cooled to room temperature. The reaction mixture was concentrated to a minimal amount before 1 M hydrochloric acid solution was added until pH reached 5.0. After filtration and concentration, Compound 9 was obtained as a pale-yellow solid (2.35 g, 85%).

4 Stereoisomers 9a, 9b, 9c, and 9d were isolated via SFC resolution of Compound 9.

Compound 10 and its 4 stereoisomers 10a, 10b, 10c, and 10d were obtained in the same way: 2-chloro-4-methylbenzoxazole instead of 2-chloro-6-methyl-benzoxazole.

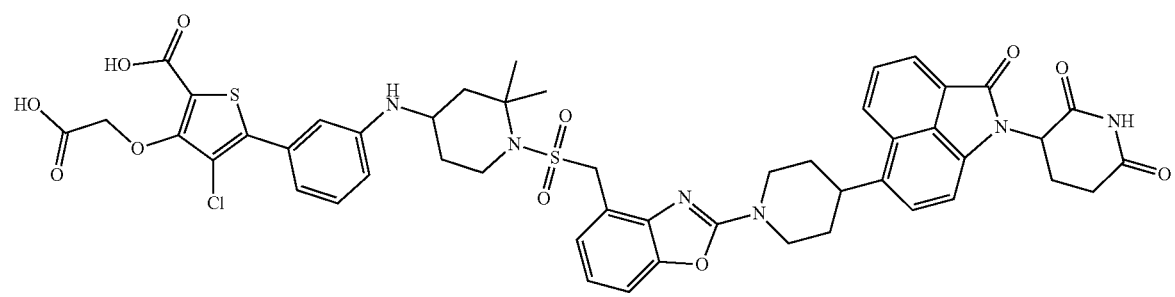

10

Synthesis of Compound 11 and its 4 stereoisomers 11a, 11b, 11c, and 11d
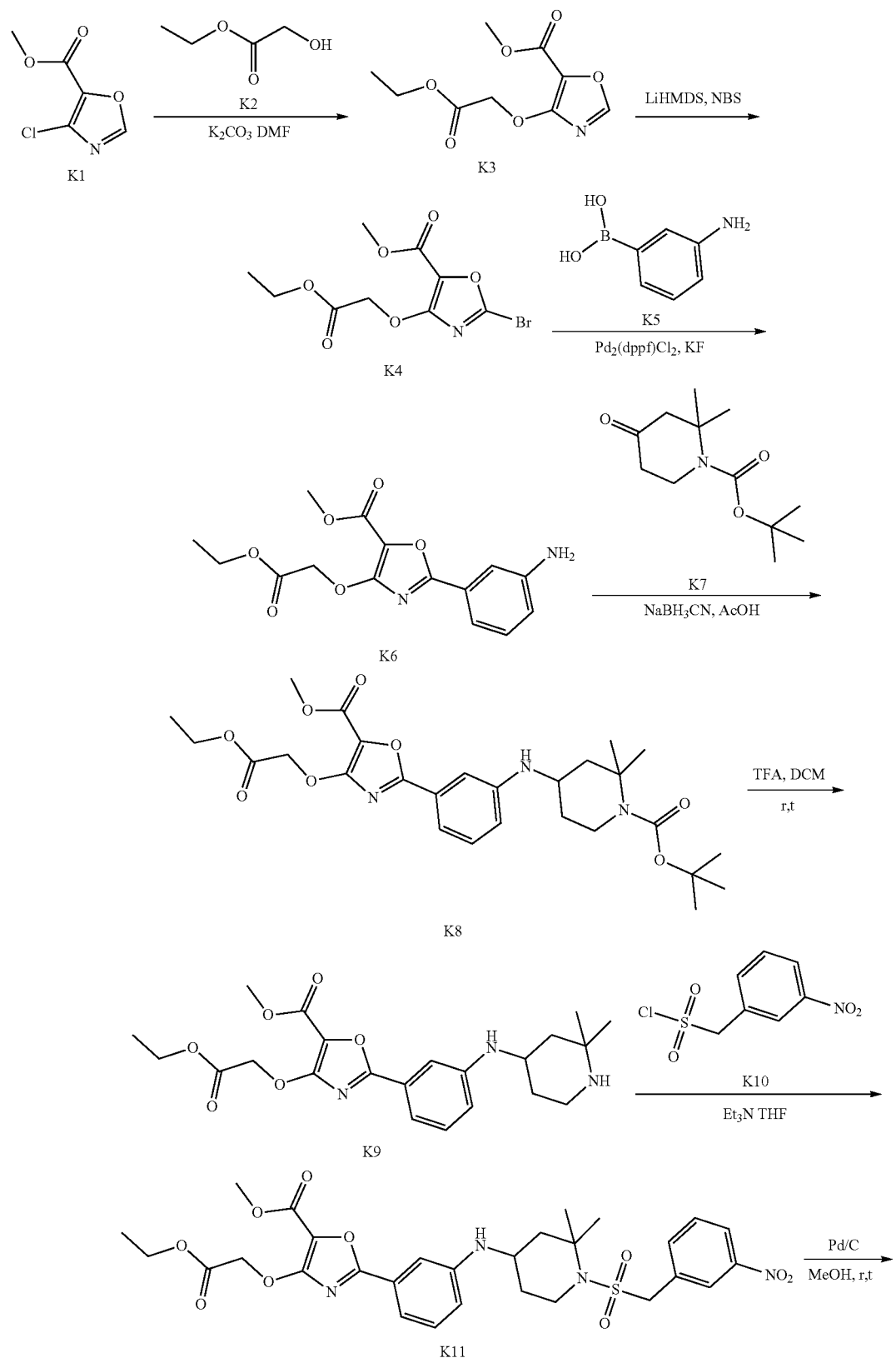

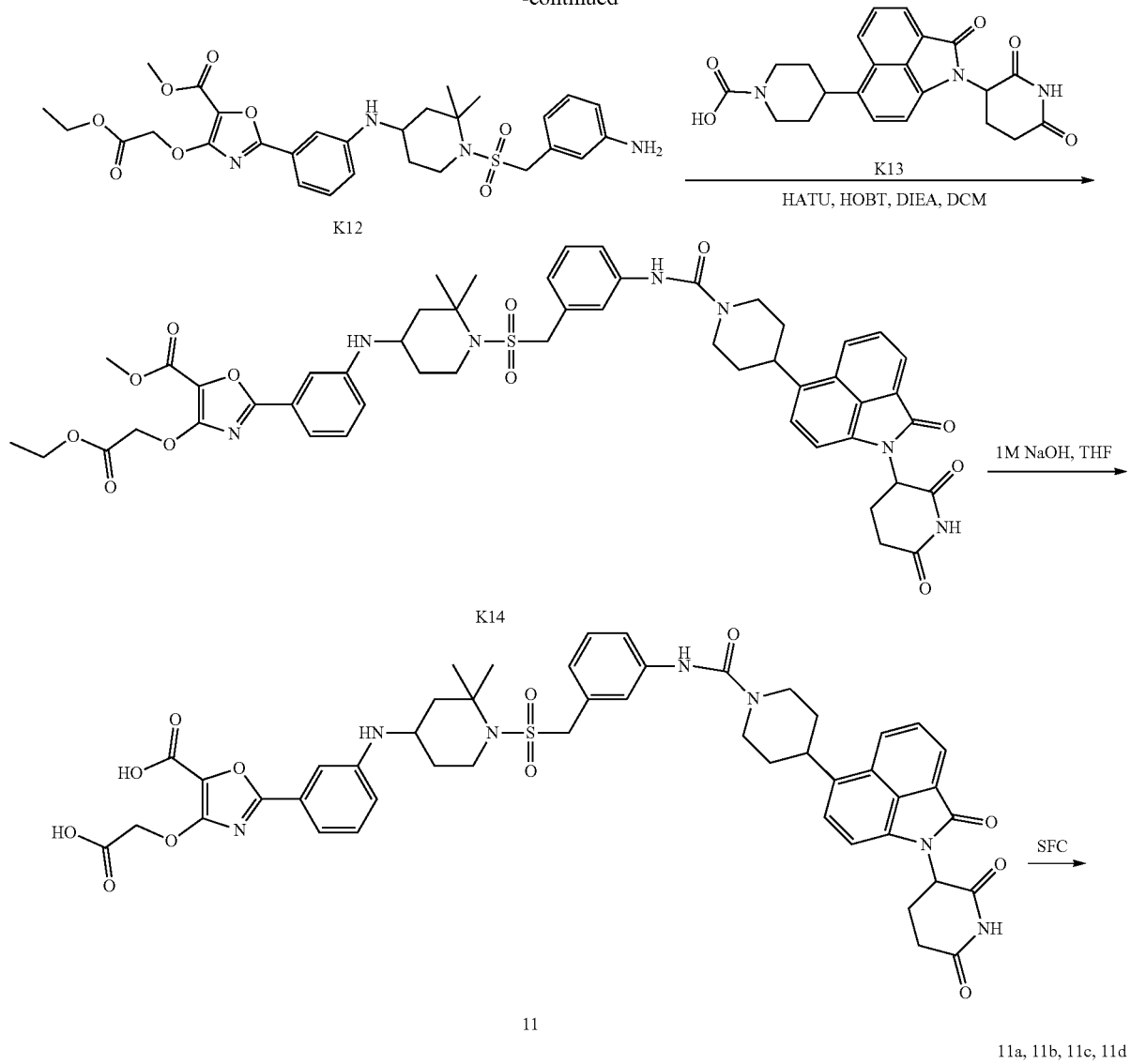

Synthesis of K3: To a solution of K1 (16.1 g, 100 mmol) and K2 (12.48 g, 120 mmol) in 100 mL N,N-dimethylformamide was added potassium carbonate (41.4 g, 300 mmol). The reaction mixture was stirred at 80° C. for 16 h before it was cooled to room temperature. 1000 mL water was used to quench the reaction, and the crude mixture was extracted with ethyl acetate. The organic layer was washed with brine and dried over anhydrous sodium sulfate. After filtration and concentration, the crude product was purified using flash chromatography to afford K3 (19.5 g, 85%). 10 Synthesis of K4: In an inert atmosphere, a solution of K3 (19.5 g, 85 mmol) in 200 mL tetrahydrofuran was stirred dropwise at 0° C. Subsequently, a tetrahydrofuran solution of lithium bis (trimethylsilyl)amide (170 mL, 1 M) was slowly added and the reaction mixture was stirred for 30 min at 0° C. Then N-bromosuccinimide (22.7 g, 127.5 mmol) was added portionwise and the reaction mixture was stirred at room temperature for another 18 h. Water was used to quench the reaction, and the crude mixture was extracted with ethyl acetate three times. The combined organic layer was dried over anhydrous sodium sulfate, and the crude product was purified using flash chromatography to afford K4 (18.3 g, 70%).

Synthesis of K6: In an inert atmosphere, a solution of K4 (18.3 g, 59.5 mmol) and K5 (12.2 g, 89.3 mmol) in 100 mL 1,4-dioxane were added Pd(dppf)Cl$_2$ (4.39 g, 6.0 mmol) and potassium fluoride (10.4 g, 178.5 mmol). The reaction mixture was stirred at 80° C. for 16 h before it was cooled to room temperature. Then the solvent was removed, and the residue was washed with brine and extracted with ethyl acetate. The organic layer was dried with anhydrous sodium sulfate, and the crude product was purified using flash chromatography to afford K6 (15.3 g, 80%).

Synthesis of K8: To a solution of K6 (15.3 g, 47.6 mmol) and K7 (16.2 g, 71.4 mmol) in 150 mL ethanol was added acetic acid (285 mg, 4.76 mmol). The reaction mixture was stirred at 80° C. for 3 h. Sodium cyanide borohydride (5.98 g, 95.2 mmol) was added dropwise and stirred at 80° C. for 5 h. The reaction mixture was poured into an ice-water mixture (30 mL) and extracted with dichloromethane (120 mL). The organic layer was washed with brine and dried over anhydrous sodium sulfate. The solvent was removed under reduced pressure and the crude product was purified using flash chromatography to afford K8 (16.4 g, 65%).

Synthesis of K9: A solution of K8 (16.4 g, 30.8 mmol) in 160 mL dichloromethane and 160 mL trifluoroacetic acid was stirred at room temperature for 19 h. Ground sodium hydroxide solid was used to neutralize the reaction mixture until pH=8.0. The organic layer was extracted with dichloromethane and dried over anhydrous sodium sulfate. The solvent was removed under reduced pressure to afford K9 (12 g, 90%).

Synthesis of K11: To a solution of K9 (12 g, 27.8 mmol) in 120 mL tetrahydrofuran were added triethylamine (8.4 g, 83.4 mmol) and K10 (9.8 g, 41.7 mmol) under an ice bath. The reaction mixture was stirred at room temperature for 16 h. The solvent was removed under reduced pressure and the crude product was purified using flash chromatography to afford K11 (14.1 g, 80%).

Synthesis of K12: To a solution of K11 (14 g, 22.2 mmol) in 140 mL methanol was added Pd/C (10 wt %, 2.8 g). Three freeze-pump-thaw cycles were used to maintain an $H_2$ atmosphere and the reaction mixture was stirred at room temperature for 8 h before it was eventually filtered. The filtrate was concentrated to afford K12 (11.3 g, 85%).

Synthesis of K14: To a solution of K13 (9.2 g, 22.5 mmol), HATU (6.84 g, 18 mmol), and 1-hydroxybenzotriazole (2.8 g, 21 mmol) in 200 mL dichloromethane was added N,N-diisopropylethylamine (5.8 g, 45 mmol). The reaction mixture was stirred at room temperature for 1 h. Subsequently, K12 (9 g, 15 mmol) was added and the reaction mixture was stirred at room temperature for 20 h before water was used to quench the reaction. The crude mixture was extracted with ethyl acetate and the combined organic layer was dried over anhydrous sodium sulfate. The solvent was removed under reduced pressure and the crude product was purified using flash chromatography to afford K14 (10.4 g, 70%).

Synthesis of Compound 11: To a solution of K14 (9.9 g, 10 mmol) in 150 mL tetrahydrofuran was added 150 mL 1 M sodium hydroxide solution. The reaction mixture was stirred at 40° C. for 18 h before 2 M hydrochloric acid was added. The pale-yellow precipitation was isolated through filtration as a crude product. The crude product was purified using preparative HPLC to afford Compound 11 (8.1 g, 86%).

4 Stereoisomers 11a, 11b, 11c, and 11d were isolated via SFC resolution of Compound 11.

Compound 12 and Compound 13 and their stereoisomers 12a, 12b, 12c, 12d, 13a, 13b, 13c, and 13d were synthesized in the same way.

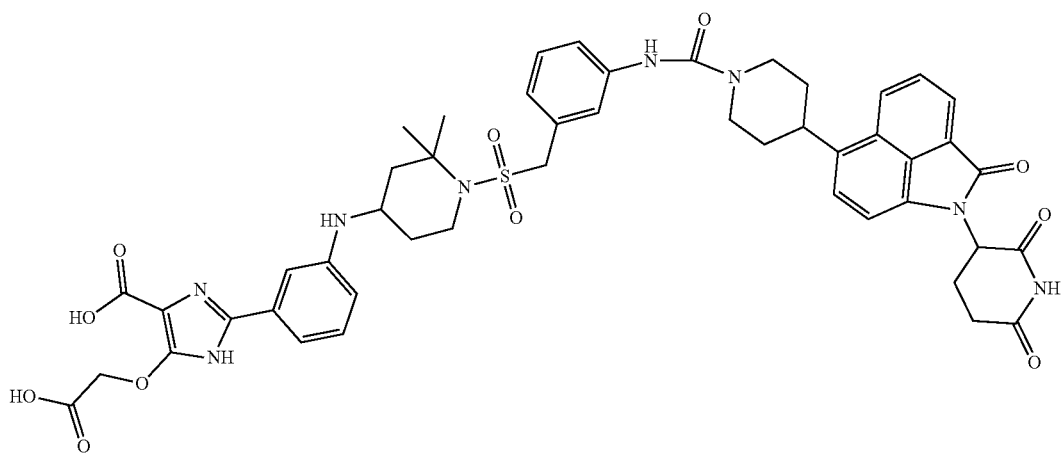

12

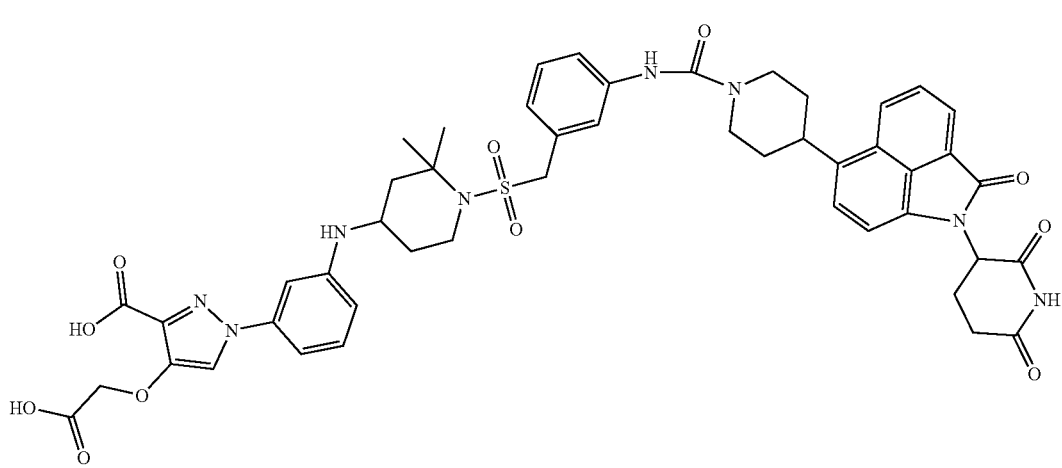

13

Compound 14 and its 4 stereoisomers 14a, 14b, 14c, and 14d were obtained in the same way as Compound 4, 6 and their stereoisomers.
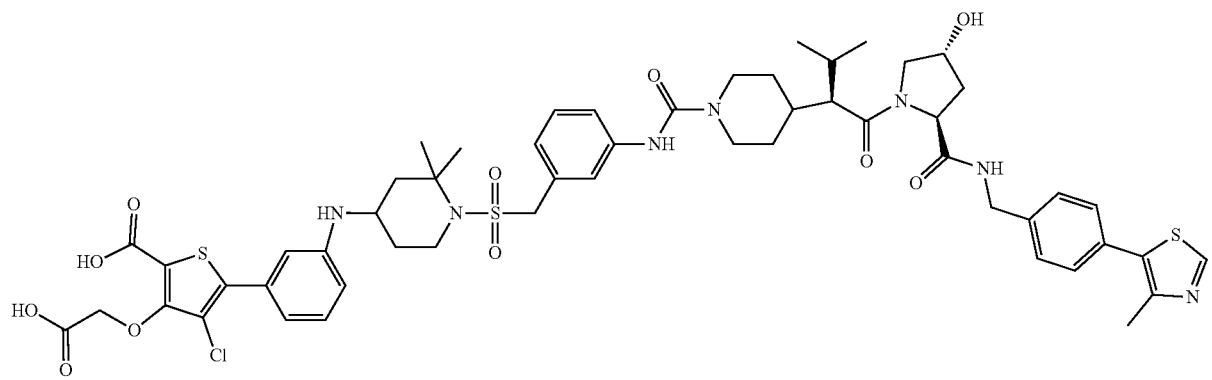
14
Compound 15 and its 4 stereoisomers 15a, 15b, 15c, and 15d were obtained in the same way as Compound 11 and its stereoisomers.
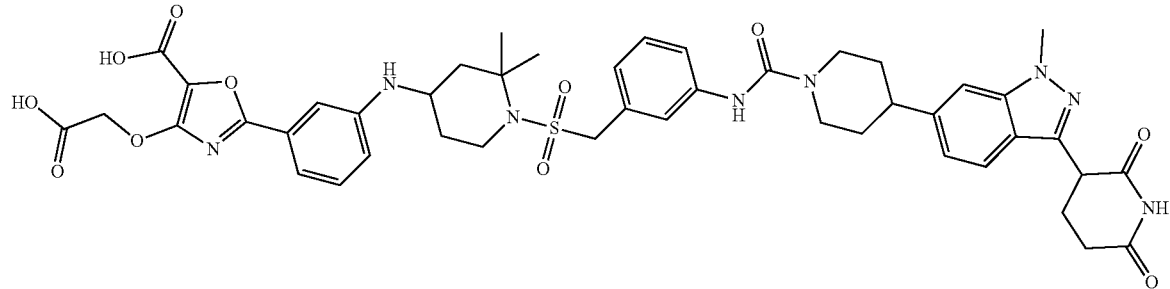
15
Compound 16 and its 4 stereoisomers 16a, 16b, 16c, and 16d were obtained in the same way as Compound 4, 6 and their stereoisomers.
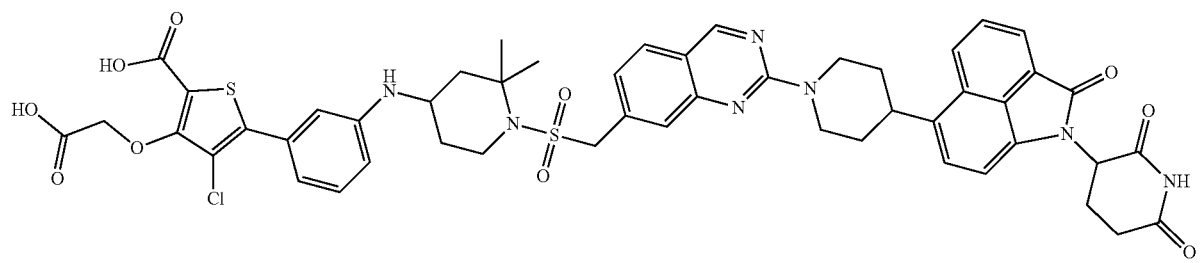
16

Compound 17 and its 4 stereoisomers 17a, 17b, 17c, and 17d were obtained in the same way as Compound 11 and its stereoisomers.
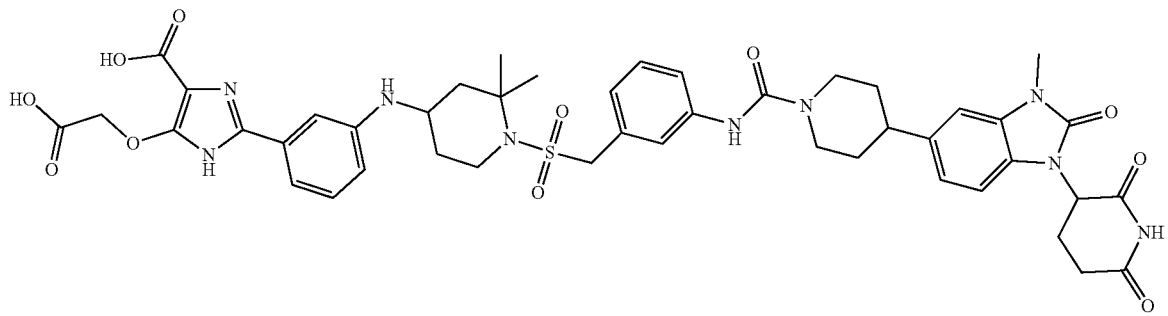
17
Compound 18 and its 4 stereoisomers 18a, 18b, 18c, and Compound 148 were obtained in the same way as Compound 4, 5, and their stereoisomers.
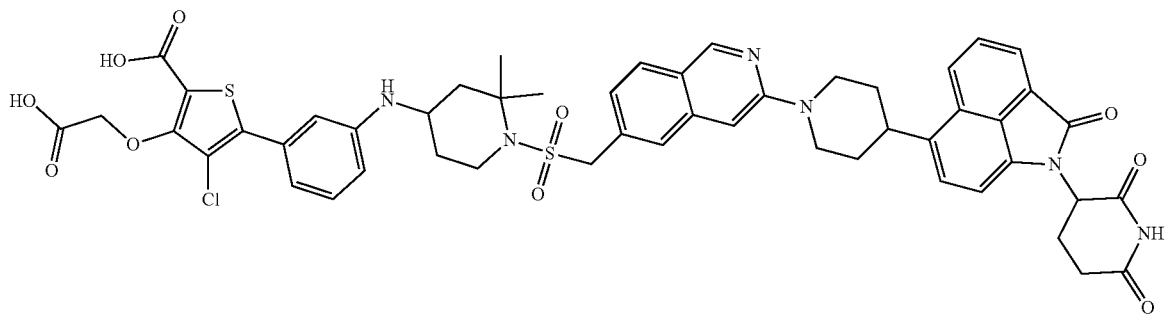
18
Compound 19 and its 4 stereoisomers 19a, 19b, 19c, and 19d were obtained in the same way as Compound 11 and its stereoisomers.
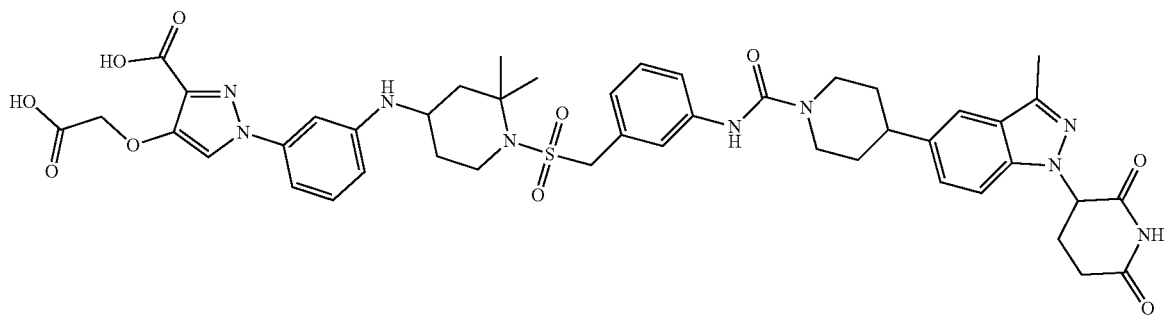
19

Compound 20 and its 4 stereoisomers 20a, 20b, 20c, and 20d were obtained in the same way as Compound 1 and its stereoisomers.
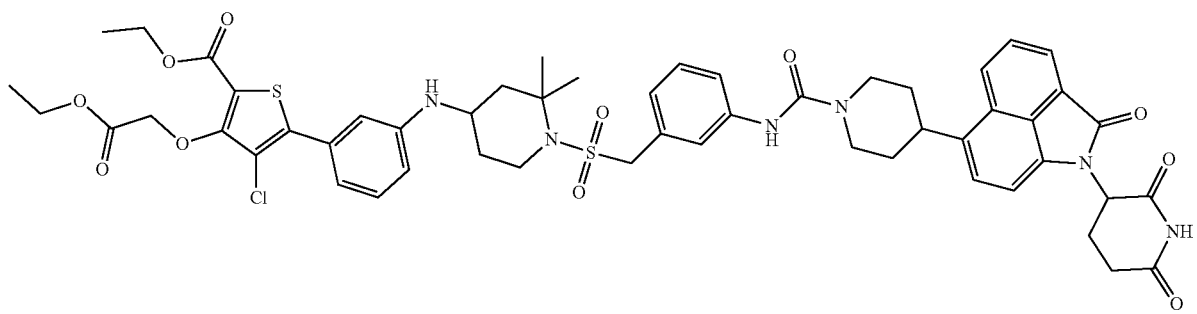
20
Synthesis of Compound 21 and its 4 Stereoisomers 21a, 21b, 21c, and 21d
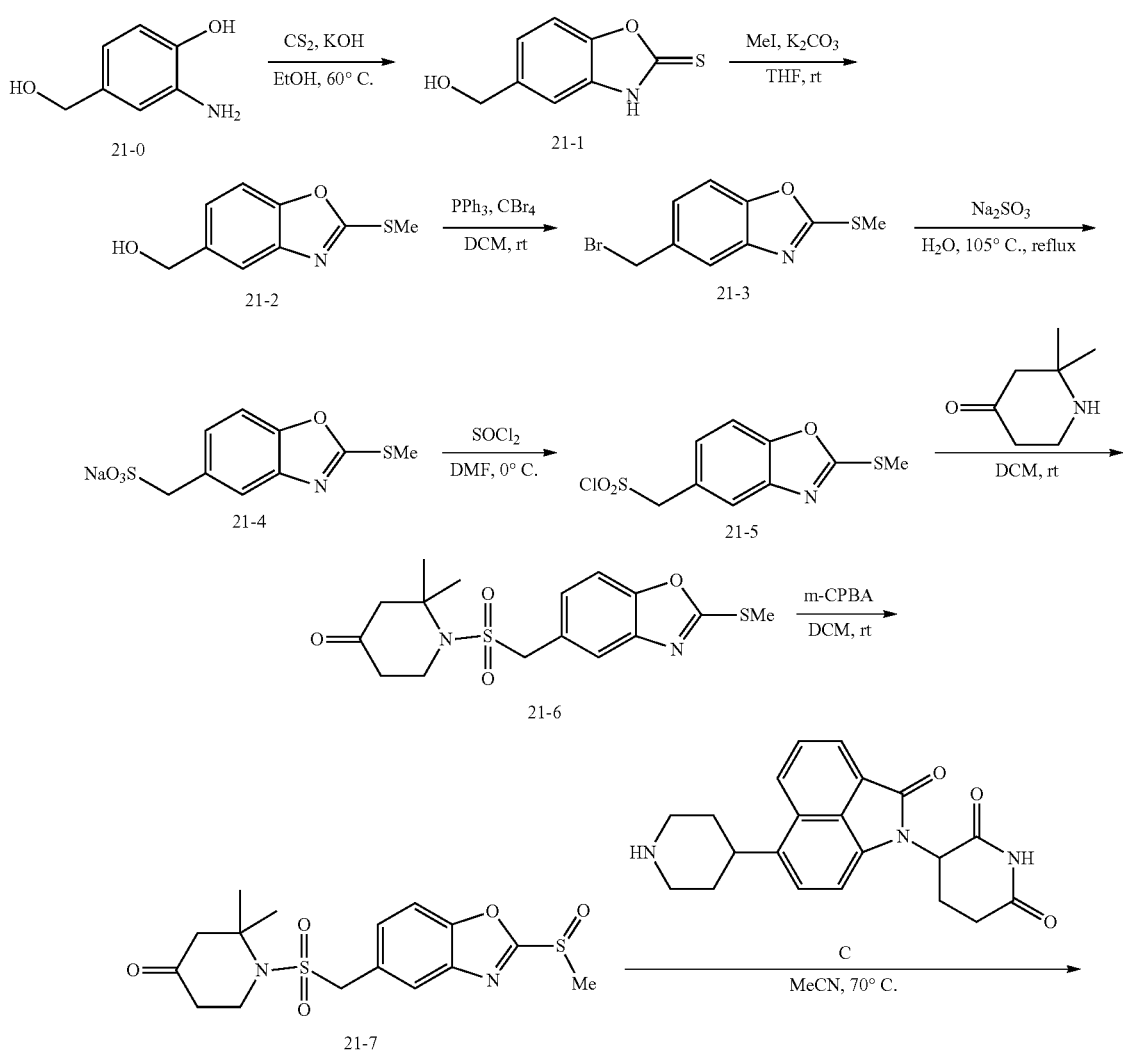

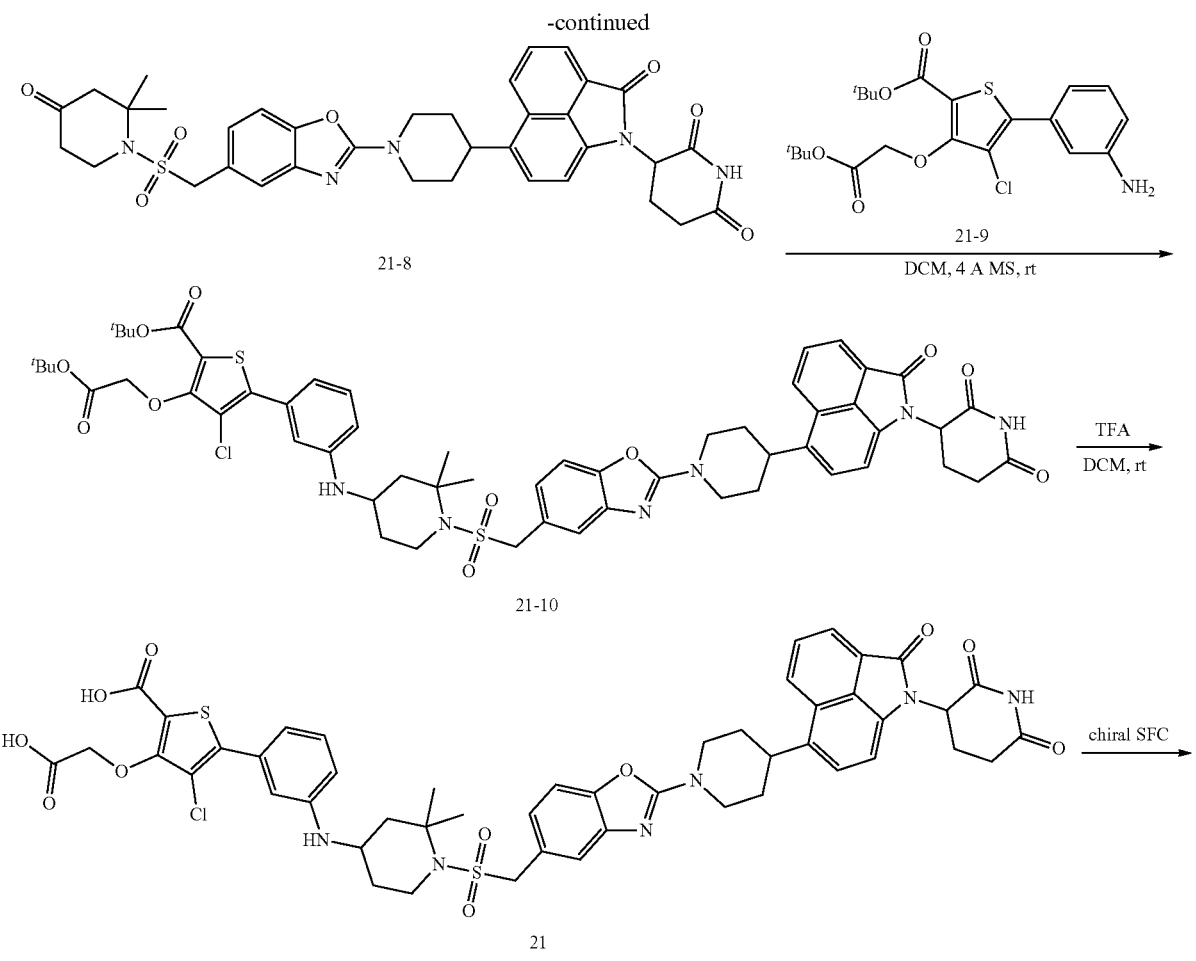

Synthesis of 21-1: To a solution of 21-0 (4.17 g, 30 mmol) in ethanol (30 mL) was added potassium hydroxide (2.02 g, 36 mmol). The mixture was stirred at room temperature for 5 min before carbon disulfide (2.2 mL, 36 mmol) was added via a syringe and the reaction mixture was stirred at 60° C. for 2 h. The mixture was cooled to room temperature, poured to ice water, and acidified with 2 M hydrochloric acid aqueous solution. The precipitate was collected by filtration and dried under vacuum to afford 21-1 (4.2 g, 77%) as an off-white solid.

Synthesis of 21-2: To a suspension of 21-1 (3.60 g, 19.87 mmol) in anhydrous tetrahydrofuran (100 mL) was added anhydrous potassium carbonate (3.30 g, 23.84 mmol). The mixture was stirred at room temperature for 10 min and iodomethane (1.48 mL, 23.84 mmol) was added. The mixture was continuously stirred at room temperature for 12 h. Water was added and the mixture was extracted with ethyl acetate. The combined organic layer was washed with brine, dried over sodium sulfate, and concentrated under reduced pressure to afford 21-2.

Synthesis of 21-3: To an ice-water bath cooled mixture of 21-2 (4.88 g, 25 mmol) and triphenylphosphine (7.87 g, 30 mmol) in anhydrous dichloromethane (100 mL), was added carbon tetrabromide (9.95 g, 30 mmol) portion-wise. The mixture was allowed to warm to room temperature and stirred for 2 h. The mixture was concentrated and purified using flash chromatography to afford 21-3 (5.25 g, 81%) as a white solid.

Synthesis of 21-4: A mixture of 21-3 (6.6 g, 25.57 mmol) and sodium thiosulfate (3.87 g, 30.68 mmol) in water (66 mL) was heated to reflux for 3 h. The mixture was cooled to room temperature, frozen in a dry-ice/acetone bath, and lyophilized under vacuum. The resulting solid was washed with dichloromethane and dried under vacuum to afford 21-4 as a white solid.

Synthesis of 21-5: In an inert atmosphere, to a suspension of crude 21-4 (5.63 g, mmol) in anhydrous N,N-dimethylformamide (20 mL) was added thionyl dichloride (10 mL, 137.85 mmol) dropwise in an ice-water cooled bath. The mixture was stirred at this temperature for 15 min and was poured carefully into an ice-water mixture. The resulting white solid was filtered and dried under vacuum to afford 21-5 (2.98 g, 54%).

Synthesis of 21-6: A suspension of 2,2-dimethylpiperidin-4-one hydrochloride (2.55 g, 15.6 mmol) and 4-dimethylaminopyridine (3.97 g, 32.5 mmol) in anhydrous dichloromethane (50 mL) was stirred in an inert atmosphere for 10 min at 0° C. A suspension of 21-5 (3.61 g, 13 mmol) in anhydrous dichloromethane (40 mL) was added slowly and the mixture was stirred at room temperature for 2 h. The reaction mixture was concentrated and purified by silica gel column chromatography to afford 21-6 (4.32 g, 90%) as a white solid.

Synthesis of 21-7: To a solution of 21-6 (4.0 g, 10.86 mmol) in anhydrous dichloromethane (100 mL) was added 85% 3-chloroperoxybenzoic acid (3.31 g, 16.29 mmol) portion-wise at 0° C. The mixture was allowed to warm to room temperature and stirred for 3 h. The reaction mixture was diluted with dichloromethane, and washed with aqueous sodium thiosulfate, aqueous sodium bicarbonate, and brine. The organic layer was dried over sodium sulfate. The solvents were evaporated under reduced pressure and the residue was purified by silica gel column chromatography to afford 21-7 (3.76 g, 90%) as a colorless solid.

Synthesis of 21-8: To a mixture of 21-7 (577 mg, 1.5 mmol) and C (477 mg, 1.8 mmol) in anhydrous acetonitrile (15 mL) was added sodium bicarbonate (630 mg, 7.5 mmol). The mixture was stirred at 70° C. for 12 h. The mixture was cooled to room temperature and diluted with ethyl acetate. The mixture was washed with brine and dried over sodium sulfate. The solvents were evaporated under reduced pressure and the residue was purified by silica gel column chromatography to afford 21-8 (820 mg, 80%) as a yellow solid.

Synthesis of 21-10: To an ice-bath cooled mixture of 21-8 (480 mg, 0.70 mmol), 21-9 (462 mg, 1.05 mmol), and diphenyl phosphate (350 mg, 1.4 mmol) in dichloromethane (60 mL) was added 4A MS (4.0 g). The mixture was stirred at this temperature for 30 min. Diethyl 1,4-dihydro-2,6-dimethyl-3,5-pyridinedicarboxylate (266 mg, 1.05 mmol) was added to the reaction mixture and the mixture was gradually warmed to room temperature and stirred overnight. The mixture was filtered and the residue was washed with dichloromethane. The combined extracts were concentrated and purified using flash chromatography to afford 21-10 (504 mg, 65%) as a yellow foam.

Synthesis of Compound 21: To an ice-water bath cooled solution of 21-10 (400 mg, 0.36 mmol) in dichloromethane (10 mL) was added trifluoroacetic acid (2.5 mL) dropwise. The reaction mixture was stirred at room temperature for 8 h. The reaction mixture was evaporated under reduced pressure and the residue was purified using preparative HPLC to afford 21 (trifluoroacetate salt, 345 mg, 85%) as a yellow solid.

4 stereoisomers 21a, 21b, 21c, and 21d were isolated via SFC resolution of Compound 21.

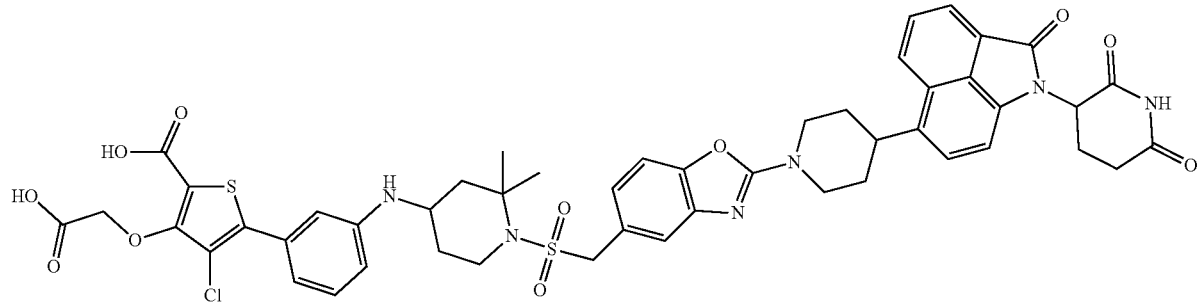

21

Compound 22 and its 4 stereoisomers 22a, 22b, 22c, and 22d were obtained in the same way as Compound 3 and its stereoisomers.

Compound 23 and its 4 stereoisomers 23a, 23b, 23c, and 23d were obtained in the same way as Compound 9 and its stereoisomers.

Compound 24 and its 4 stereoisomers 24a, 24b, 24c, and 24d were obtained in the same way as Compound 16 and its stereoisomers.

Compound 25 and its 4 stereoisomers 25a, 25b, 25c, and 25d were obtained in the same way as Compound 9 and its stereoisomers.

Compound 26 and its 4 stereoisomers 26a, 26b, 26c, and 26d were obtained in the same way as Compound 9 and its stereoisomers.

Compound 27 and its 4 stereoisomers 27a, 27b, 27c, and 27d were obtained in the same way as Compound 16 and its stereoisomers.

Compound 28 and its 4 stereoisomers 28a, 28b, 28c, and 28d were obtained in the same way as Compound 16 and its stereoisomers.

Compound 29-35, 39-43, 47-51, and their stereoisomers were obtained in the same way as Compound 1, 3, and their stereoisomers.

Synthesis of Compound 37 and its 4 Stereoisomers 37a, 37b, 37c, and 37d

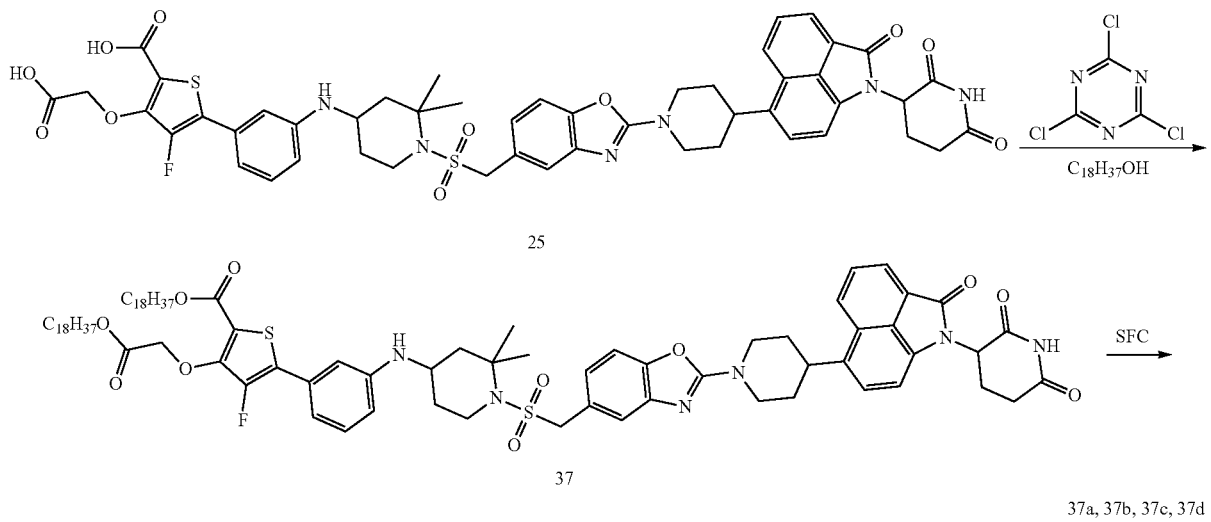

To a solution of Compound 25 (1.0 equiv.) in dichloromethane (0.01 M) were added melamine (0.7 equiv.) and triethylamine (2.0 equiv.). The reaction mixture was stirred at room temperature for 30 min. Then octadecyl alcohol was added and the reaction mixture was stirred for another 2 h. The reaction mixture was extracted with ethyl acetate. The combined organic layer was washed with brine, hydrochloric acid aqueous solution (1 M), and sodium hydroxide aqueous solution (2 M). The organic layer was separated and dried over anhydrous magnesium sulfate to afford the crude product. After column chromatography purification, 37 was obtained (68% yield).

4 stereoisomers 37, 37b, 37c, and 37d were isolated via SFC resolution of Compound 37.

Compound 38, 45, 46, and their stereoisomers were obtained in the same way as Compound 37 and its 4 stereoisomers.

Synthesis of Intermediate L

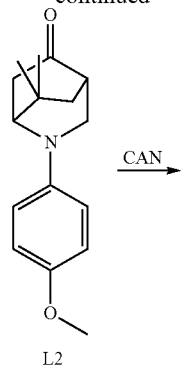

-continued

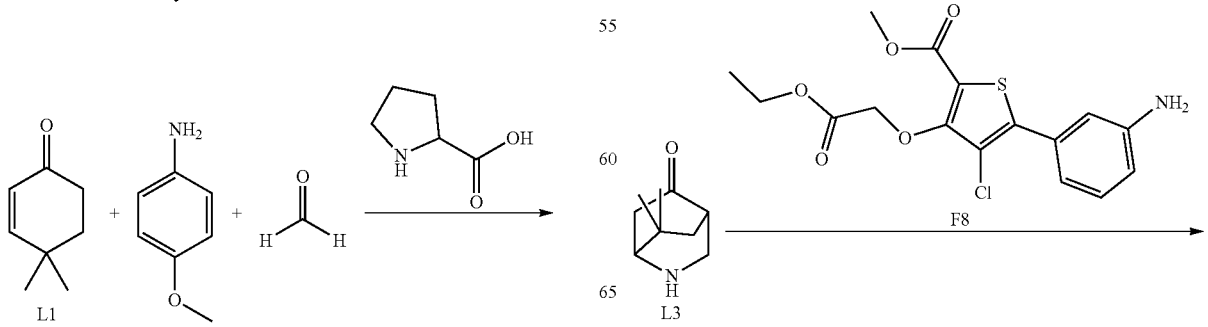

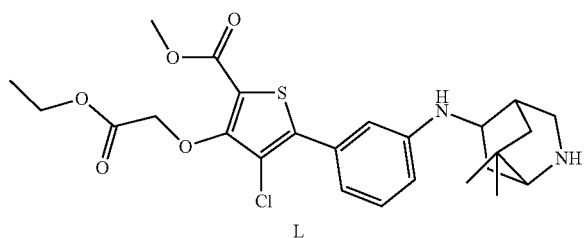

L

Synthesis of Intermediate L2

To a solution of L1 (5 g, 40.26 mmol) in dimethyl sulfoxide (30 mL) were added p-methoxyaniline (2.73 g, 22.14 mmol), formaldehyde (0.60 g, 20.13 mmol) and proline (0.70 g, 6.04 mmol) at room temperature. The reaction mixture was stirred for 16 h before it was washed with brine extracted with dichloromethane. The organic layers were combined and dried over anhydrous sodium sulfate. The filtrate was concentrated under reduced pressure, and the residue was further purified using a rapid chromatography column (SiO2, PE/EA=2/1) to afford L2 as a yellow solid (2.5 g, yield 23.94%).

Synthesis of Intermediate L3

To a solution of L2 (1.5 g, 5.78 mmol) in acetonitrile (10 mL) and water (3 mL) was added ammonium cerium nitrate (9.51 g, 17.34 mmol) at room temperature. The reaction mixture was stirred at room temperature for 1 h. The reaction mixture was extracted with dichloromethane and water, and the organic layers were combined and washed with brine. The solvent was removed under reduced pressure, and the residue was further purified by reverse phase column to afford L3 as a yellow solid (1 g, yield 67.70%).

To a solution of L3 (600 mg, 0.40 mmol) and F8 (178 mg, 0.48 mmol) in ethanol (15 mL) was added acetic acid (121 mg, 2.02 mmol). The reaction mixture was stirred at 80° C. for 3 h before it was cooled to room temperature. Sodium cyanoborohydride (133 mg, 2.02 mmol) was added portion-wise, and the reaction mixture was stirred at 80° C. for another 5 h. The reaction mixture was added dropwise to an ice-water mixture (30 mL) and extracted three times with dichloromethane (120 mL). The organic layer was washed three times with brine, dried over anhydrous sodium sulfate, and concentrated under reduced pressure to afford an oil. The oil was eventually purified using flash chromatography to afford L (163 mg, 80.7%).

Synthesis of Compound 36 and its 4 Stereoisomers 36a, 36b, 36c, and 36d

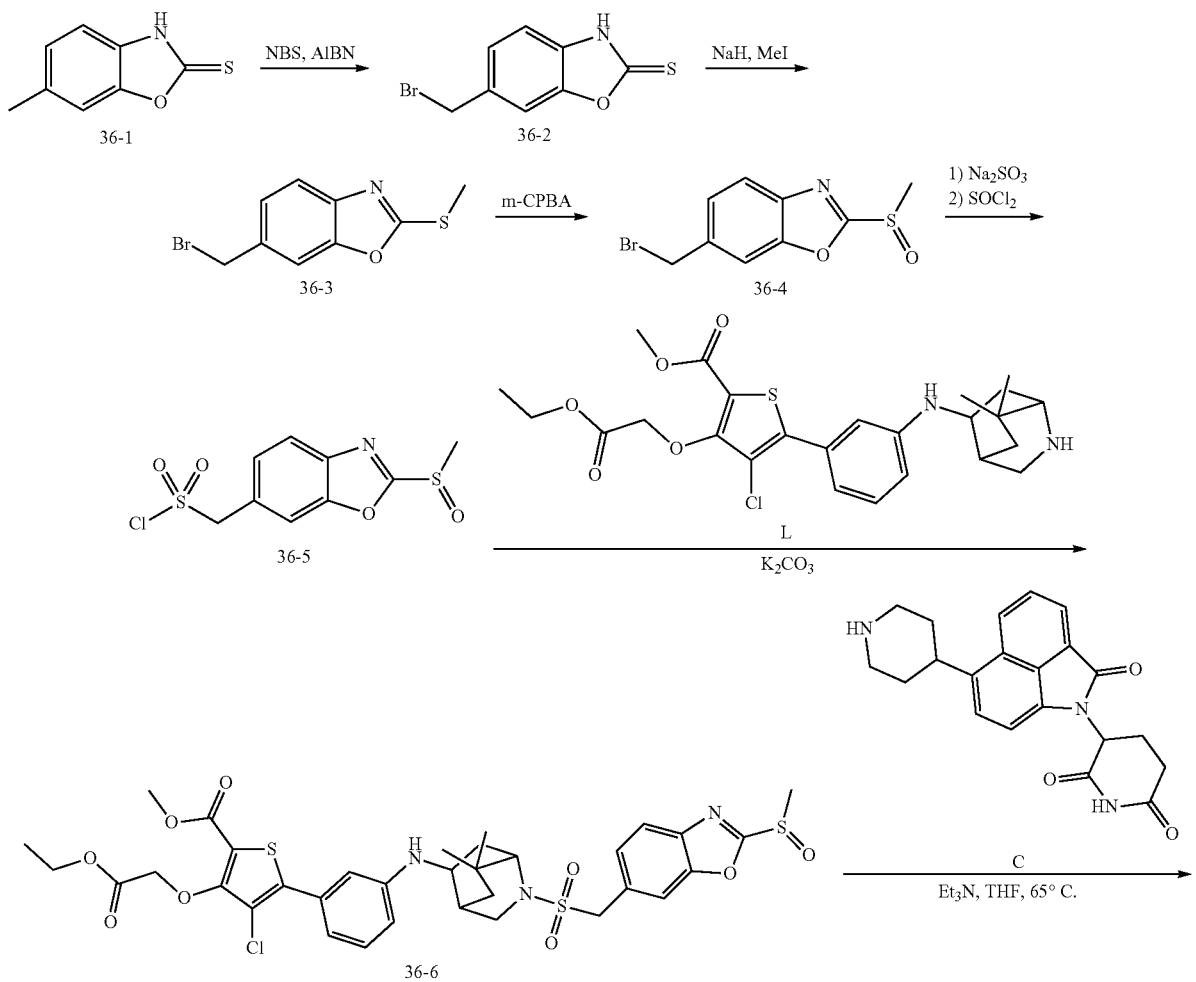

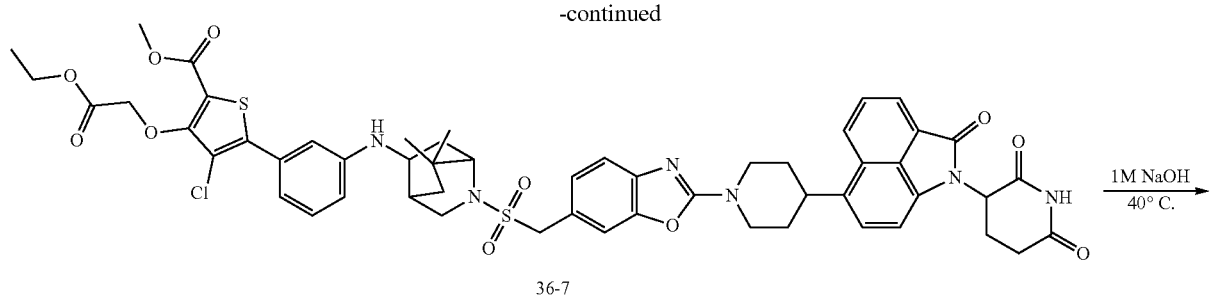

36-7

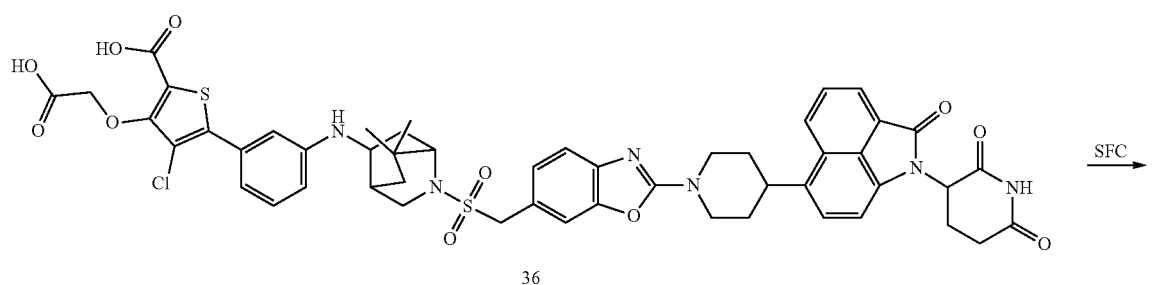

36

36a, 36b, 36c, 36d

Synthesis of 36-2: To a solution of 36-1 (10 mmol, 1.0 equiv.) in 50 mL carbon tetrachloride were added N-bromosuccinimide (12 mmol, 1.2 equiv.) and 2,2'-azobis(2-methylpropionitrile) (0.04 mmol) in an inert atmosphere. The reaction mixture was stirred at 90° C. for 5 h before it was cooled to room temperature. The reaction was quenched with water and the crude mixture was extracted with carbon tetrachloride. The combined organic layer was dried over anhydrous sodium sulfate. The solvent was removed under reduced pressure and the crude product was purified using flash chromatography to afford 36-2 as a yellow solid (60% yield).

Synthesis of 36-3: To a solution of 36-2 (6 mmol, 1.0 equiv.) in 50 mL N,N-dimethylformamide were added sodium hydride (40 wt %, 480 mg, 12 mmol) and iodomethane (1.41 g, 1.7 equiv.). The reaction mixture was stirred for 5 h before it was quenched by saturated ammonium chloride solution. The crude mixture was extracted 3 times with ethyl acetate, and the combined organic layer was dried over anhydrous sodium sulfate. The solvent was removed under reduced pressure and the crude product was purified using flash chromatography to afford 36-3 (95% yield).

Synthesis of 36-4: To a solution of 36-3 (5 mmol, 1.0 equiv.) in 10 mL dichloromethane was added 3-chloroperoxybenzoic acid (5.5 mmol, 1.1 equiv.). The reaction mixture was stirred at room temperature for 0.5 h before it was quenched by aqueous sodium bicarbonate solution. The mixture was extracted 3 times with ethyl acetate, and the combined organic layer was dried over anhydrous sodium sulfate. The solvent was removed under reduced pressure and the crude product was purified by silica gel column chromatography to afford 36-4 (100% yield).

Synthesis of 36-5: To a solution of 36-4 (5 mmol, 1.0 equiv.) in 100 mL acetone was added sodium sulfite (7.2 mmol, 1.4 equiv.) in water (100 mL). The reaction mixture was heated to reflux for 5 h. The reaction mixture was cooled to room temperature and filtrated to afford 36-5'. Then 36-5' was dissolved in 30 mL dimethyl sulfoxide and the solution was heated to reflux for 6 h. The reaction solution was cooled to room temperature before it was poured into a precooled saturated sodium bicarbonate. The crude mixture was extracted with ethyl acetate and the organic layer was dried over anhydrous sodium sulfate. The solvent was removed under reduced pressure and the crude product was purified by silica gel column chromatography to afford 36-5 (1.8 g, 60%).

Synthesis of 36-6: To a solution of 36-5 (1.78 g, 3.0 mmol) in 30 mL N,N-dimethylformamide were added L (4.5 mmol, 1.5 equiv.) and potassium carbonate (1.36 g, 9.82 mmol) and the reaction mixture was stirred at 80° C. for 16 h. The reaction solution was cooled to room temperature before water was added. The crude mixture was extracted three times with ethyl acetate, and the combined organic layer was dried over anhydrous sodium sulfate. The solvent was removed under reduced pressure and the crude product was purified by silica gel column chromatography to afford 36-6 (85% yield).

Synthesis of 36-7: To a solution of 36-6 (2.4 mmol, 1.0 equiv.) in 30 mL tetrahydrofuran were added triethylamine (7.2 mmol, 3.0 equiv.) and intermediate C (2.88 mmol, 1.2 equiv.). The reaction mixture was stirred at 65° C. for 15 h before it was cooled to room temperature. The solvent was removed under reduced pressure and the residue was purified by silica gel column chromatography to afford 36-7 (85% yield).

Synthesis of Compound 36: To a solution of 36-7 (2.0 mmol, 1.0 equiv.) in 20 mL tetrahydrofuran, was added 1 M sodium hydroxide solution (20 mL). The reaction mixture was stirred at 40° C. for 18 h before it was cooled to room temperature. The reaction mixture was concentrated to a minimal amount before 1 M hydrochloric acid solution was added until pH=5.0. After filtration and concentration, 36 was obtained with an 85% yield.

4 stereoisomers 36a, 36b, 36c, and 36d were isolated via SFC resolution of Compound 36.

Compound 44, 52, 58-74, and their stereoisomers were obtained in the same way as Compound 36 and its stereoisomers.

Synthesis of Compound 75 and its 4 Stereoisomers 36a, 36b, 36c, and 36d
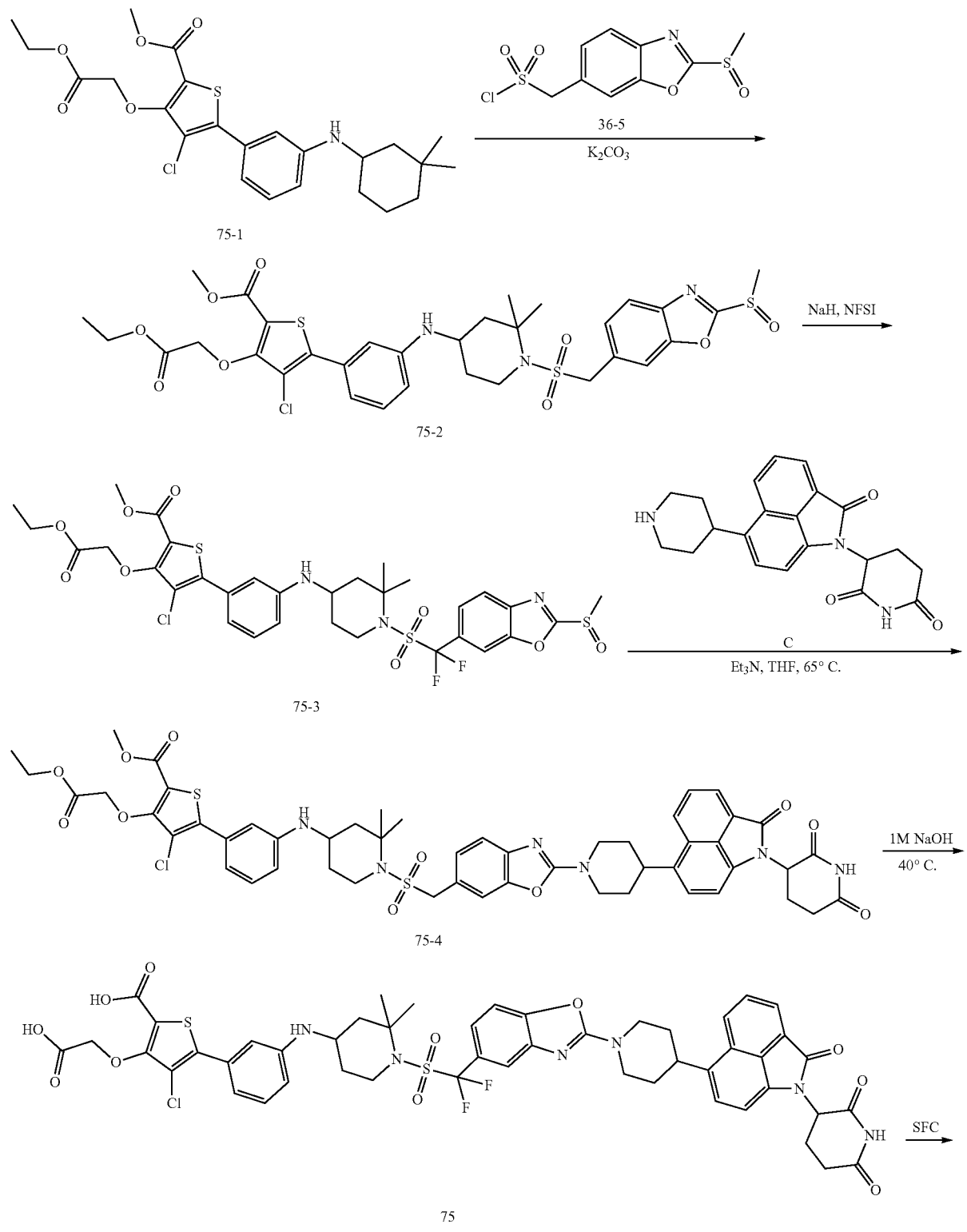

Synthesis of 75-2: To a solution of 75-1 (27.8 mmol, 1.0 equiv.) in 120 mL tetrahydrofuran were added 36-5 (41.7 mmol, 1.5 equiv.) and potassium carbonate (83.4 mmol, 3.0 equiv.). The reaction mixture was stirred at room temperature for 16 h before it was added 300 mL water. The crude mixture was extracted three times with ethyl acetate, and the combined organic layer was washed three times with brine, dried over anhydrous sodium sulfate, and purified by silica gel column chromatography to afford 75-2 (80% yield).

Synthesis of 75-3: To a solution of 75-2 (2.0 mmol, 1.0 equiv.) in 12 mL tetrahydrofuran were added sodium hydride (8.0 mmol, 4.0 equiv.) and N-fluorobenzenesulfonimide (4.17 mmol, 2.1 equiv.) at 0° C. The reaction mixture was stirred at room temperature for 16 h before it was quenched carefully with the addition of 1 M hydrochloric acid aqueous solution. The crude mixture was extracted 3 times with ethyl acetate and the combined organic layer was dried over anhydrous sodium sulfate. The mixture was filtered and concentrated to afford crude 75-3 (60% yield).

Synthesis of 75-4: To a solution of crude 75-3 (1.2 mmol, 1.0 equiv.) in 30 mL tetrahydrofuran were added triethylamine (3.6 mmol, 3.0 equiv.) and intermediate C (1.44 mmol, 1.2 equiv.). The reaction mixture was stirred at 65° C. for 15 h before it was cooled to room temperature. The solvent was removed under reduced pressure and the residue was purified by silica gel column chromatography to afford 75-4 (85% yield).

Synthesis of Compound 75: To a solution of 75-4 (1.0 mmol, 1.0 equiv.) in 20 mL tetrahydrofuran, was added 1 M sodium hydroxide solution (10 mL) and the reaction mixture was stirred at 40° C. for 18 h. 2 M hydrochloric acid aqueous solution was added to the reaction mixture and the precipitation was isolated through filtration as a crude mixture. The crude mixture was purified using preparative HPLC (acetonitrile: 0.1% formic acid aqueous solution) to afford Compound 75 (85% yield).

4 stereoisomers 75a, 75b, 75c, and 75d were isolated via SFC resolution of Compound 75.

Synthesis of Compound 77 and its 4 stereoisomers 77a, 77b, 77c, and 77d: followed the synthesis of Compound 75 and its 4 stereoisomers.

Synthesis of Intermediate M

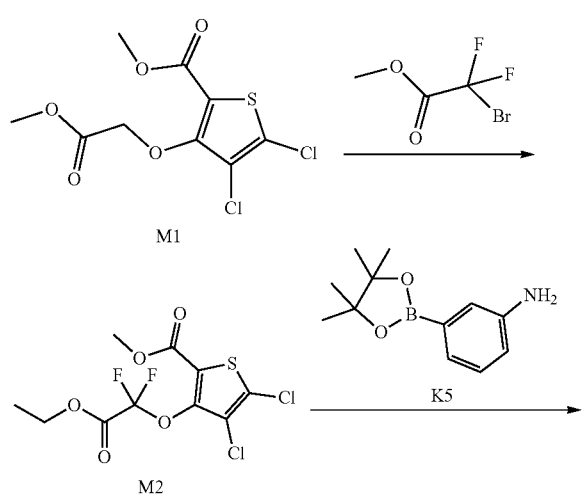

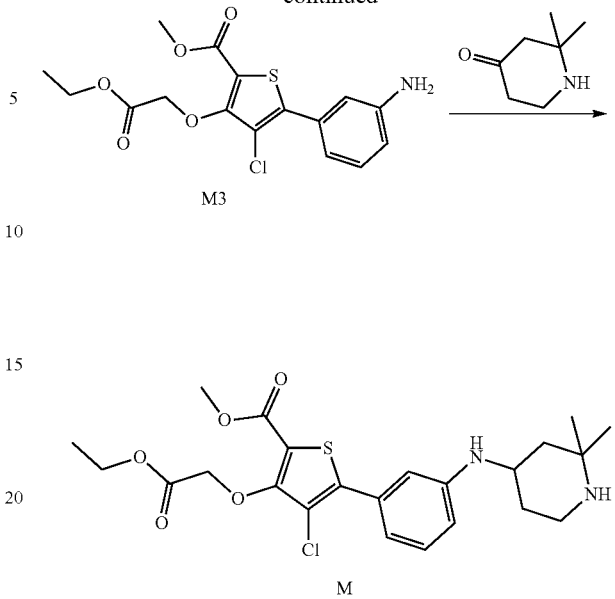

Synthesis of M2: To a solution of M1 (1.0 equiv.) in 1,4-dioxane (0.1 M) were added methyl chlorodifluoroacetate (1.4 equiv.) and sodium hydride (3 equiv.) at −78° C. The reaction mixture was stirred at 105° C. for 4 h before it was added ammonium chloride aqueous solution. The crude mixture was extracted with ethyl acetate and the combined organic layer was dried over anhydrous sodium sulfate. The solvent was removed under reduced pressure and the crude product was purified by silica gel column chromatography to afford M2 (85% yield).

Synthesis of M3: To a solution of M2 (6 mmol, 1.0 equiv.) and K5 (9 mmol, 1.5 equiv.) in 1,4-dioxane (0.6 M) were added Pd(dppf)Cl$_2$ (0.2 equiv.) and potassium fluoride (3.0 equiv.). The reaction mixture was stirred at 80° C. for 16 h before it was cooled to room temperature. The reaction mixture was concentrated to a minimal amount before water was added. The crude mixture was extracted with ethyl acetate and the combined organic layer was dried over anhydrous sodium sulfate. The solvent was removed under reduced pressure and the residue was purified by silica gel column chromatography to afford M3 (80% yield).

Synthesis of M: To a solution of M3 (4.7 mmol, 1.0 equiv.) and 2,2-dimethylpiperidin-4-one (7.1 mmol, 1.5 equiv.) in 15 mL ethanol was added acetic acid (285 mg, 4.76 mmol). The reaction mixture was stirred at 80° C. for 5 h before sodium cyanide borohydride (9.5 mmol, 2.0 equiv.) was added portion-wise. The reaction mixture was stirred at 80° C. for another 5 h before an ice-water mixture (30 mL) was added. The crude mixture was extracted with dichloromethane (120 mL) and the combined organic layer was washed with brine and dried over anhydrous sodium sulfate. The solvent was removed under reduced pressure and the residue was purified by silica gel column chromatography to afford M (65% yield).

Compound 76 and its 4 stereoisomers 76a, 76b, 76c, and 76d were obtained in the same way as Compound 75 and its 4 stereoisomers.

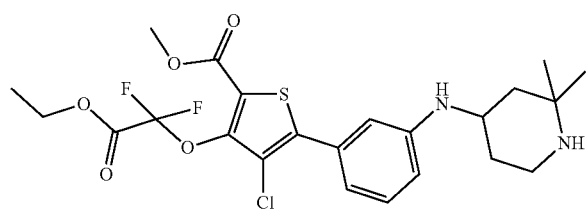
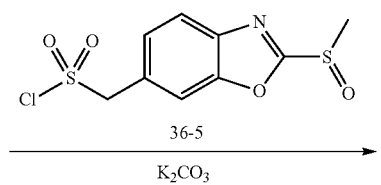
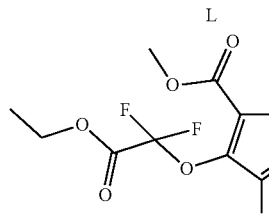
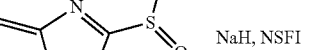
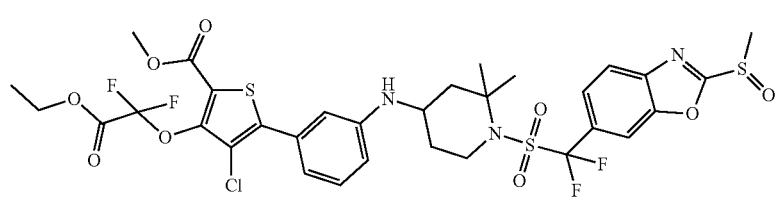
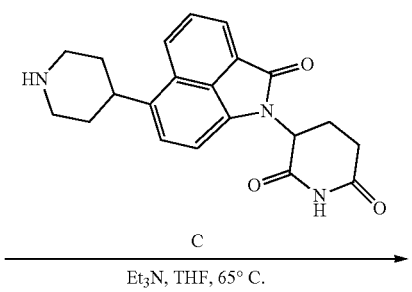
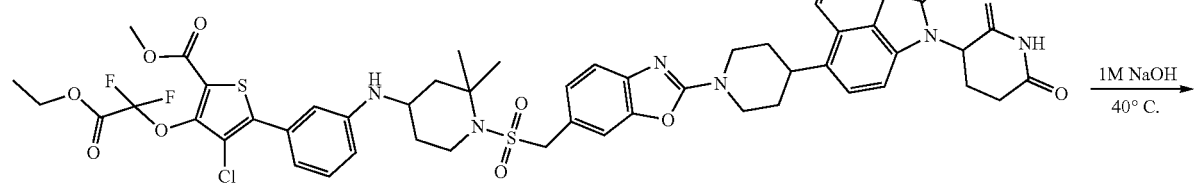
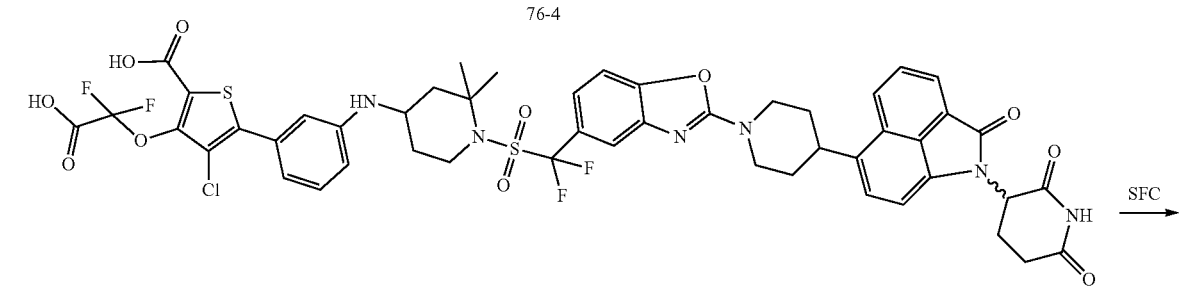

Compound 78 and its 4 stereoisomers 78a, 78b, 78c, and 78d were obtained in the same way as Compound 75 and its 4 stereoisomers.

Synthesis of Compound 79-83, 91, 94, 96-99, 106, 108, 145, and their stereoisomers: Compound 9 method was followed.

Synthesis of Compound 92, 93, 95, 100-105, 107, and their stereoisomers: Compound 5 method was followed.

Synthesis of Compound 109-144, 146, and their stereoisomers: Compound 5 method was followed.

Synthesis of Compound 147-150, and their stereoisomers: Compound 7 method was followed.

Synthesis of Compound 151, 151a, 151b, 151c, and 151d: Compound 21 method was followed.

According to the preparation method described in this article, the following compounds were prepared using appropriate starting materials and intermediates, and if necessary, appropriate protective chemical methods. The structures were confirmed by MS and 1H-NMR.

| compounds | Structure | MS [M + H⁺] | ¹H-NMR |
|---|---|---|---|
| 1 | 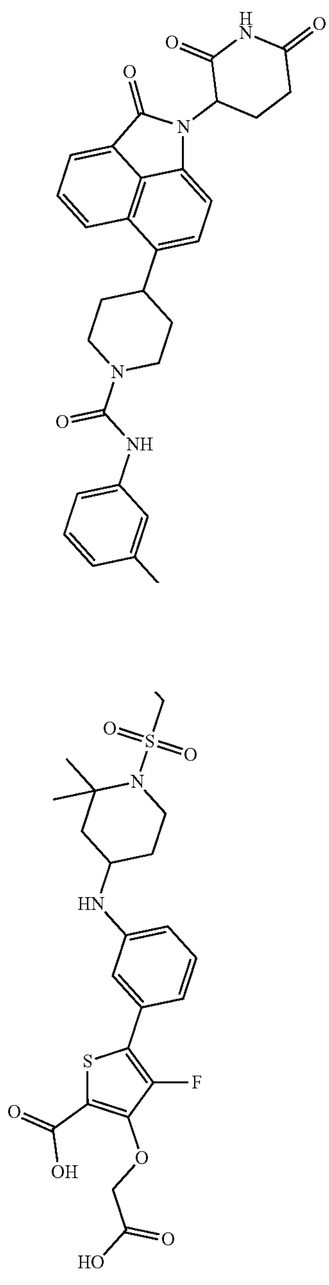 | 981.29 | ¹H NMR (400 MHZ, DMSO-d6): δ 11.09 (s, 1H), 8.64 (s, 1H), 8.46 (d, J = 8.5 Hz, 1H), 8.08 (d, J = 7.0 Hz, 1H), 7.88-7.77 (m, 1H), 7.55 (s, 1H), 7.44 (d, J= 8.3 Hz, 1H), 7.34 (d, J = 7.5 Hz, 1H), 7.20 (dd, J = 15.2, 7.3 Hz, 1H), 7.15 (d, J = 7.9 Hz, 1H), 7.05 (d, J = 7.5 Hz, 1H), 6.95 (d, J = 7.7 Hz, 1H), 6.83 (s, 1H), 6.77 (d, J = 7.4 Hz, 1H), 6.66 (d, J = 8.3 Hz, 1H), 5.41 (dd, J = 12.6, 5.3 Hz, 1H), 4.80 (s, 2H), 4.33 (d, J = 13.7 Hz, 4H), 4.22 (d, J = 13.8 Hz, 2H), 3.51 (d, J = 19.6 Hz, 2H), 3.42 (d, J = 13.7 Hz, 1H), 3.14-3.04 (m, 12H), 3.01 (d, J = 12.2 Hz, 1H), 2.79-2.65 (m, 1H), 2.61 (d, J = 17.8 Hz, 1H), 2.05 (d, J = 5.3 Hz, 1H), 1.94 (d, J = 7.4 Hz, 1H), 1.86 (d, J = 25.5 Hz, 2H), 1.82-1.70 (m, 2H), 1.68 (d, J = 11.7 Hz, 1H), 1.44 (s, 13H), 1.36 (s, 13H). |

-continued

| compounds | Structure | MS [M + H⁺] | ¹H-NMR |
|---|---|---|---|
| 2 | 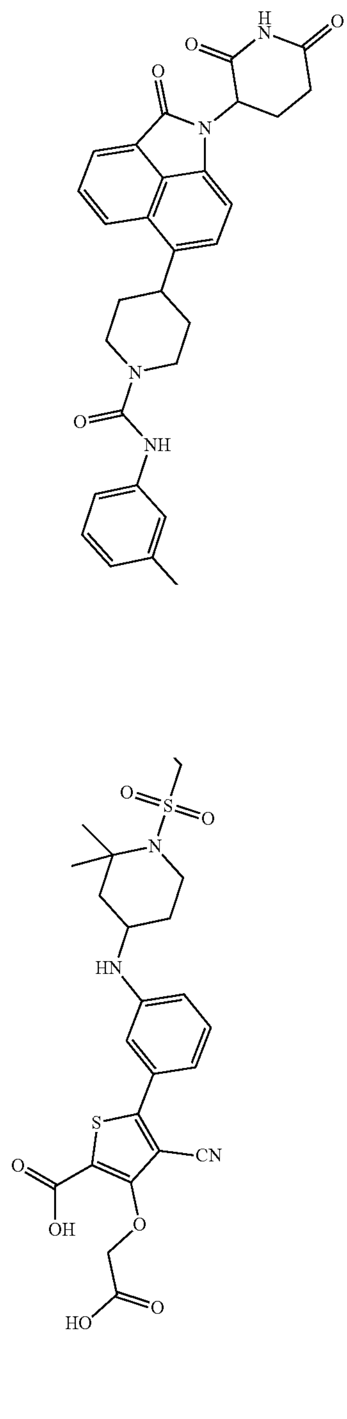 | 988.29 | ¹H NMR (400 MHZ, DMSO-d6): δ 11.10 (d, J = 7.0 Hz, 1H), 8.64 (d, J = 12.4 Hz, 1H), 8.46 (d, J = 8.4 Hz, 1H), 8.11-8.05 (m, 1H), 7.83 (dt, J = 13.4, 6.7 Hz, 1H), 7.55 (s, 1H), 7.48-7.41 (m, 1H), 7.35 (d, J= 7.6 Hz, 1H), 7.21 (dd, J = 14.6, 7.7 Hz, 2H), 7.06 (d, J = 7.5 Hz, 1H), 6.98-6.92 (m, 1H), 6.89-6.79 (m, 1H), 6.74 (dd, J = 8.3, 1.5 Hz, 1H), 5.41 (dd, J = 13.0, 5.4 Hz, 1H), 5.03 (d, J = 15.0 Hz, 2H), 4.33 (d, J = 13.8 Hz, 3H), 4.22 (d, J = 13.8 Hz, 1H), 3.60-3.35 (m, 3H), 3.06 (dt, J = 20.3, 12.4 Hz, 3H), 2.97-2.86 (m, 1H), 2.79-2.56 (m, 2H), 2.10-2.01 (m, 1H), 1.76 (ddd, J = 34.5, 28.6, 12.0 Hz, 6H), 1.45 (s, 3H), 1.41-1.33 (m, 5H), 1.08 (dt, J = 11.7, 8.2 Hz, 1H). |

| compounds | Structure | MS [M + H⁺] | ¹H-NMR |
|---|---|---|---|
| 3 | 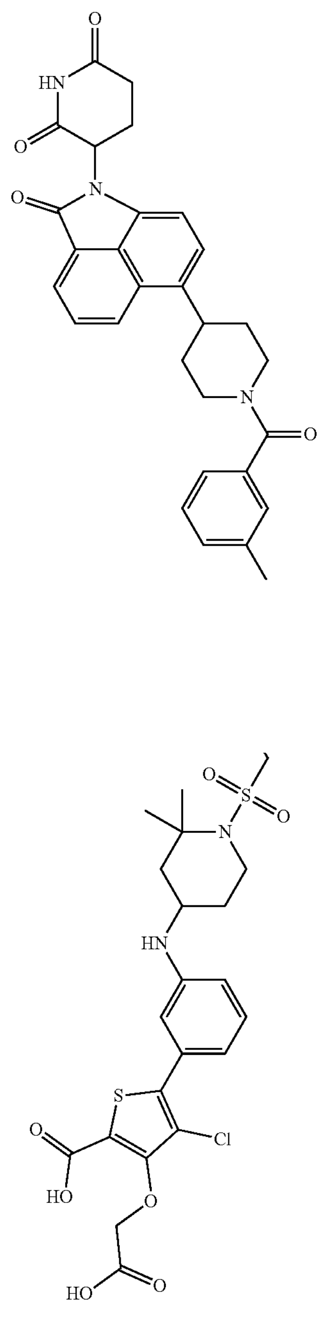 | 982.25 | ¹H NMR (400 MHZ, DMSO-d6) δ 11.06 (s, 1H), 8.19-8.18 (m, 1H), 7.99-7.97 (m, 1H), 7.88-7.87 (m, 1H), 7.63-7.61 (m, 1H), 7.60-7.59 (m, 1H), 7.51-7.49 (m, 1H), 7.48-7.46 (m, 1H), 7.39-7.38 (m, 1H), 7.37-7.36 (m, 1H), 7.34-7.33 (m, 1H), 7.30-7.26 (m, 1H), 7.17-7.16 (m, 1H), 6.78-6.76 (m, 1H), 6.64-6.62 (m, 1H), 5.15-5.13 (m, 1H), 4.67 (s, 2H), 4.51 (s, 2H), 3.77-3.72 (m, 2H), 3.67-3.59 (m, 4H), 3.39-3.37 (m, 1H), 3.33-3.25 (m, 2H), 2.78-2.73 (m, 1H), 2.67-2.62 (m, 1H), 2.39-2.33 (m, 1H), 2.30-2.24 (m, 2H), 2.20-2.15 (m, 2H), 2.06-1.99 (m, 3H), 1.93-1.90 (m, 1H), 1.77-1.70 (m, 1H), 1.36 (s, 3H), 1.24 (m, 3H). |

-continued
| compounds | Structure | MS [M + H+] | 1H-NMR |
|---|---|---|---|
| 4 | 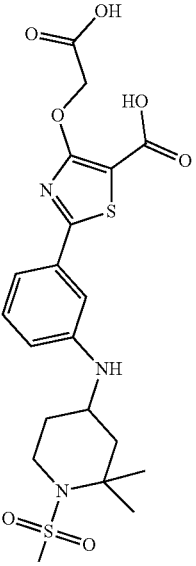 | 964.30 | 1H NMR (400 MHZ, DMSO-d6): δ 11.09 (s, 1H), 8.64 (s, 1H), 8.46 (d, J = 8.5 Hz, 1H), 8.08 (d, J = 7.0 Hz, 1H), 7.88-7.77 (m, 1H), 7.55 (s, 1H), 7.44 (d, J= 8.3 Hz, 1H), 7.34 (d, J = 7.5 Hz, 1H), 7.20 (dd, J = 15.2, 7.3 Hz, 1H), 7.15 (d, J = 7.9 Hz, 1H), 7.05 (d, J= 7.5 Hz, 1H), 6.95 (d, J = 7.7 Hz, 1H), 6.83 (s, 1H), 6.77 (d, J = 7.4 Hz, 1H), 6.66 (d, J = 8.3 Hz, 1H), 5.41 (dd, J = 12.6, 5.3 Hz, 1H), 4.80 (s, 2H), 4.33 (d, J = 13.7 Hz, 4H), 4.22 (d, J = 13.8 Hz, 2H), 3.51 (d, J = 19.6 Hz, 2H), 3.42 (d, J = 13.7 Hz, 1H), 3.14-3.04 (m, 12H), 3.01 (d, J = 12.2 Hz, 1H), 2.79-2.65 (m, 1H), 2.61 (d, J = 17.8 Hz, 1H), 2.05 (d, J = 5.3 Hz, 1H), 1.94 (d, J = 7.4 Hz, 1H), 1.86 (d, J = 25.5 Hz, 2H), 1.82-1.70 (m, 2H), 1.77-1.70 (m, 1H), 1.36 (s, 3H), 1.24 (m, 3H). |

-continued
| compounds | Structure | MS [M + H+] | 1H-NMR |
|---|---|---|---|
| 5 | 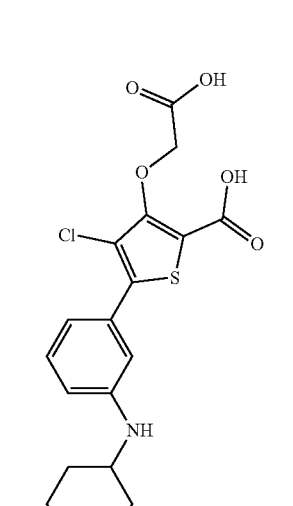 | 993.27 | 1H NMR (400 MHZ, DMSO-d6) δ 11.09 (s, 1H), 9.29 (s, 1H), 8.25-8.17 (m, 2H), 7.90-7.84 (m, 1H), 7.76-7.69 (m, 1H), 7.51-7.47 (m, 1H), 7.32-7.23 (m, 2H), 7.17 (s, 1H), 7.05-6.94 (m, 2H), 6.91-6.86 (m, 1H), 6.75-6.69 (m, 1H), 6.67-6.62 (m, 1H), 5.50-5.44 (m, 2H), 5.34-5.26 (m, 2H), 4.46 (s, 1H), 4.36-4.27 (m, 1H), 4.17-4.08 (m, 2H), 4.07-4.01 (m, 1H), 3.56-3.48 (m, 1H), 3.47-3.37 (m, 1H), 3.30-3.20 (m, 1H), 3.07-2.97 (m, 2H), 2.87-2.75 (m, 2H), 2.69-2.50 (m, 2H), 2.41-2.30 (m, 2H), 2.20-2.08 (m, 2H), 1.92-1.78 (m, 2H), 1.74-1.64 (m, 2H), 1.47-1.39 (m, 1H), 1.18 (s, 3H), 1.10 (s, 3H). |
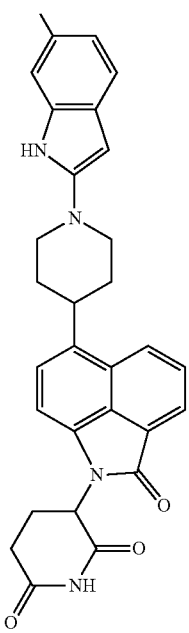

| compounds | Structure | MS [M + H⁺] | ¹H-NMR |
|---|---|---|---|
| 6 | 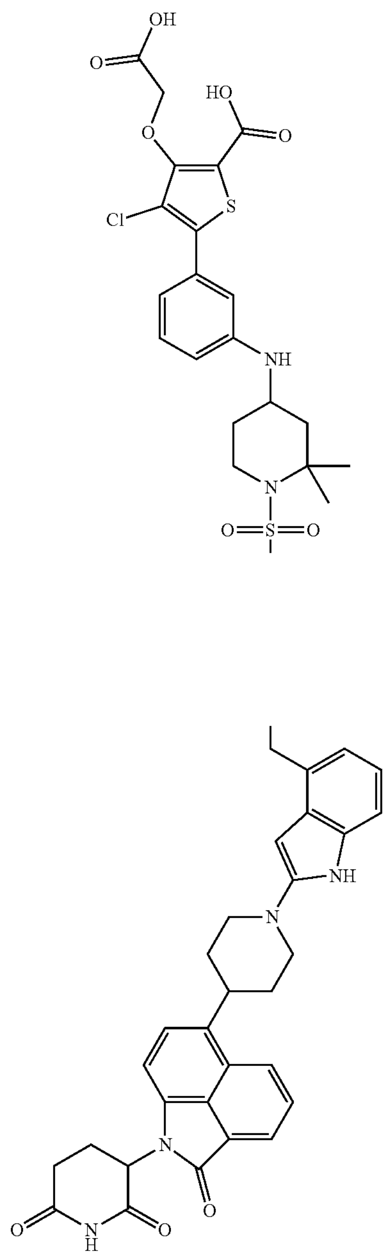 | 993.27 | ¹H NMR (400 MHZ, DMSO-d6) δ 11.09 (s, 1H), 9.35 (s, 1H), 8.43-8.37 (m, 1H), 8.25-8.19 (m, 1H), 7.92-7.85 (m, 1H), 7.58-7.50 (m, 1H), 7.32-7.24 (m, 2H), 7.09-6.95 (m, 4H), 6.83-6.78 (m, 1H), 6.76-6.70 (m, 1H), 5.45 (s, 1H), 5.37-5.24 (m, 3H), 4.62 (s, 1H), 4.46-4.40 (m, 1H), 4.32-4.23 (m, 1H), 4.22-3.96 (m, 2H), 3.82-3.74 (m, 1H), 3.56-3.46 (m, 1H), 3.38-3.16 (m, 4H), 3.08-2.96 (m, 1H), 2.69-2.52 (m, 2H), 2.43-2.29 (m, 2H), 2.25-2.11 (m, 2H), 1.88-1.76 (m, 2H), 1.76-1.60 (m, 2H), 1.49-1.41 (m, 1H), 1.08 (s, 3H), 0.92 (s, 3H). |

| compounds | Structure | MS [M + H+] | 1H-NMR |
|---|---|---|---|
| 7 | 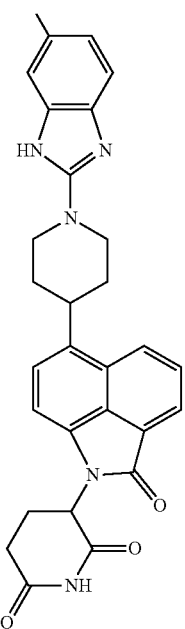 | 994.27 | 1H NMR (400 MHZ, DMSO-d6) δ 11.12 (s, 1H), 8.53 (d, J = 8.3 Hz, 1H), 8.12 (d, J = 7.0 Hz, 1H), 7.89 (dd, J = 8.2, 7.1 Hz, 1H), 7.41 (t, J = 8.0 Hz, 2H), 7.33 (s, 1H), 7.20 (t, J = 7.9 Hz, 1H), 7.08 (t, J = 7.1 Hz, 2H), 6.88 (s, 1H), 6.81 (d, J = 7.4 Hz, 1H), 6.70 (d, J = 7.9 Hz, 1H), 5.44 (dd, J = 12.5, 5.6 Hz, 1H), 4.92 (s, 2H), 4.48 (d, J = 13.7 Hz, 1H), 4.35 (d, J = 13.5 Hz, 3H), 3.68 (dd, J = 16.8, 9.4 Hz, 1H), 3.51 (t, J = 12.3 Hz, 1H), 3.42 (dd, J = 15.3, 7.4 Hz, 3H), 3.17-3.04 (m, 1H), 2.95 (dd, J = 23.0, 8.1 Hz, 1H), 2.81-2.69 (m, 1H), 2.64 (d, J = 19.1 Hz, 1H), 2.12-2.04 (m, 1H), 1.99 (d, J = 10.3 Hz, 2H), 1.95-1.73 (m, 4H), 1.44 (s, 3H), 1.41-1.31 (m, 4H), 1.17-1.02 (m, 1H). |

-continued
| compounds | Structure | MS [M + H+] | 1H-NMR |
|---|---|---|---|
| 8 | 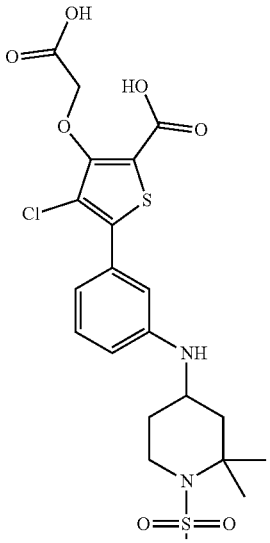 | 994.27 | 1H NMR (400 MHz, DMSO-d6) δ 11.15 (s, 1H), 8.48 (d, J = 8.4 Hz, 1H), 8.10 (d, J = 6.9 Hz, 1H), 7.85 (d, J = 7.9 Hz, 1H), 7.41 (d, J = 7.9 Hz, 1H), 7.25-7.13 (m, 3H), 7.04 (t, J = 7.9 Hz, 1H), 6.85 (dd, J = 13.8, 8.9 Hz, 3H), 6.67 (t, J = 7.5 Hz, 1H), 5.40 (dd, J = 12.4, 4.5 Hz, 1H), 4.90 (s, 2H), 4.56 (dd, J = 17.8, 14.2 Hz, 2H), 4.46-4.35 (m, 2H), 3.64 (t, J = 12.9 Hz, 1H), 3.43 (t, J = 14.1 Hz, 3H), 3.24 (d, J = 16.7 Hz, 1H), 3.15-2.84 (m, 2H), 2.63 (t, J = 11.3 Hz, 2H), 2.11-1.73 (m, 7H), 1.66 (d, J = 20.6 Hz, 4H), 1.36 (s, 5H), 0.76-0.60 (m, 1H). |

-continued
| compounds | Structure | MS [M + H⁺] | ¹H-NMR |
|---|---|---|---|
| 9 | 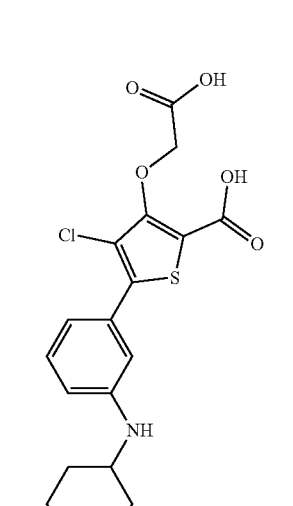 | 995.25 | ¹H NMR (400 MHZ, DMSO-d6): δ 11.09 (s, 1H), 8.64 (s, 1H), 8.46 (d, J = 8.5 Hz, 1H), 8.08 (d, J = 7.0 Hz, 1H), 7.88-7.77 (m, 1H), 7.55 (s, 1H), 7.44 (d, J= 8.3 Hz, 1H), 7.34 (d, J = 7.5 Hz, 1H), 7.20 (dd, J = 15.2, 7.3 Hz, 1H), 7.15 (d, J = 7.9 Hz, 1H), 7.05 (d, J= 7.5 Hz, 1H), 6.95 (d, J = 7.7 Hz, 1H), 6.83 (s, 1H), 6.77 (d, J = 7.4 Hz, 1H), 6.66 (d, J = 8.3 Hz, 1H), 5.41 (dd, J = 12.6, 5.3 Hz, 1H), 4.80 (s, 2H), 4.33 (d, J = 13.7 Hz, 4H), 4.22 (d, J = 13.8 Hz, 2H), 3.51 (d, J = 19.6 Hz, 2H), 3.42 (d, J = 13.7 Hz, 1H), 3.14-3.04 (m, 12H), 3.01 (d, J = 12.2 Hz, 1H), 2.79-2.65 (m, 1H), 2.61 (d, J = 17.8 Hz, 1H), 2.05 (d, J = 5.3 Hz, 1H), 1.94 (d, J = 7.4 Hz, 1H), 1.86 (d, J = 25.5 Hz, 2H), 1.82-1.70 (m, 2H), 1.68 (d, J = 11.7 Hz, 1H), 1.48-0.84 (m, 8H). |
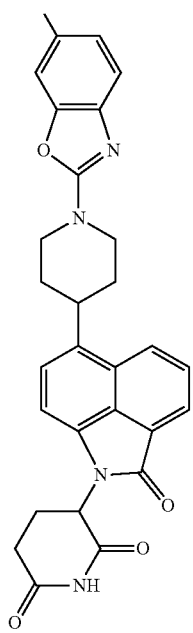

-continued
| compounds | Structure | MS [M + H+] | 1H-NMR |
|---|---|---|---|
| 10 | 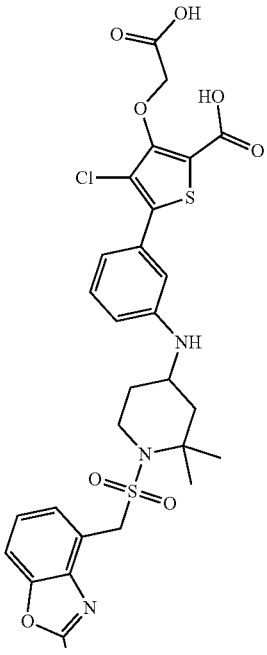 | 995.25 | 1H NMR (400 MHZ, DMSO-d6) δ 11.15 (s, 1H), 8.48 (d, J = 8.4 Hz, 1H), 8.10 (d, J = 6.9 Hz, 1H), 7.85 (d, J = 7.9 Hz, 1H), 7.41 (d, J = 7.9 Hz, 1H), 7.25-7.13 (m, 3H), 7.04 (t, J = 7.9 Hz, 1H), 6.85 (dd, J = 13.8, 8.9 Hz, 3H), 6.67 (t, J = 7.5 Hz, 1H), 5.40 (dd, J = 12.4, 4.5 Hz, 1H), 4.90 (s, 2H), 4.56 (dd, J = 17.8, 14.2 Hz, 2H), 4.46-4.35 (m, 2H), 3.64 (t, J = 12.9 Hz, 1H), 3.43 (t, J = 14.1 Hz, 3H), 3.24 (d, J = 16.7 Hz, 1H), 3.15-2.84 (m, 2H), 2.63 (t, J = 11.3 Hz, 2H), 2.11-1.73 (m, 7H), 1.66 (d, J = 20.6 Hz, 4H), 1.36 (s, 5H), 0.76-0.60 (m, 1H). |

| compounds | Structure | MS [M + H+] | 1H-NMR |
|---|---|---|---|
| 11 | | 948.32 | 1H NMR (400 MHZ, DMSO-d6): δ 11.09 (s, 1H), 8.64 (s, 1H), 8.46 (d, J = 8.5 Hz, 1H), 8.08 (d, J = 7.0 Hz, 1H), 7.88-7.77 (m, 1H), 7.55 (s, 1H), 7.44 (d, J= 8.3 Hz, 1H), 7.34 (d, J = 7.5 Hz, 1H), 7.20 (dd, J = 15.2, 7.3 Hz, 1H), 7.15 (d, J = 7.9 Hz, 1H), 7.05 (d, J= 7.5 Hz, 1H), 6.95 (d, J = 7.7 Hz, 1H), 6.83 (s, 1H), 6.77 (d, J = 7.4 Hz, 1H), 6.66 (d, J = 8.3 Hz, 1H), 5.41 (dd, J = 12.6, 5.3 Hz, 1H), 4.80 (s, 2H), 4.33 (d, J = 13.7 Hz, 4H), 4.22 (d, J = 13.8 Hz, 2H), 3.51 (d, J = 19.6 Hz, 2H), 3.42 (d, J = 13.7 Hz, 1H), 3.14-3.04 (m, 12H), 3.01 (d, J = 12.2 Hz, 1H), 2.79-2.65 (m, 1H), 2.61 (d, J = 17.8 Hz, 1H), 2.05 (d, J = 5.3 Hz, 1H), 1.94 (d, J = 7.4 Hz, 1H), 1.86 (d, J = 25.5 Hz, 2H), 1.82-1.70 (m, 2H), 1.68-1.36 (s, 13H). |

-continued

| compounds | Structure | MS [M + H+] | 1H-NMR |
|---|---|---|---|
| 12 | 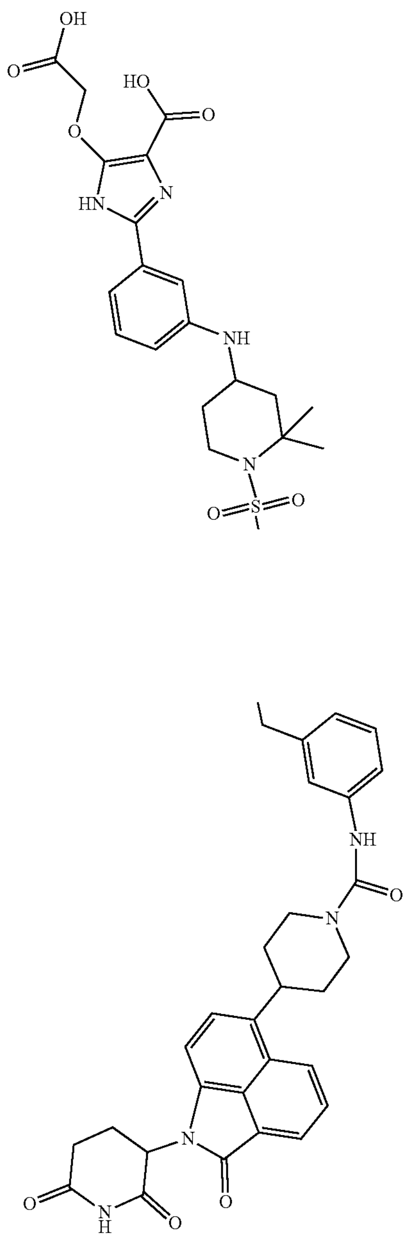 | 947.34 | 1H NMR (400 MHZ, DMSO-d6) δ 12.88 (s, 1H), 12.74 (s, 1H), 12.49 (s, 1H), 10.75 (s, 1H), 8.98 (s, 1H), 8.83 (m, 2H), 7.78-7.71 (m, 2H), 7.49-7.42 (m, 3H), 7.38-7.26 (m, 2H), 7.17 (m, 1H), 6.96-6.85 (m, 1H), 6.80-6.72 (m, 2H), 5.23 (s, 1H), 4.95 (s, 2H), 4.77 (s, 2H), 4.66-4.61 (m, 1H), 3.47-3.63 (m, 4H), 3.36-3.21 (m, 2H), 2.86-2.64 (m, 2H), 2.18-1.43 (m, 12H), 1.30 (s, 6H) |

-continued

| compounds | Structure | MS [M + H⁺] | ¹H-NMR |
|---|---|---|---|
| 13 | 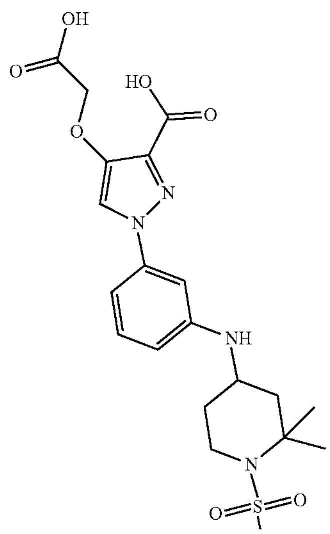 | 947.34 | ¹H NMR (400 MHZ, DMSO-d6) δ 12.78 (s, 1H), 12.31 (s, 1H), 11.05 (s, 1H), 9.05 (s, 1H), 8.52 (s, 1H), 8.22-8.18 (m, 2H), 7.78-7.73 (m, 2H), 7.53-7.46 (m, 1H), 7.29-7.23 (m, 3H), 7.13-7.08 (m, 2H), 6.91-6.86 (m, 2H), 6.68-6.62 (m, 1H), 5.18 (s, 1H), 4.81 (s, 2H), 4.69 (s, 2H), 4.42-4.39 (m, 1H), 3.59-3.49 (m, 4H), 3.34-3.21 (m, 2H), 2.73-2.63 (m, 2H), 1.98-1.41 (m, 12H), 1.28 (s, 6H) |

-continued

| compounds | Structure | MS [M + H⁺] | ¹H-NMR |
|---|---|---|---|
| 14 | 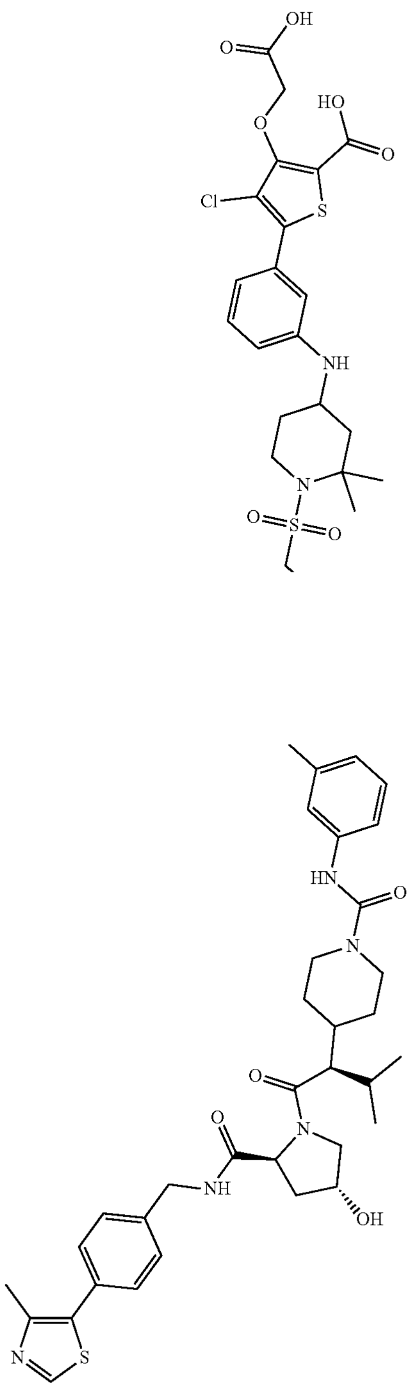 | 1118.36 | ¹H NMR (500 MHZ, Chloroform-d) δ 11.05 (s, 1H), 8.54 (s, 1H), 8.35 (s, 1H), 7.63-7.61 (m, 1H), 7.46-7.43 (m, 3H), 7.42 (m, 1H), 7.39-7.36 (m, 1H), 7.36-7.31 (m, 5H), 7.22 (m, 1H), 7.20-7.16 (m, 1H), 6.87 (m, 1H), 6.58 (m, 1H), 4.83-4.59 (m, 2H), 4.48-4.33 (m, 5H), 4.32-4.19 (m, 4H), 3.75 (m, 3H), 3.70-3.57 (m, 7H), 3.54 (m, 1H), 3.45-3.34 (m, 3H), 2.53-2.42 (m, 4H), 2.22-1.99 (m, 5H), 1.93 (m, 1H), 1.88-1.69 (m, 9H), 1.27 (m, 6H), 0.94 (m, 8H). |

-continued
| compounds | Structure | MS [M + H⁺] | ¹H-NMR |
|---|---|---|---|
| 15 | 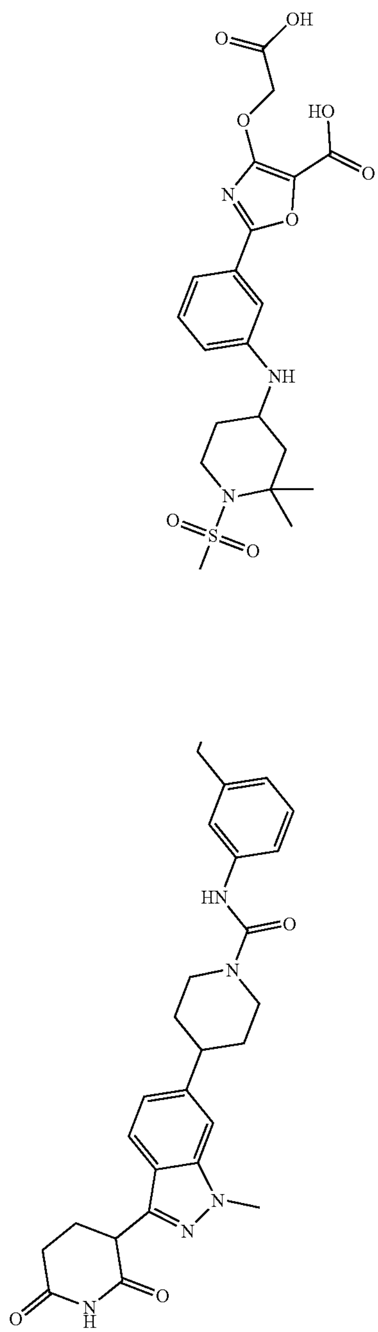 | 911.34 | ¹H NMR (400 MHZ, DMSO-d6) δ 12.82 (s, 1H), 12.52 (s, 1H), 10.83 (s, 1H), 9.03 (s, 1H), 8.23 (m, 2H), 7.75-7.70 (m, 2H), 7.55-7.42 (m, 2H), 7.30-7.22 (m, 1H), 6.98-6.85 (m, 1H), 6.82-6.77 (m, 2H), 5.21 (s, 1H), 4.96 (s, 2H), 4.75 (s, 2H), 4.69-4.64 (m, 1H), 3.47-3.63 (m, 4H), 3.35-3.20 (m, 2H), 2.73-2.63 (m, 5H), 2.21-1.42 (m, 12H), 1.25 (s, 6H) |
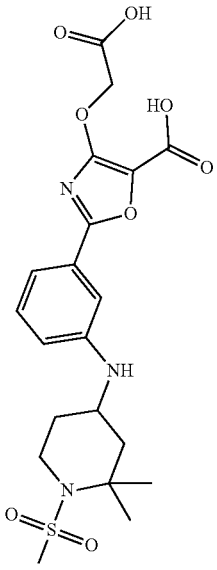

-continued
| compounds | Structure | MS [M + H⁺] | ¹H-NMR |
|---|---|---|---|
| 16 | 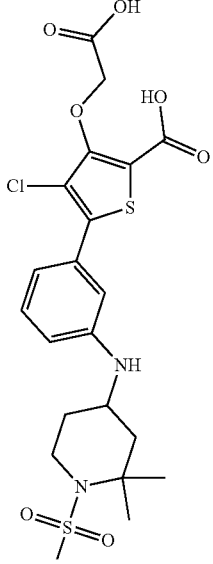 | 1006.27 | ¹H NMR (500 MHZ, DMSO-d6) δ 11.08 (s, 1H), 9.24 (s, 1H), 8.50 (d, J = 8.4 Hz, 1H), 8.08 (d, J = 7.0 Hz), 7.94-7.70 (m, 2H), 7.58 (s, 1H), 7.31 (dd, J = 11.4, 8.1 Hz, 2H), 7.15 (t, J = 7.9 Hz, 1H), 7.03 (d, J= 7.6 Hz, 1H), 6.84 (s, 1H), 6.76 (d, J = 8.3 Hz, 1H), (d, J = 10.3 Hz, 1H), 5.40 (dd, J = 13.4, 4.9 Hz, 1H), 5.03 (d, J = 15.7 Hz, 2H), 4.85 (s, 2H), 4.61 (d, J = 13.7 Hz, 1H), 4.50 (d, J = 13.4 Hz, 1H), 3.69 (t, J= 11.3 Hz, 1H), 3.55-3.39 (m, 1H), 3.33-3.04 (m, 2H), 2.98-2.83 (m, 1H), 2.77-2.56 (m, 1H), 2.11-1.82 (m, 2H), 1.76 (t, J = 11.1 Hz, 2H), 1.45 (s, 3H), 1.42-1.29 (m, 4H). |

| compounds | Structure | MS [M + H⁺] | ¹H-NMR |
|---|---|---|---|
| 17 | 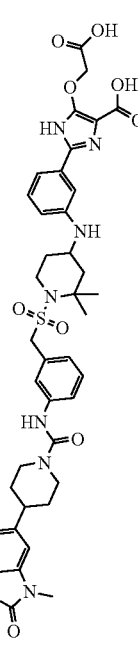 | 926.35 | ¹H NMR (400 MHZ, DMSO-d6) δ 12.84 (s, 1H), 12.54 (s, 1H), 10.84 (s, 1H), 9.04 (s, 1H), 8.24-8.20 (m, 2H), 7.73-7.70 (m, 2H), 7.53-7.42 (m, 2H), 7.33-7.22 (m, 1H), 6.94-6.85 (m, 1H), 6.82-6.77 (m, 2H), 5.23 (s, 1H), 4.93 (s, 2H), 4.73 (s, 2H), 4.63-4.61 (m, 1H), 3.47-3.63 (m, 4H), 3.32-3.20 (m, 2H), 2.75-2.63 (m, 5H), 2.24-1.44 (m, 12H), 1.24 (s, 6H) |
| 18 | 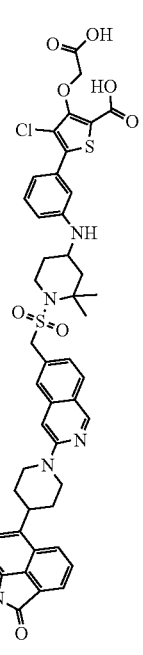 | 1005.27 | ¹H NMR (500 MHZ, Chloroform-d) δ 11.05 (s, 1H), 8.98 (s, 1H), 8.74-8.72 (m, 1H), 8.19-8.01 (m, 2H), 7.93-7.90 (m, 1H), 7.76-7.75 (m, 1H), 7.60-7.46 (m, 3H), 7.48-7.32 (m, 2H), 7.22-7.21 (m, 1H), 7.11-7.09 (m, 1H), 6.87-6.85 (m, 1H), 6.58-6.55 (m, 1H), 4.82-4.64 (m, 2H), 4.54-5.51 (m, 1H), 4.44-4.10 (m, 3H), 3.76-3.55 (m, 7H), 3.50-3.33 (m, 3H), 3.27-3.07 (m, 1H), 2.76-2.58 (m, 3H), 2.46-2.23 (m, 5H), 2.02-1.98 (m, 3H), 1.93-1.90 (m, 1H), 1.88-1.67 (m, 4H), 1.27-1.24 (m, 6H). |

| compounds | Structure | MS [M + H⁺] | ¹H-NMR |
|---|---|---|---|
| 19 | 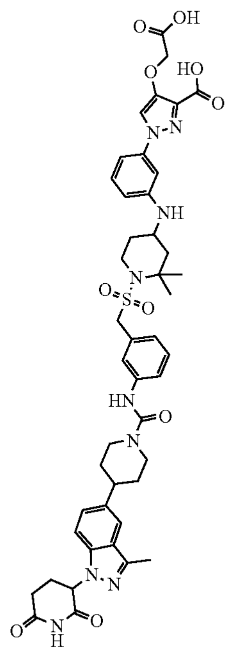 [SMILES: Cc1nn(C2CCC(=O)NC2=O)c2ccc(C3CCN(C(=O)Nc4cccc(CS(=O)(=O)N5CCC(Nc6cccc(-n7cc(OCC(=O)O)c(C(=O)O)n7)c6)CC5(C)C)c4)CC3)cc12] | 910.36 | ¹H NMR (400 MHZ, DMSO-d6) δ 12.81 (s, 1H), 12.51 (s, 1H), 10.81 (s, 1H), 9.01 (s, 1H), 8.21-8.18 (m, 2H), 7.73-7.70 (m, 2H), 7.53-7.42 (m, 2H), 7.31-7.22 (m, 1H), 6.96-6.85 (m, 1H), 6.81-6.77 (m, 2H), 5.22 (s, 1H), 4.93 (s, 2H), 4.74 (s, 2H), 4.66-4.64 (m, 1H), 3.45-3.63 (m, 4H), 3.34-3.20 (m, 2H), 2.71-2.63 (m, 5H), 2.20-1.42 (m, 12H), 1.24 (s, 6H) |
| 20 | 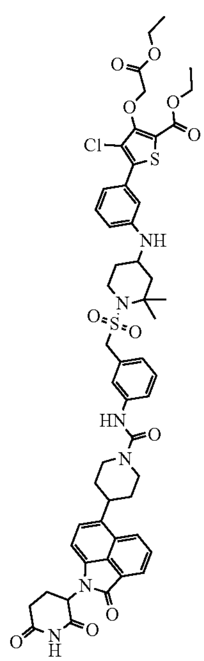 [SMILES: CCOC(=O)COc1c(C(=O)OCC)sc(-c2cccc(NC3CCN(S(=O)(=O)Cc4cccc(NC(=O)N5CCC(c6ccc7c8c(cccc68)C(=O)N7C6CCC(=O)NC6=O)CC5)c4)C(C)(C)C3)c2)c1Cl] | 1053.33 | ¹H NMR (400 MHZ, DMSO-d6): δ 13.32 (s, 1H), 11.13 (s, 1H), 8.66 (s, 1H), 8.52-7.50 (m, 1H), 8.12-8.10 (m, 1H), 7.90-7.86 (m, 1H), 7.59-7.53 (m, 1H), 7.49-7.43 (m, 1H), 7.39-7.36 (m, 1H), 7.28-7.18 (m, 2H), 7.10-7.05 (m, 1H), 7.03-7.00 (m, 1H), 6.88-6.85 (m, 1H), 6.81-6.80 (m, 1H), 6.73-6.70 (m, 1H), 5.46-5.43 (m, 1H), 4.91 (s, 2H), 4.93-4.25 (m, 4H), 4.13-3.96 (m, 4H), 3.61-3.45 (m, 3H), 3.13-2.96 (m, 4H), 2.78-2.64 (m, 2H), 2.11-2.08 (m, 1H), 1.93-1.71 (m, 5H), 1.50-1.40 (m, 7H), 1.25-1.14 (m, 6H), 1.15-1.04 (m, 1H) |

-continued

| compounds | Structure | MS [M + H⁺] | ¹H-NMR |
|---|---|---|---|
| 21 | 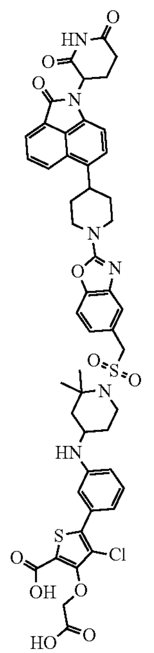 [SMILES: CC1(C)CC(Nc2cccc(-c3sc(C(=O)O)c(OCC(=O)O)c3Cl)c2)CCN1S(=O)(=O)Cc1ccc2oc(N3CCC(c4ccc5c6c(cccc46)C(=O)N5C4CCC(=O)NC4=O)CC3)nc2c1] | 995.25 | ¹H NMR (400 MHZ, DMSO-d6) δ 11.12 (s, 1H), 8.53 (d, J = 8.3 Hz, 1H), 8.12 (d, J = 7.0 Hz, 1H), 7.89 (dd, J = 8.2, 7.1 Hz, 1H), 7.41 (t, J = 8.0 Hz, 2H), 7.33 (s, 1H), 7.20 (t, J = 7.9 Hz, 1H), 7.08 (t, J = 7.1 Hz, 2H), 6.88 (s, 1H), 6.81 (d, J = 7.4 Hz, 1H), 6.70 (d, J = 7.9 Hz, 1H), 5.44 (dd, J = 12.5, 5.6 Hz, 1H), 4.92 (s, 2H), 4.48 (d, J = 13.7 Hz, 1H), 4.35 (d, J = 13.5 Hz, 3H), 3.68 (dd, J = 16.8, 9.4 Hz, 1H), 3.51 (t, J = 12.3 Hz, 1H), 3.42 (dd, J = 15.3, 7.4 Hz, 3H), 3.17-3.04 (m, 1H), 2.95 (dd, J = 23.0, 8.1 Hz, 1H), 2.81-2.69 (m, 1H), 2.64 (d, J = 19.1 Hz, 1H), 2.12-2.04 (m, 1H), 1.99 (d, J = 10.3 Hz, 2H), 1.95-1.73 (m, 4H), 1.44 (s, 3H), 1.41-1.31 (m, 4H), 1.17-1.02 (m, 1H). |
| 22 | 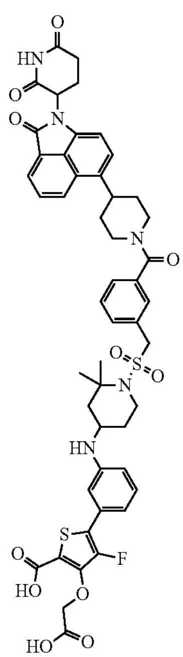 [SMILES: CC1(C)CC(Nc2cccc(-c3sc(C(=O)O)c(OCC(=O)O)c3F)c2)CCN1S(=O)(=O)Cc1cccc(C(=O)N2CCC(c3ccc4c5c(cccc35)C(=O)N4C3CCC(=O)NC3=O)CC2)c1] | 966.29 | ¹H NMR (400 MHZ, DMSO-d6): δ 11.06 (s, 1H), 8.19-8.18 (m, 1H), 7.99-7.97 (m, 1H), 7.88-7.87 (m, 1H), 7.63-7.61 (m, 1H), 7.60-7.59 (m, 1H), 7.51-7.49 (m, 1H), 7.48-7.46 (m, 1H), 7.39-7.38 (m, 1H), 7.37-7.33 (m, 2H), 7.30-7.26 (m, 1H), 7.17-7.16 (m, 1H), 6.78-6.76 (m, 1H), 6.64-6.62 (m, 1H), 5.15-5.13 (m, 1H), 4.67 (s, 2H), 4.51 (s, 2H), 3.77-3.72 (m, 2H), 3.67-3.59 (m, 4H), 3.39-3.25 (m, 3H), 2.78-2.73 (m, 1H), 2.67-2.62 (m, 1H), 2.39-2.33 (m, 1H), 2.30-2.24 (m, 2H), 2.20-2.15 (m, 2H), 2.06-1.99 (m, 3H), 1.93-1.90 (m, 1H), 1.77-1.70 (m, 1H), 1.36-0.81 (m, 6H). |

-continued

| compounds | Structure | MS [M + H+] | 1H-NMR |
|---|---|---|---|
| 23 | 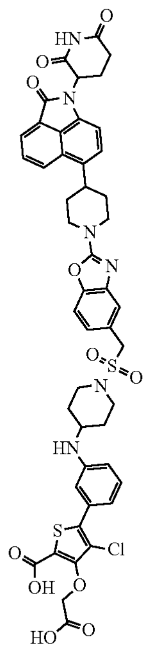 [SMILES: O=C(O)COc1c(C(=O)O)sc(-c2cccc(NC3CCN(S(=O)(=O)Cc4ccc5oc(N6CCC(c7ccc8c9c(cccc79)C(=O)N8C7CCC(=O)NC7=O)CC6)nc5c4)CC3)c2)c1Cl] | 967.22 | 1H NMR (400 MHZ, DMSO-d6) δ 11.12 (s, 1H), 8.53 (d, J = 8.3 Hz, 1H), 8.12 (d, J = 7.0 Hz, 1H), 7.89 (dd, J = 8.2, 7.1 Hz, 1H), 7.41 (t, J = 8.0 Hz, 2H), 7.33 (s, 1H), 7.20 (t, J = 7.9 Hz, 1H), 7.08 (t, J = 7.1 Hz, 2H), 6.88 (s, 1H), 6.81 (d, J = 7.4 Hz, 1H), 6.70 (d, J = 7.9 Hz, 1H), 5.44 (dd, J = 12.5, 5.6 Hz, 1H), 4.92 (s, 2H), 4.48 (d, J = 13.7 Hz, 1H), 4.35 (d, J = 13.5 Hz, 3H), 3.68 (dd, J = 16.8, 9.4 Hz, 1H), 3.51 (t, J = 12.3 Hz, 1H), 3.42 (dd, J = 15.3, 7.4 Hz, 3H), 3.17-2.95 (m, 4H), 2.81-2.69 (m, 1H), 2.64 (d, J = 19.1 Hz, 1H), 2.12-2.04 (m, 1H), 1.99 (d, J = 10.3 Hz, 2H), 1.95-1.73 (m, 1H), 1.41-1.31 (m, 4H), 1.17-1.02 (m, 1H). |
| 24 | 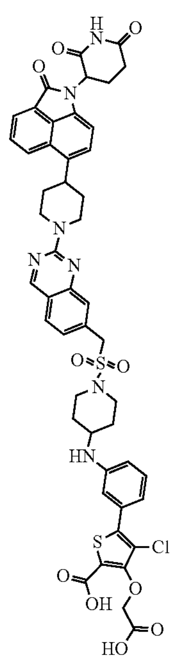 [SMILES: O=C(O)COc1c(C(=O)O)sc(-c2cccc(NC3CCN(S(=O)(=O)Cc4ccc5cnc(N6CCC(c7ccc8c9c(cccc79)C(=O)N8C7CCC(=O)NC7=O)CC6)nc5c4)CC3)c2)c1Cl] | 978.24 | 1H NMR (400 MHZ, DMSO-d6) δ 11.08 (s, 1H), 9.24 (s, 1H), 8.50 (d, J = 8.4 Hz, 1H), 8.08 (d, J = 7.0 Hz, 1H), 7.94-7.70 (m, 2H), 7.58 (s, 1H), 7.31 (dd, J = 11.4, 8.1 Hz, 2H), 7.15 (t, J = 7.9 Hz, 1H), 7.03 (d, J= 7.6 Hz, 1H), 6.84 (s, 1H), 6.76 (d, J = 8.3 Hz, 1H), 6.65 (d, J = 10.3 Hz, 1H), 5.40 (dd, J = 13.4, 4.9 Hz, 1H), 5.03 (d, J = 15.7 Hz, 2H), 4.61 (t, J = 13.7 Hz, 1H), 4.50 (d, J = 13.4 Hz, 1H), 3.69 (t, J = 11.3 Hz, 1H), 3.55-3.39 (m, 1H), 3.33-3.04 (m, 2H), 2.98-2.83 (m, 1H), 2.77-2.56 (m, 1H), 2.11-1.82 (m, 2H), 1.76 (t, J = 11.1 Hz, 2H), 1.45 (s, 3H), 1.42-1.29 (m, 4H). |

-continued

| compounds | Structure | MS [M + H⁺] | ¹H-NMR |
|---|---|---|---|
| 25 | 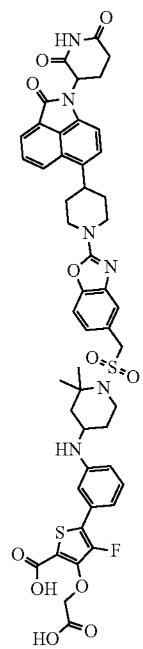 [SMILES: CC1(C)CC(Nc2cccc(-c3sc(C(=O)O)c(OCC(=O)O)c3F)c2)CCN1S(=O)(=O)Cc1ccc2oc(N3CCC(c4ccc5c6c(cccc46)C(=O)N5C4CCC(=O)NC4=O)CC3)nc2c1] | 979.28 | ¹H NMR (400 MHZ, DMSO-d6) δ 11.09 (s, 1H), 8.71-8.49 (m, 1H), 8.09-8.02 (m, 1H), 7.86-7.83 (m, 1H), 7.69-7.36 (m, 3H), 7.31-7.27 (m, 1H), 7.26-7.25 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.48-0.84 (m, 8H). |
| 26 | 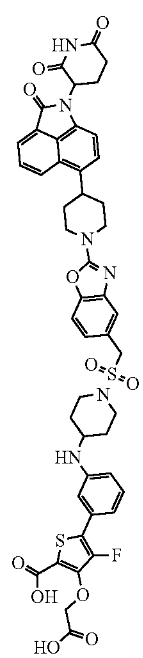 [SMILES: O=C(O)COc1c(C(=O)O)sc(-c2cccc(NC3CCN(S(=O)(=O)Cc4ccc5oc(N6CCC(c7ccc8c9c(cccc79)C(=O)N8C7CCC(=O)NC7=O)CC6)nc5c4)CC3)c2)c1F] | 951.25 | ¹H NMR (400 MHZ, DMSO-d6) δ 11.10 (s, 1H), 8.52-8.47 (m, 1H), 8.08-8.02 (m, 1H), 7.87-7.83 (m, 1H), 7.38-7.36 (m, 1H), 7.31-7.27 (m, 1H), 7.22-7.15 (m, 1H), 7.08-7.03 (m, 2H), 6.86-6.78 (m, 2H), 6.67-6.65 (m, 1H), 5.42-5.39 (m, 1H), 4.89 (s, 2H), 4.38-4.36 (m, 3H), 3.70-3.28 (m, 4H), 3.18-2.80 (m, 2H), 2.75-2.70 (m, 1H), 2.13-1.62 (m, 7H), 1.50-0.84 (m, 2H). |

| compounds | Structure | MS [M + H⁺] | ¹H-NMR |
|---|---|---|---|
| 27 | 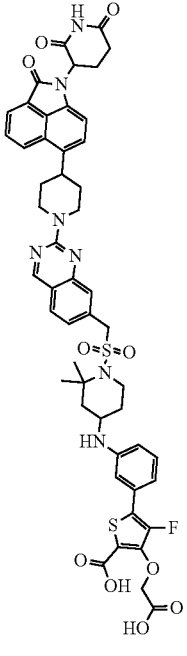 [SMILES: CC1(C)CC(Nc2cccc(-c3sc(C(=O)O)c(OCC(=O)O)c3F)c2)CCN1S(=O)(=O)Cc1ccc2cnc(N3CCC(c4ccc5c6c(cccc46)C(=O)N5C4CCC(=O)NC4=O)CC3)nc2c1] | 990.30 | ¹H NMR (400 MHZ, DMSO-d6) δ 11.08 (s, 1H), 9.24 (s, 1H), 8.50 (d, J = 8.4 Hz, 1H), 8.08 (d, J = 7.0 Hz, 1H), 7.94-7.70 (m, 2H), 7.58 (s, 1H), 7.31 (dd, J = 11.4, 8.1 Hz, 2H), 7.15 (t, J = 7.9 Hz, 1H), 7.03 (d, J= 7.6 Hz, 1H), 6.84 (s, 1H), 6.76 (d, J = 8.3 Hz, 1H), 6.65 (d, J = 10.3 Hz, 1H), 5.40 (dd, J = 13.4, 4.9 Hz, 1H), 5.03 (d, J = 15.7 Hz, 2H), 4.61 (d, J = 13.7 Hz, 1H), 4.50 (d, J = 13.4 Hz, 1H), 3.69 (t, J = 11.3 Hz, 1H), 3.55-3.39 (m, 1H), 3.33-3.04 (m, 2H), 2.98-2.83 (m, 1H), 2.77-2.56 (m, 1H), 2.11-1.82 (m, 2H), 1.76 (t, J = 11.1 Hz, 2H), 1.45 (s, 3H), 1.42-1.29 (m, 4H). |
| 28 | 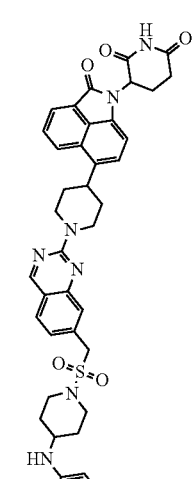 | 962.26 | ¹H NMR (400 MHZ, DMSO-d6) δ 11.08 (s, 1H), 9.24 (s, 1H), 8.50 (d, J = 8.4 Hz, 1H), 8.08 (d, J = 7.0 Hz, 1H), 7.94-7.70 (m, 2H), 7.58 (s, 1H), 7.31 (dd, J = 11.4, 8.1 Hz, 2H), 7.15 (t, J = 7.9 Hz, 1H), 7.03 (d, J= 7.6 Hz, 1H), 6.84 (s, 1H), 6.76 (d, J = 8.3 Hz, 1H), 6.65 (d, J = 10.3 Hz, 1H), 5.40 (dd, J = 13.4, 4.9 Hz, 1H), 5.03 (d, J = 15.7 Hz, 2H), 4.61 (d, J = 13.7 Hz, 1H), 4.50 (d, J = 13.4 Hz, 1H), 3.69 (t, J = 11.3 Hz, 1H), 3.55-3.39 (m, 1H), 3.33-3.04 (m, 2H), 2.98-2.83 (m, 2H), 2.77-2.56 (m, 2H), 2.11-1.82 (m, 2H), 1.76 (t, J = 11.1 Hz, 2H), 1.42-1.29 (m, 1H). |

-continued
| compounds | Structure | MS [M + H+] | 1H-NMR |
|---|---|---|---|
| 29 | 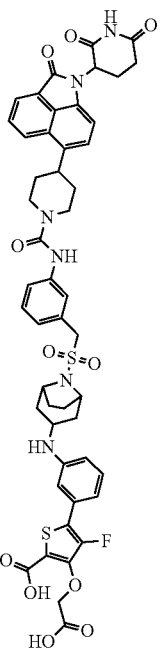 [SMILES: O=C(O)COc1c(C(=O)O)sc(-c2cccc(NC3CC4CCC(C3)N4S(=O)(=O)Cc3cccc(NC(=O)N4CCC(c5ccc6c7c(cccc57)C(=O)N6C5CCC(=O)NC5=O)CC4)c3)c2)c1F] | 979.28 | 1H NMR (400 MHZ, DMSO-d6): δ 10.62 (s, 1H), 8.66 (s, 1H), 8.52-7.50 (m, 1H), 8.12-8.10 (m, 1H), 7.90-7.86 (m, 1H), 7.59-7.53 (m, 1H), 7.49-7.43 (m, 1H), 7.39-7.36 (m, 1H), 7.28-7.18 (m, 2H), 7.10-7.05 (m, 1H), 7.03-7.00 (m, 1H), 6.88-6.85 (m, 1H), 6.81-6.80 (m, 1H), 6.73-6.70 (m, 1H), 5.46-5.43 (m, 1H), 4.91 (s, 2H), 4.93-4.25 (m, 4H), 3.61-3.45 (m, 3H), 3.13-2.96 (m, 4H), 2.78-2.64 (m, 2H), 2.11-2.08 (m, 1H), 1.93-1.71 (m, 5H), 1.50-1.40 (m, 5H), 1.15-1.04 (m, 1H). |
| 30 | 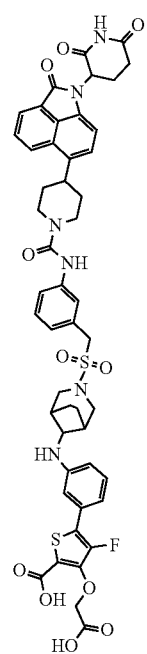 [SMILES: O=C(O)COc1c(C(=O)O)sc(-c2cccc(NC3C4CCC3CN(S(=O)(=O)Cc3cccc(NC(=O)N5CCC(c6ccc7c8c(cccc68)C(=O)N7C6CCC(=O)NC6=O)CC5)c3)C4)c2)c1F] | 979.28 | 1H NMR (400 MHZ, DMSO-d6): δ 11.12 (s, 1H), 8.65 (s, 1H), 8.53-7.51 (m, 1H), 8.11-8.09 (m, 1H), 7.89-7.85 (m, 1H), 7.58-7.52 (m, 1H), 7.48-7.43 (m, 1H), 7.38-7.36 (m, 1H), 7.28-7.18 (m, 2H), 7.10-7.05 (m, 1H), 7.03-7.00 (m, 1H), 6.88-6.85 (m, 1H), 6.81-6.80 (m, 1H), 6.73-6.70 (m, 1H), 5.46-5.43 (m, 1H), 4.91 (s, 2H), 4.93-4.25 (m, 4H), 3.61-3.45 (m, 3H), 3.13-2.96 (m, 6H), 2.78-2.64 (m, 2H), 2.11-2.08 (m, 1H), 1.93-1.71 (m, 5H), 1.50-1.40 (m, 7H), 1.15-1.04 (m, 1H). |

-continued

| compounds | Structure | MS [M + H⁺] | ¹H-NMR |
|---|---|---|---|
| 31 | 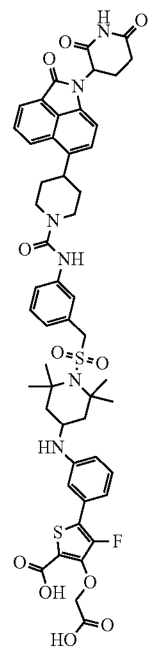 [SMILES: CC1(C)CC(Nc2cccc(-c3sc(C(=O)O)c(OCC(=O)O)c3F)c2)CC(C)(C)N1S(=O)(=O)Cc1cccc(NC(=O)N2CCC(c3ccc4c5c(cccc35)C(=O)N4C3CCC(=O)NC3=O)CC2)c1] | 1009.33 | ¹H NMR (400 MHz, DMSO-d6): δ 11.12 (s, 1H), 8.66 (s, 1H), 8.52-7.50 (m, 1H), 8.11-8.10 (m, 1H), 7.92-7.86 (m, 1H), 7.58-7.53 (m, 1H), 7.49-7.43 (m, 1H), 7.38-7.35 (m, 1H), 7.28-7.18 (m, 2H), 7.10-7.05 (m, 1H), 7.03-7.00 (m, 1H), 6.89-6.85 (m, 1H), 6.83-6.80 (m, 1H), 6.72-6.70 (m, 1H), 5.45-5.43 (m, 1H), 4.92 (s, 2H), 4.93-4.25 (m, 4H), 3.62-3.45 (m, 3H), 3.14-2.96 (m, 3H), 2.77-2.64 (m, 2H), 2.12-2.08 (m, 1H), 1.94-1.71 (m, 5H), 1.51-1.40 (m, 7H), 1.15-1.04 (m, 7H). |
| 32 | 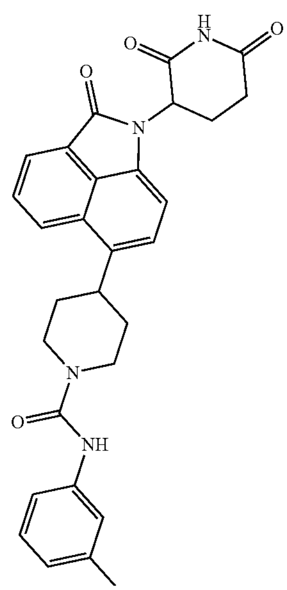 | 1005.30 | ¹H NMR (400 MHZ, DMSO-d6): δ 11.11 (s, 1H), 8.66 (s, 1H), 8.52-7.50 (m, 1H), 8.12-8.10 (m, 1H), 7.90-7.86 (m, 1H), 7.59-7.53 (m, 1H), 7.49-7.43 (m, 1H), 7.39-7.36 (m, 1H), 7.28-7.18 (m, 2H), 7.10-7.05 (m, 1H), 7.03-7.00 (m, 1H), 6.88-6.85 (m, 1H), 6.81-6.80 (m, 1H), 6.73-6.70 (m, 1H), 5.46-5.43 (m, 1H), 4.91 (s, 2H), 4.93-4.25 (m, 4H), 3.61-3.45 (m, 3H), 3.13-2.96 (m, 3H), 2.76-2.64 (m, 2H), 2.12-2.08 (m, 1H), 1.93-1.71 (m, 5H), 1.50-1.40 (m, 5H), 1.15-1.04 (m, 5H). |

| compounds | Structure | MS [M + H+] | 1H-NMR |
|---|---|---|---|
| | 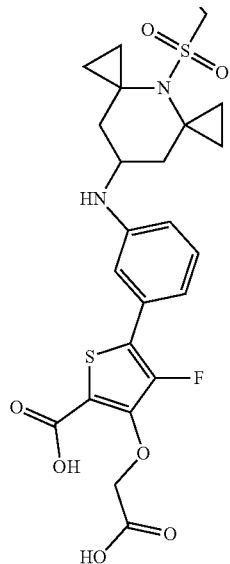 | | |
| 33 | 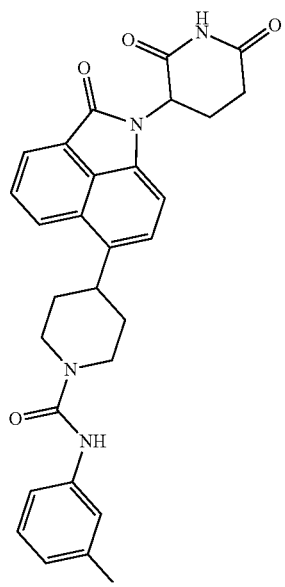 | 1033.33 | 1H NMR (400 MHZ, DMSO-d6): δ 11.12 (s, 1H), 8.66 (s, 1H), 8.53-7.50 (m, 1H), 8.13-8.10 (m, 1H), 7.91-7.86 (m, 1H), 7.61-7.53 (m, 1H), 7.49-7.43 (m, 1H), 7.39-7.36 (m, 1H), 7.28-7.18 (m, 2H), 7.10-7.05 (m, 1H), 7.03-7.00 (m, 1H), 6.88-6.85 (m, 1H), 6.81-6.80 (m, 1H), 6.73-6.70 (m, 1H), 5.46-5.43 (m, 1H), 4.91 (s, 2H), 4.93-4.25 (m, 4H), 3.61-3.45 (m, 3H), 3.13-2.96 (m, 3H), 2.78-2.64 (m, 2H), 2.11-2.08 (m, 1H), 1.93-1.71 (m, 5H), 1.50-1.40 (m, 7H), 1.15-1.04 (m, 7H). |

| compounds | Structure | MS [M + H+] | 1H-NMR |
|---|---|---|---|
| | 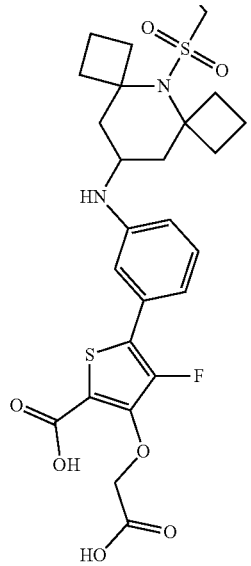 | | |
| 34 | 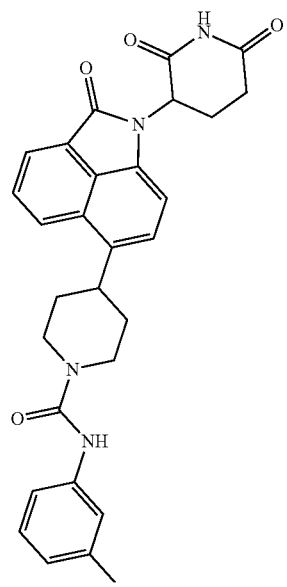 | 1061.36 | 1H NMR (400 MHZ, DMSO-d6): 811.13 (s, 1H), 8.64 (s, 1H), 8.51-7.50 (m, 1H), 8.13-8.10 (m, 1H), 7.89-7.86 (m, 1H), 7.59-7.53 (m, 1H), 7.48-7.43 (m, 1H), 7.37-7.36 (m, 1H), 7.29-7.18 (m, 2H), (m, 1H), 7.05-7.00 (m, 1H), 6.87-6.85 (m, 1H), 6.83-6.80 (m, 1H), 6.73-6.70 (m, 1H), 5.44-5.43 (m, 1H), 4.92 (s, 2H), 4.94-4.25 (m, 4H), 3.61-3.45 (m, 3H), 3.13-2.96 (m, 3H), 2.76-2.64 (m, 2H), 2.12-2.08 (m, 1H), 1.93-1.71 (m, 5H), 1.50-1.40 (m, 9H), 1.15-1.04 (m, 9H). |

| compounds | Structure | MS [M + H+] | 1H-NMR |
|---|---|---|---|
| | 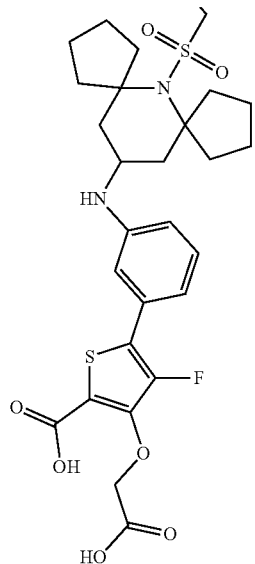 | | |
| 35 | 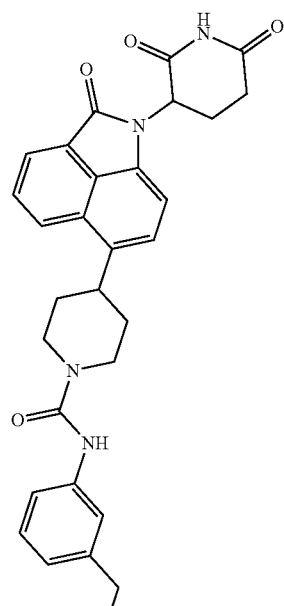 | 965.26 | 1H NMR (400 MHZ, DMSO-d6): δ 13.33 (s, 1H), 11.13 (s, 1H), 8.66 (s, 1H), 8.53-7.50 (m, 1H), 8.13-8.10 (m, 1H), 7.91-7.86 (m, 1H), 7.58-7.53 (m, 1H), 7.48-7.43 (m, 1H), 7.38-7.36 (m, 1H), 7.29-7.18 (m, 2H), 7.10-7.05 (m, 1H), 7.04-7.00 (m, 1H), 6.90-6.85 (m, 1H), 6.81-6.80 (m, 1H), 6.72-6.70 (m, 1H), 5.45-5.43 (m, 1H), 4.91 (s, 2H), 4.93-4.25 (m, 4H), 3.61-3.45 (m, 3H), 3.13-2.96 (m, 5H), 2.75-2.64 (m, 2H), 2.12-2.08 (m, 1H), 1.91-1.71 (m, 2H), 1.51-1.40 (m, 7H), 1.15-1.04 (m, 1H). |

| compounds | Structure | MS [M + H+] | 1H-NMR |
|---|---|---|---|
| | 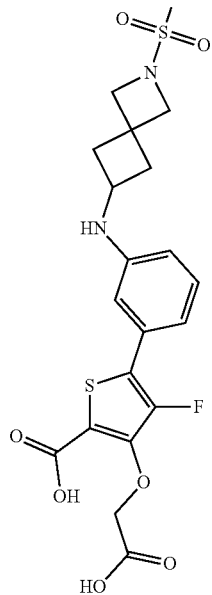 | | |
| 36 | 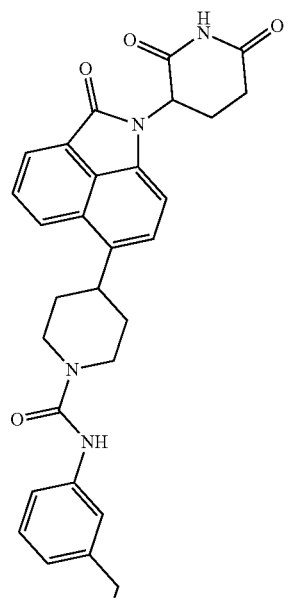 | 1007.31 | 1H NMR (400 MHZ, DMSO-d6): δ 11.06 (d, J = 28.5 Hz, 1H), 8.63 (d, J = 25.8 Hz, 1H), 8.46 (d, J = 8.4 Hz, 1H), 8.08 (d, J = 7.0 Hz, 1H), 7.93-7.73 (m, 1H), 7.64 (s, 1H), 7.47-7.32 (m, 2H), 7.23-7.10 (m, 2H), 7.06 (d, J = 7.6 Hz, 1H), 6.99 (d, J = 7.4 Hz, 1H), 6.87 (s, 1H), 6.82 (d, J = 10.0 Hz, 1H), 6.77 (dd, J = 12.5, 4.1 Hz, 1H), 6.67 (dd, J = 11.9, 10.3 Hz, 1H), 5.39 (dt, J = 29.6, 14.7 Hz, 1H), 4.88 (s, 2H), 4.45-4.03 (m, 4H), 3.70-3.39 (m, 2H), 3.20-2.84 (m, 4H), 2.80-2.59 (m, 2H), 2.09-1.98 (m, 2H), 1.87 (d, J = 11.6 Hz, 3H), 1.75-1.45 (m, 4H), 1.45-1.29 (m, 1H), 1.27-1.11 (m, 2H), 1.00 (d, J = 4.4 Hz, 5H), 0.89 (dd, J = 8.5, 6.4 Hz, 3H). |

-continued
| compounds | Structure | MS [M + H+] | 1H-NMR |
|---|---|---|---|
|  | 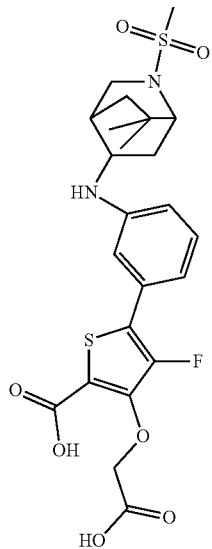 |  |  |
| 37 | 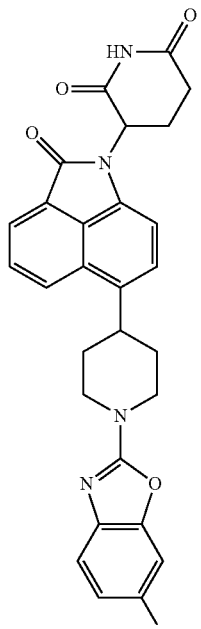 | 1483.84 | 1H NMR (400 MHZ, DMSO-d6) δ 11.12 (s, 1H), 8.53 (d, J = 8.3 Hz, 1H), 8.12 (d, J = 7.0 Hz, 1H), 7.89 (dd, J = 8.2, 7.1 Hz, 1H), 7.45-7.38 (m, 2H), 7.30-7.28 (m, 1H), 7.20 (t, J = 7.9 Hz, 1H), 7.08 (t, J = 7.1 Hz, 2H), 6.88 (s, 1H), 6.81 (d, J = 7.4 Hz, 1H), 6.70 (d, J= 7.9 Hz, 1H), 5.44 (dd, J = 12.5, 5.6 Hz, 1H), 4.92 (s, 2H), 4.48 (d, J = 13.7 Hz, 1H), 4.35 (d, J = 13.5 Hz, 3H), 3.68-3.51 (m, 6H), 3.42 (dd, J = 15.3, 7.4 Hz, 3H), 3.17-3.04 (m, 1H), 2.95 (dd, J = 23.0, 8.1 Hz, 1H), 2.81-2.69 (m, 1H), 2.64 (d, J = 19.1 Hz, 1H), 2.12-2.04 (m, 1H), 1.99 (d, J = 10.3 Hz, 2H), 1.95-1.73 (m, 4H), 1.44 (s, 3H), 1.41-1.31 (m, 4H), 1.17-1.02 (m, 70H). |

| compounds | Structure | MS [M + H+] | 1H-NMR |
|---|---|---|---|
| | 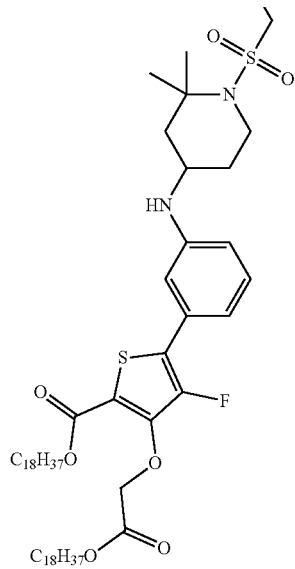 | | |
| 38 | 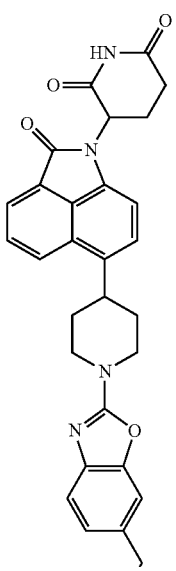 | 1229.55 | 1H NMR (400 MHZ, DMSO-d6) δ 11.12 (s, 1H), 8.53 (d, J = 8.3 Hz, 1H), 8.12 (d, J = 7.0 Hz, 1H), 7.89 (dd, J = 8.2, 7.1 Hz, 1H), 7.45-7.38 (m, 2H), 7.30-7.28 (m, 1H), 7.20 (t, J = 7.9 Hz, 1H), 7.08 (t, J = 7.1 Hz, 2H), 6.88 (s, 1H), 6.81 (d, J = 7.4 Hz, 1H), 6.70 (d, J= 7.9 Hz, 1H), 5.44 (dd, J = 12.5, 5.6 Hz, 1H), 4.92 (s, 2H), 4.48 (d, J = 13.7 Hz, 1H), 4.35 (d, J = 13.5 Hz, 3H), 3.68-3.51 (m, 6H), 3.42 (dd, J = 15.3, 7.4 Hz, 3H), 3.17-3.04 (m, 1H), 2.95 (dd, J = 23.0, 8.1 Hz, 1H), 2.81-2.69 (m, 1H), 2.64 (d, J = 19.1 Hz, 1H), 2.12-2.04 (m, 1H), 1.99 (d, J = 10.3 Hz, 2H), 1.95-1.73 (m, 4H), 1.44 (s, 3H), 1.41-1.31 (m, 4H), 1.17-1.02 (m, 37H). |

| compounds | Structure | MS [M + H⁺] | ¹H-NMR |
|---|---|---|---|
| | 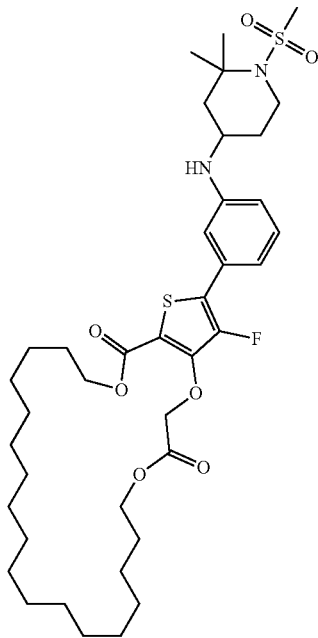 | | |
| 39 | 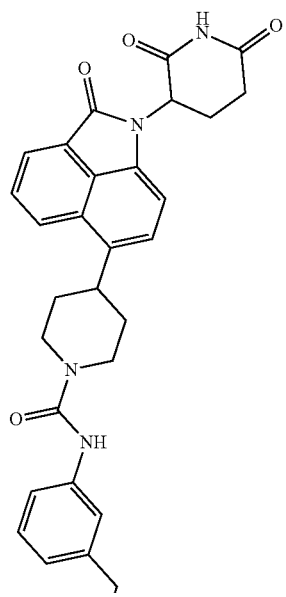 | 995.25 | ¹H NMR (400 MHZ, DMSO-d6): δ 11.12 (s, 1H), 8.66 (s, 1H), 8.52-7.50 (m, 1H), 8.12-8.10 (m, 1H), 7.90-7.86 (m, 1H), 7.59-7.53 (m, 1H), 7.49-7.43 (m, 1H), 7.39-7.36 (m, 1H), 7.28-7.18 (m, 2H), 7.10-7.05 (m, 1H), 7.03-7.00 (m, 1H), 6.88-6.85 (m, 1H), 6.81-6.80 (m, 1H), 6.73-6.70 (m, 1H), 5.46-5.43 (m, 1H), 4.91 (s, 2H), 4.93-4.25 (m, 4H), 3.61-3.45 (m, 3H), 3.13-2.96 (m, 4H), 2.78-2.64 (m, 2H), 2.11-2.08 (m, 1H), 1.93-1.71 (m, 5H), 1.50-1.40 (m, 5H), 1.15-1.04 (m, 1H). |

| compounds | Structure | MS [M + H+] | 1H-NMR |
|---|---|---|---|
| 40 | 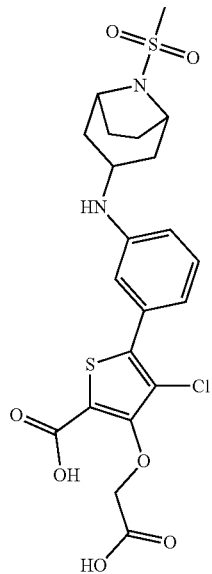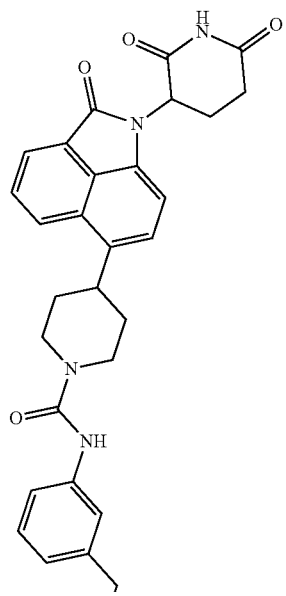 | 995.25 | 1H NMR (400 MHZ, DMSO-d6): δ 11.12 (s, 1H), 8.66 (s, 1H), 8.52-7.50 (m, 1H), 8.12-8.10 (m, 1H), 7.90-7.86 (m, 1H), 7.59-7.53 (m, 1H), 7.49-7.43 (m, 1H), 7.39-7.36 (m, 1H), 7.28-7.18 (m, 2H), 7.10-7.05 (m, 1H), 7.03-7.00 (m, 1H), 6.88-6.85 (m, 1H), 6.81-6.80 (m, 1H), 6.73-6.70 (m, 1H), 5.46-5.43 (m, 1H), 4.91 (s, 2H), 4.93-4.25 (m, 4H), 3.61-3.45 (m, 3H), 3.13-2.96 (m, 6H), 2.78-2.64 (m, 2H), 2.11-2.08 (m, 1H), 1.93-1.71 (m, 5H), 1.50-1.40 (m, 7H), 1.15-1.04 (m, 1H). |

| compounds | Structure | MS [M + H⁺] | ¹H-NMR |
|---|---|---|---|
| | 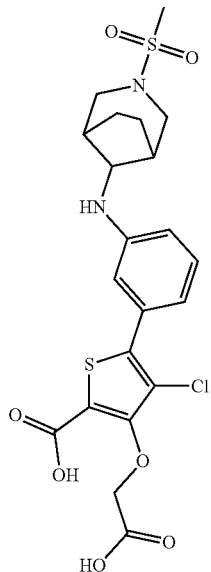 | | |
| 41 | 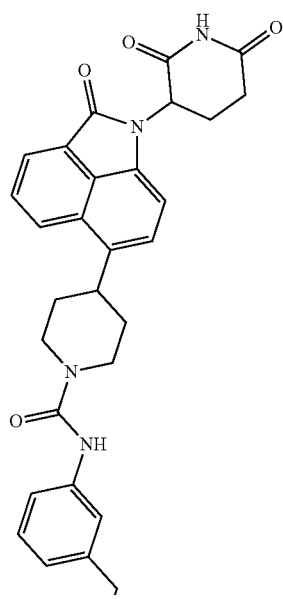 | 1025.30 | ¹H NMR (400 MHZ, DMSO-d6): δ 11.12 (s, 1H), 8.66 (s, 1H), 8.52-7.50 (m, 1H), 8.12-8.10 (m, 1H), 7.90-7.86 (m, 1H), 7.59-7.53 (m, 1H), 7.49-7.43 (m, 1H), 7.39-7.36 (m, 1H), 7.28-7.18 (m, 2H), 7.10-7.05 (m, 1H), 7.03-7.00 (m, 1H), 6.88-6.85 (m, 1H), 6.81-6.80 (m, 1H), 6.73-6.70 (m, 1H), 5.46-5.43 (m, 1H), 4.91 (s, 2H), 4.93-4.25 (m, 4H), 3.61-3.45 (m, 3H), 3.13-2.96 (m, 3H), 2.78-2.64 (m, 2H), 2.11-2.08 (m, 1H), 1.93-1.71 (m, 5H), 1.50-1.40 (m, 7H), 1.15-1.04 (m, 7H). |

| compounds | Structure | MS [M + H+] | 1H-NMR |
|---|---|---|---|
| | 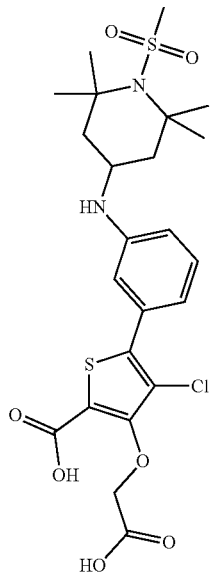 | | |
| 42 | 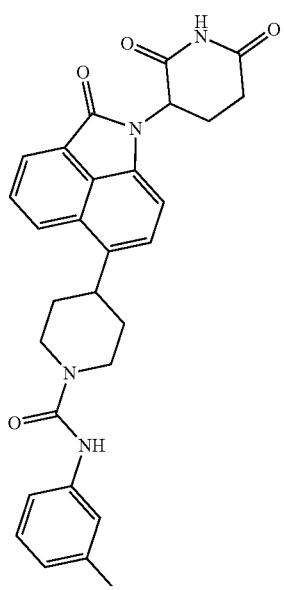 | 1021.27 | 1H NMR (400 MHZ, DMSO-d6): δ 11.12 (s, 1H), 8.66 (s, 1H), 8.52-7.50 (m, 1H), 8.12-8.10 (m, 1H), 7.90-7.86 (m, 1H), 7.59-7.53 (m, 1H), 7.49-7.43 (m, 1H), 7.39-7.36 (m, 1H), 7.28-7.18 (m, 2H), 7.10-7.05 (m, 1H), 7.03-7.00 (m, 1H), 6.88-6.85 (m, 1H), 6.81-6.80 (m, 1H), 6.73-6.70 (m, 1H), 5.46-5.43 (m, 1H), 4.91 (s, 2H), 4.93-4.25 (m, 4H), 3.61-3.45 (m, 3H), 3.13-2.96 (m, 3H), 2.78-2.64 (m, 2H), 2.11-2.08 (m, 1H), 1.93-1.71 (m, 5H), 1.50-1.40 (m, 5H), 1.15-1.04 (m, 5H). |

-continued
| compounds | Structure | MS [M + H+] | 1H-NMR |
|---|---|---|---|
| 43 | 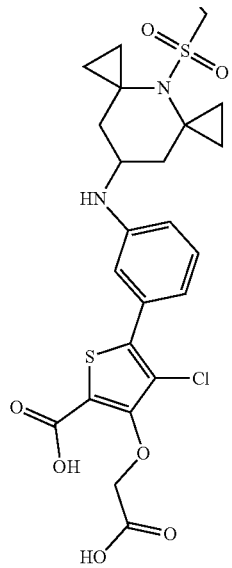<br>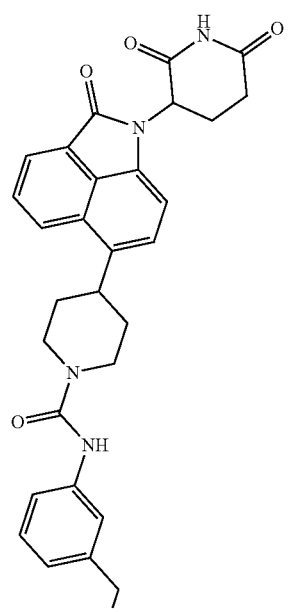 | 981.23 | 1H NMR (400 MHZ, DMSO-d6): δ 11.12 (s, 1H), 8.66 (s, 1H), 8.52-7.50 (m, 1H), 8.12-8.10 (m, 1H), 7.90-7.86 (m, 1H), 7.59-7.53 (m, 1H), 7.49-7.43 (m, 1H), 7.39-7.36 (m, 1H), 7.28-7.18 (m, 2H), 7.10-7.05 (m, 1H), 7.03-7.00 (m, 1H), 6.88-6.85 (m, 1H), 6.81-6.80 (m, 1H), 6.73-6.70 (m, 1H), 5.46-5.43 (m, 1H), 4.91 (s, 2H), 4.93-4.25 (m, 4H), 3.61-3.45 (m, 3H), 3.13-2.96 (m, 5H), 2.78-2.64 (m, 2H), 2.11-2.08 (m, 1H), 1.93-1.71 (m, 2H), 1.50-1.40 (m, 7H), 1.15-1.04 (m, 1H). |

| compounds | Structure | MS [M + H+] | 1H-NMR |
|---|---|---|---|
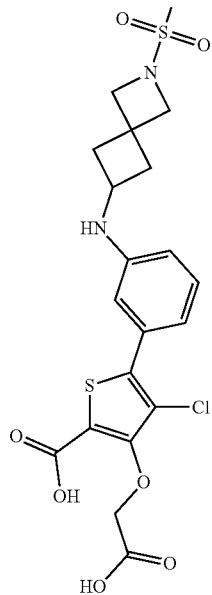
| 44 | 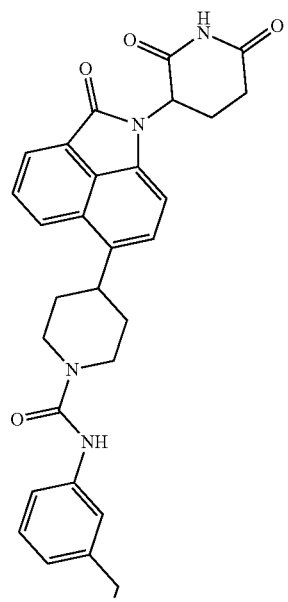 | 1023.28 | 1H NMR (400 MHZ, DMSO-d6): δ 11.06 (d, J = 28.5 Hz, 1H), 8.63 (d, J = 25.8 Hz, 1H), 8.46 (d, J = 8.4 Hz, 1H), 8.08 (d, J = 7.0 Hz, 1H), 7.93-7.73 (m, 1H), 7.64 (s, 1H), 7.47-7.32 (m, 2H), 7.23-7.10 (m, 2H), 7.06 (d, J = 7.6 Hz, 1H), 6.99 (d, J = 7.4 Hz, 1H), 6.87 (s, 1H), 6.82 (d, J = 10.0 Hz, 1H), 6.77 (dd, J = 12.5, 4.1 Hz, 1H), 6.67 (dd, J = 11.9, 10.3 Hz, 1H), 5.39 (dt, J = 29.6, 14.7 Hz, 1H), 4.88 (s, 2H), 4.45-4.03 (m, 4H), 3.70-3.39 (m, 2H), 3.20-2.84 (m, 4H), 2.80-2.59 (m, 2H), 2.09-1.98 (m, 2H), 1.87 (d, J = 11.6 Hz, 3H), 1.75-1.45 (m, 4H), 1.45-1.29 (m, 1H), 1.27-1.11 (m, 2H), 1.00 (d, J = 4.4 Hz, 5H), 0.89 (dd, J = 8.5, 6.4 Hz, 3H). |

| compounds | Structure | MS [M + H+] | 1H-NMR |
|---|---|---|---|
| 45 | 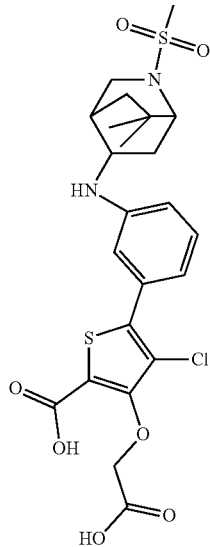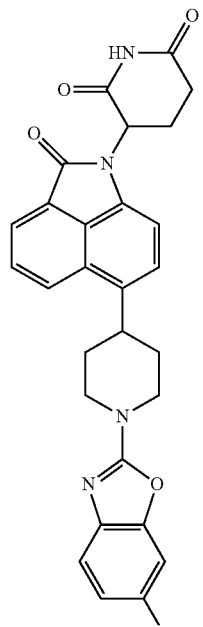 | 1499.81 | 1H NMR (400 MHZ, DMSO-d6) δ 11.12 (s, 1H), 8.53 (d, J = 8.3 Hz, 1H), 8.12 (d, J = 7.0 Hz, 1H), 7.89 (dd, J = 8.2, 7.1 Hz, 1H), 7.45-7.38 (m, 2H), 7.30-7.28 (m, 1H), 7.20 (t, J = 7.9 Hz, 1H), 7.08 (t, J = 7.1 Hz, 2H), 6.88 (s, 1H), 6.81 (d, J = 7.4 Hz, 1H), 6.70 (d, J= 7.9 Hz, 1H), 5.44 (dd, J = 12.5, 5.6 Hz, 1H), 4.92 (s, 2H), 4.48 (d, J = 13.7 Hz, 1H), 4.35 (d, J = 13.5 Hz, 3H), 3.68-3.51 (m, 6H), 3.42 (dd, J = 15.3, 7.4 Hz, 3H), 3.17-3.04 (m, 1H), 2.95 (dd, J = 23.0, 8.1 Hz, 1H), 2.81-2.69 (m, 1H), 2.64 (d, J = 19.1 Hz, 1H), 2.12-2.04 (m, 1H), 1.99 (d, J = 10.3 Hz, 2H), 1.95-1.73 (m, 4H), 1.44 (s, 3H), 1.41-1.31 (m, 4H), 1.17-1.02 (m, 70H). |

-continued
| compounds | Structure | MS [M + H+] | 1H-NMR |
|---|---|---|---|
| 46 | 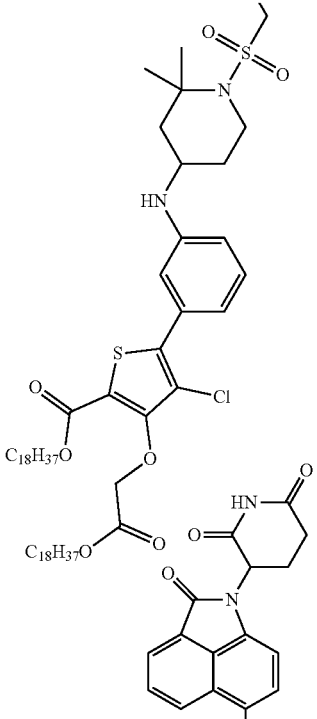 | 1245.52 | 1H NMR (400 MHZ, DMSO-d6) δ 11.12 (s, 1H), 8.53 (d, J = 8.3 Hz, 1H), 8.12 (d, J = 7.0 Hz, 1H), 7.89 (dd, J = 8.2, 7.1 Hz, 1H), 7.45-7.38 (m, 2H), 7.30-7.28 (m, 1H), 7.20 (t, J = 7.9 Hz, 1H), 7.08 (t, J = 7.1 Hz, 2H), 6.88 (s, 1H), 6.81 (d, J = 7.4 Hz, 1H), 6.70 (d, J= 7.9 Hz, 1H), 5.44 (dd, J = 12.5, 5.6 Hz, 1H), 4.92 (s, 2H), 4.48 (d, J = 13.7 Hz, 1H), 4.35 (d, J = 13.5 Hz, 3H), 3.68-3.51 (m, 6H), 3.42 (dd, J = 15.3, 7.4 Hz, 3H), 3.17-3.04 (m, 1H), 2.95 (dd, J = 23.0, 8.1 Hz, 1H), 2.81-2.69 (m, 1H), 2.64 (d, J = 19.1 Hz, 1H), 2.12-2.04 (m, 1H), 1.99 (d, J = 10.3 Hz, 2H), 1.95-1.73 (m, 4H), 1.44 (s, 3H), 1.41-1.31 (m, 4H), 1.17-1.02 (m, 37H). |

-continued

| compounds | Structure | MS [M + H⁺] | ¹H-NMR |
|---|---|---|---|
| 47 | 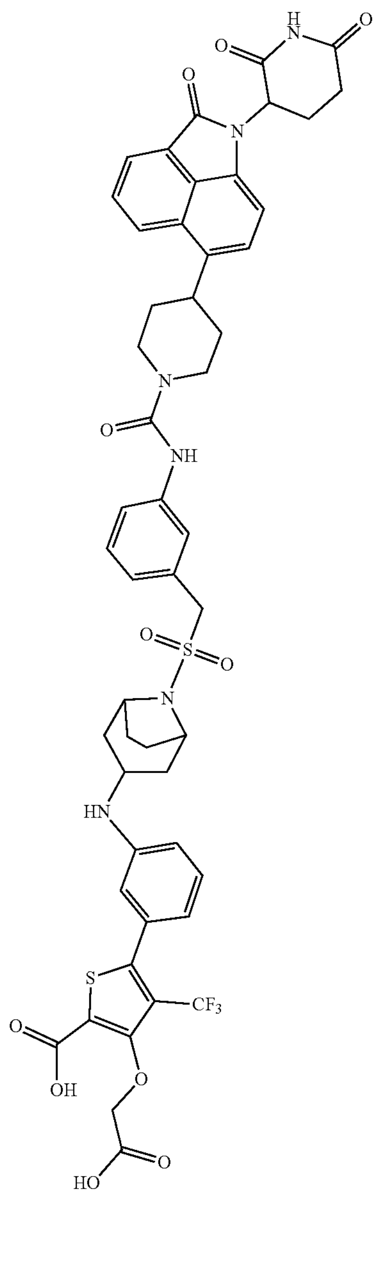 [SMILES: O=C(O)COc1c(C(=O)O)sc(-c2cccc(NC3CC4CCC(C3)N4S(=O)(=O)Cc3cccc(NC(=O)N4CCC(c5ccc6c7c(cccc57)C(=O)N6C5CCC(=O)NC5=O)CC4)c3)c2)c1C(F)(F)F] | 1029.28 | ¹H NMR (400 MHZ, DMSO-d6): δ 11.12 (s, 1H), 8.65 (s, 1H), 8.52-7.50 (m, 1H), 8.12-8.10 (m, 1H), 7.91-7.86 (m, 1H), 7.58-7.53 (m, 1H), 7.49-7.43 (m, 1H), 7.38-7.36 (m, 1H), 7.29-7.18 (m, 2H), 7.11-7.05 (m, 1H), 7.04-7.00 (m, 1H), 6.88-6.85 (m, 1H), 6.81-6.80 (m, 1H), 6.74-6.70 (m, 1H), 5.45-5.43 (m, 1H), 4.91 (s, 2H), 4.91-4.25 (m, 4H), 3.62-3.45 (m, 3H), 3.14-2.96 (m, 4H), 2.79-2.64 (m, 2H), 2.11-2.08 (m, 1H), 1.91-1.71 (m, 5H), 1.49-1.40 (m, 5H), 1.14-1.04 (m, 1H). |

| compounds | Structure | MS [M + H⁺] | ¹H-NMR |
|---|---|---|---|
| 48 | 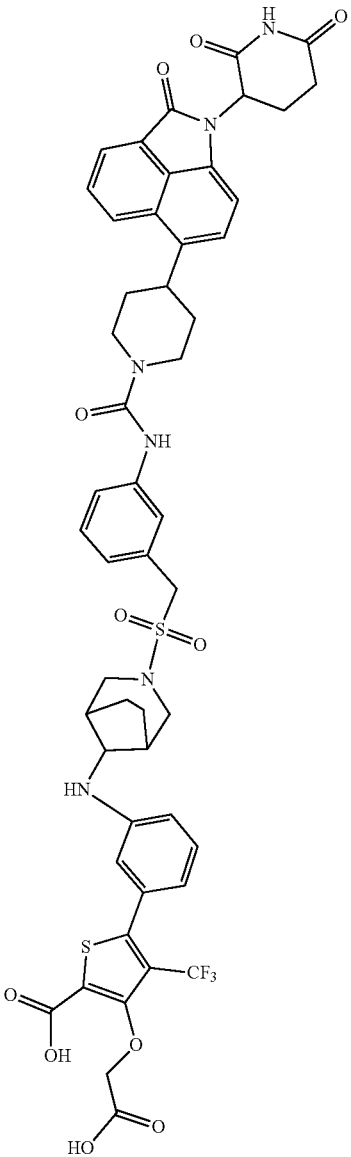 [SMILES: O=C(O)COc1c(C(=O)O)sc(-c2cccc(NC3C4CCC3CN(S(=O)(=O)Cc3cccc(NC(=O)N5CCC(c6ccc7c8c(cccc68)C(=O)N7C6CCC(=O)NC6=O)CC5)c3)C4)c2)c1C(F)(F)F] | 1029.28 | ¹H NMR (400 MHZ, DMSO-d6): δ 11.10 (s, 1H), 8.65 (s, 1H), 8.53-7.50 (m, 1H), 8.11-8.10 (m, 1H), 7.89-7.86 (m, 1H), 7.61-7.53 (m, 1H), 7.48-7.43 (m, 1H), 7.39-7.36 (m, 1H), 7.28-7.18 (m, 2H), 7.10-7.05 (m, 1H), 7.03-7.00 (m, 1H), 6.88-6.85 (m, 1H), 6.82-6.80 (m, 1H), 6.75-6.70 (m, 1H), 5.45-5.43 (m, 1H), 4.91 (s, 2H), 4.92-4.25 (m, 4H), 3.63-3.45 (m, 3H), 3.15-2.96 (m, 6H), 2.79-2.64 (m, 2H), 2.12-2.08 (m, 1H), 1.93-1.71 (m, 5H), 1.50-1.40 (m, 7H), 1.15-1.04 (m, 1H). |

| compounds | Structure | MS [M + H⁺] | ¹H-NMR |
|---|---|---|---|
| 49 | 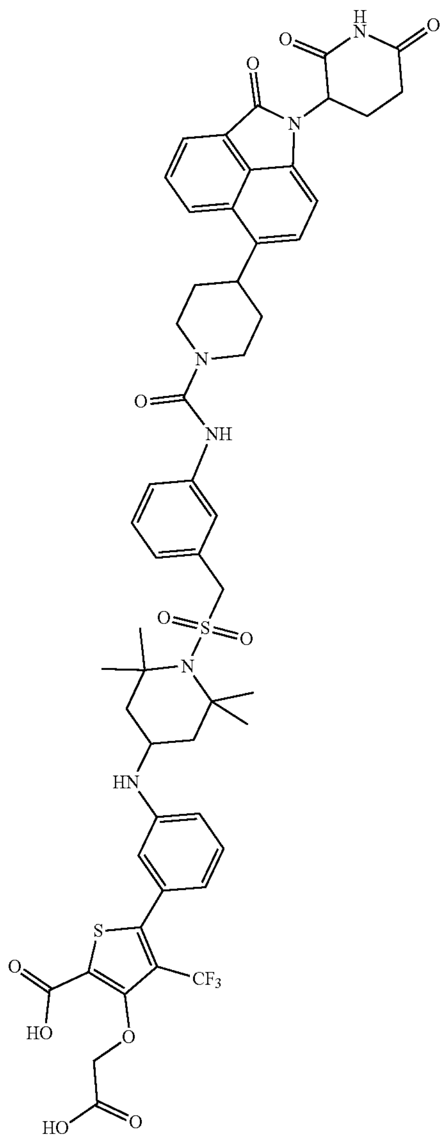 [SMILES: CC1(C)CC(Nc2cccc(-c3sc(C(=O)O)c(OCC(=O)O)c3C(F)(F)F)c2)CC(C)(C)N1S(=O)(=O)Cc1cccc(NC(=O)N2CCC(c3ccc4c5c(cccc35)C(=O)N4C3CCC(=O)NC3=O)CC2)c1] | 1059.32 | ¹H NMR (400 MHZ, DMSO-d6): δ 11.12 (s, 1H), 8.64 (s, 1H), 8.51-7.50 (m, 1H), 8.11-8.10 (m, 1H), 7.91-7.86 (m, 1H), 7.60-7.53 (m, 1H), 7.50-7.43 (m, 1H), 7.41-7.36 (m, 1H), 7.29-7.18 (m, 2H), 7.11-7.05 (m, 1H), 7.04-7.00 (m, 1H), 6.89-6.85 (m, 1H), 6.81-6.80 (m, 1H), 6.74-6.70 (m, 1H), 5.46-5.43 (m, 1H), 4.91 (s, 2H), 4.93-4.25 (m, 4H), 3.61-3.45 (m, 3H), 3.13-2.96 (m, 3H), 2.78-2.64 (m, 2H), 2.10-2.08 (m, 1H), 1.92-1.71 (m, 5H), 1.51-1.40 (m, 7H), 1.14-1.04 (m, 7H). |

| compounds | Structure | MS [M + H+] | 1H-NMR |
|---|---|---|---|
| 50 | 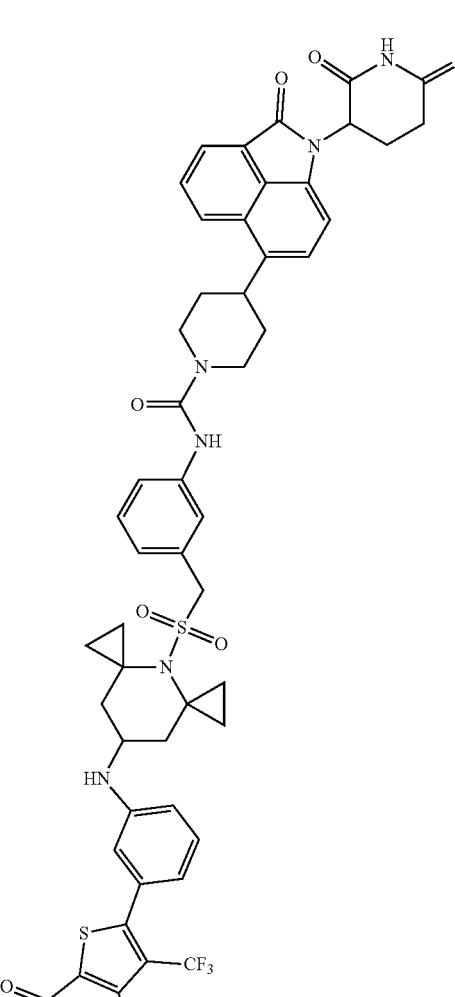 | 1055.29 | 1H NMR (400 MHZ, DMSO-d6): δ 11.14 (s, 1H), 8.65 (s, 1H), 8.53-7.50 (m, 1H), 8.11-8.10 (m, 1H), 7.91-7.86 (m, 1H), 7.59-7.53 (m, 1H), 7.49-7.43 (m, 1H), 7.39-7.36 (m, 1H), 7.28-7.18 (m, 2H), 7.10-7.05 (m, 1H), 7.03-7.00 (m, 1H), 6.88-6.85 (m, 1H), 6.81-6.80 (m, 1H), 6.73-6.70 (m, 1H), 5.46-5.43 (m, 1H), 4.91 (s, 2H), 4.93-4.25 (m, 4H), 3.61-3.45 (m, 3H), 3.13-2.96 (m, 3H), 2.78-2.64 (m, 2H), 2.11-2.08 (m, 1H), 1.93-1.71 (m, 5H), 1.50-1.40 (m, 5H), 1.15-1.04 (m, 5H). |

-continued

| compounds | Structure | MS [M + H+] | 1H-NMR |
|---|---|---|---|
| 51 | 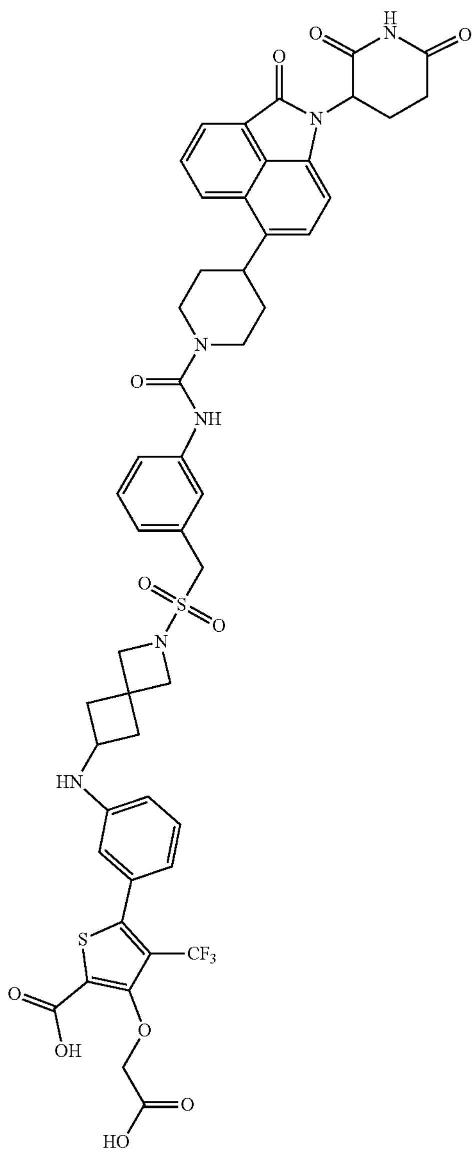 [SMILES: O=C(O)COc1c(C(=O)O)sc(-c2cccc(NC3CC4(C3)CN(S(=O)(=O)Cc3cccc(NC(=O)N5CCC(c6ccc7c8c(cccc68)C(=O)N7C6CCC(=O)NC6=O)CC5)c3)C4)c2)c1C(F)(F)F] | 1015.26 | 1H NMR (400 MHZ, DMSO-d6): δ 11.13 (s, 1H), 8.67 (s, 1H), 8.54-7.50 (m, 1H), 8.11-8.10 (m, 1H), 7.91-7.86 (m, 1H), 7.57-7.53 (m, 1H), 7.51-7.43 (m, 1H), 7.38-7.36 (m, 1H), 7.29-7.18 (m, 2H), 7.11-7.05 (m, 1H), 7.04-7.00 (m, 1H), 6.89-6.85 (m, 1H), 6.82-6.80 (m, 1H), 6.74-6.70 (m, 1H), 5.47-5.43 (m, 1H), 4.92 (s, 2H), 4.91-4.25 (m, 4H), 3.62-3.45 (m, 3H), 3.11-2.96 (m, 5H), 2.77-2.64 (m, 2H), 2.12-2.08 (m, 1H), 1.93-1.71 (m, 2H), 1.50-1.40 (m, 7H), 1.15-1.04 (m, 1H). |

-continued

| compounds | Structure | MS [M + H+] | 1H-NMR |
|---|---|---|---|
| 52 | 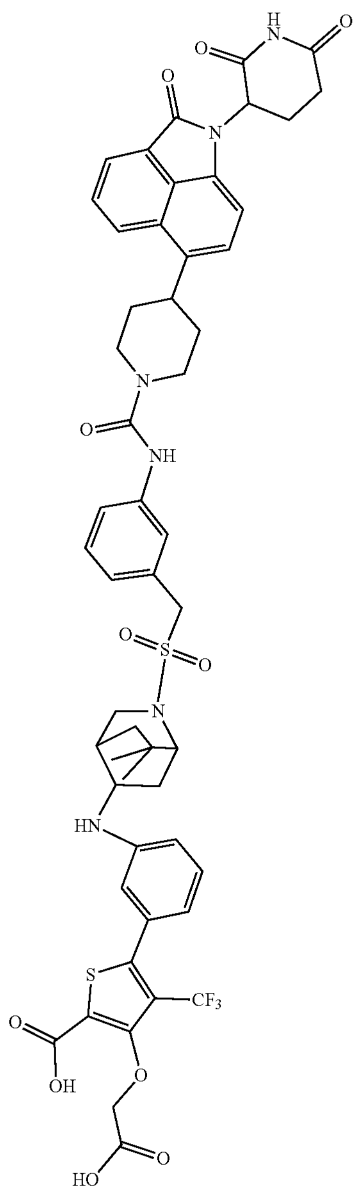 [SMILES: CC1(C)CC2CN(S(=O)(=O)Cc3cccc(NC(=O)N4CCC(c5ccc6c7c(cccc57)C(=O)N6C5CCC(=O)NC5=O)CC4)c3)C1CC2Nc1cccc(-c2sc(C(=O)O)c(OCC(=O)O)c2C(F)(F)F)c1] | 1057.31 | 1H NMR (400 MHZ, DMSO-d6): δ 11.06 (d, J = 28.5 Hz, 1H), 8.63 (d, J = 25.8 Hz, 1H), 8.46 (d, J = 8.4 Hz, 1H), 8.08 (d, J = 7.0 Hz, 1H), 7.93-7.73 (m, 1H), 7.64 (s, 1H), 7.47-7.32 (m, 2H), 7.23-7.10 (m, 2H), 7.06 (d, J = 7.6 Hz, 1H), 6.99 (d, J = 7.4 Hz, 1H), 6.87 (s, 1H), 6.82 (d, J = 10.0 Hz, 1H), 6.77 (dd, J = 12.5, 4.1 Hz, 1H), 6.67 (dd, J = 11.9, 10.3 Hz, 1H), 5.39 (dt, J = 29.6, 14.7 Hz, 1H), 4.88 (s, 2H), 4.45-4.03 (m, 4H), 3.70-3.39 (m, 2H), 3.20-2.84 (m, 4H), 2.80-2.59 (m, 2H), 2.09-1.98 (m, 2H), 1.87 (d, J = 11.6 Hz, 3H), 1.75-1.45 (m, 4H), 1.45-1.29 (m, 1H), 1.27-1.11 (m, 2H), 1.00 (d, J = 4.4 Hz, 5H), 0.89 (dd, J = 8.5, 6.4 Hz, 3H). |

| compounds | Structure | MS [M + H+] | 1H-NMR |
|---|---|---|---|
| 53 | 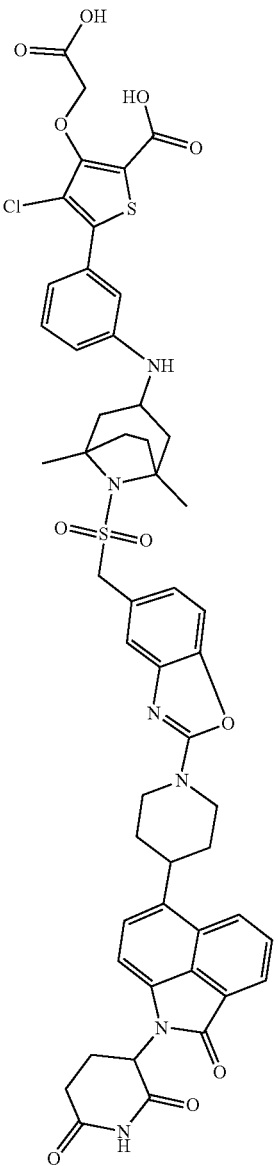 [SMILES: CC12CCC(C)(CC(Nc3cccc(-c4sc(C(=O)O)c(OCC(=O)O)c4Cl)c3)C1)N2S(=O)(=O)Cc1ccc2oc(N3CCC(c4ccc5c6c(cccc46)C(=O)N5C4CCC(=O)NC4=O)CC3)nc2c1] | 1021.27 | 1H NMR (400 MHZ, DMSO-d6): δ 11.14 (s, 1H), 8.66 (s, 1H), 8.52-7.50 (m, 1H), 8.11-8.10 (m, 1H), 7.91-7.86 (m, 1H), 7.58-7.53 (m, 1H), 7.49-7.43 (m, 1H), 7.39-7.36 (m, 1H), 7.28-7.18 (m, 2H), 7.10-7.05 (m, 1H), 7.03-7.00 (m, 1H), 6.88-6.85 (m, 1H), 6.81-6.80 (m, 1H), 6.73-6.70 (m, 1H), 5.46-5.43 (m, 1H), 4.91 (s, 2H), 4.93-4.25 (m, 4H), 3.61-3.45 (m, 3H), 3.13-2.96 (m, 3H), 2.78-2.64 (m, 2H), 2.11-2.08 (m, 1H), 1.93-1.71 (m, 5H), 1.50-1.40 (m, 5H), 1.15-0.88 (m, 7H). |

| compounds | Structure | MS [M + H+] | 1H-NMR |
|---|---|---|---|
| 54 | 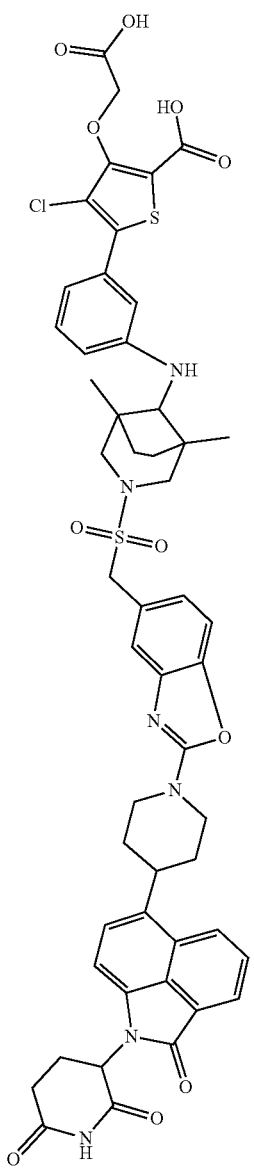 [SMILES: CC12CCC(C)(CN(S(=O)(=O)Cc3ccc4oc(N5CCC(c6ccc7c8c(cccc68)C(=O)N7C6CCC(=O)NC6=O)CC5)nc4c3)C1)C2Nc1cccc(-c2sc(C(=O)O)c(OCC(=O)O)c2Cl)c1] | 1021.27 | 1H NMR (400 MHz, DMSO-d6): δ 11.14 (s, 1H), 8.65 (s, 1H), 8.53-7.50 (m, 1H), 8.11-8.10 (m, 1H), 7.91-7.86 (m, 1H), 7.59-7.53 (m, 1H), 7.49-7.43 (m, 1H), 7.39-7.36 (m, 1H), 7.28-7.18 (m, 2H), 7.10-7.05 (m, 1H), 7.03-7.00 (m, 1H), 6.88-6.85 (m, 1H), 6.81-6.80 (m, 1H), 6.73-6.70 (m, 1H), 5.46-5.43 (m, 1H), 4.91 (s, 2H), 4.93-4.25 (m, 4H), 3.61-3.45 (m, 3H), 3.13-2.96 (m, 7H), 2.78-2.64 (m, 2H), 2.11-2.08 (m, 1H), 1.93-1.71 (m, 5H), 1.50-1.40 (m, 3H), 1.15-0.88 (m, 5H). |

-continued
| compounds | Structure | MS [M + H⁺] | ¹H-NMR |
|---|---|---|---|
| 55 | 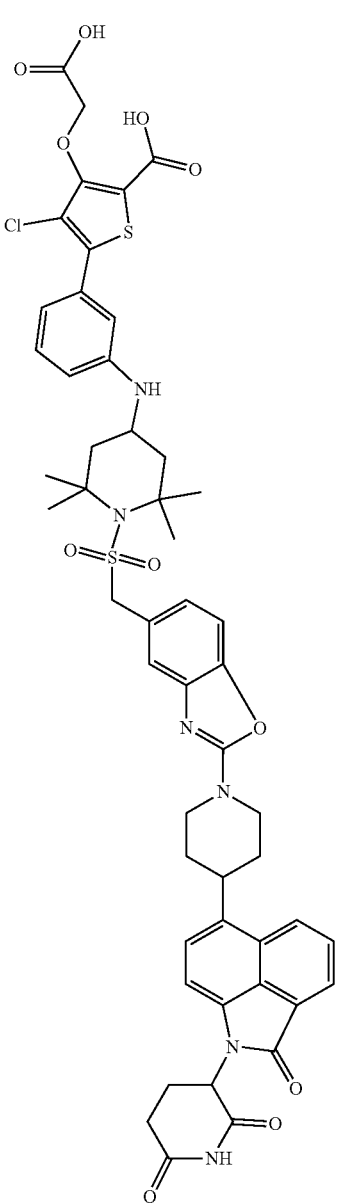 [SMILES: CC1(C)CC(Nc2cccc(-c3sc(C(=O)O)c(OCC(=O)O)c3Cl)c2)CC(C)(C)N1S(=O)(=O)Cc1ccc2oc(N3CCC(c4ccc5c6c(cccc46)C(=O)N5C4CCC(=O)NC4=O)CC3)nc2c1] | 1023.28 | ¹H NMR (400 MHZ, DMSO-d6): δ 11.14 (s, 1H), 8.65 (s, 1H), 8.53-7.50 (m, 1H), 8.11-8.10 (m, 1H), 7.91-7.86 (m, 1H), 7.59-7.53 (m, 1H), 7.49-7.43 (m, 1H), 7.39-7.36 (m, 1H), 7.28-7.18 (m, 2H), 7.10-7.05 (m, 1H), 7.03-7.00 (m, 1H), 6.88-6.85 (m, 1H), 6.81-6.80 (m, 1H), 6.73-6.70 (m, 1H), 5.46-5.43 (m, 1H), 4.91 (s, 2H), 4.93-4.25 (m, 4H), 3.61-3.45 (m, 3H), 3.13-2.96 (m, 3H), 2.78-2.64 (m, 2H), 2.11-2.08 (m, 1H), 1.93-1.71 (m, 5H), 1.50-1.40 (m, 6H), 1.15-0.82 (m, 8H). |

-continued
| compounds | Structure | MS [M + H+] | 1H-NMR |
|---|---|---|---|
| 56 | 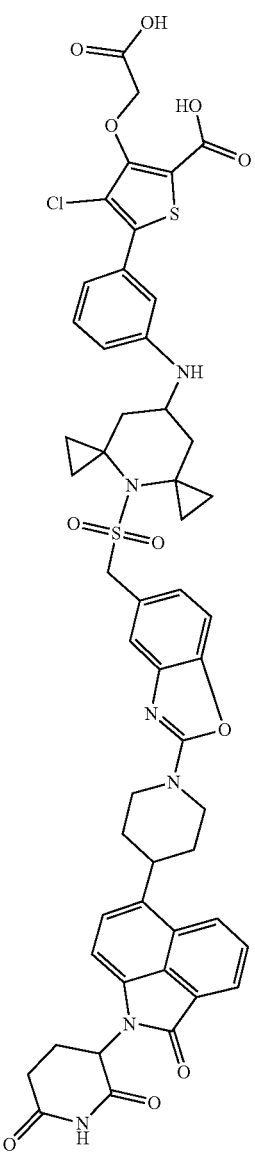 [SMILES: O=C(O)COc1c(C(=O)O)sc(-c2cccc(NC3CC4(CC4)N(S(=O)(=O)Cc4ccc5oc(N6CCC(c7ccc8c9c(cccc79)C(=O)N8C7CCC(=O)NC7=O)CC6)nc5c4)C4(CC4)C3)c2)c1Cl] | 1019.25 | 1H NMR (400 MHZ, DMSO-d6): δ 11.14 (s, 1H), 8.65 (s, 1H), 8.53-7.50 (m, 1H), 8.11-8.10 (m, 1H), 7.91-7.86 (m, 1H), 7.59-7.53 (m, 1H), 7.49-7.43 (m, 1H), 7.39-7.36 (m, 1H), 7.28-7.18 (m, 2H), 7.10-7.05 (m, 1H), 7.03-7.00 (m, 1H), 6.88-6.85 (m, 1H), 6.81-6.80 (m, 1H), 6.73-6.70 (m, 1H), 5.46-5.43 (m, 1H), 4.91 (s, 2H), 4.93-4.25 (m, 4H), 3.61-3.45 (m, 3H), 3.13-2.96 (m, 3H), 2.78-2.64 (m, 2H), 2.11-2.08 (m, 1H), 1.93-1.71 (m, 5H), 1.50-1.40 (m, 6H), 1.15-1.04 (m, 6H). |

-continued
| compounds | Structure | MS [M + H⁺] | ¹H-NMR |
|---|---|---|---|
| 57 | 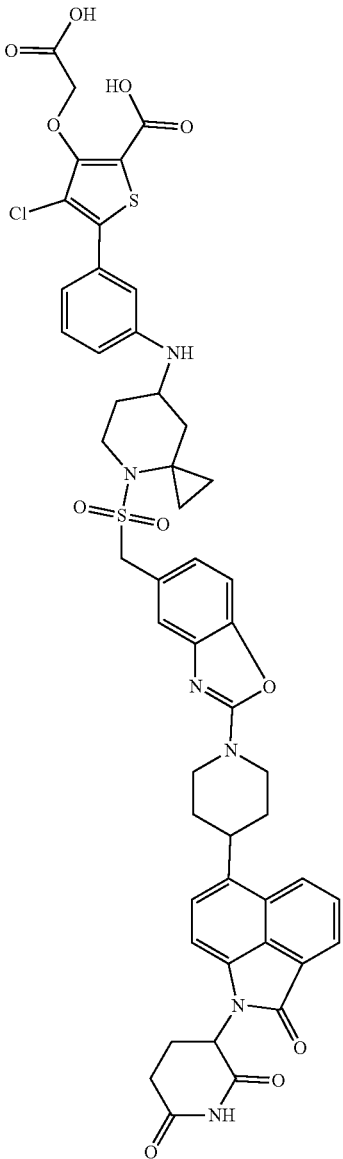 [SMILES: O=C(O)COc1c(C(=O)O)sc(-c2cccc(NC3CCN(S(=O)(=O)Cc4ccc5oc(N6CCC(c7ccc8c9c(cccc79)C(=O)N8C7CCC(=O)NC7=O)CC6)nc5c4)C4(CC4)C3)c2)c1Cl] | 993.24 | ¹H NMR (400 MHZ, DMSO-d6): δ 11.13 (s, 1H), 8.53 (d, J = 8.5 Hz, 1H), 8.13 (d, J = 7.0 Hz, 1H), 7.96-7.79 (m, 1H), 7.41 (d, J = 8.3 Hz, 2H), 7.20 (s, 2H), 7.10 (d, J = 7.5 Hz, 1H), 6.96-6.87 (m, 1H), 6.84 (d, J = 6.8 Hz, 1H), 6.72 (d, J = 6.6 Hz, 1H), 5.45 (dd, J = 12.8, 5.1 Hz, 1H), 4.92 (s, 2H), 4.35 (dt, J = 25.9, 13.7 Hz, 4H), 3.78-3.34 (m, 5H), 2.95 (dt, J = 17.4, 8.9 Hz, 2H), 2.84-2.58 (m, 2H), 2.17-1.79 (m, 6H), 1.64 (dd, J = 87.4, 10.1 Hz, 3H), 1.37-1.16 (m, 3H), 0.90-0.26 (m, 6H). |

-continued
| compounds | Structure | MS [M + H+] | 1H-NMR |
|---|---|---|---|
| 58 | 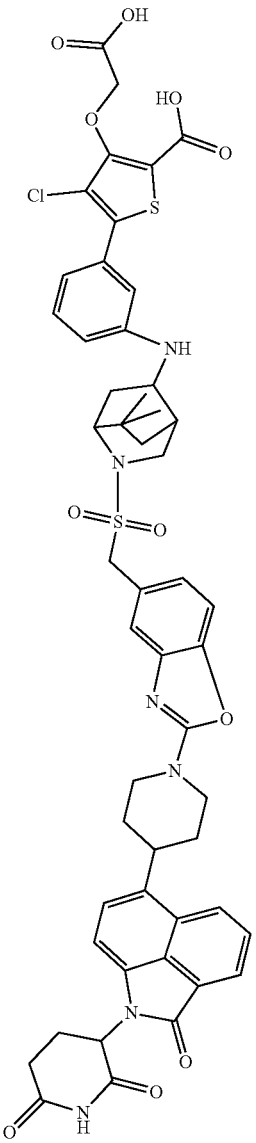 [SMILES: CC1(C)CC2CN(S(=O)(=O)Cc3ccc4oc(N5CCC(c6ccc7c8c(cccc68)C(=O)N7C6CCC(=O)NC6=O)CC5)nc4c3)C1CC2Nc1cccc(-c2sc(C(=O)O)c(OCC(=O)O)c2Cl)c1] | 1021.27 | 1H NMR (400 MHZ, DMSO-d6): δ 11.06 (d, J = 28.5 Hz, 1H), 8.63 (d, J = 25.8 Hz, 1H), 8.46 (d, J = 8.4 Hz, 1H), 8.08 (d, J = 7.0 Hz, 1H), 7.93-7.73 (m, 1H), 7.64 (s, 1H), 7.47-7.32 (m, 2H), 7.23-7.10 (m, 2H), 7.06 (d, J = 7.6 Hz, 1H), 6.99 (d, J = 7.4 Hz, 1H), 6.87 (s, 1H), 6.82 (d, J = 10.0 Hz, 1H), 6.77 (dd, J = 12.5, 4.1 Hz, 1H), 6.67 (dd, J = 11.9, 10.3 Hz, 1H), 5.39 (dt, J = 29.6, 14.7 Hz, 1H), 4.88 (s, 2H), 4.45-4.03 (m, 4H), 3.70-3.39 (m, 2H), 3.20-2.84 (m, 4H), 2.80-2.59 (m, 2H), 2.09-1.98 (m, 2H), 1.87 (d, J = 11.6 Hz, 3H), 1.75-1.45 (m, 4H), 1.45-1.29 (m, 1H), 1.27-1.11 (m, 2H), 1.00 (d, J = 4.4 Hz, 5H), 0.89 (dd, J = 8.5, 6.4 Hz, 3H). |

-continued
| compounds | Structure | MS [M + H+] | 1H-NMR |
|---|---|---|---|
| 59 | 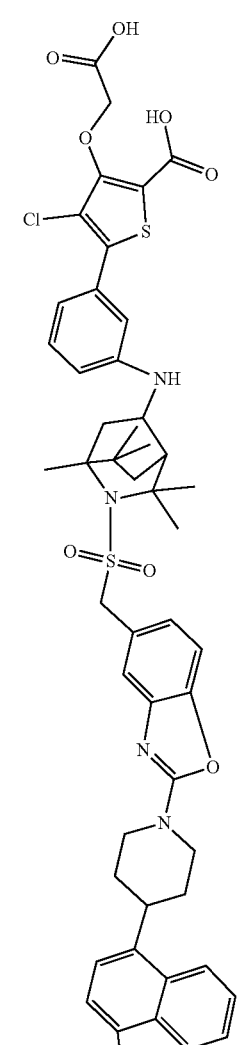 | 1063.31 | 1HNMR (400 MHZ, DMSO-d6) δ 10.60 (s, 1H), 8.62 (s, 1H), 8.43-8.38 (m, 1H), 8.10-8.03 (m, 1H), 7.90-7.78 (m, 1H), 7.68-7.62 (m, 1H), 7.49-7.42 (m, 1H), 7.33-7.27 (m, 1H), 7.23-7.15 (m, 2H), 7.06-6.98 (m, 2H), 6.87-6.82 (m, 1H), 6.77-6.75 (m, 1H), 6.65-6.59 (m, 1H), 5.43-5.39 (m, 2H), 4.91-4.86 (m, 2H), 4.45-4.30 (m, 3H), 4.27-4.18 (m, 2H), 3.52-3.40 (m, 2H), 3.32-3.16 (m, 3H), 3.08-3.03 (m, 2H), 3.00-2.83 (m, 4H), 2.80-2.57 (m, 2H), 2.11-1.96 (m, 1H), 1.90-1.79 (m, 1H), 1.76-1.55 (m, 2H), 1.38-1.20 (m, 2H), 1.02-0.84 (m, 15H). |

| compounds | Structure | MS [M + H$^+$] | $^1$H-NMR |
|---|---|---|---|
| 60 | 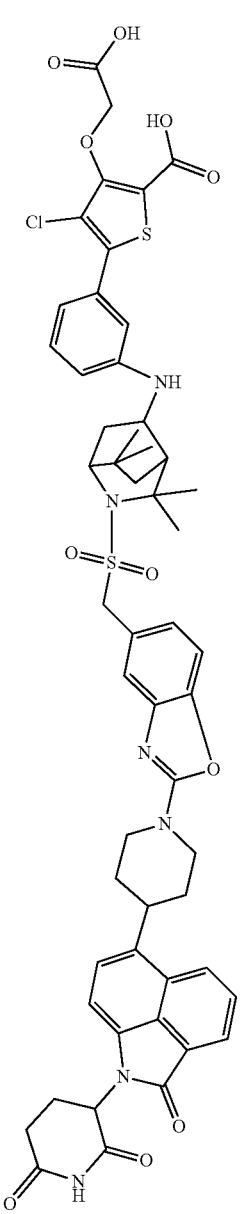 [SMILES: CC1(C)CC2C(Nc3cccc(-c4sc(C(=O)O)c(OCC(=O)O)c4Cl)c3)CC1N(S(=O)(=O)Cc1ccc3oc(N4CCC(c5ccc6c7c(cccc57)C(=O)N6C5CCC(=O)NC5=O)CC4)nc3c1)C2(C)C] | 1049.30 | $^1$HNMR (400 MHZ, DMSO-d6) δ 10.56 (s, 1H), 8.61 (s, 1H), 8.43-8.38 (m, 1H), 8.10-8.03 (m, 1H), 7.90-7.78 (m, 1H), 7.68-7.62 (m, 1H), 7.49-7.42 (m, 1H), 7.33-7.27 (m, 1H), 7.23-7.15 (m, 2H), 7.06-6.98 (m, 2H), 6.87-6.82 (m, 1H), 6.77-6.75 (m, 1H), 6.65-6.59 (m, 1H), 5.43-5.39 (m, 2H), 4.91-4.86 (m, 2H), 4.45-4.30 (m, 3H), 4.27-4.18 (m, 2H), 3.52-3.40 (m, 2H), 3.32-3.16 (m, 3H), 3.08-3.03 (m, 2H), 3.00-2.83 (m, 4H), 2.80-2.57 (m, 2H), 2.11-1.96 (m, 1H), 1.90-1.79 (m, 1H), 1.76-1.55 (m, 2H), 1.38-1.20 (m, 2H), 1.02-0.85 (m, 12H). |

-continued
| compounds | Structure | MS [M + H+] | 1H-NMR |
|---|---|---|---|
| 61 | 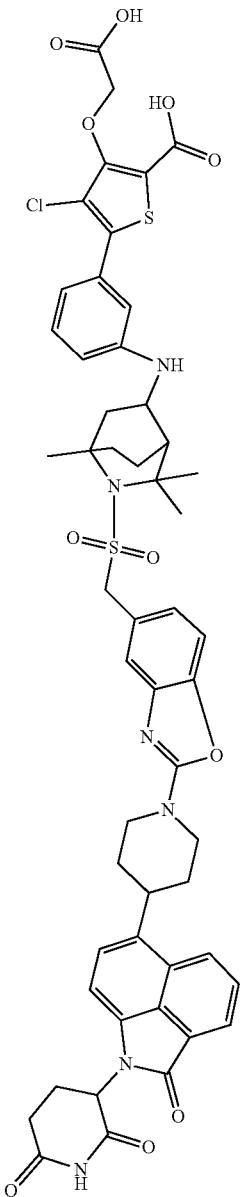 [SMILES: CC12CCC(C(Nc3cccc(-c4sc(C(=O)O)c(OCC(=O)O)c4Cl)c3)C1)C(C)(C)N2S(=O)(=O)Cc1ccc2oc(N3CCC(c4ccc5c6c(cccc46)C(=O)N5C4CCC(=O)NC4=O)CC3)nc2c1] | 1035.28 | 1HNMR (400 MHZ, DMSO-d6) δ 10.56 (s, 1H), 8.60 (s, 1H), 8.43-8.38 (m, 1H), 8.10-8.03 (m, 1H), 7.90-7.78 (m, 1H), 7.68-7.62 (m, 1H), 7.49-7.42 (m, 1H), 7.33-7.27 (m, 1H), 7.23-7.15 (m, 2H), 7.06-6.98 (m, 2H), 6.87-6.82 (m, 1H), 6.77-6.75 (m, 1H), 6.65-6.59 (m, 1H), 5.43-5.39 (m, 2H), 4.91-4.86 (m, 2H), 4.45-4.30 (m, 3H), 4.27-4.18 (m, 2H), 3.52-3.40 (m, 2H), 3.32-3.16 (m, 3H), 3.08-3.03 (m, 2H), 3.00-2.83 (m, 4H), 2.80-2.57 (m, 2H), 2.11-1.96 (m, 1H), 1.90-1.79 (m, 1H), 1.76-1.55 (m, 2H), 1.38-1.20 (m, 2H), 1.02-0.83 (m, 9H). |

| compounds | Structure | MS [M + H+] | 1H-NMR |
|---|---|---|---|
| 62 | 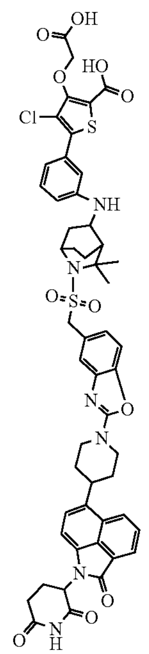 [SMILES: CC1(C)C2CCC(CC2Nc2cccc(-c3sc(C(=O)O)c(OCC(=O)O)c3Cl)c2)N1S(=O)(=O)Cc1ccc2oc(N3CCC(c4ccc5c6c(cccc46)C(=O)N5C4CCC(=O)NC4=O)CC3)nc2c1] | 1021.27 | 1HNMR (400 MHZ, DMSO-d6) δ 10.55 (s, 1H), 8.60 (s, 1H), 8.43-8.38 (m, 1H), 8.10-8.03 (m, 1H), 7.90-7.78 (m, 1H), 7.68-7.62 (m, 1H), 7.49-7.42 (m, 1H), 7.33-7.27 (m, 1H), 7.23-7.15 (m, 2H), 7.06-6.98 (m, 2H), 6.87-6.82 (m, 1H), 6.77-6.75 (m, 1H), 6.65-6.59 (m, 1H), 5.43-5.39 (m, 2H), 4.91-4.86 (m, 2H), 4.45-4.30 (m, 3H), 4.27-4.18 (m, 2H), 3.52-3.40 (m, 2H), 3.32-3.16 (m, 3H), 3.08-3.03 (m, 2H), 3.00-2.83 (m, 4H), 2.80-2.57 (m, 2H), 2.11-1.96 (m, 1H), 1.90-1.79 (m, 1H), 1.76-1.55 (m, 2H), 1.38-1.20 (m, 2H), 1.02-0.95 (m, 6H). |
| 63 | 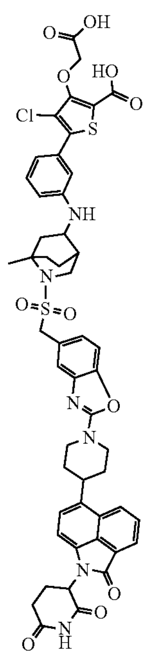 [SMILES: CC12CCC(CN1S(=O)(=O)Cc1ccc3oc(N4CCC(c5ccc6c7c(cccc57)C(=O)N6C5CCC(=O)NC5=O)CC4)nc3c1)C(Nc1cccc(-c3sc(C(=O)O)c(OCC(=O)O)c3Cl)c1)C2] | 1007.25 | 1HNMR (400 MHZ, DMSO-d6) δ 10.65 (s, 1H), 8.60 (s, 1H), 8.43-8.38 (m, 1H), 8.10-8.03 (m, 1H), 7.90-7.78 (m, 1H), 7.68-7.62 (m, 1H), 7.49-7.42 (m, 1H), 7.33-7.27 (m, 1H), 7.23-7.15 (m, 2H), 7.06-6.98 (m, 2H), 6.87-6.82 (m, 1H), 6.77-6.75 (m, 1H), 6.65-6.59 (m, 1H), 5.43-5.39 (m, 2H), 4.91-4.86 (m, 2H), 4.45-4.30 (m, 3H), 4.27-4.18 (m, 2H), 3.52-3.40 (m, 2H), 3.32-3.16 (m, 3H), 3.08-3.03 (m, 2H), 3.00-2.83 (m, 4H), 2.80-2.57 (m, 2H), 2.11-1.96 (m, 1H), 1.90-1.79 (m, 1H), 1.76-1.55 (m, 2H), 1.38-1.20 (m, 2H), 1.02-0.95 (m, 3H). |

-continued

| compounds | Structure | MS [M + H⁺] | ¹H-NMR |
|---|---|---|---|
| 64 | 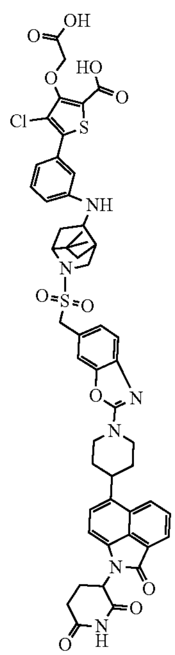 [SMILES: CC1(C)CC2CN(S(=O)(=O)Cc3ccc4nc(N5CCC(c6ccc7c8c(cccc68)C(=O)N7C6CCC(=O)NC6=O)CC5)oc4c3)C1CC2Nc1cccc(-c2sc(C(=O)O)c(OCC(=O)O)c2Cl)c1] | 1021.27 | ¹H NMR (400 MHz, DMSO-d6): δ 11.06 (d, J = 28.5 Hz, 1H), 8.63 (d, J = 25.8 Hz, 1H), 8.46 (d, J = 8.4 Hz, 1H), 8.08 (d, J = 7.0 Hz, 1H), 7.93-7.73 (m, 1H), 7.64 (s, 1H), 7.47-7.32 (m, 2H), 7.23-7.10 (m, 2H), 7.06 (d, J = 7.6 Hz, 1H), 6.99 (d, J = 7.4 Hz, 1H), 6.87 (s, 1H), 6.82 (d, J = 10.0 Hz, 1H), 6.77 (dd, J = 12.5, 4.1 Hz, 1H), 6.67 (dd, J = 11.9, 10.3 Hz, 1H), 5.39 (dt, J = 29.6, 14.7 Hz, 1H), 4.88 (s, 2H), 4.45-4.03 (m, 4H), 3.70-3.39 (m, 2H), 3.20-2.84 (m, 4H), 2.80-2.59 (m, 2H), 2.09-1.98 (m, 2H), 1.87 (d, J = 11.6 Hz, 3H), 1.75-1.45 (m, 4H), 1.45-1.29 (m, 1H), 1.27-1.11 (m, 2H), 1.00 (d, J = 4.4 Hz, 5H), 0.89 (dd, J = 8.5, 6.4 Hz, 3H). |
| 65 | 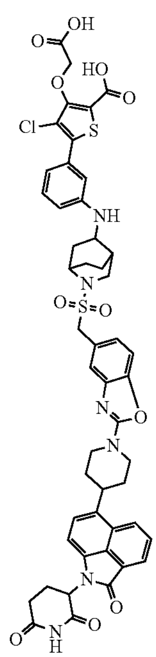 [SMILES: O=C(O)COc1c(C(=O)O)sc(-c2cccc(NC3CC4CCC3CN4S(=O)(=O)Cc3ccc4oc(N5CCC(c6ccc7c8c(cccc68)C(=O)N7C6CCC(=O)NC6=O)CC5)nc4c3)c2)c1Cl] | 993.24 | ¹HNMR (400 MHZ, DMSO-d6) δ 10.65 (s, 1H), 8.60 (s, 1H), 8.43-8.38 (m, 1H), 8.10-8.03 (m, 1H), 7.90-7.78 (m, 1H), 7.68-7.62 (m, 1H), 7.49-7.42 (m, 1H), 7.33-7.27 (m, 1H), 7.23-7.15 (m, 2H), 7.06-6.98 (m, 2H), 6.87-6.82 (m, 1H), 6.77-6.75 (m, 1H), 6.65-6.59 (m, 1H), 5.43-5.39 (m, 2H), 4.91-4.86 (m, 2H), 4.45-4.30 (m, 3H), 4.27-4.18 (m, 2H), 3.52-3.40 (m, 2H), 3.32-3.16 (m, 3H), 3.08-3.03 (m, 2H), 3.00-2.83 (m, 4H), 2.80-2.57 (m, 2H), 2.11-1.96 (m, 1H), 1.90-1.79 (m, 1H), 1.76-1.55 (m, 2H), 1.38-1.20 (m, 2H). |

-continued

| compounds | Structure | MS [M + H⁺] | ¹H-NMR |
|---|---|---|---|
| 66 | 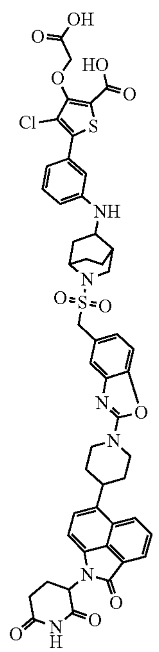 [SMILES: O=C(O)COc1c(C(=O)O)sc(-c2cccc(NC3CC4CCC3CN4S(=O)(=O)Cc3ccc4oc(N5CCC(c6ccc7c8c(cccc68)C(=O)N7C6CCC(=O)NC6=O)CC5)nc4c3)c2)c1Cl] | 979.22 | ¹HNMR (400 MHZ, DMSO-d6) δ 10.64 (s, 1H), 8.60 (s, 1H), 8.43-8.38 (m, 1H), 8.10-8.03 (m, 1H), 7.90-7.78 (m, 1H), 7.68-7.62 (m, 1H), 7.49-7.42 (m, 1H), 7.33-7.27 (m, 1H), 7.23-7.15 (m, 2H), 7.06-6.98 (m, 2H), 6.87-6.82 (m, 1H), 6.77-6.75 (m, 1H), 6.65-6.59 (m, 1H), 5.43-5.39 (m, 2H), 4.91-4.86 (m, 2H), 4.45-4.30 (m, 3H), 4.27-4.18 (m, 2H), 3.52-3.40 (m, 2H), 3.32-3.16 (m, 3H), 3.08-3.03 (m, 2H), 3.00-2.83 (m, 4H), 2.80-2.57 (m, 2H), 2.11-1.96 (m, 1H), 1.90-1.79 (m, 1H), 1.76-1.55 (m, 2H), 1.38-1.20 (m, 2H). |
| 67 | 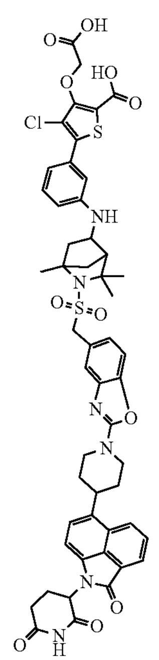 [SMILES: CC12CC(Nc3cccc(-c4sc(C(=O)O)c(OCC(=O)O)c4Cl)c3)C(C1)C(C)(C)N2S(=O)(=O)Cc1ccc2oc(N3CCC(c4ccc5c6c(cccc46)C(=O)N5C4CCC(=O)NC4=O)CC3)nc2c1] | 1021.27 | ¹HNMR (400 MHZ, DMSO-d6) δ 10.63 (s, 1H), 8.60 (s, 1H), 8.43-8.38 (m, 1H), 8.10-8.03 (m, 1H), 7.90-7.78 (m, 1H), 7.68-7.62 (m, 1H), 7.49-7.42 (m, 1H), 7.33-7.27 (m, 1H), 7.23-7.15 (m, 2H), 7.06-6.98 (m, 2H), 6.87-6.82 (m, 1H), 6.77-6.75 (m, 1H), 6.65-6.59 (m, 1H), 5.43-5.39 (m, 2H), 4.91-4.86 (m, 2H), 4.45-4.30 (m, 3H), 4.27-4.18 (m, 2H), 3.52-3.40 (m, 2H), 3.32-3.16 (m, 3H), 3.08-3.03 (m, 2H), 3.00-2.83 (m, 4H), 2.80-2.57 (m, 2H), 2.11-1.96 (m, 1H), 1.90-1.79 (m, 1H), 1.76-1.55 (m, 2H), 1.38-1.20 (m, 2H), 1.02-0.95 (m, 12H). |

-continued

| compounds | Structure | MS [M + H⁺] | ¹H-NMR |
|---|---|---|---|
| 68 | 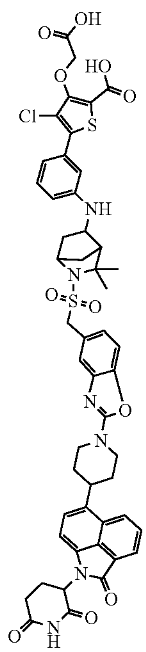 [SMILES: CC1(C)C2CC(CC2Nc2cccc(-c3sc(C(=O)O)c(OCC(=O)O)c3Cl)c2)N1S(=O)(=O)Cc1ccc2oc(N3CCC(c4ccc5c6c(cccc46)C(=O)N5C4CCC(=O)NC4=O)CC3)nc2c1] | 1007.25 | ¹HNMR (400 MHZ, DMSO-d6) δ 10.62 (s, 1H), 8.60 (s, 1H), 8.43-8.38 (m, 1H), 8.10-8.03 (m, 1H), 7.90-7.78 (m, 1H), 7.68-7.62 (m, 1H), 7.49-7.42 (m, 1H), 7.33-7.27 (m, 1H), 7.23-7.15 (m, 2H), 7.06-6.98 (m, 2H), 6.87-6.82 (m, 1H), 6.77-6.75 (m, 1H), 6.65-6.59 (m, 1H), 5.43-5.39 (m, 2H), 4.91-4.86 (m, 2H), 4.45-4.30 (m, 3H), 4.27-4.18 (m, 2H), 3.52-3.40 (m, 2H), 3.32-3.16 (m, 3H), 3.08-3.03 (m, 2H), 3.00-2.83 (m, 4H), 2.80-2.57 (m, 2H), 2.11-1.96 (m, 1H), 1.90-1.79 (m, 1H), 1.76-1.55 (m, 2H), 1.38-1.20 (m, 2H), 1.02-0.95 (m, 6H). |
| 69 | 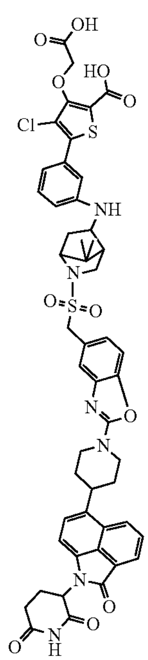 [SMILES: CC1(C)C2CN(S(=O)(=O)Cc3ccc4oc(N5CCC(c6ccc7c8c(cccc68)C(=O)N7C6CCC(=O)NC6=O)CC5)nc4c3)C1CC2Nc1cccc(-c2sc(C(=O)O)c(OCC(=O)O)c2Cl)c1] | 1007.25 | ¹HNMR (400 MHZ, DMSO-d6) δ 10.61 (s, 1H), 8.60 (s, 1H), 8.43-8.38 (m, 1H), 8.10-8.03 (m, 1H), 7.90-7.78 (m, 1H), 7.68-7.62 (m, 1H), 7.49-7.42 (m, 1H), 7.33-7.27 (m, 1H), 7.23-7.15 (m, 2H), 7.06-6.98 (m, 2H), 6.87-6.82 (m, 1H), 6.77-6.75 (m, 1H), 6.65-6.59 (m, 1H), 5.43-5.39 (m, 2H), 4.91-4.86 (m, 2H), 4.45-4.30 (m, 3H), 4.27-4.18 (m, 2H), 3.52-3.40 (m, 2H), 3.32-3.16 (m, 3H), 3.08-3.03 (m, 2H), 3.00-2.83 (m, 4H), 2.80-2.57 (m, 2H), 2.11-1.96 (m, 1H), 1.90-1.79 (m, 1H), 1.76-1.55 (m, 2H), 1.38-1.20 (m, 2H), 1.02-0.95 (m, 6H). |

-continued

| compounds | Structure | MS [M + H+] | 1H-NMR |
|---|---|---|---|
| 70 | 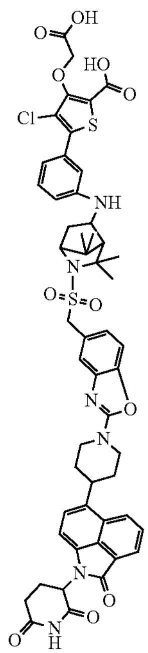 [SMILES: CC1(C)C2CC(Nc3cccc(-c4sc(C(=O)O)c(OCC(=O)O)c4Cl)c3)C1C(C)(C)N2S(=O)(=O)Cc1ccc2oc(N3CCC(c4ccc5c6c(cccc46)C(=O)N5C4CCC(=O)NC4=O)CC3)nc2c1] | 1035.28 | 1HNMR (400 MHZ, DMSO-d6) δ 10.55 (s, 1H), 8.60 (s, 1H), 8.43-8.38 (m, 1H), 8.10-8.03 (m, 1H), 7.90-7.78 (m, 1H), 7.68-7.62 (m, 1H), 7.49-7.42 (m, 1H), 7.33-7.27 (m, 1H), 7.23-7.15 (m, 2H), 7.06-6.98 (m, 2H), 6.87-6.82 (m, 1H), 6.77-6.75 (m, 1H), 6.65-6.59 (m, 1H), 5.43-5.39 (m, 2H), 4.91-4.86 (m, 2H), 4.45-4.30 (m, 3H), 4.27-4.18 (m, 2H), 3.52-3.40 (m, 2H), 3.32-3.16 (m, 3H), 3.08-3.03 (m, 2H), 3.00-2.83 (m, 4H), 2.80-2.57 (m, 2H), 2.11-1.96 (m, 1H), 1.90-1.79 (m, 1H), 1.76-1.55 (m, 2H), 1.38-1.20 (m, 2H), 1.02-0.95 (m, 12H). |
| 71 | 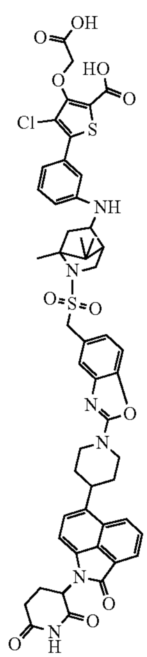 | 1021.27 | 1HNMR (400 MHZ, DMSO-d6) δ 10.61 (s, 1H), 8.60 (s, 1H), 8.43-8.38 (m, 1H), 8.10-8.03 (m, 1H), 7.90-7.78 (m, 1H), 7.68-7.62 (m, 1H), 7.49-7.42 (m, 1H), 7.33-7.27 (m, 1H), 7.23-7.15 (m, 2H), 7.06-6.98 (m, 2H), 6.87-6.82 (m, 1H), 6.77-6.75 (m, 1H), 6.65-6.59 (m, 1H), 5.43-5.39 (m, 2H), 4.91-4.86 (m, 2H), 4.45-4.30 (m, 3H), 4.27-4.18 (m, 2H), 3.52-3.40 (m, 2H), 3.32-3.16 (m, 3H), 3.08-3.03 (m, 2H), 3.00-2.83 (m, 4H), 2.80-2.57 (m, 2H), 2.11-1.96 (m, 1H), 1.90-1.79 (m, 1H), 1.76-1.55 (m, 2H), 1.38-1.20 (m, 2H), 1.02-0.95 (m, 9H). |

-continued

| compounds | Structure | MS [M + H+] | 1H-NMR |
|---|---|---|---|
| 72 | 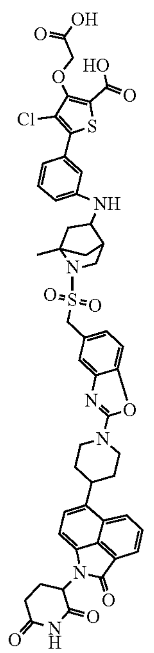 [SMILES: CC12CC(CN1S(=O)(=O)Cc1ccc3oc(N4CCC(c5ccc6c7c(cccc57)C(=O)N6C5CCC(=O)NC5=O)CC4)nc3c1)C(Nc1cccc(-c3sc(C(=O)O)c(OCC(=O)O)c3Cl)c1)C2] | 993.24 | 1HNMR (400 MHz, DMSO-d6) δ 10.60 (s, 1H), 8.60 (s, 1H), 8.43-8.38 (m, 1H), 8.10-8.03 (m, 1H), 7.90-7.78 (m, 1H), 7.68-7.62 (m, 1H), 7.49-7.42 (m, 1H), 7.33-7.27 (m, 1H), 7.23-7.15 (m, 2H), 7.06-6.98 (m, 2H), 6.87-6.82 (m, 1H), 6.77-6.75 (m, 1H), 6.65-6.59 (m, 1H), 5.43-5.39 (m, 2H), 4.91-4.86 (m, 2H), 4.45-4.30 (m, 3H), 4.27-4.18 (m, 2H), 3.52-3.40 (m, 2H), 3.32-3.16 (m, 3H), 3.08-3.03 (m, 2H), 3.00-2.83 (m, 4H), 2.80-2.57 (m, 2H), 2.11-1.96 (m, 1H), 1.90-1.79 (m, 1H), 1.76-1.55 (m, 2H), 1.38-1.20 (m, 2H), 1.02-0.95 (m, 3H). |
| 73 | 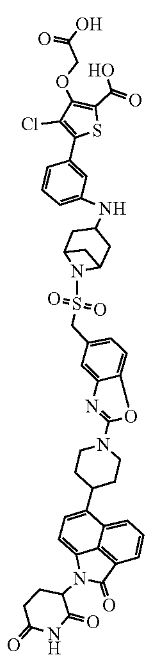 [SMILES: O=C(O)COc1c(C(=O)O)sc(-c2cccc(NC3CC4CC(C3)N4S(=O)(=O)Cc3ccc4oc(N5CCC(c6ccc7c8c(cccc68)C(=O)N7C6CCC(=O)NC6=O)CC5)nc4c3)c2)c1Cl] | 979.22 | 1HNMR (400 MHZ, DMSO-d6) δ 10.60 (s, 1H), 8.60 (s, 1H), 8.43-8.38 (m, 1H), 8.10-8.03 (m, 1H), 7.90-7.78 (m, 1H), 7.68-7.62 (m, 1H), 7.49-7.42 (m, 1H), 7.33-7.27 (m, 1H), 7.23-7.15 (m, 2H), 7.06-6.98 (m, 2H), 6.87-6.82 (m, 1H), 6.77-6.75 (m, 1H), 6.65-6.59 (m, 1H), 5.43-5.39 (m, 2H), 4.91-4.86 (m, 2H), 4.45-4.30 (m, 3H), 4.27-4.18 (m, 2H), 3.52-3.40 (m, 2H), 3.32-3.16 (m, 3H), 3.08-3.03 (m, 2H), 3.00-2.83 (m, 4H), 2.80-2.57 (m, 2H), 2.11-1.96 (m, 1H), 1.90-1.79 (m, 1H), 1.76-1.55 (m, 2H), 1.38-1.20 (m, 2H). |

-continued

| compounds | Structure | MS [M + H⁺] | ¹H-NMR |
|---|---|---|---|
| 74 | 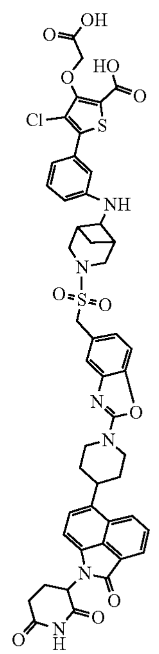 [SMILES: O=C(O)COc1c(C(=O)O)sc(-c2cccc(NC3C4CC3CN(S(=O)(=O)Cc3ccc5oc(N6CCC(c7ccc8c9c(cccc79)C(=O)N8C7CCC(=O)NC7=O)CC6)nc5c3)C4)c2)c1Cl] | 979.22 | ¹HNMR (400 MHZ, DMSO-d6) δ 10.59 (s, 1H), 8.60 (s, 1H), 8.43-8.38 (m, 1H), 8.10-8.03 (m, 1H), 7.90-7.78 (m, 1H), 7.68-7.62 (m, 1H), 7.49-7.42 (m, 1H), 7.33-7.27 (m, 1H), 7.23-7.15 (m, 2H), 7.06-6.98 (m, 2H), 6.87-6.82 (m, 1H), 6.77-6.75 (m, 1H), 6.65-6.59 (m, 1H), 5.43-5.39 (m, 2H), 4.91-4.86 (m, 2H), 4.45-4.30 (m, 3H), 4.27-4.18 (m, 2H), 3.52-3.40 (m, 2H), 3.32-3.16 (m, 3H), 3.08-3.03 (m, 2H), 3.00-2.83 (m, 4H), 2.80-2.57 (m, 2H), 2.11-1.96 (m, 1H), 1.90-1.79 (m, 1H), 1.76-1.55 (m, 2H), 1.38-1.20 (m, 2H). |
| 75 | 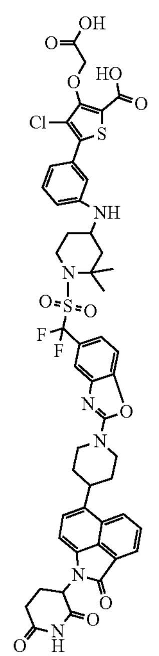 [SMILES: CC1(C)CC(Nc2cccc(-c3sc(C(=O)O)c(OCC(=O)O)c3Cl)c2)CCN1S(=O)(=O)C(F)(F)c1ccc2oc(N3CCC(c4ccc5c6c(cccc46)C(=O)N5C4CCC(=O)NC4=O)CC3)nc2c1] | 1031.23 | ¹H NMR (400 MHZ, DMSO-d6) δ 11.09 (s, 1H), 8.48 (d, J = 8.7 Hz, 1H), 8.08 (d, J = 7.1 Hz, 1H), 7.85 (dd, J = 8.5, 7.1 Hz, 1H), 7.47-7.31 (m, 3H), 7.18 (ddd, J = 21.7, 10.0, 5.0 Hz, 2H), 7.08-7.02 (m, 1H), 6.88-6.79 (m, 1H), 6.76 (d, J = 9.3 Hz, 1H), 6.67-6.57 (m, 1H), 5.40 (dd, J = 13.1, 5.2 Hz, 1H), 4.92-4.84 (m, 2H), 3.36 (d, J = 13.2 Hz, 7H), 3.14-3.02 (m, 2H), 2.98-2.78 (m, 2H), 2.63 (dd, J = 3.7, 1.9 Hz, 1H), 1.96 (ddd, J = 69.4, 32.5, 8.9 Hz, 5H), 1.75-1.39 (m, 2H), 1.27-0.89 (m, 4H). |

-continued

| compounds | Structure | MS [M + H⁺] | ¹H-NMR |
|---|---|---|---|
| 76 | 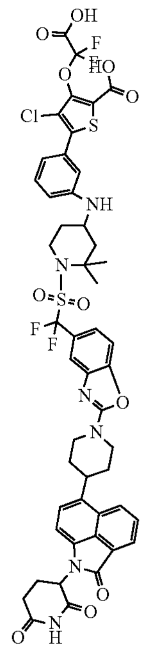 [SMILES: CC1(C)CC(Nc2cccc(-c3sc(C(=O)O)c(OC(F)(F)C(=O)O)c3Cl)c2)CCN1S(=O)(=O)C(F)(F)c1ccc2oc(N3CCC(c4ccc5c6c(cccc46)C(=O)N5C4CCC(=O)NC4=O)CC3)nc2c1] | 1067.21 | ¹H NMR (400 MHZ, DMSO-d6) δ 11.09 (s, 1H), 8.48 (d, J = 8.7 Hz, 1H), 8.08 (d, J = 7.1 Hz, 1H), 7.85 (dd, J = 8.5, 7.1 Hz, 1H), 7.47-7.31 (m, 3H), 7.18 (ddd, J = 21.7, 10.0, 5.0 Hz, 2H), 7.08-7.02 (m, 1H), 6.88-6.79 (m, 1H), 6.76 (d, J = 9.3 Hz, 1H), 6.67-6.57 (m, 1H), 5.40 (dd, J = 13.1, 5.2 Hz, 1H), 3.36 (d, J = 13.2 Hz, 7H), 3.14-3.02 (m, 2H), 2.98-2.78 (m, 2H), 2.63 (dd, J = 3.7, 1.9 Hz, 1H), 1.96 (ddd, J = 69.4, 32.5, 8.9 Hz, 5H), 1.75-1.39 (m, 2H), 1.27-0.89 (m, 4H). |
| 77 | 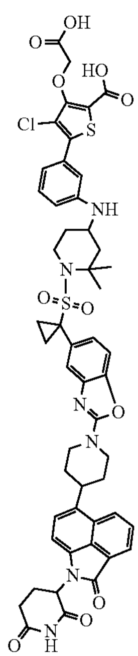 [SMILES: CC1(C)CC(Nc2cccc(-c3sc(C(=O)O)c(OCC(=O)O)c3Cl)c2)CCN1S(=O)(=O)C1(c2ccc3oc(N4CCC(c5ccc6c7c(cccc57)C(=O)N6C5CCC(=O)NC5=O)CC4)nc3c2)CC1] | 1021.27 | ¹H NMR (400 MHZ, DMSO-d6) δ 11.09 (s, 1H), 8.48 (d, J = 8.7 Hz, 1H), 8.08 (d, J = 7.1 Hz, 1H), 7.85 (dd, J = 8.5, 7.1 Hz, 1H), 7.47-7.31 (m, 3H), 7.18 (ddd, J = 21.7, 10.0, 5.0 Hz, 2H), 7.08-7.02 (m, 1H), 6.88-6.79 (m, 1H), 6.76 (d, J = 9.3 Hz, 1H), 6.67-6.57 (m, 1H), 5.40 (dd, J = 13.1, 5.2 Hz, 1H), 4.92-4.84 (m, 2H), 3.36 (d, J = 13.2 Hz, 7H), 3.14-3.02 (m, 2H), 2.98-2.78 (m, 2H), 2.63 (dd, J = 3.7, 1.9 Hz, 1H), 1.96 (ddd, J = 69.4, 32.5, 8.9 Hz, 5H), 1.75-1.39 (m, 4H), 1.27-0.89 (m, 6H). |

-continued

| compounds | Structure | MS [M + H⁺] | ¹H-NMR |
|---|---|---|---|
| 78 | 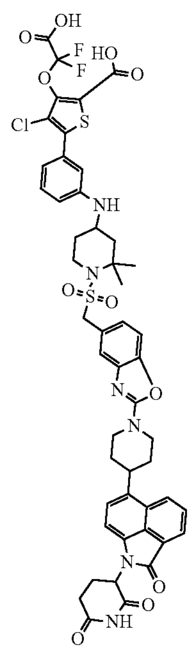 [SMILES: CC1(C)CC(Nc2cccc(-c3sc(C(=O)O)c(OC(F)(F)C(=O)O)c3Cl)c2)CCN1S(=O)(=O)Cc1ccc2oc(N3CCC(c4ccc5c6c(cccc46)C(=O)N5C4CCC(=O)NC4=O)CC3)nc2c1] | 1031.23 | ¹H NMR (400 MHZ, DMSO-d6) δ 11.12 (s, 1H), 8.53 (d, J = 8.3 Hz, 1H), 8.12 (d, J = 7.0 Hz, 1H), 7.89 (dd, J = 8.2, 7.1 Hz, 1H), 7.41 (t, J = 8.0 Hz, 2H), 7.33 (s, 1H), 7.20 (t, J = 7.9 Hz, 1H), 7.08 (t, J = 7.1 Hz, 2H), 6.88 (s, 1H), 6.81 (d, J = 7.4 Hz, 1H), 6.70 (d, J = 7.9 Hz, 1H), 5.44 (dd, J = 12.5, 5.6 Hz, 1H), 4.92 (s, 2H), 4.35 (d, J = 13.5 Hz, 2H), 3.68 (dd, J = 16.8, 9.4 Hz, 1H), 3.51 (t, J = 12.3 Hz, 1H), 3.42 (dd, J = 15.3, 7.4 Hz, 3H), 3.17-3.04 (m, 1H), 2.95 (dd, J = 23.0, 8.1 Hz, 1H), 2.81-2.69 (m, 1H), 2.64 (d, J = 19.1 Hz, 1H), 2.12-2.04 (m, 1H), 1.99 (d, J = 10.3 Hz, 2H), 1.95-1.73 (m, 4H), 1.44 (s, 3H), 1.41-1.31 (m, 4H), 1.17-1.02 (m, 1H). |
| 79 | 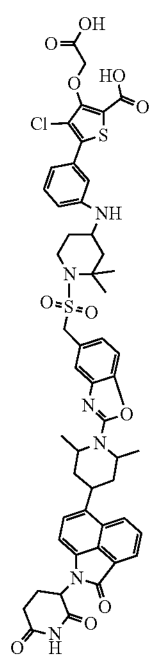 [SMILES: CC1CC(c2ccc3c4c(cccc24)C(=O)N3C2CCC(=O)NC2=O)CC(C)N1c1nc2cc(CS(=O)(=O)N3CCC(Nc4cccc(-c5sc(C(=O)O)c(OCC(=O)O)c5Cl)c4)CC3(C)C)ccc2o1] | 1023.28 | ¹H NMR (400 MHZ, DMSO-d6) δ 10.58 (s, 1H), 8.51-8.47 (m, 1H), 8.06-8.02 (m, 1H), 7.85-7.83 (m, 1H), 7.38-7.36 (m, 1H), 7.33-7.27 (m, 1H), 7.19-7.15 (m, 1H), 7.07-7.03 (m, 2H), 6.85-6.78 (m, 2H), 6.68-6.65 (m, 1H), 5.43-5.39 (m, 1H), 4.88 (s, 2H), 4.39-4.36 (m, 1H), 3.71-3.28 (m, 2H), 3.17-2.80 (m, 1H), 2.74-2.70 (m, 1H), 2.12-1.62 (m, 7H), 1.49-0.84 (m, 14H). |

-continued

| compounds | Structure | MS [M + H+] | 1H-NMR |
|---|---|---|---|
| 80 | 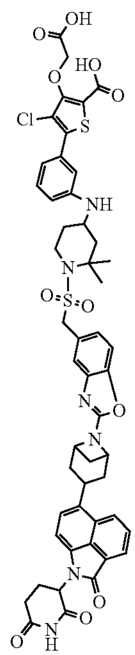 [SMILES: CC1(C)CC(Nc2cccc(-c3sc(C(=O)O)c(OCC(=O)O)c3Cl)c2)CCN1S(=O)(=O)Cc1ccc2oc(N3C4CC(c5ccc6c7c(cccc57)C(=O)N6C5CCC(=O)NC5=O)CC3C4)nc2c1] | 1007.25 | 1H NMR (400 MHZ, DMSO-d6) δ 10.59 (s, 1H), 8.51-8.47 (m, 1H), 8.08-8.02 (m, 1H), 7.87-7.83 (m, 1H), 7.39-7.36 (m, 1H), 7.32-7.27 (m, 1H), 7.19-7.15 (m, 1H), 7.08-7.03 (m, 2H), 6.85-6.78 (m, 2H), 6.68-6.65 (m, 1H), 5.42-5.39 (m, 1H), 4.88 (s, 2H), 4.39-4.36 (m, 1H), 3.70-3.28 (m, 4H), 3.17-2.80 (m, 2H), 2.74-2.70 (m, 1H), 2.12-1.62 (m, 7H), 151-0.84 (m, 10H). |
| 81 | 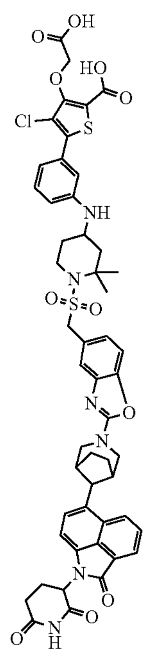 [SMILES: CC1(C)CC(Nc2cccc(-c3sc(C(=O)O)c(OCC(=O)O)c3Cl)c2)CCN1S(=O)(=O)Cc1ccc2oc(N3CC4CCC(C3)C4c3ccc4c5c(cccc35)C(=O)N4C3CCC(=O)NC3=O)nc2c1] | 1021.27 | 1H NMR (400 MHZ, DMSO-d6) δ 10.59 (s, 1H), 8.52-8.47 (m, 1H), 8.07-8.02 (m, 1H), 7.86-7.83 (m, 1H), 7.41-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 1H), 3.72-3.28 (m, 4H), 3.17-2.80 (m, 4H), 2.74-2.70 (m, 1H), 2.12-1.62 (m, 7H), 1.48-0.84 (m, 10H). |

-continued

| compounds | Structure | MS [M + H⁺] | ¹H-NMR |
|---|---|---|---|
| 82 | 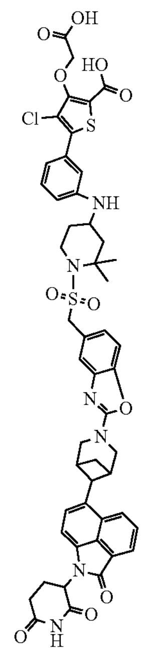 [SMILES: CC1(C)CC(Nc2cccc(-c3sc(C(=O)O)c(OCC(=O)O)c3Cl)c2)CCN1S(=O)(=O)Cc1ccc2oc(N3CC4CC(C3)C4c3ccc4c5c(cccc35)C(=O)N4C3CCC(=O)NC3=O)nc2c1] | 1007.25 | ¹H NMR (400 MHZ, DMSO-d6) δ 10.59 (s, 1H), 8.51-8.47 (m, 1H), 8.07-8.02 (m, 1H), 7.87-7.83 (m, 1H), 7.39-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 1H), 3.70-3.28 (m, 4H), 3.17-2.80 (m, 4H), 2.74-2.70 (m, 1H), 2.12-1.62 (m, 7H), 1.48-0.84 (m, 10H). |
| 83 | 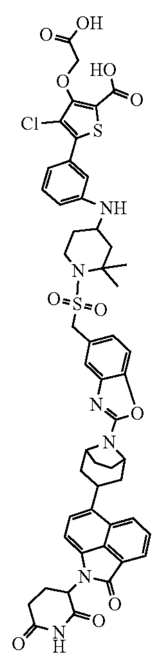 [SMILES: CC1(C)CC(Nc2cccc(-c3sc(C(=O)O)c(OCC(=O)O)c3Cl)c2)CCN1S(=O)(=O)Cc1ccc2oc(N3C4CCC3CC(c3ccc5c6c(cccc36)C(=O)N5C3CCC(=O)NC3=O)C4)nc2c1] | 1021.27 | ¹H NMR (400 MHZ, DMSO-d6) δ 10.55 (s, 1H), 8.51-8.47 (m, 1H), 8.06-8.02 (m, 1H), 7.87-7.83 (m, 1H), 7.41-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 1H), 3.70-3.28 (m, 4H), 3.17-2.80 (m, 2H), 2.74-2.70 (m, 1H), 2.12-1.62 (m, 7H), 1.45-0.84 (m, 12H). |

-continued

| compounds | Structure | MS [M + H⁺] | ¹H-NMR |
|---|---|---|---|
| 84 | 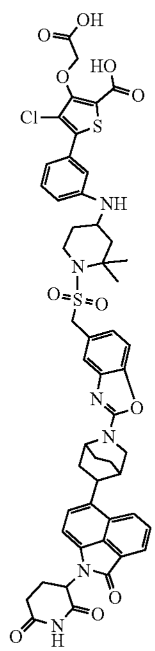 [SMILES: CC1(C)CC(Nc2cccc(-c3sc(C(=O)O)c(OCC(=O)O)c3Cl)c2)CCN1S(=O)(=O)Cc1ccc2oc(N3CC4CCC3CC4c3ccc4c5c(cccc35)C(=O)N4C3CCC(=O)NC3=O)nc2c1] | 1021.27 | ¹H NMR (400 MHZ, DMSO-d6) δ 10.59 (s, 1H), 8.51-8.47 (m, 1H), 8.06-8.02 (m, 1H), 7.87-7.83 (m, 1H), 7.39-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 1H), 3.70-3.28 (m, 4H), 3.17-2.80 (m, 3H), 2.74-2.70 (m, 1H), 2.12-1.62 (m, 7H), 1.52-0.84 (m, 11H). |
| 85 | 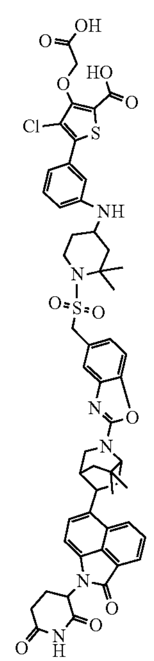 [SMILES: CC1(C)CC2CN(c3nc4cc(CS(=O)(=O)N5CCC(Nc6cccc(-c7sc(C(=O)O)c(OCC(=O)O)c7Cl)c6)CC5(C)C)ccc4o3)C1CC2c1ccc2c3c(cccc13)C(=O)N2C1CCC(=O)NC1=O] | 1049.30 | ¹H NMR (400 MHZ, DMSO-d6) δ 10.54 (s, 1H), 8.52-8.47 (m, 1H), 8.07-8.02 (m, 1H), 7.86-7.83 (m, 1H), 7.37-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 1H), 3.70-3.28 (m, 4H), 3.17-2.80 (m, 3H), 2.74-2.70 (m, 1H), 2.12-1.62 (m, 7H), 1.58-0.83 (m, 17H). |

-continued

| compounds | Structure | MS [M + H⁺] | ¹H-NMR |
|---|---|---|---|
| 86 | 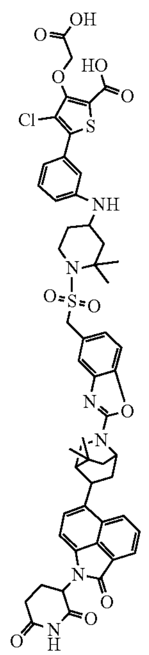 [SMILES: CC1(C)CC2CC(c3ccc4c5c(cccc35)C(=O)N4C3CCC(=O)NC3=O)C1CN2c1nc2cc(CS(=O)(=O)N3CCC(Nc4cccc(-c5sc(C(=O)O)c(OCC(=O)O)c5Cl)c4)CC3(C)C)ccc2o1] | 1049.30 | ¹H NMR (400 MHZ, DMSO-d6) δ 10.55 (s, 1H), 8.51-8.47 (m, 1H), 8.07-8.02 (m, 1H), 7.87-7.83 (m, 1H), 7.38-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 1H), 3.70-3.28 (m, 4H), 3.17-2.80 (m, 3H), 2.74-2.70 (m, 1H), 2.12-1.62 (m, 7H), 1.49-0.84 (m, 11H). |
| 87 | 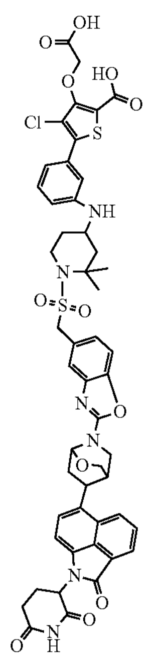 [SMILES: CC1(C)CC(Nc2cccc(-c3sc(C(=O)O)c(OCC(=O)O)c3Cl)c2)CCN1S(=O)(=O)Cc1ccc2oc(N3CC4COC3CC4c3ccc4c5c(cccc35)C(=O)N4C3CCC(=O)NC3=O)nc2c1] | 1023.24 | ¹H NMR (400 MHZ, DMSO-d6) δ 10.69 (s, 1H), 8.51-8.47 (m, 1H), 8.07-8.02 (m, 1H), 7.86-7.83 (m, 1H), 7.39-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.82-4.50 (m, 3H), 4.39-4.36 (m, 1H), 3.70-3.28 (m, 6H), 3.17-2.80 (m, 3H), 2.74-2.70 (m, 1H), 2.12-1.62 (m, 9H), 1.48-0.84 (m, 5H). |

-continued

| compounds | Structure | MS [M + H⁺] | ¹H-NMR |
|---|---|---|---|
| 88 | 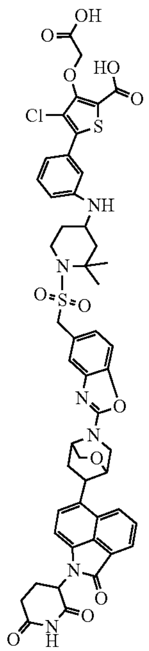 [SMILES: CC1(C)CC(Nc2cccc(-c3sc(C(=O)O)c(OCC(=O)O)c3Cl)c2)CCN1S(=O)(=O)Cc1ccc2oc(N3CC4OCC3CC4c3ccc4c5c(cccc35)C(=O)N4C3CCC(=O)NC3=O)nc2c1] | 1023.24 | ¹H NMR (400 MHZ, DMSO-d6) δ 10.59 (s, 1H), 8.51-8.47 (m, 1H), 8.05-8.02 (m, 1H), 7.85-7.83 (m, 1H), 7.39-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.82-4.50 (m, 2H), 4.39-4.36 (m, 1H), 3.70-3.28 (m, 7H), 3.17-2.80 (m, 3H), 2.74-2.70 (m, 1H), 2.12-1.62 (m, 9H), 1.48-0.84 (m, 5H). |
| 89 | 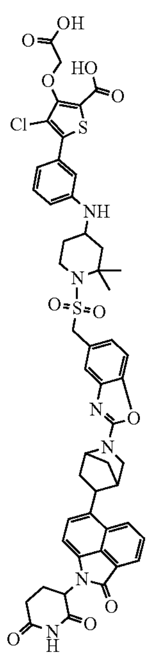 [SMILES: CC1(C)CC(Nc2cccc(-c3sc(C(=O)O)c(OCC(=O)O)c3Cl)c2)CCN1S(=O)(=O)Cc1ccc2oc(N3CC4CC3CC4c3ccc4c5c(cccc35)C(=O)N4C3CCC(=O)NC3=O)nc2c1] | 1007.25 | ¹H NMR (400 MHZ, DMSO-d6) δ 10.59 (s, 1H), 8.50-8.47 (m, 1H), 8.07-8.02 (m, 1H), 7.87-7.83 (m, 1H), 7.39-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 1H), 3.70-3.28 (m, 4H), 3.17-2.80 (m, 3H), 2.74-2.70 (m, 1H), 2.12-1.62 (m, 5H), 1.48-0.84 (m, 11H). |

| compounds | Structure | MS [M + H⁺] | ¹H-NMR |
|---|---|---|---|
| 90 | 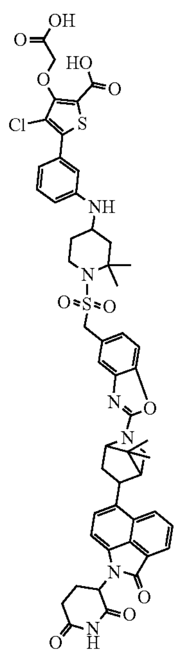 [SMILES: CC1(C)C2CN(c3nc4cc(CS(=O)(=O)N5CCC(Nc6cccc(-c7sc(C(=O)O)c(OCC(=O)O)c7Cl)c6)CC5(C)C)ccc4o3)C1CC2c1ccc2c3c(cccc13)C(=O)N2C1CCC(=O)NC1=O] | 1035.28 | ¹H NMR (400 MHZ, DMSO-d6) δ 10.59 (s, 1H), 8.51-8.47 (m, 1H), 8.07-8.02 (m, 1H), 7.87-7.83 (m, 1H), 7.39-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 1H), 3.70-3.28 (m, 4H), 3.17-2.80 (m, 3H), 2.74-2.70 (m, 1H), 2.12-1.62 (m, 5H), 1.46-0.84 (m, 17H). |
| 91 | 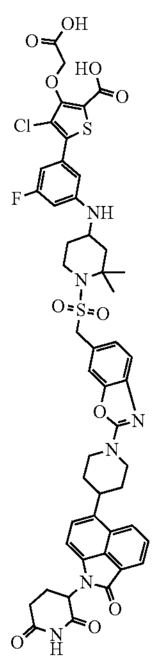 [SMILES: CC1(C)CC(Nc2cc(F)cc(-c3sc(C(=O)O)c(OCC(=O)O)c3Cl)c2)CCN1S(=O)(=O)Cc1ccc2nc(N3CCC(c4ccc5c6c(cccc46)C(=O)N5C4CCC(=O)NC4=O)CC3)oc2c1] | 1013.24 | ¹H NMR (400 MHZ, DMSO-d6) δ 11.07 (s, 1H), 8.52-8.47 (m, 1H), 8.07-8.02 (m, 1H), 7.87-7.83 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.48-0.84 (m, 8H). |

-continued

| compounds | Structure | MS [M + H+] | 1H-NMR |
|---|---|---|---|
| 92 | 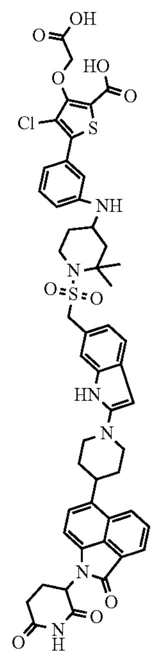 [SMILES: CC1(C)CC(Nc2cccc(-c3sc(C(=O)O)c(OCC(=O)O)c3Cl)c2)CCN1S(=O)(=O)Cc1ccc2cc(N3CCC(c4ccc5c6c(cccc46)C(=O)N5C4CCC(=O)NC4=O)CC3)[nH]c2c1] | 993.27 | 1H NMR (400 MHZ, DMSO-d6) δ 11.11 (s, 1H), 8.52-8.47 (m, 1H), 8.07-8.02 (m, 1H), 7.87-7.83 (m, 1H), 7.39-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 2H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.49-0.84 (m, 8H). |
| 93 | 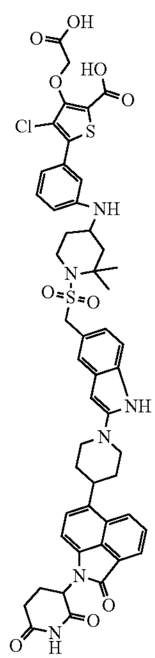 [SMILES: CC1(C)CC(Nc2cccc(-c3sc(C(=O)O)c(OCC(=O)O)c3Cl)c2)CCN1S(=O)(=O)Cc1ccc2[nH]c(N3CCC(c4ccc5c6c(cccc46)C(=O)N5C4CCC(=O)NC4=O)CC3)cc2c1] | 993.27 | 1H NMR (400 MHZ, DMSO-d6) δ 11.09 (s, 1H), 8.51-8.47 (m, 1H), 8.08-8.02 (m, 1H), 7.87-7.83 (m, 1H), 7.39-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 2H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.48-0.84 (m, 8H). |

-continued
| compounds | Structure | MS [M + H⁺] | ¹H-NMR |
|---|---|---|---|
| 94 | 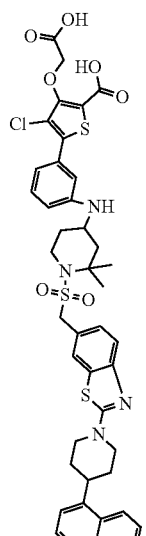 | 1011.23 | ¹H NMR (400 MHZ, DMSO-d6) δ 11.12 (s, 1H), 8.53 (d, J = 8.3 Hz, 1H), 8.12 (d, J = 7.0 Hz, 1H), 7.89 (dd, J = 8.2, 7.1 Hz, 1H), 7.41 (t, J = 8.0 Hz, 2H), 7.33 (s, 1H), 7.20 (t, J = 7.9 Hz, 1H), 7.08 (t, J = 7.1 Hz, 2H), 6.88 (s, 1H), 6.81 (d, J = 7.4 Hz, 1H), 6.70 (d, J = 7.9 Hz, 1H), 5.44 (dd, J = 12.5, 5.6 Hz, 1H), 4.92 (s, 2H), 4.48 (d, J = 13.7 Hz, 1H), 4.35 (d, J = 13.5 Hz, 3H), 3.68 (dd, J = 16.8, 9.4 Hz, 1H), 3.51 (t, J = 12.3 Hz, 1H), 3.42 (dd, J = 15.3, 7.4 Hz, 3H), 3.17-3.04 (m, 1H), 2.95 (dd, J = 23.0, 8.1 Hz, 1H), 2.81-2.69 (m, 1H), 2.64 (d, J = 19.1 Hz, 1H), 2.12-2.04 (m, 1H), 1.99 (d, J = 10.3 Hz, 2H), 1.95-1.73 (m, 4H), 1.44 (s, 3H), 1.41-1.31 (m, 4H), 1.17-1.02 (m, 1H). |
| 95 | 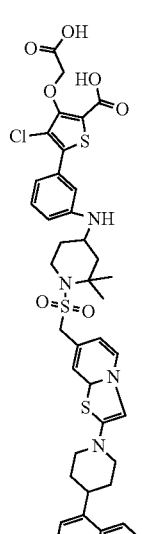 | 1013.24 | ¹H NMR (400 MHZ, DMSO-d6) δ 11.12 (s, 1H), 8.51-8.47 (m, 1H), 8.07-8.02 (m, 1H), 7.87-7.83 (m, 1H), 7.39-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 3H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.49-0.84 (m, 8H). |

-continued

| compounds | Structure | MS [M + H⁺] | ¹H-NMR |
|---|---|---|---|
| 96 | 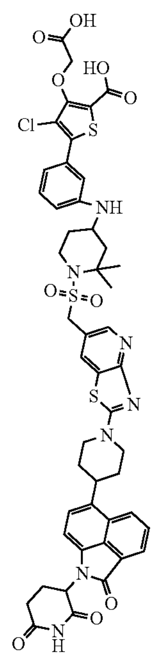 [SMILES: CC1(C)CC(Nc2cccc(-c3sc(C(=O)O)c(OCC(=O)O)c3Cl)c2)CCN1S(=O)(=O)Cc1cnc2nc(N3CCC(c4ccc5c6c(cccc46)C(=O)N5C4CCC(=O)NC4=O)CC3)sc2c1] | 1012.22 | ¹H NMR (400 MHZ, DMSO-d6) δ 11.12 (s, 1H), 8.51-8.47 (m, 1H), 8.07-8.02 (m, 1H), 7.87-7.83 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.48-0.84 (m, 8H). |
| 97 | 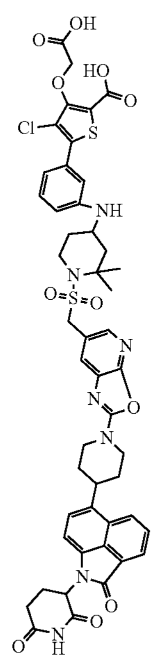 [SMILES: CC1(C)CC(Nc2cccc(-c3sc(C(=O)O)c(OCC(=O)O)c3Cl)c2)CCN1S(=O)(=O)Cc1cnc2oc(N3CCC(c4ccc5c6c(cccc46)C(=O)N5C4CCC(=O)NC4=O)CC3)nc2c1] | 996.24 | ¹H NMR (400 MHZ, DMSO-d6) δ 11.09 (s, 1H), 8.51-8.47 (m, 1H), 8.07-8.02 (m, 1H), 7.87-7.83 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.48-0.84 (m, 8H). |

-continued
| compounds | Structure | MS [M + H+] | 1H-NMR |
|---|---|---|---|
| 98 | 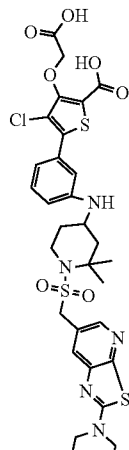 | 1012.22 | 1H NMR (400 MHZ, DMSO-d6) δ 11.07 (s, 1H), 8.51-8.47 (m, 1H), 8.07-8.02 (m, 1H), 7.39-7.36 (m, 1H), 7.32-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.51-0.84 (m, 8H). |
| 99 | 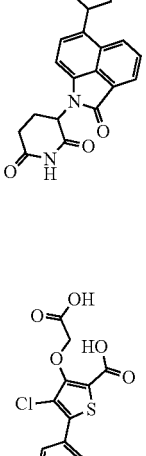 | 996.24 | 1H NMR (400 MHZ, DMSO-d6) δ 11.10 (s, 1H), 8.53-8.47 (m, 1H), 8.06-8.02 (m, 1H), 7.87-7.83 (m, 1H), 7.31-7.27 (m, 1H), 7.18-7.15 (m, 1H), 7.06-7.03 (m, 2H), 6.86-6.78 (m, 2H), 6.68-6.65 (m, 1H), 5.43-5.39 (m, 1H), 4.88 (s, 2H), 4.39-4.36 (m, 3H), 3.73-3.28 (m, 4H), 3.17-2.80 (m, 1H), 2.74-2.70 (m, 1H), 2.12-1.62 (m, 7H), 1.49-0.84 (m, 8H). |

| compounds | Structure | MS [M + H⁺] | ¹H-NMR |
|---|---|---|---|
| 100 | 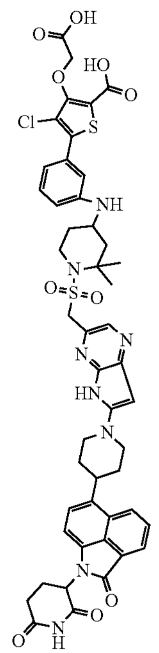 [SMILES: CC1(C)CC(Nc2cccc(-c3sc(C(=O)O)c(OCC(=O)O)c3Cl)c2)CCN1S(=O)(=O)Cc1cnc2cc(N3CCC(c4ccc5c6c(cccc46)C(=O)N5C4CCC(=O)NC4=O)CC3)[nH]c2n1] | 995.26 | ¹H NMR (400 MHZ, DMSO-d6) δ 11.09 (s, 1H), 8.51-8.47 (m, 1H), 8.07-8.02 (m, 1H), 7.19-7.15 (m, 1H), 7.07-7.03 (m, 2H), 6.85-6.78 (m, 2H), 6.68-6.65 (m, 1H), 5.42-5.39 (m, 2H), 4.88 (s, 2H), 4.39-4.36 (m, 3H), 3.70-3.28 (m, 4H), 3.17-2.80 (m, 1H), 2.74-2.70 (m, 1H), 2.14-1.62 (m, 7H), 1.50-0.84 (m, 8H). |
| 101 | 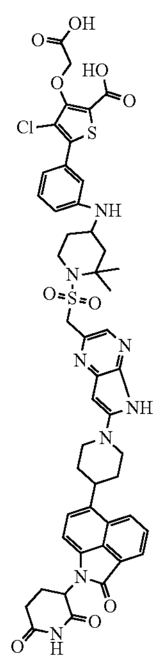 [SMILES: CC1(C)CC(Nc2cccc(-c3sc(C(=O)O)c(OCC(=O)O)c3Cl)c2)CCN1S(=O)(=O)Cc1cnc2[nH]c(N3CCC(c4ccc5c6c(cccc46)C(=O)N5C4CCC(=O)NC4=O)CC3)cc2n1] | 995.26 | ¹H NMR (400 MHZ, DMSO-d6) δ 11.12 (s, 1H), 8.52-8.47 (m, 1H), 8.06-8.02 (m, 1H), 7.18-7.15 (m, 1H), 7.06-7.03 (m, 2H), 6.86-6.78 (m, 2H), 6.68-6.66 (m, 1H), 5.43-5.39 (m, 2H), 4.88 (s, 2H), 4.39-4.36 (m, 3H), 3.71-3.28 (m, 4H), 3.18-2.80 (m, 1H), 2.75-2.70 (m, 1H), 2.13-1.62 (m, 7H), 1.49-0.84 (m, 8H). |

| compounds | Structure | MS [M + H⁺] | ¹H-NMR |
|---|---|---|---|
| 102 | 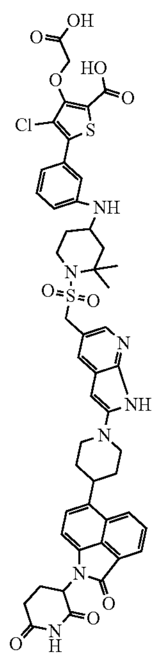 [SMILES: CC1(C)CC(Nc2cccc(-c3sc(C(=O)O)c(OCC(=O)O)c3Cl)c2)CCN1S(=O)(=O)Cc1cnc2[nH]c(N3CCC(c4ccc5c6c(cccc46)C(=O)N5C4CCC(=O)NC4=O)CC3)cc2c1] | 994.27 | ¹H NMR (400 MHZ, DMSO-d6) δ 11.11 (s, 1H), 8.51-8.47 (m, 1H), 8.07-8.02 (m, 1H), 7.39-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 2H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.50-0.84 (m, 8H). |
| 103 | 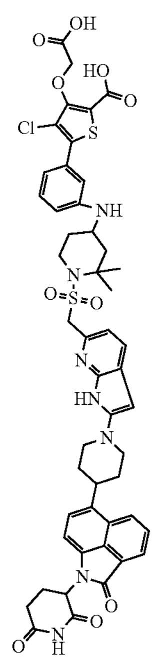 | 994.27 | ¹H NMR (400 MHZ, DMSO-d6) δ 11.09 (s, 1H), 8.31-8.27 (m, 1H), 8.17-8.12 (m, 1H), 7.39-7.36 (m, 1H), 7.31-7.27 (m, 1H), 7.19-7.15 (m, 1H), 7.07-7.03 (m, 2H), 6.86-6.78 (m, 2H), 6.68-6.65 (m, 1H), 5.42-5.39 (m, 2H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.48-0.84 (m, 8H). |

-continued

| compounds | Structure | MS [M + H+] | 1H-NMR |
|---|---|---|---|
| 104 | 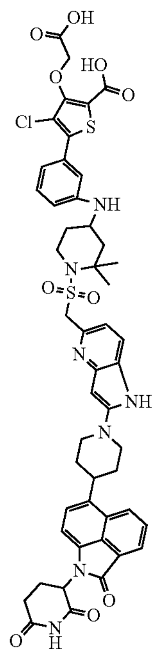 [SMILES: CC1(C)CC(Nc2cccc(-c3sc(C(=O)O)c(OCC(=O)O)c3Cl)c2)CCN1S(=O)(=O)Cc1ccc2[nH]c(N3CCC(c4ccc5c6c(cccc46)C(=O)N5C4CCC(=O)NC4=O)CC3)cc2n1] | 994.27 | 1H NMR (400 MHZ, DMSO-d6) δ 10.59 (s, 1H), 8.51-8.47 (m, 1H), 8.07-8.02 (m, 1H), 7.39-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 2H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.48-0.84 (m, 8H). |
| 105 | 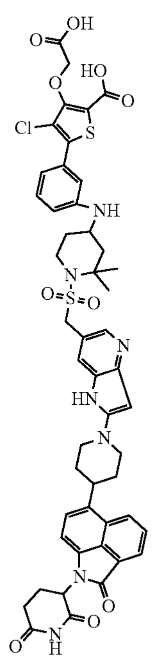 | 994.27 | 1H NMR (400 MHZ, DMSO-d6) δ 11.04 (s, 1H), 8.52-8.47 (m, 2H), 8.07-8.02 (m, 1H), 7.39-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 2H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.53-0.84 (m, 8H). |

-continued

| compounds | Structure | MS [M + H⁺] | ¹H-NMR |
|---|---|---|---|
| 106 | 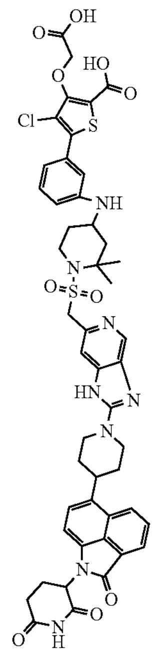 [SMILES: CC1(C)CC(Nc2cccc(-c3sc(C(=O)O)c(OCC(=O)O)c3Cl)c2)CCN1S(=O)(=O)Cc1cc2[nH]c(N3CCC(c4ccc5c6c(cccc46)C(=O)N5C4CCC(=O)NC4=O)CC3)nc2cn1] | 995.26 | ¹H NMR (400 MHZ, DMSO-d6) δ 11.05 (s, 1H), 8.51-8.47 (m, 2H), 8.07-8.02 (m, 1H), 7.39-7.36 (m, 2H), 7.19-7.15 (m, 1H), 7.07-7.03 (m, 2H), 6.85-6.78 (m, 2H), 6.68-6.65 (m, 1H), 5.42-5.39 (m, 2H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.52-0.84 (m, 8H). |
| 107 | 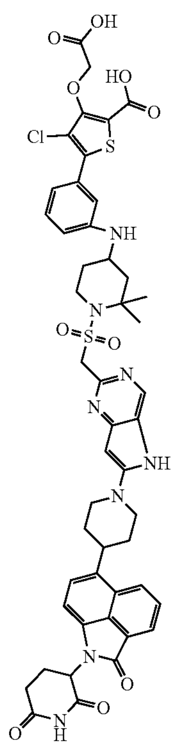 [SMILES: CC1(C)CC(Nc2cccc(-c3sc(C(=O)O)c(OCC(=O)O)c3Cl)c2)CCN1S(=O)(=O)Cc1ncc2[nH]c(N3CCC(c4ccc5c6c(cccc46)C(=O)N5C4CCC(=O)NC4=O)CC3)cc2n1] | 995.26 | ¹H NMR (400 MHZ, DMSO-d6) δ 11.09 (s, 1H), 8.51-8.47 (m, 2H), 8.07-8.02 (m, 1H), 7.39-7.36 (m, 2H), 7.19-7.15 (m, 1H), 7.07-7.03 (m, 2H), 6.85-6.78 (m, 1H), 6.68-6.65 (m, 1H), 5.42-5.39 (m, 2H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.48-0.84 (m, 8H). |

-continued
| compounds | Structure | MS [M + H+] | 1H-NMR |
|---|---|---|---|
| 108 | 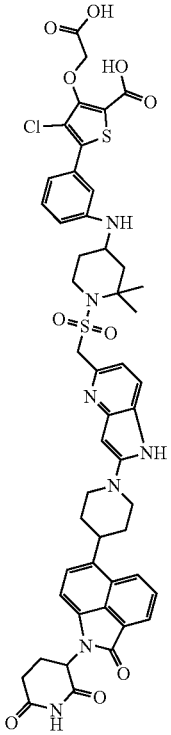 [SMILES: CC1(C)CC(Nc2cccc(-c3sc(C(=O)O)c(OCC(=O)O)c3Cl)c2)CCN1S(=O)(=O)Cc1ccc2[nH]c(N3CCC(c4ccc5c6c(cccc46)C(=O)N5C4CCC(=O)NC4=O)CC3)cc2n1] | 995.26 | 1H NMR (400 MHZ, DMSO-d6) δ 11.07 (s, 1H), 8.51-8.47 (m, 1H), 8.07-8.02 (m, 2H), 7.87-7.83 (m, 1H), 7.39-7.36 (m, 1H), 7.31-7.27 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.55-0.84 (m, 8H). |
| 109 | 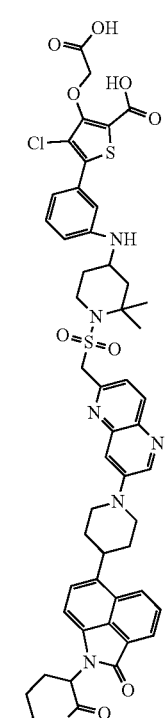 | 1006.27 | 1H NMR (400 MHZ, DMSO-d6) δ 11.09 (s, 1H), 8.51-8.47 (m, 2H), 8.47-8.42 (m, 1H), 8.07-8.02 (m, 1H), 7.87-7.83 (m, 1H), 7.39-7.36 (m, 1H), 7.31-7.27 (m, 1H), 7.19-7.15 (m, 1H), 7.07-7.03 (m, 3H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.52-0.84 (m, 8H). |

-continued

| compounds | Structure | MS [M + H+] | 1H-NMR |
|---|---|---|---|
| 110 | 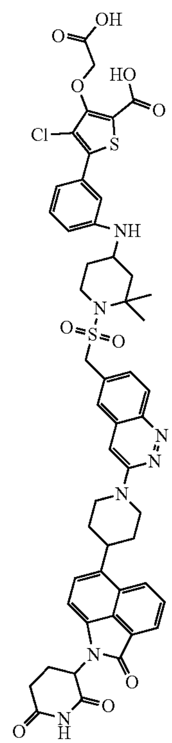 [SMILES: CC1(C)CC(Nc2cccc(-c3sc(C(=O)O)c(OCC(=O)O)c3Cl)c2)CCN1S(=O)(=O)Cc1ccc2nnc(N3CCC(c4ccc5c6c(cccc46)C(=O)N5C4CCC(=O)NC4=O)CC3)cc2c1] | 1006.27 | 1H NMR (400 MHZ, DMSO-d6) δ 11.09 (s, 1H), 8.51-8.47 (m, 1H), 8.07-8.02 (m, 1H), 7.87-7.83 (m, 2H), 7.39-7.36 (m, 1H), 7.31-7.27 (m, 1H), 7.19-7.15 (m, 1H), 7.07-7.03 (m, 3H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.54-0.84 (m, 8H). |
| 111 | 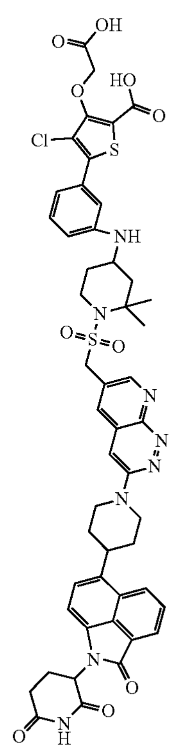 [SMILES: CC1(C)CC(Nc2cccc(-c3sc(C(=O)O)c(OCC(=O)O)c3Cl)c2)CCN1S(=O)(=O)Cc1cnc2nnc(N3CCC(c4ccc5c6c(cccc46)C(=O)N5C4CCC(=O)NC4=O)CC3)cc2c1] | 1007.26 | 1H NMR (400 MHZ, DMSO-d6) δ 11.15 (s, 1H), 8.52-8.47 (m, 1H), 8.07-8.02 (m, 1H), 7.39-7.36 (m, 1H), 7.31-7.27 (m, 1H), 7.19-7.15 (m, 1H), 7.07-7.03 (m, 3H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.51-0.84 (m, 8H). |

-continued

| compounds | Structure | MS [M + H⁺] | ¹H-NMR |
|---|---|---|---|
| 112 | 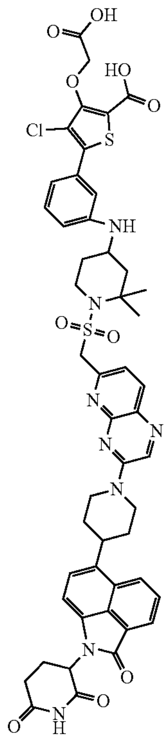 [SMILES: CC1(C)CC(Nc2cccc(-c3sc(C(=O)O)c(OCC(=O)O)c3Cl)c2)CCN1S(=O)(=O)Cc1ccc2ncc(N3CCC(c4ccc5c6c(cccc46)C(=O)N5C4CCC(=O)NC4=O)CC3)nc2n1] | 1007.26 | ¹H NMR (400 MHZ, DMSO-d6) δ 11.19 (s, 1H), 8.51-8.47 (m, 2H), 8.07-8.02 (m, 1H), 7.87-7.83 (m, 1H), 7.39-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.52-0.84 (m, 8H). |
| 113 | 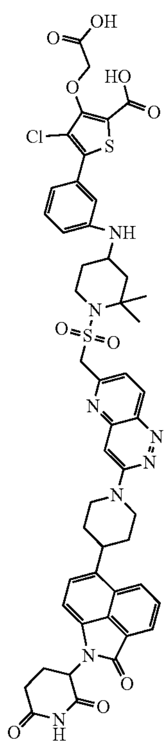 [SMILES: CC1(C)CC(Nc2cccc(-c3sc(C(=O)O)c(OCC(=O)O)c3Cl)c2)CCN1S(=O)(=O)Cc1ccc2nnc(N3CCC(c4ccc5c6c(cccc46)C(=O)N5C4CCC(=O)NC4=O)CC3)cc2n1] | 1007.26 | ¹H NMR (400 MHZ, DMSO-d6) δ 10.73 (s, 1H), 8.53-8.47 (m, 1H), 8.07-8.02 (m, 1H), 7.87-7.83 (m, 1H), 7.31-7.27 (m, 1H), 7.19-7.15 (m, 2H), 7.07-7.03 (m, 3H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.48-0.84 (m, 8H). |

-continued

| compounds | Structure | MS [M + H⁺] | ¹H-NMR |
|---|---|---|---|
| 114 | 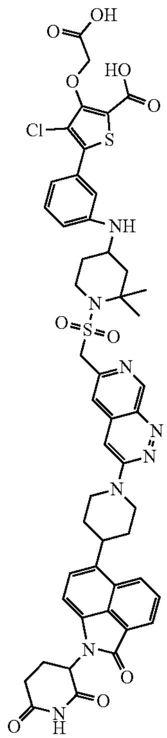 [SMILES: CC1(C)CC(Nc2cccc(-c3sc(C(=O)O)c(OCC(=O)O)c3Cl)c2)CCN1S(=O)(=O)Cc1cc2cc(N3CCC(c4ccc5c6c(cccc46)C(=O)N5C4CCC(=O)NC4=O)CC3)nnc2cn1] | 1007.26 | ¹H NMR (400 MHZ, DMSO-d6) δ 11.11 (s, 1H), 8.51-8.47 (m, 2H), 8.07-8.02 (m, 1H), 7.39-7.36 (m, 1H), 7.31-7.27 (m, 1H), 7.19-7.15 (m, 1H), 7.07-7.03 (m, 3H), 6.85-6.78 (m, 2H), 6.68-6.65 (m, 1H), 5.42-5.39 (m, 1H), 4.89 (s, 2H), 4.39-4.36 (m, 3H), 3.72-3.28 (m, 4H), 3.17-2.80 (m, 1H), 2.74-2.70 (m, 1H), 2.15-1.62 (m, 7H), 1.49-0.84 (m, 8H). |
| 115 | 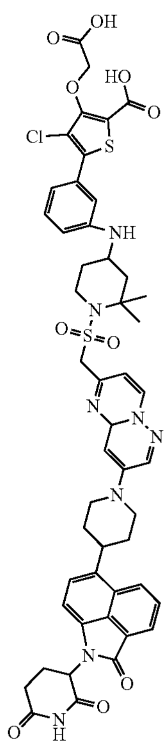 [SMILES: CC1(C)CC(Nc2cccc(-c3sc(C(=O)O)c(OCC(=O)O)c3Cl)c2)CCN1S(=O)(=O)CC1=NC2C=C(N3CCC(c4ccc5c6c(cccc46)C(=O)N5C4CCC(=O)NC4=O)CC3)C=NN2C=C1] | 1009.28 | ¹H NMR (400 MHz, DMSO-d6) δ 11.09 (s, 1H), 8.53-8.47 (m, 2H), 8.06-8.02 (m, 1H), 7.39-7.36 (m, 2H), 7.32-7.27 (m, 1H), 7.21-7.15 (m, 1H), 7.06-7.03 (m, 2H), 6.85-6.78 (m, 3H), 6.68-6.65 (m, 1H), 5.43-5.39 (m, 2H), 4.88 (s, 2H), 4.41-4.36 (m, 3H), 3.70-3.28 (m, 4H), 3.17-2.80 (m, 1H), 2.75-2.70 (m, 1H), 2.12-1.62 (m, 7H), 1.48-0.84 (m, 8H). |

-continued

| compounds | Structure | MS [M + H+] | 1H-NMR |
|---|---|---|---|
| 116 | 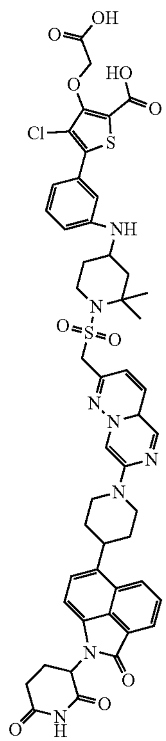 [SMILES: CC1(C)CC(Nc2cccc(-c3sc(C(=O)O)c(OCC(=O)O)c3Cl)c2)CCN1S(=O)(=O)CC1=NN2C=C(N3CCC(c4ccc5c6c(cccc46)C(=O)N5C4CCC(=O)NC4=O)CC3)N=CC2C=C1] | 1009.28 | 1H NMR (400 MHZ, DMSO-d6) δ 11.12 (s, 1H), 8.50-8.47 (m, 1H), 8.07-8.02 (m, 1H), 7.39-7.36 (m, 2H), 7.31-7.27 (m, 1H), 7.19-7.15 (m, 1H), 7.07-7.03 (m, 2H), 6.85-6.78 (m, 3H), 6.68-6.65 (m, 1H), 5.42-5.39 (m, 2H), 4.88 (s, 2H), 4.39-4.36 (m, 3H), 3.70-3.28 (m, 4H), 3.17-2.80 (m, 1H), 2.74-2.70 (m, 1H), 2.14-1.62 (m, 7H), 1.47-0.84 (m, 8H). |
| 117 | 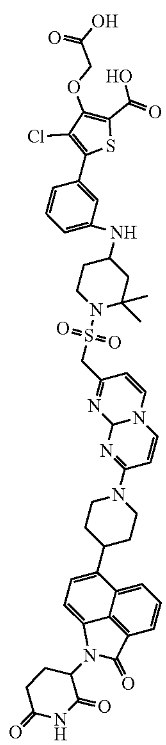 [SMILES: CC1(C)CC(Nc2cccc(-c3sc(C(=O)O)c(OCC(=O)O)c3Cl)c2)CCN1S(=O)(=O)CC1=NC2N=C(N3CCC(c4ccc5c6c(cccc46)C(=O)N5C4CCC(=O)NC4=O)CC3)C=CN2C=C1] | 1009.28 | 1H NMR (400 MHZ, DMSO-d6) δ 11.07 (s, 1H), 8.52-8.47 (m, 2H), 8.07-8.02 (m, 2H), 7.49-7.42 (m, 2H), 7.39-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.46-0.84 (m, 8H). |

-continued

| compounds | Structure | MS [M + H⁺] | ¹H-NMR |
|---|---|---|---|
| 118 | 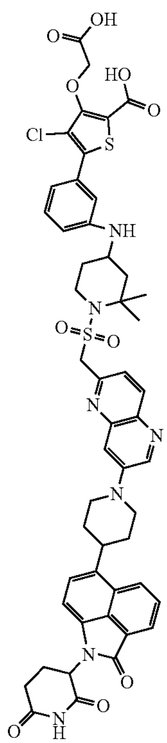 [SMILES: CC1(C)CC(Nc2cccc(-c3sc(C(=O)O)c(OCC(=O)O)c3Cl)c2)CCN1S(=O)(=O)Cc1ccc2ncc(N3CCC(c4ccc5c6c(cccc46)C(=O)N5C4CCC(=O)NC4=O)CC3)cc2n1] | 1006.27 | ¹H NMR (400 MHZ, DMSO-d6) δ 11.09 (s, 1H), 8.51-8.47 (m, 2H), 8.47-8.42 (m, 1H), 8.07-8.02 (m, 1H), 7.87-7.83 (m, 1H), 7.39-7.36 (m, 1H), 7.31-7.27 (m, 1H), 7.19-7.15 (m, 1H), 7.07-7.03 (m, 3H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.15-1.62 (m, 7H), 1.51-0.84 (m, 8H). |
| 119 | 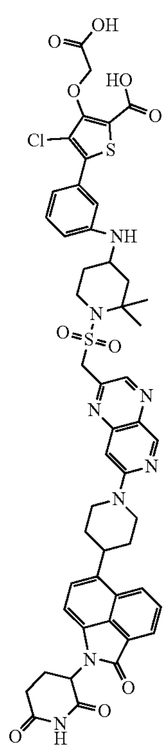 [SMILES: CC1(C)CC(Nc2cccc(-c3sc(C(=O)O)c(OCC(=O)O)c3Cl)c2)CCN1S(=O)(=O)Cc1cnc2cnc(N3CCC(c4ccc5c6c(cccc46)C(=O)N5C4CCC(=O)NC4=O)CC3)cc2n1] | 1007.26 | ¹H NMR (400 MHZ, DMSO-d6) δ 11.06 (s, 1H), 8.52-8.47 (m, 2H), 7.87-7.83 (m, 1H), 7.49-7.42 (m, 1H), 7.39-7.36 (m, 1H), 7.19-7.15 (m, 1H), 7.07-7.03 (m, 3H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.75-2.70 (m, 1H), 2.12-1.62 (m, 7H), 1.49-0.84 (m, 8H). |

-continued

| compounds | Structure | MS [M + H⁺] | ¹H-NMR |
|---|---|---|---|
| 120 | 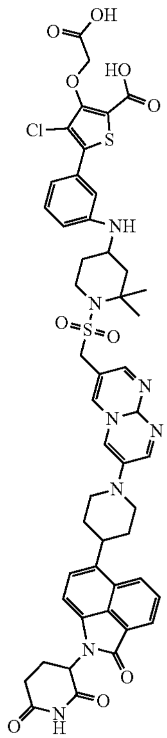 [SMILES: CC1(C)CC(Nc2cccc(-c3sc(C(=O)O)c(OCC(=O)O)c3Cl)c2)CCN1S(=O)(=O)CC1=CN2C=C(N3CCC(c4ccc5c6c(cccc46)C(=O)N5C4CCC(=O)NC4=O)CC3)C=NC2N=C1] | 1009.28 | ¹H NMR (400 MHZ, DMSO-d6) δ 11.05 (s, 1H), 8.50-8.47 (m, 2H), 8.07-8.02 (m, 2H), 7.49-7.42 (m, 2H), 7.39-7.36 (m, 1H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.13-1.62 (m, 7H), 1.48-0.84 (m, 8H). |
| 121 | 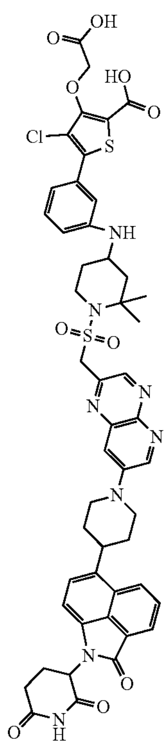 [SMILES: CC1(C)CC(Nc2cccc(-c3sc(C(=O)O)c(OCC(=O)O)c3Cl)c2)CCN1S(=O)(=O)Cc1cnc2ncc(N3CCC(c4ccc5c6c(cccc46)C(=O)N5C4CCC(=O)NC4=O)CC3)cc2n1] | 1007.26 | ¹H NMR (400 MHZ, DMSO-d6) δ 11.10 (s, 1H), 8.71-8.57 (m, 2H), 8.07-8.02 (m, 2H), 7.87-7.83 (m, 1H), 7.49-7.42 (m, 1H), 7.39-7.36 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.45-0.84 (m, 8H). |

-continued

| compounds | Structure | MS [M + H+] | 1H-NMR |
|---|---|---|---|
| 122 | 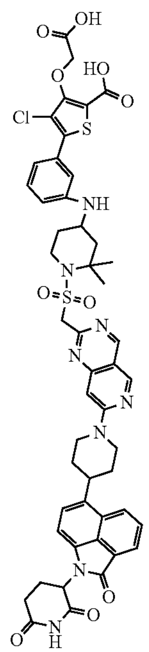 [SMILES: CC1(C)CC(Nc2cccc(-c3sc(C(=O)O)c(OCC(=O)O)c3Cl)c2)CCN1S(=O)(=O)Cc1ncc2cnc(N3CCC(c4ccc5c6c(cccc46)C(=O)N5C4CCC(=O)NC4=O)CC3)cc2n1] | 1007.26 | 1H NMR (400 MHZ, DMSO-d6) δ 11.11 (s, 1H), 8.51-8.47 (m, 3H), 8.08-8.02 (m, 1H), 7.49-7.42 (m, 1H), 7.39-7.36 (m, 2H), 7.19-7.15 (m, 1H), 7.07-7.03 (m, 1H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.49-0.84 (m, 8H). |
| 123 | 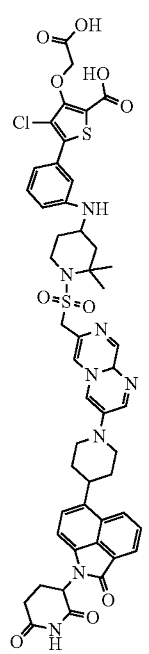 [SMILES: CC1(C)CC(Nc2cccc(-c3sc(C(=O)O)c(OCC(=O)O)c3Cl)c2)CCN1S(=O)(=O)CC1=CN2C=C(N3CCC(c4ccc5c6c(cccc46)C(=O)N5C4CCC(=O)NC4=O)CC3)C=NC2C=N1] | 1009.28 | 1H NMR (400 MHZ, DMSO-d6) δ 11.02 (s, 1H), 8.51-8.47 (m, 1H), 8.07-8.02 (m, 2H), 7.49-7.42 (m, 1H), 7.39-7.36 (m, 2H), 7.19-7.15 (m, 2H), 7.07-7.03 (m, 3H), 6.85-6.78 (m, 2H), 6.68-6.65 (m, 1H), 5.42-5.39 (m, 2H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.45-0.84 (m, 8H). |

| compounds | Structure | MS [M + H+] | 1H-NMR |
|---|---|---|---|
| 124 | 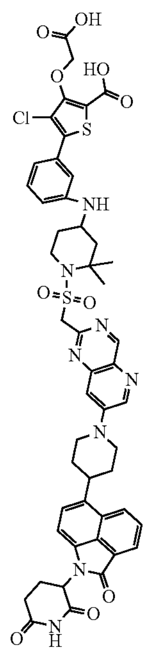 [SMILES: CC1(C)CC(Nc2cccc(-c3sc(C(=O)O)c(OCC(=O)O)c3Cl)c2)CCN1S(=O)(=O)Cc1ncc2ncc(N3CCC(c4ccc5c6c(cccc46)C(=O)N5C4CCC(=O)NC4=O)CC3)cc2n1] | 1007.26 | 1H NMR (400 MHz, DMSO-d6) δ 11.08 (s, 1H), 8.91-8.87 (m, 1H), 8.51-8.47 (m, 1H), 8.07-8.02 (m, 1H), 7.47-7.42 (m, 1H), 7.38-7.36 (m, 2H), 7.21-7.15 (m, 1H), 7.09-7.03 (m, 3H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.48-0.84 (m, 8H). |
| 125 | 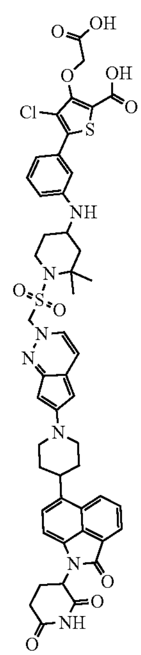 [SMILES: CC1(C)CC(Nc2cccc(-c3sc(C(=O)O)c(OCC(=O)O)c3Cl)c2)CCN1S(=O)(=O)Cn1ccc2cc(N3CCC(c4ccc5c6c(cccc46)C(=O)N5C4CCC(=O)NC4=O)CC3)cc-2n1] | 994.27 | 1H NMR (400 MHZ, DMSO-d6) δ 11.07 (s, 1H), 8.51-8.47 (m, 1H), 8.07-8.02 (m, 2H), 7.39-7.36 (m, 1H), 7.17-7.15 (m, 1H), 7.08-7.03 (m, 2H), 6.85-6.78 (m, 2H), 6.68-6.65 (m, 1H), 5.42-5.39 (m, 3H), 4.88-4.59 (m, 5H), 4.39-4.36 (m, 3H), 3.70-3.28 (m, 4H), 3.17-2.80 (m, 1H), 2.74-2.70 (m, 1H), 2.12-1.62 (m, 7H), 1.51-0.84 (m, 8H). |

| compounds | Structure | MS [M + H+] | ¹H-NMR |
|---|---|---|---|
| 126 | 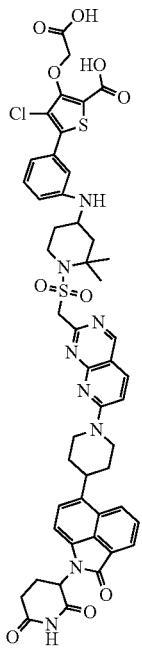 [SMILES: CC1(C)CC(Nc2cccc(-c3sc(C(=O)O)c(OCC(=O)O)c3Cl)c2)CCN1S(=O)(=O)Cc1ncc2ccc(N3CCC(c4ccc5c6c(cccc46)C(=O)N5C4CCC(=O)NC4=O)CC3)nc2n1] | 1007.26 | ¹H NMR (400 MHZ, DMSO-d6) δ 11.09 (s, 1H), 8.51-8.47 (m, 2H), 8.07-8.02 (m, 1H), 7.38-7.36 (m, 3H), 7.19-7.15 (m, 1H), 7.09-7.03 (m, 2H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.16-2.80 (m, 1H), 2.74-2.70 (m, 1H), 2.13-1.62 (m, 7H), 1.52-0.84 (m, 8H). |
| 127 | 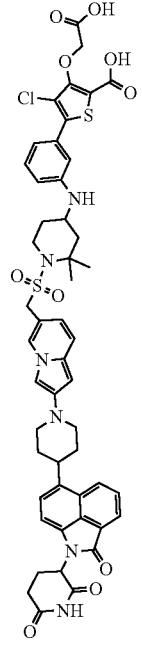 | 993.27 | ¹H NMR (400 MHZ, DMSO-d6) δ 11.01 (s, 1H), 8.51-8.47 (m, 2H), 8.07-8.02 (m, 2H), 7.87-7.83 (m, 1H), 7.38-7.36 (m, 1H), 7.31-7.27 (m, 1H), 7.19-7.15 (m, 1H), 7.06-7.03 (m, 2H), 6.85-6.78 (m, 2H), 6.68-6.65 (m, 1H), 5.42-5.39 (m, 2H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.47-0.84 (m, 8H). |

-continued
| compounds | Structure | MS [M + H⁺] | ¹H-NMR |
|---|---|---|---|
| 128 | 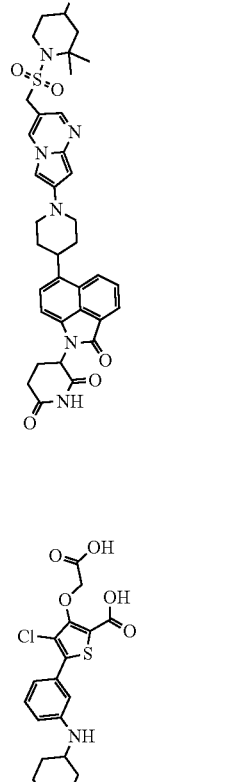 | 994.27 | ¹H NMR (400 MHZ, DMSO-d6) δ 11.08 (s, 1H), 8.52-8.47 (m, 3H), 8.06-8.02 (m, 1H), 7.39-7.36 (m, 1H), 7.32-7.27 (m, 1H), 7.17-7.15 (m, 1H), 7.07-7.03 (m, 1H), 6.85-6.78 (m, 2H), 6.68-6.65 (m, 1H), 5.42-5.39 (m, 1H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.49-0.84 (m, 8H). |
| 129 | 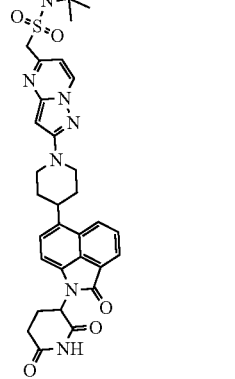 | 995.26 | ¹H NMR (400 MHZ, DMSO-d6) δ 11.09 (s, 1H), 9.31-9.27 (m, 1H), 8.51-8.47 (m, 1H), 8.07-8.02 (m, 1H), 7.39-7.36 (m, 2H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 2H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.51-0.84 (m, 8H). |

-continued

| compounds | Structure | MS [M + H⁺] | ¹H-NMR |
|---|---|---|---|
| 130 | 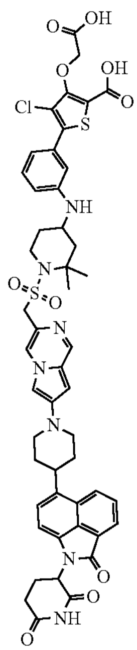 [SMILES: CC1(C)CC(Nc2cccc(-c3sc(C(=O)O)c(OCC(=O)O)c3Cl)c2)CCN1S(=O)(=O)Cc1ccc2cc(N3CCC(c4ccc5c6c(cccc46)C(=O)N5C4CCC(=O)NC4=O)CC3)cn2c1] | 994.27 | ¹H NMR (400 MHZ, DMSO-d6) δ 11.03 (s, 1H), 9.33-9.27 (m, 1H), 8.51-8.47 (m, 1H), 8.07-8.02 (m, 1H), 7.39-7.36 (m, 2H), 7.31-7.27 (m, 1H), 7.19-7.15 (m, 1H), 7.07-7.03 (m, 2H), 6.85-6.78 (m, 2H), 6.68-6.65 (m, 2H), 5.42-5.39 (m, 2H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.45-0.84 (m, 8H). |
| 131 | 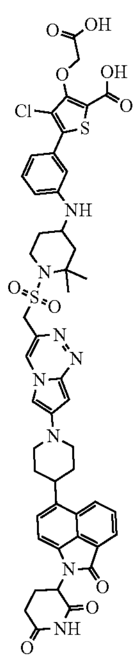 [SMILES: CC1(C)CC(Nc2cccc(-c3sc(C(=O)O)c(OCC(=O)O)c3Cl)c2)CCN1S(=O)(=O)Cc1cn2cc(N3CCC(c4ccc5c6c(cccc46)C(=O)N5C4CCC(=O)NC4=O)CC3)cc2nn1] | 995.26 | ¹H NMR (400 MHZ, DMSO-d6) δ 11.05 (s, 1H), 9.31-9.27 (m, 1H), 7.39-7.36 (m, 2H), 7.31-7.27 (m, 1H), 7.19-7.15 (m, 1H), 7.07-7.03 (m, 2H), 6.85-6.78 (m, 2H), 6.68-6.65 (m, 1H), 5.42-5.39 (m, 2H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.47-0.84 (m, 8H). |

| compounds | Structure | MS [M + H+] | 1H-NMR |
|---|---|---|---|
| 132 | 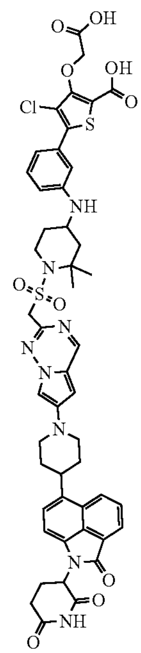 [SMILES: CC1(C)CC(Nc2cccc(-c3sc(C(=O)O)c(OCC(=O)O)c3Cl)c2)CCN1S(=O)(=O)Cc1ncc2cc(N3CCC(c4ccc5c6c(cccc46)C(=O)N5C4CCC(=O)NC4=O)CC3)cn2n1] | 995.26 | 1H NMR (400 MHZ, DMSO-d6) δ 11.09 (s, 1H), 9.31-9.27 (m, 1H), 8.51-8.47 (m, 1H), 8.07-8.02 (m, 1H), 7.39-7.36 (m, 2H), 7.31-7.27 (m, 1H), 7.19-7.15 (m, 1H), 7.07-7.03 (m, 2H), 6.84-6.78 (m, 2H), 6.68-6.65 (m, 1H), 5.42-5.39 (m, 2H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.46-0.84 (m, 8H). |
| 133 | 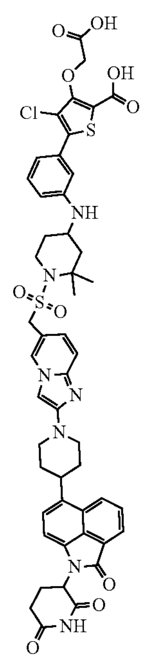 [SMILES: CC1(C)CC(Nc2cccc(-c3sc(C(=O)O)c(OCC(=O)O)c3Cl)c2)CCN1S(=O)(=O)Cc1ccc2nc(N3CCC(c4ccc5c6c(cccc46)C(=O)N5C4CCC(=O)NC4=O)CC3)cn2c1] | 994.27 | 1H NMR (400 MHZ, DMSO-d6) δ 11.11 (s, 1H), 8.81-8.77 (m, 1H), 8.51-8.47 (m, 1H), 8.07-8.02 (m, 1H), 7.39-7.36 (m, 2H), 7.31-7.27 (m, 1H), 7.19-7.15 (m, 1H), 7.07-7.03 (m, 2H), 6.85-6.78 (m, 2H), 6.68-6.65 (m, 2H), 5.42-5.39 (m, 2H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.50-0.83 (m, 8H). |

-continued

| compounds | Structure | MS [M + H⁺] | ¹H-NMR |
|---|---|---|---|
| 134 | 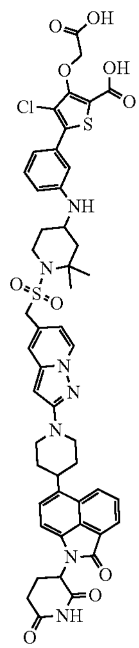 [SMILES: CC1(C)CC(Nc2cccc(-c3sc(C(=O)O)c(OCC(=O)O)c3Cl)c2)CCN1S(=O)(=O)Cc1ccn2nc(N3CCC(c4ccc5c6c(cccc46)C(=O)N5C4CCC(=O)NC4=O)CC3)cc2c1] | 994.27 | ¹H NMR (400 MHZ, DMSO-d6) δ 11.08 (s, 1H), 9.47-9.42 (m, 2H), 8.47-8.42 (m, 2H), 8.07-8.02 (m, 2H), 7.57-7.42 (m, 1H), 7.39-7.36 (m, 3H), 7.31-7.27 (m, 1H), 7.18-7.15 (m, 1H), 7.06-7.03 (m, 2H), 6.85-6.78 (m, 2H), 6.68-6.65 (m, 1H), 5.42-5.39 (m, 2H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.49-0.84 (m, 8H). |
| 135 | 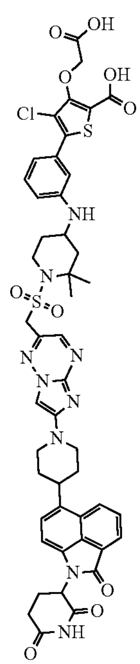 [SMILES: CC1(C)CC(Nc2cccc(-c3sc(C(=O)O)c(OCC(=O)O)c3Cl)c2)CCN1S(=O)(=O)Cc1cnc2nc(N3CCC(c4ccc5c6c(cccc46)C(=O)N5C4CCC(=O)NC4=O)CC3)cn2n1] | 996.26 | ¹H NMR (400 MHZ, DMSO-d6) δ 11.09 (s, 1H), 8.97-8.92 (m, 1H), 8.07-8.02 (m, 2H), 7.57-7.42 (m, 1H), 7.19-7.15 (m, 1H), 7.07-7.03 (m, 2H), 6.85-6.78 (m, 2H), 6.68-6.65 (m, 1H), 5.42-5.39 (m, 2H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.48-0.83 (m, 8H). |

-continued
| compounds | Structure | MS [M + H+] | 1H-NMR |
|---|---|---|---|
| 136 | 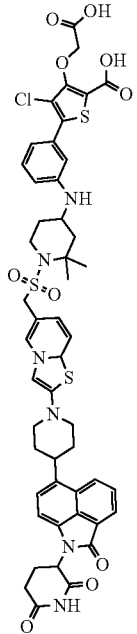 | 1013.24 | 1H NMR (400 MHZ, DMSO-d6) δ 11.09 (s, 1H), 8.81-8.77 (m, 1H), 8.51-8.47 (m, 1H), 8.07-8.02 (m, 1H), 7.39-7.36 (m, 2H), 7.31-7.27 (m, 1H), 7.19-7.15 (m, 1H), 7.07-7.03 (m, 2H), 6.85-6.78 (m, 2H), 6.68-6.65 (m, 2H), 5.42-5.39 (m, 2H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.48-0.84 (m, 8H). |
| 137 | 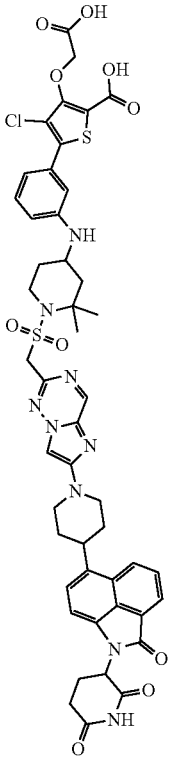 [SMILES: CC1(C)CC(Nc2cccc(-c3sc(C(=O)O)c(OCC(=O)O)c3Cl)c2)CCN1S(=O)(=O)Cc1ncc2nc(N3CCC(c4ccc5c6c(cccc46)C(=O)N5C4CCC(=O)NC4=O)CC3)cn2n1] | 996.26 | 1H NMR (400 MHZ, DMSO-d6) δ 11.08 (s, 1H), 8.82-8.77 (m, 1H), 8.51-8.47 (m, 1H), 7.39-7.36 (m, 2H), 7.31-7.27 (m, 1H), 7.19-7.15 (m, 1H), 7.07-7.03 (m, 2H), 6.85-6.78 (m, 2H), 6.68-6.65 (m, 2H), 5.42-5.39 (m, 2H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.51-0.84 (m, 8H). |

| compounds | Structure | MS [M + H+] | 1H-NMR |
|---|---|---|---|
| 138 | 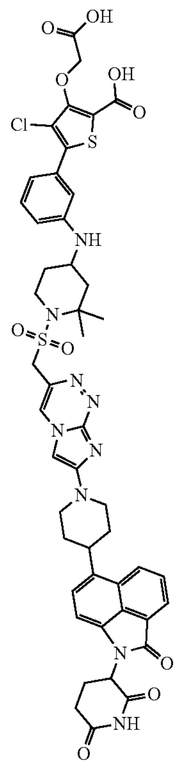 [SMILES: CC1(C)CC(Nc2cccc(-c3sc(C(=O)O)c(OCC(=O)O)c3Cl)c2)CCN1S(=O)(=O)Cc1cn2cc(N3CCC(c4ccc5c6c(cccc46)C(=O)N5C4CCC(=O)NC4=O)CC3)nc2nn1] | 996.26 | 1H NMR (400 MHZ, DMSO-d6) δ 11.09 (s, 1H), 9.81-9.77 (m, 1H), 8.81-8.77 (m, 1H), 7.39-7.36 (m, 2H), 7.31-7.27 (m, 1H), 7.07-7.03 (m, 2H), 6.85-6.78 (m, 2H), 6.68-6.65 (m, 2H), 5.42-5.39 (m, 2H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.49-0.84 (m, 8H). |
| 139 | 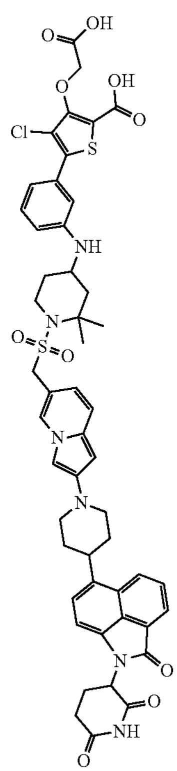 [SMILES: CC1(C)CC(Nc2cccc(-c3sc(C(=O)O)c(OCC(=O)O)c3Cl)c2)CCN1S(=O)(=O)Cc1ccc2cc(N3CCC(c4ccc5c6c(cccc46)C(=O)N5C4CCC(=O)NC4=O)CC3)cn2c1] | 993.27 | 1H NMR (400 MHZ, DMSO-d6) δ 11.11 (s, 1H), 8.82-8.77 (m, 2H), 8.27-8.22 (m, 1H), 8.17-8.12 (m, 1H), 7.39-7.36 (m, 2H), 7.31-7.27 (m, 1H), 7.19-7.15 (m, 1H), 7.07-7.03 (m, 2H), 6.85-6.78 (m, 2H), 6.68-6.65 (m, 3H), 5.42-5.39 (m, 3H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.52-0.84 (m, 8H). |

-continued
| compounds | Structure | MS [M + H+] | 1H-NMR |
|---|---|---|---|
| 140 | 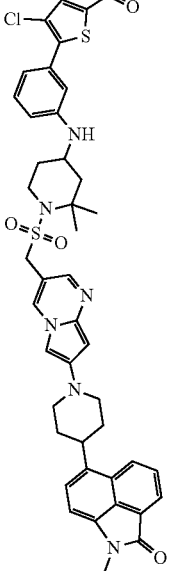 | 994.27 | 1H NMR (400 MHZ, DMSO-d6) δ 11.08 (s, 1H), 8.81-8.77 (m, 1H), 8.27-8.22 (m, 1H), 7.39-7.36 (m, 2H), 7.31-7.27 (m, 1H), 7.19-7.15 (m, 1H), 6.85-6.78 (m, 2H), 6.68-6.65 (m, 3H), 5.42-5.39 (m, 3H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.49-0.85 (m, 8H). |
| 141 | 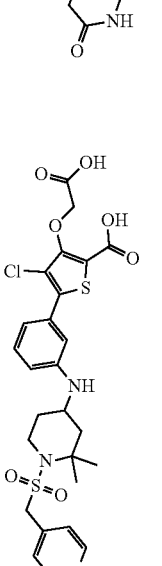 | 994.27 | 1H NMR (400 MHZ, DMSO-d6) δ 11.11 (s, 1H), 8.51-8.47 (m, 1H), 8.27-8.22 (m, 1H), 8.07-8.02 (m, 1H), 7.39-7.36 (m, 2H), 7.31-7.27 (m, 1H), 7.19-7.15 (m, 1H), 7.07-7.03 (m, 1H), 6.85-6.78 (m, 2H), 6.68-6.65 (m, 2H), 5.42-5.39 (m, 3H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.48-0.84 (m, 8H). |

-continued
| compounds | Structure | MS [M + H⁺] | ¹H-NMR |
|---|---|---|---|
| 142 | 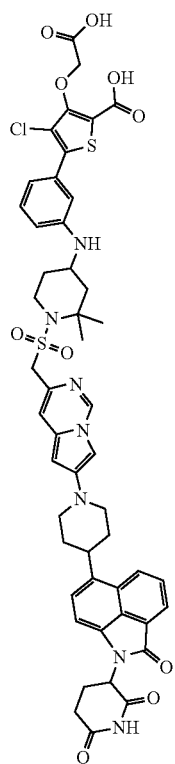 [SMILES: CC1(C)CC(Nc2cccc(-c3sc(C(=O)O)c(OCC(=O)O)c3Cl)c2)CCN1S(=O)(=O)Cc1cc2cc(N3CCC(c4ccc5c6c(cccc46)C(=O)N5C4CCC(=O)NC4=O)CC3)cn2cn1] | 994.27 | ¹H NMR (400 MHZ, DMSO-d6) δ 11.09 (s, 1H), 10.09-9.87 (m, 1H), 8.81-8.77 (m, 1H), 7.39-7.36 (m, 2H), 7.31-7.27 (m, 1H), 7.19-7.15 (m, 1H), 7.07-7.03 (m, 1H), 6.85-6.78 (m, 2H), 6.68-6.65 (m, 3H), 5.42-5.39 (m, 3H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.47-0.84 (m, 8H). |

-continued
| compounds | Structure | MS [M + H⁺] | ¹H-NMR |
|---|---|---|---|
| 143 | 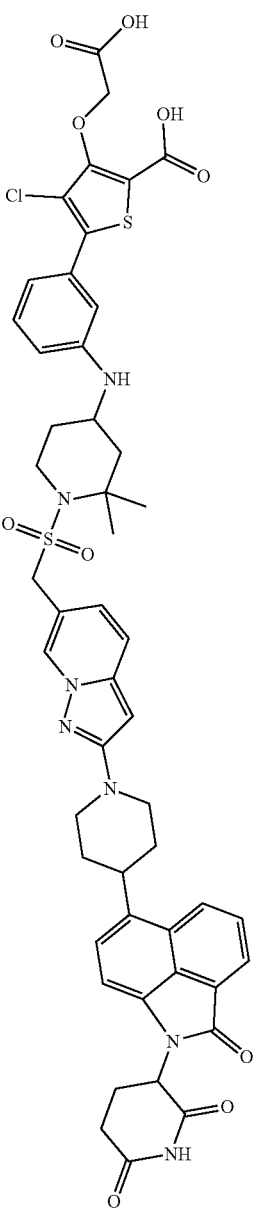 [SMILES: CC1(C)CC(Nc2cccc(-c3sc(C(=O)O)c(OCC(=O)O)c3Cl)c2)CCN1S(=O)(=O)Cc1ccc2cc(N3CCC(c4ccc5c6c(cccc46)C(=O)N5C4CCC(=O)NC4=O)CC3)nn2c1] | 994.27 | ¹H NMR (400 MHZ, DMSO-d6) δ 11.09 (s, 1H), 8.82-8.77 (m, 1H), 8.41-8.37 (m, 1H), 8.27-8.22 (m, 2H), 7.39-7.36 (m, 2H), 7.31-7.27 (m, 1H), 7.19-7.15 (m, 2H), 7.07-7.03 (m, 1H), 6.85-6.78 (m, 1H), 6.68-6.65 (m, 2H), 5.42-5.39 (m, 3H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.49-0.84 (m, 8H). |

-continued
| compounds | Structure | MS [M + H⁺] | ¹H-NMR |
|---|---|---|---|
| 144 | 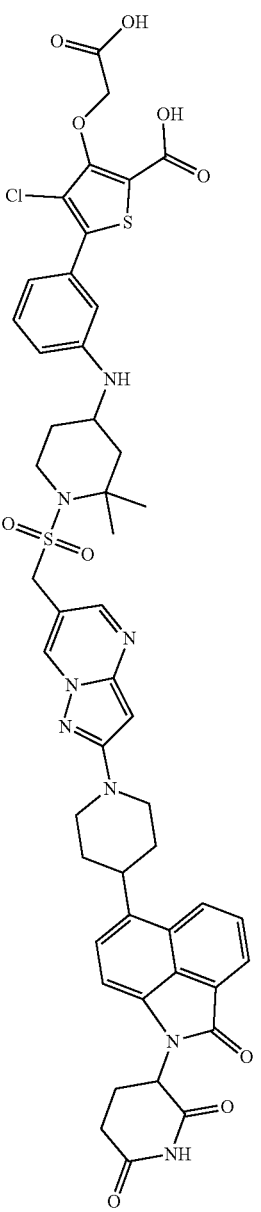 [SMILES: CC1(C)CC(Nc2cccc(-c3sc(C(=O)O)c(OCC(=O)O)c3Cl)c2)CCN1S(=O)(=O)Cc1cnc2cc(N3CCC(c4ccc5c6c(cccc46)C(=O)N5C4CCC(=O)NC4=O)CC3)nn2c1] | 995.26 | ¹H NMR (400 MHZ, DMSO-d6) δ 11.09 (s, 1H), 8.81-8.77 (m, 3H), 8.27-8.22 (m, 1H), 7.39-7.36 (m, 2H), 7.31-7.27 (m, 1H), 7.19-7.15 (m, 1H), 7.07-7.03 (m, 1H), 6.85-6.78 (m, 1H), 6.68-6.65 (m, 2H), 5.42-5.39 (m, 3H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.51-0.84 (m, 8H). |

| compounds | Structure | MS [M + H+] | 1H-NMR |
|---|---|---|---|
| 145 | 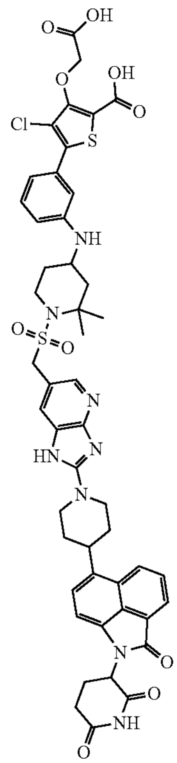 [SMILES: CC1(C)CC(Nc2cccc(-c3sc(C(=O)O)c(OCC(=O)O)c3Cl)c2)CCN1S(=O)(=O)Cc1cnc2nc(N3CCC(c4ccc5c6c(cccc46)C(=O)N5C4CCC(=O)NC4=O)CC3)[nH]c2c1] | 995.26 | 1H NMR (400 MHZ, DMSO-d6) δ 11.09 (s, 1H), 8.81-8.77 (m, 1H), 8.47-8.42 (m, 1H), 8.27-8.22 (m, 1H), 7.39-7.36 (m, 2H), 7.31-7.27 (m, 1H), 7.19-7.15 (m, 1H), 7.07-7.03 (m, 1H), 6.85-6.78 (m, 1H), 6.68-6.65 (m, 2H), 5.42-5.39 (m, 3H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.52-0.84 (m, 8H). |
| 146 | 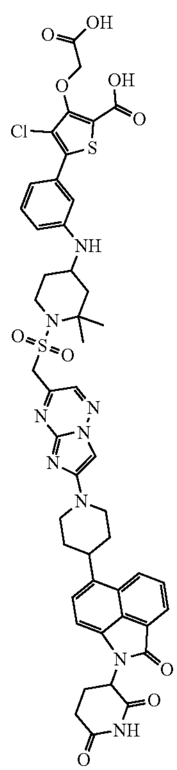 [SMILES: CC1(C)CC(Nc2cccc(-c3sc(C(=O)O)c(OCC(=O)O)c3Cl)c2)CCN1S(=O)(=O)Cc1cnn2cc(N3CCC(c4ccc5c6c(cccc46)C(=O)N5C4CCC(=O)NC4=O)CC3)nc2n1] | 995.26 | 1H NMR (400 MHZ, DMSO-d6) δ 11.09 (s, 1H), 8.81-8.77 (m, 1H), 8.27-8.22 (m, 1H), 7.39-7.36 (m, 2H), 7.31-7.27 (m, 1H), 7.19-7.15 (m, 1H), 7.07-7.03 (m, 1H), 6.85-6.78 (m, 1H), 6.68-6.65 (m, 2H), 5.42-5.39 (m, 3H), 4.88-4.59 (m, 4H), 4.39-4.36 (m, 3H), 3.70-3.28 (m, 4H), 3.17-2.80 (m, 1H), 2.74-2.70 (m, 1H), 2.12-1.62 (m, 7H), 1.48-0.84 (m, 8H). |

-continued

| compounds | Structure | MS [M + H⁺] | ¹H-NMR |
|---|---|---|---|
| 147 | 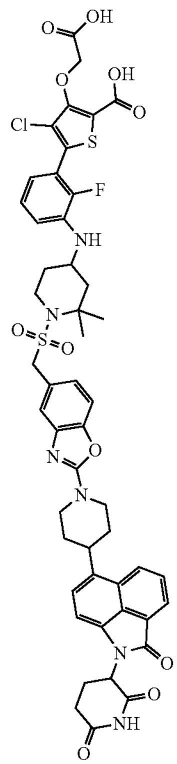 [SMILES: CC1(C)CC(Nc2cccc(-c3sc(C(=O)O)c(OCC(=O)O)c3Cl)c2F)CCN1S(=O)(=O)Cc1ccc2oc(N3CCC(c4ccc5c6c(cccc46)C(=O)N5C4CCC(=O)NC4=O)CC3)nc2c1] | 1013.24 | ¹H NMR (400 MHZ, DMSO-d6) δ 11.09 (s, 1H), 8.51-8.47 (m, 1H), 8.07-8.02 (m, 1H), 7.87-7.83 (m, 1H), 7.35-7.36 (m, 1H), 7.31-7.27 (m, 1H), 7.19-7.15 (m, 1H), 7.07-7.03 (m, 1H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.47-0.84 (m, 8H). |
| 148 | 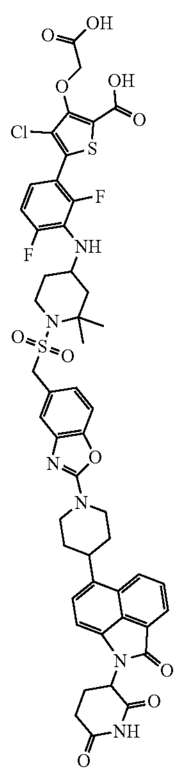 [SMILES: CC1(C)CC(Nc2c(F)ccc(-c3sc(C(=O)O)c(OCC(=O)O)c3Cl)c2F)CCN1S(=O)(=O)Cc1ccc2oc(N3CCC(c4ccc5c6c(cccc46)C(=O)N5C4CCC(=O)NC4=O)CC3)nc2c1] | 1031.23 | ¹H NMR (400 MHZ, DMSO-d6) δ 11.08 (s, 1H), 8.51-8.47 (m, 1H), 8.09-8.02 (m, 1H), 7.88-7.83 (m, 1H), 7.39-7.36 (m, 1H), 7.31-7.27 (m, 1H), 7.19-7.15 (m, 1H), 7.07-7.03 (m, 1H), 6.85-6.78 (m, 1H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.49-0.84 (m, 8H). |

-continued

| compounds | Structure | MS [M + H⁺] | ¹H-NMR |
|---|---|---|---|
| 149 | 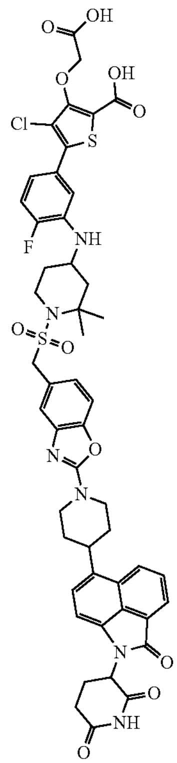 [SMILES: CC1(C)CC(Nc2cc(-c3sc(C(=O)O)c(OCC(=O)O)c3Cl)ccc2F)CCN1S(=O)(=O)Cc1ccc2oc(N3CCC(c4ccc5c6c(cccc46)C(=O)N5C4CCC(=O)NC4=O)CC3)nc2c1] | 1013.24 | ¹H NMR (400 MHZ, DMSO-d6) δ 11.05 (s, 1H), 8.53-8.45 (m, 1H), 8.08-8.02 (m, 1H), 7.85-7.83 (m, 1H), 7.35-7.36 (m, 1H), 7.31-7.27 (m, 1H), 7.19-7.15 (m, 1H), 7.06-7.03 (m, 2H), 6.85-6.78 (m, 1H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.12-1.62 (m, 7H), 1.49-0.83 (m, 8H). |
| 150 | 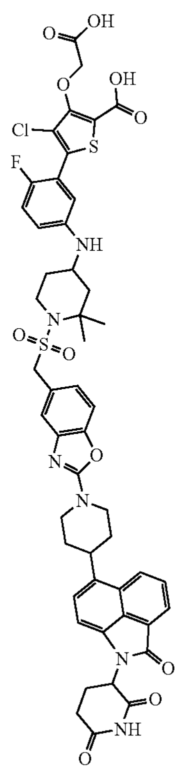 | 1013.24 | ¹H NMR (400 MHZ, DMSO-d6) δ 11.09 (s, 1H), 8.51-8.47 (m, 1H), 8.07-8.02 (m, 1H), 7.87-7.83 (m, 1H), 7.39-7.36 (m, 1H), 7.19-7.15 (m, 1H), 7.07-7.03 (m, 2H), 6.85-6.78 (m, 2H), 6.68-6.65 (m, 1H), 5.42-5.39 (m, 1H), 4.88 (s, 2H), 4.39-4.36 (m, 3H), 3.70-3.28 (m, 4H), 3.17-2.80 (m, 1H), 2.74-2.70 (m, 1H), 2.13-1.62 (m, 7H), 1.48-0.84 (m, 8H). |

| compounds | Structure | MS [M + H⁺] | ¹H-NMR |
|---|---|---|---|
| 151 | 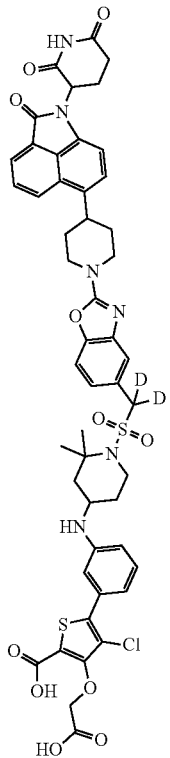 [SMILES: [2H]C([2H])(c1ccc2oc(N3CCC(c4ccc5c6c(cccc46)C(=O)N5C4CCC(=O)NC4=O)CC3)nc2c1)S(=O)(=O)N1CCC(Nc2cccc(-c3sc(C(=O)O)c(OCC(=O)O)c3Cl)c2)CC1(C)C] | 997.26 | ¹H NMR (400 MHZ, DMSO-d6) δ 11.09 (s, 1H), 8.48 (d, J = 8.7 Hz, 1H), 8.08 (d, J = 7.1 Hz, 1H), 7.85 (dd, J = 8.5, 7.1 Hz, 1H), 7.47-7.31 (m, 3H), 7.18 (ddd, J = 21.7, 10.0, 5.0 Hz, 2H), 7.08-7.02 (m, 1H), 6.88-6.79 (m, 1H), 6.76 (d, J = 9.3 Hz, 1H), 6.67-6.57 (m, 1H), 5.40 (dd, J = 13.1, 5.2 Hz, 1H), 4.92-4.84 (m, 2H), 3.36 (d, J = 13.2 Hz, 7H), 3.14-3.02 (m, 2H), 2.98-2.78 (m, 2H), 2.63 (dd, J = 3.7, 1.9 Hz, 1H), 1.96 (ddd, J = 69.4, 32.5, 8.9 Hz, 5H), 1.75-1.39 (m, 2H), 1.27-0.89 (m, 4H). |

Example 2: Luciferase Reporter Assay

HEK293/Luc (IFN-γ) stable cell line (Cat: M00953) and Fire-Lumi luciferase detection kit (Cat: L00877C) were purchased from GenScript. The complete culture medium formulation was DMEM containing 10% FBS and 1% Penicillin-Streptomycin. For $EC_{50}$ detection, 60 μL HEK293/Luc (IFN-γ) cells were seeded at the density of 10,000 cells/well into 384 well assay plates (761601, NEST) using the medium above mentioned.

The working solutions for each sample were prepared triplicated at 9 gradient doses, starting from 10 UM and diluted by 4 folds. The IFN-γ working solution was prepared at 0.8 ng/mL concentration. The sample working solution and IFN-γ working solution were mixed at the volume of 1:1, and then 20 μl/well of the aliquot was added into the 384-well plate and cells were incubated at 37° C./5% $CO_2$ for 6 h. 40 μL/well prewarmed detection reagents were added into the cells. Luminescent signals could be determined after 5-minute incubation. The data were plotted and four-parameter fitting was performed on the test data to obtain the relative $EC_{50}$ value of the curve by Prism GraphPad 9 software (Table 1).

TABLE 1

Response of compounds stimulated with 30 ng/mL IFN-γ in HEK293/Luc

| Compounds | Absolute $EC_{50}$(nM) | Compounds | Absolute $EC_{50}$(nM) |
|---|---|---|---|
| Ref. Cpd | 473.1 | 21 | 48.05 |

*Ref. Cpd refers to compound 187b in patent publication No. WO 2023/019166, the structure was shown as below:

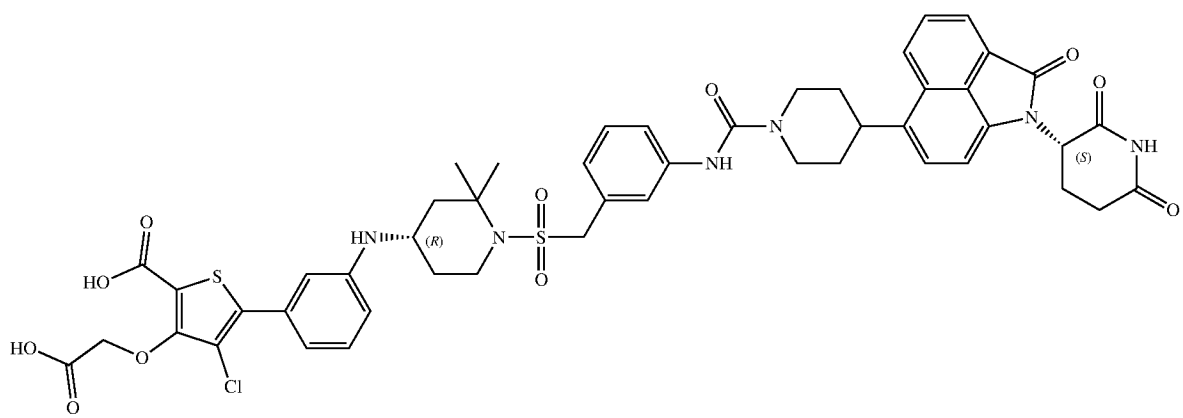

Examplee 187b

Example 3: Western Blot

1. Sample preparation: 150,000 HEK293T cells per well were seeded in a 24-well plate and incubated overnight. Compounds were added to the wells at the final concentrations of 20 µM, 10 µM, 5 µM, 2 µM, 1 µM, 500 nM, 200 nM, 100 nM, 50 nM, 20 nM, 5 nM, 0 nM (solvent control) and medium (negative control) and incubated for 48 hours. After incubation, the supernatants were discarded. Cells were washed with pre-chilled PBS once, 40 µL cell lysis buffer were added to lyse the cells and then centrifuged at 14000 g, 4° C. for 20 mins. The supernatant was aspirated and the protein concentration were quantified. 5× loading buffer was added into the samples, and the samples were heated at 70° C. for 10 minutes.

2. Experimental procedure: 20 µg protein were added to each well then start SDS-PAGE electrophoresis. The protein was transferred to the PVDF membrane.

The blotting current was set at 250 mA for 90 min. 5% BSA in TBST was used to block the membrane for 1 h at room temperature. After diluting the primary antibody according to Table 2, the membrane was hybridized overnight at 4° C. The membrane was washed three times with TBST, 7 minutes each time. After diluting the secondary antibody, the membrane was incubated for 2 h at room temperature. The membrane was washed three times with TBST for 7 min each time.

TABLE 2

Antibody dilution ratio and corresponding secondary antibody species information

| Antibody | Cat | dilution | Host species |
|---|---|---|---|
| PTPN2 | CST#58935S | 1:1000 | Rabbit |
| PTP1B | CST#8311S | 1:1000 | Rabbit |
| GAPDH | CST#97166 | 1:10000 | mouse |
| β-actin | CST#3700 | 1:10000 | mouse |

ImageJ software was used to detect the gray value of each band and enter it into the following formula as the degradation rate (D):

$$D(\%) = \frac{V_{target}(Lane\ X)}{V_{housekeeping}(Lane\ X)} \times \frac{V_{housekeeping}(Lane\ Y)}{V_{DMSO}(Lane\ Y)} \times 100\%$$

D is the degradation rate, V refers to the gray value: target refers to the name of the protein targeted for degradation, housekeeping refers to housekeeping proteins such as GAPDH and beta-actin: DMSO refers to the solvent DMSO added only to dissolve PROTAC and incubate cells: Lane X refers to a lane with a specific incubation concentration; Lane Y refers to a lane where only the solvent DMSO is added to incubate cells.

As shown in FIG. 1, after incubation with compound 21 for 48 hours, the PTPN2 protein was completely degraded at high concentrations, and the protein degradation ability gradually weakened as the compound concentration decreased, showing a good dose-dependent effect. Meanwhile, compound 21 showed good selectivity, and the inhibition of PTP1B at the same concentration was much weaker than that of PTPN2.

A graph was drawn with degradation rate as the vertical axis and drug incubation concentration as the horizontal axis, and $DC_{50}$ and $D_{max}$ were read and recorded in Tables 3, 4, 5 and 6.

TABLE 3

Summary of $DC_{50}$ and $D_{max}$ of compounds on PTPN2 degradation

| Compounds | Relative $DC_{50}$ (nM) | $D_{max}(\%)$ |
|---|---|---|
| 16 | 38.76 | 96.45 |
| 21 | 10.14 | 100.0 |
| 57 | 51.19 | 97.23 |
| 78 | 55.17 | 100.0 |

TABLE 4

Summary of $DC_{50}$ and $D_{max}$ of compounds for PTP1B degradation

| Compounds | Relative $DC_{50}$ (nM) | $D_{max}(\%)$ |
|---|---|---|
| 21 | 860.6 | 97.3 |

TABLE 5

Summary of DC$_{50}$ and D$_{max}$ of compounds on PTPN2 degradation

| Compounds | Relative DC$_{50}$ (nM) | D$_{max}$(%) |
|---|---|---|
| Ref Cpd | 29.32 | 96.34 |

TABLE 6

Summary of DC$_{50}$ and D$_{max}$ of compounds for PTP1B degradation

| Compounds | Relative DC$_{50}$ (nM) | D$_{max}$(%) |
|---|---|---|
| Ref Cpd | 271.0 | 96.77 |

Example 4: PK Studies in SD Rats

A PK study of the compounds after a single intravenous administration.

The scheme was as follows:

SD rats were randomly assigned to 5 groups (3 rats/group). Blood samples were collected from animals at 0.083 h, 0.25 h, 0.5 h, 1 h, 2 h, 4 h, 8 h, 10 h and 24 h after administration. Blood samples were collected in an anticoagulant tube containing EDTA-K2. The concentration of compounds in plasma were determined by an LC-MS/MS method with the lower limit of quantitation (LLOQ) of 0.50 ng/mL. Pharmacokinetic parameters were calculated with WinNonlin to assess the PK characteristics in SD rats. The formulation prescription was DMSO: Cremophor EL: 5% Glucose Solution=5:5:90 (v/v/v). The blood collection time points and plasma drug concentrations were shown in Table 7.

TABLE 7

Plasma concentrations of different compounds after intravenous injection

| | Compounds | | | | |
|---|---|---|---|---|---|
| | Ref. Cpd | 21 | 151 | 23 | 57 |
| | Dose (mg/kg) | | | | |
| | 2 | 1 | 1 | 1 | 1 |
| Time (h) | Concentration (ng/mL) | | | | |
| 0.083 | 22700 | 18100 | 19400 | 21700 | 21900 |
| 0.25 | 8300 | 14600 | 14900 | 17900 | 17000 |
| 0.5 | 1290 | 9660 | 11500 | 12600 | 13200 |
| 1 | 318 | 5980 | 7920 | 7110 | 8730 |
| 2 | 148 | 2890 | 3810 | 2420 | 5430 |
| 4 | 79.4 | 1000 | 1050 | 525 | 2870 |
| 8 | 29.3 | 372 | 345 | 110 | 1090 |
| 10 | 18.9 | 321 | 279 | 95.1 | 809 |
| 24 | BLOQ | 98.6 | 57.5 | 39.6 | 206 |
| AUC$_{0-24 h}$ (ng · h/mL) | 7490 | 27200 | 29700 | 24700 | 48700 |
| CL (mL/kg/min) | 4.46 | 0.661 | 0.568 | 0.684 | 0.351 |

*Ref. Cpd refers to compound 187b in patent publication No. WO 2023/019166.

What is claimed is:

1. A compound or a pharmaceutically acceptable salt thereof, wherein the compound is selected from the group consisting of:

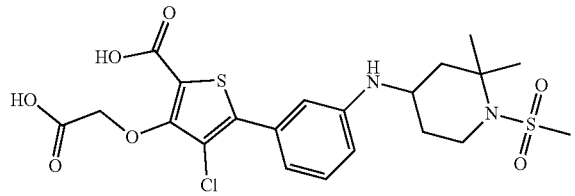

16

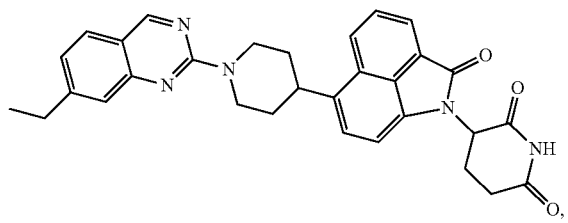

21

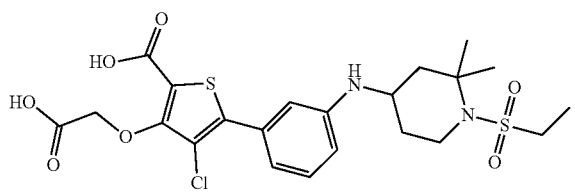

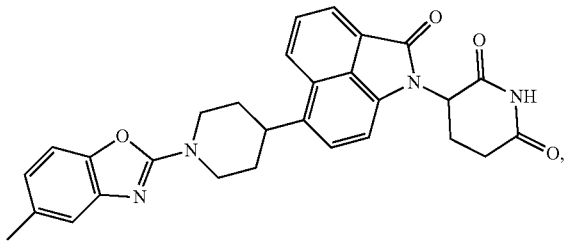

57

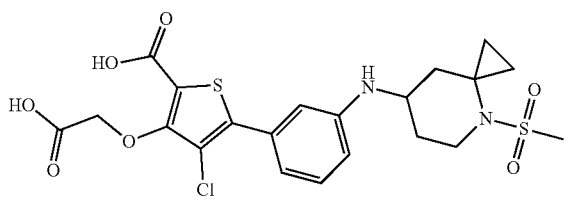

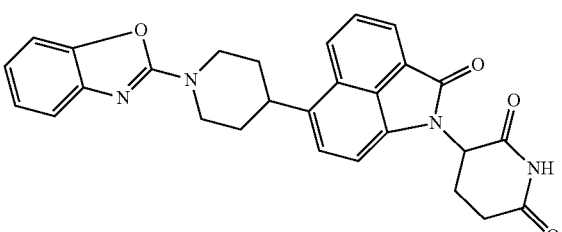

78

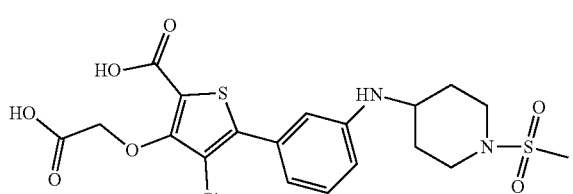

421
-continued

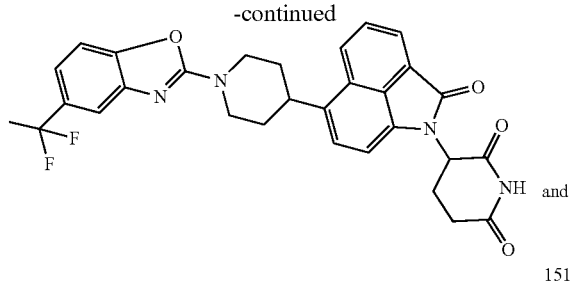

151

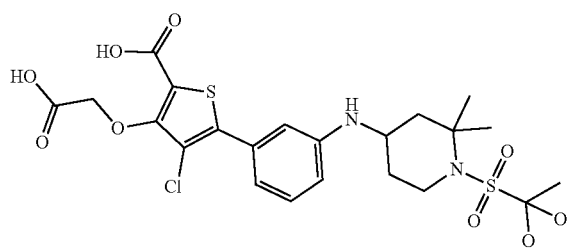

422
-continued

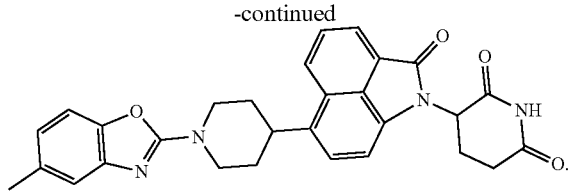

and

2. The compound or the pharmaceutically acceptable salt thereof of claim 1, wherein the pharmaceutically acceptable salt is selected from the group consisting of an acetate, a benzenesulfonate, a bromide, a camphorsulfonate, a chloride, a citrate, a fumarate, a lactate, a malate, a maleate, a fumarate, an oxalate, a phosphate, a succinate, a sulfate, a tartrate, a sodium salt, a potassium salt, an ammonium salt, a tetra-n-butylammonium salt, and an ethanolamine salt.

3. The compound or the pharmaceutically acceptable salt thereof of claim 1, wherein the compound is

16

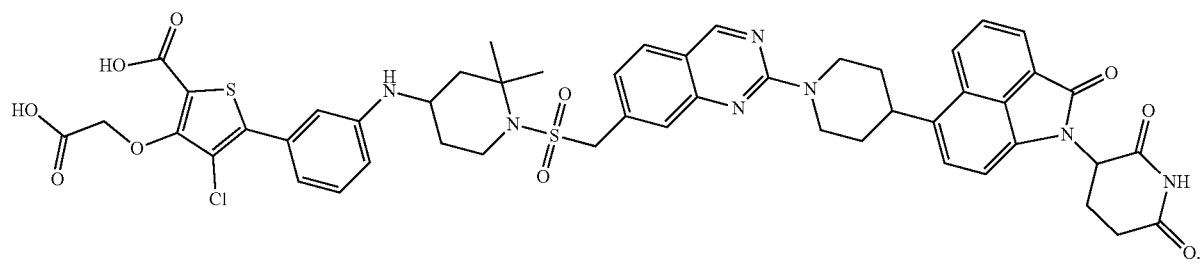

40

4. The compound or the pharmaceutically acceptable salt thereof of claim 1, wherein the compound is

21

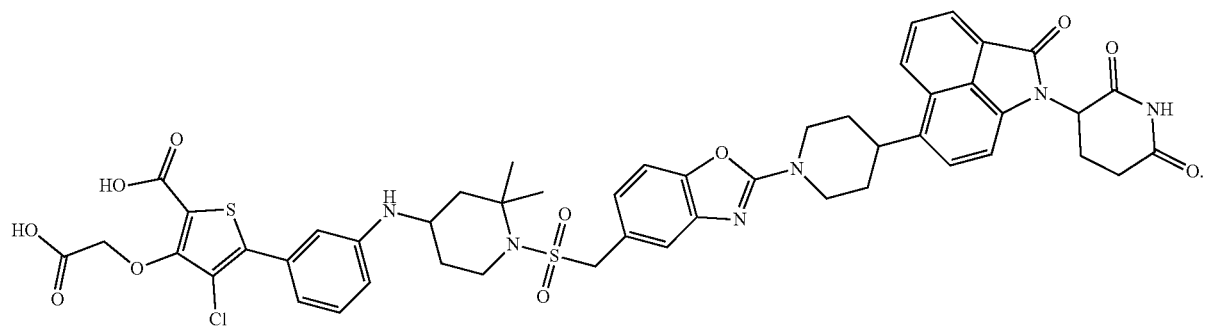

5. The compound or the pharmaceutically acceptable salt thereof of claim 1, wherein the compound is

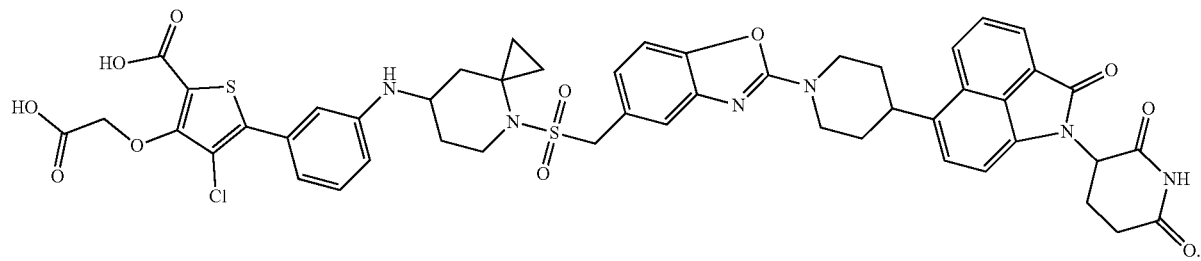

57

6. The compound or the pharmaceutically acceptable salt thereof of claim 1, wherein the compound is

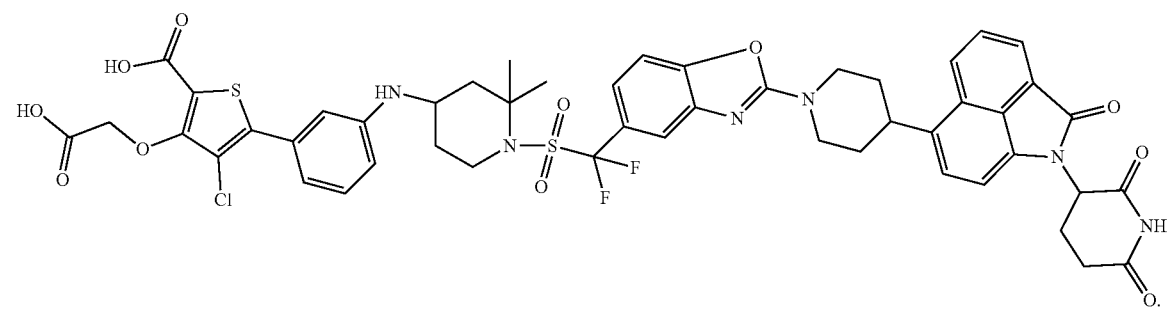

78

7. The compound or the pharmaceutically acceptable salt thereof of claim 1, wherein the compound is

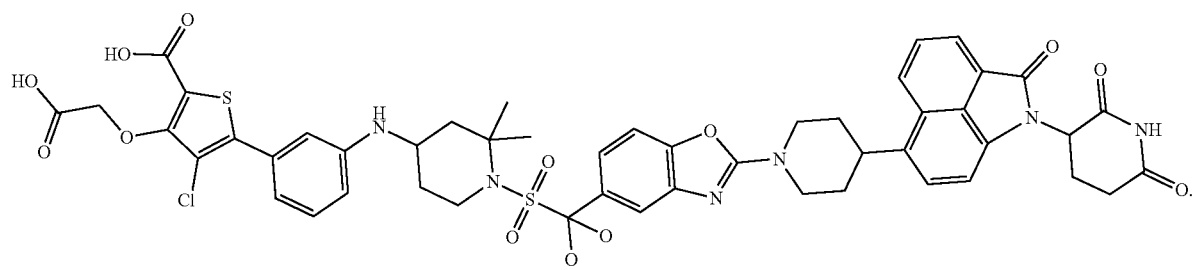

151

8. A pharmaceutical composition, comprising the compound or the pharmaceutically acceptable salt thereof of claim 1, and a pharmaceutically acceptable excipient.

* * * * *